(12) United States Patent  
Caniggia et al.

(10) Patent No.: US 8,889,132 B2  
(45) Date of Patent: Nov. 18, 2014

(54) ANTIBODIES AGAINST HUMAN HIF-1α

(75) Inventors: Isabella Caniggia, Toronto (CA);  
Martin Post, Toronto (CA)

(73) Assignee: Mount Sinai Hospital, Toronto, CA (US)

( * ) Notice: Subject to any disclaimer, the term of this patent is extended or adjusted under 35 U.S.C. 154(b) by 0 days.

(21) Appl. No.: 13/807,093

(22) PCT Filed: Jun. 30, 2011

(86) PCT No.: PCT/CA2011/000763  
§ 371 (c)(1),  
(2), (4) Date: Dec. 27, 2012

(87) PCT Pub. No.: WO2012/000094  
PCT Pub. Date: Jan. 5, 2012

(65) Prior Publication Data  
US 2013/0280736 A1 Oct. 24, 2013

Related U.S. Application Data

(60) Provisional application No. 61/360,058, filed on Jun. 30, 2010, provisional application No. 61/381,575, filed on Sep. 10, 2010.

(51) Int. Cl.  
*A61K 39/395* (2006.01)  
*A61K 39/00* (2006.01)  
*G01N 33/68* (2006.01)  
*C07K 16/18* (2006.01)  
*G01N 33/53* (2006.01)

(52) U.S. Cl.  
CPC ........ *G01N 33/689* (2013.01); *G01N 2800/368* (2013.01); *C07K 16/18* (2013.01); *G01N 2800/7038* (2013.01)  
USPC .................. 424/130.1; 424/135.1; 424/139.1; 424/141.1; 424/142.1; 435/7.1; 436/510

(58) Field of Classification Search  
None  
See application file for complete search history.

(56) References Cited

U.S. PATENT DOCUMENTS

| 7,279,160 B2* | 10/2007 | Zhou et al. ................. 424/143.1 |
| 7,604,800 B2* | 10/2009 | Lin et al. .................... 424/154.1 |
| 2005/0202450 A1 | 9/2005 | Huang |

FOREIGN PATENT DOCUMENTS

| KR | 1130786 | * 6/2011 | ............. C07K 16/40 |
| WO | WO 03/077858 | 9/2003 | |
| WO | WO 03/77858 | 9/2003 | |
| WO | WO 2005/110475 | 11/2005 | |
| WO | WO 2007/024535 | 3/2007 | |
| WO | WO 2007/146172 | 12/2007 | |

OTHER PUBLICATIONS

Pascallis et al., Grafting of "abbreviated" complementarity-determining regions containing specificity-determining residues essential for ligand contact to engineer a less immunogenic humanized monoclonal antibody, Journal of Immunology, 169: 3076-3084, 2002.*

Vajdos et al., .Comprehensive functional maps of the antigen binding site of an Anti-ErbB2 antibody obtained with shotgun scanning mutagenesis, J. Mol. Biol. 320: 415-428, 2002.*

Lamminmaki et al., Crystal structure of a recombinant Anti-estradiol Fab fragment in complex with 17 beta-estradiol, JBC 276:36687-36694, 2001.*

Rolfo et al, Abnormalities in oxygen sensing define early and late onset preeclampsia as distinct pathologies, PLoS One. Oct. 12, 2010; 5(10):e13288.

International Search Report mailed Oct. 18, 2011 issued in corresponding international application No. PCT/CA11/000763.

International Preliminary Report on Patentability mailed Jan. 17, 2013 issued in corresponding international application No. PCT/CA11/000763.

ACOG practice bulletin. Diagnosis and management of preeclampsia and eclampsia. Obstetrics and Gynecology, No. 33, Jan. 2002;99(1):159-67.

Adelman DM et al, Placental cell fates are regulated in vivo by HIF-mediated hypoxia responses. Genes and Development. Dec. 15, 2000;14(24):3191-203.

Ahmad S and Ahmed A, Elevated placental soluble vascular endothelial growth factor receptor-1 inhibits angiogenesis in preeclampsia. Circulation Research, Oct. 29, 2004;95(9):884-91. Epub Oct. 7, 2004.

Appelhoff RJ et al, Differential function of the prolyl hydroxylases PHD1, PHD2, and PHD3 in the regulation of hypoxia-inducible factor. Journal of Biological Chemistry. Sep. 10, 2004;279(37):38458-65. Epub Jul. 7, 2004.

Barber A et al, Heme oxygenase expression in human placenta and placental bed: reduced expression of placenta endothelial HO-2 in preeclampsia and fetal growth restriction. Faseb Journal. May 2001;15(7):1158-68.

Berra E, et al, HIF prolyl-hydroxylase 2 is the key oxygen sensor setting low steady-state levels of HIF-1alpha in normoxia. EMBO J. Aug. 15, 2003;22(16):4082-90.

Caniggia I and Winter JL, Adriana and Luisa Castellucci Award lecture 2001. Hypoxia inducible factor-1: oxygen regulation of trophoblast differentiation in normal and pre-eclamptic pregnancies—a review. Placenta. Apr. 2002;23 Suppl A:S47-57.

Caniggia I et al, Hypoxia-inducible factor-1 mediates the biological effects of oxygen on human trophoblast differentiation through TGFbeta(3). Journal of Clinical Investigation. Mar. 2000;105(5):577-87.

(Continued)

*Primary Examiner* — Elly-Gerald Stoica  
(74) *Attorney, Agent, or Firm* — Howson & Howson LLP

(57) ABSTRACT

The invention relates to reagents and methods for detecting, diagnosing and screening for conditions associated with hydroxylated hypoxia inducible factor 1-α (HIF-1α). The invention also relates to novel monoclonal antibodies specific for hydroxylated HIF-1α, or binding fragments thereof, and related nucleic acids, vectors, cells and compositions, as well as methods of using the antibodies in methods of the invention.

8 Claims, 22 Drawing Sheets

(56) References Cited

OTHER PUBLICATIONS

Caniggia I et al, Oxygen and placental development during the first trimester: implications for the pathophysiology of pre-eclampsia. Placenta Mar.-Apr. 2000;21 Suppl A:S25-30.

Chandel NS et al, Reactive oxygen species generated at mitochondrial complex III stabilize hypoxia-inducible factor-1alpha during hypoxia: a mechanism of O2 sensing. Journal of Biological Chemistry, Aug. 18, 2000;275(33):25130-8.

Chandel NS et al. Mitochondrial reactive oxygen species trigger hypoxia-induced transcription. Proceedings of the National Academy of Sciences U S A,Sep. 29, 1998;96(20):11715-20.

Chen YR et al, Differential and reciprocal regulation between hypoxia-inducible factor-alpha subunits and their prolyl hydroxylases in pulmonary arteries of rat with hypoxia-induced hypertension. Acta Biochim Biophys Sin (Shanghai). Jun. 2006;38(6):423-34.

Chun JY et al, Differential expression of vascular endothelial growth factor (VEGF), endocrine gland derived-VEGF, and VEGF receptors in human placentas from normal and preeclamptic pregnancies. Journal of Clinical Endocrinology and Metabolism, May 2004;89(5):2484-90.

Cockman ME et al, Hypoxia inducible factor-alpha binding and ubiquitylation by th evon Hippel-Lindau tumor suppresor protein. Journal of Biological Chemistry, Aug. 18, 2000;275(33):25733-41.

Cui XL et al, Expression of NADPH oxidase isoform 1 (Nox1) in human placenta: involvement in preeclampsia. Placenta Apr.-May 2006;27(4-5):422-31. Epub Jul. 1, 2005.

D'Angelo G et al, Hypoxia up-regulates prolyl hydroxylase activity: a feedback mechanism that limits HIF-1 responses during reoxygenation. Journal of Biological Chemistry. Oct. 3, 2003;278(40):38183-7. Epub Jul. 21, 2003.

Dayan F et al, The oxygen sensor factor-inhibiting hypoxia-inducible factor-1 controls expression of distinct genes through the bifunctional transcriptional character of hypoxia-inducible factor-1alpha. Cancer Research, Apr. 1, 2006;66(7):3688-98.

del Peso L et al, The von Hippel Lindau/hypoxia-inducible factor (HIF) pathway regulates the transcription of the HIF-proline hydroxylase genes in response to low oxygen. Journal of Biological Chemistry. Dec. 5, 2003;278(49):48690-5. Epub Sep. 23, 2003.

Erez N et al, Expression of prolyl-hydroxylase-1 (PHD1/EGLN2) suppresses hypoxia inducible factor-1alpha activation and inhibits tumor growth. Cancer Research, Dec. 15, 2003;63(24):8777-83.

Genbacev O et al, Hypoxia alters early gestation human cytotrophoblast differentiation/invasion in vitro and models the placental defects that occur in preeclampsia. Journal of Clinical Investigation, Jan. 15, 1996;97(2):540-50.

Hewitson KS et al, Hypoxia-inducible factor (HIF) asparagine hydroxylase is identical to factor inhibiting HIF (FIH) and is related to the cupin structural family. J Biological Chemistry, Jul. 19, 2002;277(29):26351-5. Epub May 31, 2002.

Hung TH et al, Hypoxia-reoxygenation: a potent inducer of apoptotic changes in the human placenta and possible etiological factor in preeclampsia. Circulation Research, Jun. 28, 2002;90(12):1274-81.

Hung TH et al, In vitro ischemia-reperfusion injury in term human placenta as a model for oxidative stress in pathological pregnancies. Americal Journal of Pathology, Sep. 2001;159(3):1031-43.

Ietta F et al, Dynamic HIF1A regulation during human placental development. Biology of Reproduction. Jul. 2006;75(1):112-21. Epub Apr. 12, 2006.

Ivan M, et al, HIFalpha targeted for VHL-mediated destruction by proline hydroxylation: implications for O2 sensing. Science. Apr. 20, 2001;292(5516):464-8. Epub Apr. 5, 2001.

Jaakkola P, et al, Targeting of HIF-alpha to the von Hippel-Lindau ubiquitylation complex by O2-regulated prolyl hydroxylation. Science. Apr. 20, 2001;292(5516):468-72. Epub Apr. 5, 2001.

Koga K et al. Elevated serum soluble vascular endothelial growth factor receptor 1 (sVEGFR-1) levels in women with preeclampsia. Journal of Clinical Endocrinology and Metabolism, May 2003;88(5):2348-51.

Koivunen P et al, Catalytic properties of the asparaginyl hydroxylase (FIH) in the oxygen sensing pathway are distinct from those of its prolyl 4-hydroxylases. Journal of Biological Chemistry, Mar. 12, 2004;279(11):9899-904. Epub Dec. 29, 2003.

Lando D et al, FIH-1 is an asparaginyl hydroxylase enzyme that regulates the transcriptional activity of hypoxia-inducible factor. Genes and Development. Jun. 15, 2002;16(12):1466-71.

Levine RJ et al, Circulating angiogenic factors and the risk of preeclampsia. New England Journal of Medicine, Feb. 12, 2004;350(7):672-83. Epub Feb. 5, 2004.

Livak KJ and Schmittgen TD, Analysis of relative gene expression data using real-time quantitative PCR and the 2(-Delta Delta C(T)) Method. Methods, Dec. 2001;25(4):402-8.

Lopez-Lazaro M, HIF-1: hypoxia-inducible factor or dysoxia-inducible factor? Faseb Journal, May 2006;20(7):828-32.

Mahon PC et al, FIH-1: a novel protein that interacts with HIF-1alpha and VHL to mediate repression of HIF-1 transcriptional activity. Genes and Development. Oct. 15, 2001;15(20):2675-86.

Mansfield KD et al, Mitochondrial dysfunction resulting from loss of cytochrome c impairs cellular oxygen sensing and hypoxic HIF-alpha activation. Cell Metabolism, Jun. 2005;1(6):393-9.

Masson N and Ratcliffe PJ, HIF prolyl and asparaginyl hydroxylases in the biological response to intracellular O(2) levels. Journal of Cell Science. Aug. 1, 2003;116(Pt 15):3041-9.

McMahon S et al, Transforming growth factor betal induces hypoxia-inducible factor-1 stabilization through selective inhibition of PHD2 expression. Journal of Biological Chemistry, Aug. 25, 2006;281(34):24171-81. Epub Jun. 30, 2006.

Nakayama K and Ronai Z, Siah: new players in the cellular resonse to hypoxia. Cell Cycle. Nov. 2004;3(11):1345-7. Epub Nov. 6, 2004.

Nakayama K et al, Hypoxia-induced assembly of prolyl hydroxylase PHD3 into complexes: implications for its activity and susceptibility for degradation by the E3 ligase Siah2. Biochemical Journal, Jan. 1, 2007;401(1):214-26.

Nevo O et al. Increased expression of sFlt-1 in in vivo and in vitro models of human placental hypoxia id mediated by HIF-1. American Journal of Physiology, Regulatory, Integrative and Comparative Physiology, Oct. 2006;291(4):R1085-93. Epub Apr. 20, 2006.

Rajakumar A and Conrad KP, Expression, ontogeny, and regulation of hypoxia-inducible transcription factors in the human placenta. Biology of Reproduction. Aug. 2000;63(2):559-69.

Soleymanlou N et al. Molecular evidence of placental hypoxia in preeclampsia, Journal of Clinical Endocrinology and Metabolism, Jul. 2005;90(7):4299-308.Epub Apr. 19, 2005.

Takeda K et al, Placental but not heart defects are associated with elevated hypoxia-inducible factor alpha levels in mice lacking prolyl hydroxylase domain protein 2. Mol Cell Biol Nov. 2006;26(22):8336-46. Epub Sep. 11, 2006.

Tian YM et al, Characterization of different isoforms of the HIF prolyl hydroxylase PHD1 generated by alternative initiation. Biochemical Journal, Jul. 1, 2006;397(1):179-86.

Zamudio S et al. Human placental hypoxia-inducible factor-1alpha expression correlates with clinical outcomes in chronic hypoxia in vivo. American Journal of Pathology, Jun. 2007;170(6):2171-9.

Zhou Y et al. Vascular endothelial growth factor ligands and receptors that regulate human cytotrophoblast survival are dysregulated in severe preeclampsia and hemolysis, elevated liver enzymes, and low platelets syndrome. American Journal of Pathology, Apr. 2002;160(4):1405-23.

Ahmed A and Kilby MD Hypoxia or hyperoxia in placental insufficiency? Lancet, Sep. 1997, 350(9801): 826-827.

Ahmed A et al. Colocalisation of vascular endothelial growth factor and its Flt-1 receptor in human placenta. Growth Factors, Jan. 1995;12(3):235-43.

Anson-Cartwright L et al. The glial cells missing-1 protein is essential for branching morphogenesis in the chorioallantoic placenta. Nat Genet Nature Genetics. Jul. 2000;25(3):311-4.

Aprelikova O et al. Regulation of HIF prolyl hydroxylases by hypoxia-inducible factors. Journal of Cellular Biochemistry. Jun. 1, 2004;92(3):491-501.

Bruick RK and McKnight SL, Transcription. Oxygen sensing gets a second wind. Science, Feb. 1, 2002;295(5556):807-8.

(56) References Cited

OTHER PUBLICATIONS

Brunelle JK et al, Oxygen sensing requires mitochondrial ROS but not oxidative phosphorylation. Cell Metabolism, Jun. 2005;1(6):409-14.
Burton GJ et al, Maternal arterial connections to the placental intervillous space during the first trimester of human pregnancy: the Boyd collection revisited. American Journal of Obstetrics & Gynecology Sep. 1999;181(3):718-24.
Callapina M et al, NO restores HIF-1 alpha hydroxylation during hypoxia: role of reactive oxygen species. Free Radicical Biology and Medicine, Oct. 1, 2005;39(7):925-36.
Caniggia I et al, Inhibition of TGF-beta 3 restores the invasive capability of extravillous trophoblasts in preeclamptic pregnancies. Journal of Clinical Investigation, Jun. 1999;103(12):1641-50.
Chen CP et al, Decreased placental GCM1 (glial cells missing) gene expression in pre-eclampsia. Placenta.May 2004;25(5):413-21.
Chesley LC, Diagnosis of preeclampsia. Obstetrics and Gynecol Mar. 1985;65(3):423-5.
Epstein AC, et al, C. elegans EGL-9 and mammalian homologs define a family of dioxygenases that regulate HIF by prolyl hydroxylation. Cell. Oct. 5, 2001;107(1):43-54.
Guzy RD et al, Mitochondrial complex III is required for hypoxia-induced ROS production and cellular oxygen sensing. Cell Metabolism, Jun. 2005;1(6):401-8.
Huppertz B et al, Apoptosis and its role in the trophoblast. American Journal of Obstetrics and Gynecology, Jul. 2006;195(1):29-39. Epub Mar. 31, 2006.
Iwai A et al, Siah-1L, a novel transcript variant belonging to the human Siah family of proteins, regulates beta-catenin activity in a p53-dependent manner. Oncogene, Sep. 30, 2004;23(45):7593-600.
Kibel A, et al, Binding of the von Hippel-Lindau tumor suppressor protein to Elongin B and C. Science, Sep. 8, 1995;269(5229):1444-6.
Kozak KR et al, ARNT-deficient mice and placental differentiation. Developmental Biology. Nov. 15, 1997;191(2):297-305.
Krebs C et al, Intrauterine growth restriction with absent end-diastolic flow velocity in the umbilical artery is associated with maldevelopment of the placental terminal villous tree. American Journal of Obstetrics and Gynecology, Dec. 1996;175(6):1534-42.
Li H et al, Hypoxia-induced increase in soluble Flt-1 production correlates with enhanced oxidative stress in trophoblast cells from the human placenta. Placenta. Feb.-Mar. 2005;26(2-3):210-7.
Macara L et al, Structural analysis of placental terminal villi from growth-restricted pregnancies with abnormal umbilical artery Doppler waveforms. Placenta, Jan. 1996;17(1):37-48.
Maxwell PH et al, The tumour suppressor protein VHL targets hypoxia-inducible factors for oxygen-dependent proteolysis. Nature May 20, 1999;399(6733):271-5.
Nakayama K et al, Siah2 regulates stability of prolyl-hydroxylases, controls HIF1alpha abundance, and modulates physiological responses to hypoxia. Cell. Jun. 25, 2004;117(7):941-52.
Ohh M et al, Ubiquitination of hypoxia-inducible factor requires direct binding to the beta-domain of the von Hippel-Lindau protein. Nature Cell Biology, Jul. 2000;2(7):423-7.
Pijnenborg et al, Interaction of interstitial trophoblast with placental bed capillaries and venules of normotensive and pre-eclamptic pregnancies. Placenta, Nov. 1998;19(8):569-75.
Rajakumar A et al, Evidence for the functional activity of hypoxia-inducible transcription factors overexpressed in preeclamptic placentae. Placenta Nov. 2004;25(10):763-9.
Redman CW and Sargent IL, Latest advances in understanding preeclampsia. Science, Jun. 10, 2005;308(5728):1592-4.
Rodesch F et al, Oxygen measurements in endometrial and trophoblastic tissues during early pregnancy. Obstetrics & Gynecology, Aug. 1992;80(2):283-5.
Semenza GL, Hypoxia-inducible factor 1: master regulator of O2 homeostasis. Current Opinions in Genetics and Development, Oct. 1998;8(5):588-94.

Zhou J and Brune B, Cytokines and hormones in the regulation of hypoxia inducible factor-1alpha (HIF-1alpha). Cardiovascular and Hematological Agents in Medicinal Chemistry, Jul. 2006;4(3):189-97.
Ahmad S and Ahmed A, Elevated placental soluble vascular endothelial growth factor receptor-1 inhibits angiogenesis in preeclampsia. Circulation Research, Oct. 29, 2004;95(9):884-91. Epub 2004 Oct 7.
Berra E, et al, HIF prolyl-hydroxylase 2 is the key oxygen sensor setting low steady-state levels of HIF-1alpha in normoxia. EMBO J. Aug. 15, 2003;22(16):4082-90.
Caniggia I and Winter JL, Adriana and Luisa Castellucci Award lecture 2001. Hypoxia inducible factor-1: oxygen regulation of trophoblast differentiation in normal and pre-eclamptic pregnancies—a review. Placenta. Apr. 23, 2002; Suppl A:S47-57.
Chandel NS. et al, Reactive oxygen species generated at mitochondrial complex III stabilize hypoxia-inducible factor-1 alpha during hypoxia: a mechanism of O2 sensing. Journal of Biological Chemistry, Aug. 18, 2000;275(33):25130-8.
Chandel NS et al. Mitochondrial reactive oxygen species trigger hypoxia-induced transcription. Proceedings of the National Academy of Sciences USA, Sep. 29, 1998;95(20):11715-20.
Chung JY et al, Differential expression of vascular endothelial growth factor (VEGF), endocrine gland derived-VEGF, and VEGF receptors in human placentas from normal and preeclamptic pregnancies. Journal of Clinical Endocrinology and Metabolism, May 2004;89(5):2484-90.
Cockman ME et al, Hypoxia inducible factor-alpha binding and ubiquitylation by the von Hippel-Lindau tumor suppressor protein. Journal of Biologcial Chemistry, Aug. 18, 2000;275(33):25733-41.
Dayan F et al, The oxygen sensor factor-inhibiting hypoxia-inducible factor-1 controls expression of distinct genes through the bifunctional transcriptional character of hypoxia-inducible factor-1alpha. Cancer Research, Apr. 1, 2006;66(7):3688-98.
Erez N. et al, Expression of prolyl-hydroxylase-1 (PHD1/EGLN2) suppresses hypoxia inducible factor-1 alpha activation and inhibits tumor growth. Cancer Research, Dec. 15, 2003;63(24):8777-83.
Koivunen P. et al, Catalytic properties of the asparaginyl hydroxylase (FIH) in the oxygen sensing pathway are distinct from those of its prolyl 4-hydroxylases. Journal of Biological Chemistry, Mar. 12, 2004;279(11):9899-904. Epub Dec. 29, 2003.
Levine RJ et al, Circulating angiogenic factors and the risk of preeclampsia. New England Journal of Medicine, Feb. 12, 2004; 350(7):672-83. Epub Feb. 5, 2004.
Masson N. and Ratcliffe PJ, HIF prolyl and asparaginyl hydroxylases in the biological response to intracellular O(2) levels. Journal of Cell Science. Aug. 1, 2003;116(Pt 15):3041-9.
Nakayama K and Ronai Z, Siah: new players in the cellular response to hypoxia. Cell Cycle. Nov. 2004;3(11):1345-7. Epub Nov. 6, 2004.
Nakayama K et al, Hypoxia-induced assembly of prolyl hydroxylase PHD3 into complexes: implications for its activity and susceptibility for degradation by the E3 ligase Siah2. Biochemical Journal, Jan. 1, 2007;401(1):217-26.
Nevo O et al. Increased expression of sFlt-1 in in vivo and in vitro models of human placental hypoxia is mediated by HIF-1. American Journal of Physiology, Regulatory, Integrative and Comparative Physiology, Oct. 2006;291(4):R1085-93. Epub Apr. 20, 2006.
Rajakumar A and Conrad KP, Expression, ontogeny, and regulation of hypoxia-inducible tramscription factors in the human placenta. Biology of Reproduction. Aug. 2000;63(2):559-69.
Soleymanlou N. et al. Molecular evidence of placental hypoxia in preeclampsia, Journal of Clinical Endocrinology and Metabolism, Jul. 2005;90(7):4299-308. Epub Apr. 19, 2005.
Tian YM et al, Characterization of different isoforms of the HIF prolyl hydroxylase PHD1 generated by alternative initiation. Biochemical Journal, Jul. 1, 2006;1;397(1):179-86.
Zamudio S et al. Human placental hypoxia-inducible factor-1alpha expression correlates with clinical outcomes in chronic hypoxia in vivo. American Journal of Pathology, Jun. 2007;170(6):2171-9.
Tian et al, Differential Sensitivity of Hypoxia Inducible Factor Hydroxylation Sites to Hypoxia and Hydroxylase Inhibitors, J. Biological Chemistry, 286(15):13041-51 (Apr. 2011).

(56) References Cited

OTHER PUBLICATIONS

Chan et al, Coordinate regulation of the oxygen-dependent degradation domains of hypoxia-inducible factor 1 alpha, Molecular and Cellular Biology, 25(15):6415-26 (Aug. 2005).
Chan et al, Role of prolyl hydroxylation in oncogenically stabilized hypoxia-inducible factor-1 alpha, J. Biological Chemistry, 277(42):40112-7 (Oct. 2002).
Rajakumar A et al. (Feb. 2004) Evidence for the functional activity of hypoxia-inducible transcription factors overexpressed in preeclamptic placentae. Placenta; 25(10): 763-769.
Carmeliet P, Dor Y, Herbert J-M, Fukumuras D, Brusselmans K, et al. (Jul. 1998) Role of HIF-1α in hypoxia-mediated apoptosis, cell proliferation and tumour angiogenesis. *Nature*, 394, 485-490.
Chun Y-S, Choi E, Kim G-T, Lee M-J, Lee S-E, Kim M-S & Park J-W (Jan. 2000) Zinc induces the accumulation of hypoxia-inducible factor (HIF)-1α, but inhibits the nuclear translocation of HIF-1, causing HIF-1 inactivation.*Biochem Biophys Res Commun*, 268, 652-656.
Cowden Dahl, KD et al, Hypoxia-Inducible Factors 1α and 2α Regulate Trophoblast Differentiation. *Molecular and Cellular Biology*, (Dec. 2005), vol. 25(23) p. 10479-10491.
Feldser D, Agani F, Iyer NV, Pak B, Ferreira G & Semenza GL (Aug. 1999) Reciprocal positive regulation of hypoxia-inducible factor 1a and insulinlike growth factor 2. *Cancer Research*, 59, 3915-3918.
Forsythe JA, Jiang B-H, Iyer NV, Agani F, Leung SW, et al. (Sep. 1996) Activation of vascular endothelial growth factor gene transcription by hypoxia inducible factor 1. *Mol Cell Biol*, 16, 4604-4613.
Genbacev O, Krtolica A, Kaelin W & Fisher SJ (May 2001) Human cytotrophoblast expression of the von Hippel-Lindau protein is down-regulated during uterine invasion *in situ* and up-regulated by hypoxia in vitro. *Developmental Biology*, 233, 526-536.
Goldberg MA, Dunning SP & Bunn HF (Dec. 1988) Regulation of the erythropoietin gene: evidence that the oxygen sensor is a heme protein. *Science*, 242, 1412-1415.
Huang LE, Arany Z, Livingston DM & Bunn HF (Dec. 1996) Activation of hypoxia- inducible transcription factor depends primarily upon redoxsensitive stabilization of its α subunit. *J Biol Chem*, 271, 32253-32259.
Huang LE, Gu J, Schau M & Bunn HF (Jul. 1998) Regulation of hypoxiainducible factor 1α is mediated by an oxygen-dependent degradation domain via the ubiquitin-proteasome pathway. *Proc Natl Acad Sci USA*, 95, 7987-7992.
Huang LE, Willmore WG, Gu J, Goldberg MA & Bunn HF (Mar. 1999) Inhibition of hypoxia-inducible factor 1 activation by carbon monoxide and nitric oxide. *J Biol Chem*, 274(13):9038-9044.
Iyer NV, Kotch Le, Agani F, Leung SW, Laughner E, Wenger RH, Gassman M, Gearhart JD, Lawler AM, Yu A & Semenza GL (Nov. 1997) Cellular and developmental control of oxygen homeostasis by hypoxiainducible factor 1α. *Genes and Development*, 12, 149-162.
James et al, (Mar. 2006) the regulation of trophoblast differentiation by oxygen in the first trimester of pregnancy. *Hum Reprod Update* 12(2): 137-144, Epub Oct. 18, 2005.
Jiang B-H, Zheng JC, Semenza GL & Roe R (Aug. 1997) Transactivation and inhibitory domains of hypoxia-inducible factor 1a: modulation of transcriptional activity by oxygen tension. *J Biol Chem*, 272, 19253-19260.
Makino Y, Cao R, Svensson K, Bertilsson G, Asman M, Tanaka H, Cao Y, Berkenstam A & Poellinger L (Oct. 2001) Inhibitory PAS domain protein is a negative regulator of hypoxia-inducible gene expression. *Nature*, 414, 550-554.
Maltepe E, Schmidt JV, Baunoch D, Bradfield CA & Simon MC (Mar. 1997) Abnormal angiogenesis and response to glucose and oxygen deprivation in mice lacking the protein ARNT. *Nature*, 386, 403-407.
Park, Jong-Wan et al, (Mar. 2004) Hypoxia-Inducible Factor 1-Related Diseases and Prospective Therapeutic Tools. *J Pharmacol Sci* 94, 221-232.
Peng, M et al. (Feb. 2010) Change of HIF-1 alpha protein expression in the placenta bed and concentration of vWF in maternal peripheral blood of pre-eclampsia. Zhong Nan Da Xue Xue Bao Yi Xue Ban (Journal of Central South University—Medical Sciences) 35(2): 134-9. (English Abstract).
Rajakumar A, Whitelock KA, Weissfeld LA, Daftary AR, Markovic N & Conrad KP (Feb. 2001) Selective overexpression of the hypoxia-inducible transcription factor, HIF-2α, in placentas from women with preeclampsia. *Biol Reprod*, 64, 499-506.
Rajakumar A, Doty K, Daftary A, Markovic N, Conrad KP. (Apr. 2006) Expression of von Hippel-Lindau (pVHL) protein in placentae from normal pregnant women and women with preeclampsia. *Placenta*; 27(4-5):411-421.
Rajakumar A, et al. (May 2007) Placental HIF- 1α, HIF-2α, membrane and soluble VEGF receptor-1 proteins are not increased in normotensive pregnancies complicated by late-onset intrauterine growth restriction. *Am J Physiol Regul Integr Comp Physiol* 293: R766-R774.
Rajakumar A, et al. (Mar. 2008) Proteasomal Activity in Placentas from Women with Preeclampsia and Intrauterine Growth Restriction: Implications for Expression of HIF-αProteins. Placenta 29: 290-299.
Ryan HE, Lo J & Johnson RS (Jun. 1998) HIF- 1αis required for solid tumor formation and embryonic vascularization. *EMBO J*, 17, 3005-3015.
Salceda S & Caro J (Sep. 1997) Hypoxia-inducible factor 1α (HIF-1α) is rapidly degraded by the ubiquitin-proteasome system under normoxic conditions. *J. Biol Chem*, 272, 22642-22647.
Semenza GL (Jun. 2000) Expression of hypoxia-inducible factor 1: mechanisms and consequences. *Biochem Pharmacol*, 59, 47-53.
Semenza, GL (May 2001) Hypoxia-Inducible Factor 1: Control of Oxygen Homeostasis in Health and Disease. *Pediatric Research* 49(5): 614-617.
Semenza GL & Wang GL (Sep. 1992) A nuclear factor induced by hypoxia via de novo protein synthesis binds to the human erythropoietin gene enhancer at a site required for transcriptional activation. *Mol Cell Biol*, 12, 5447-5454.
Semenza GL, Roth PH, Fang H-M & Wang GL (Jul. 1994) Transcriptional regulation of genes encoding glycolytic enzymes by hypoxia inducible factor 1. *J Biol Chem*, 269, 23757-23763.
Stroka DM, Burkhardt T, Desbaillets I, Wenger RH, Neil Dah, Bauer C, Gassmann M & Candinas D (Nov. 2001) HIF-1 is expressed in normoxic tissue and displays an organ-specific regulation under systemic hypoxia. *FASEB J*, 15, 2445-2453.
Sun SG, et al (Jul. 2006) Expression of hypoxia-inducible factor 1alpha, vascular endothelial growth factor and sFlt-1 in preeclampsia placenta. *Zhonghua Fu Chan Ke Za Zhi*, 41(7): 440-4 (English Abstract).
Tal R (Oct. 2012) The Role of Hypoxia and Hypoxia-Inducible Factor-1 Alpha in Preeclampsia Pathogenesis. *Biol Reprod*, 87(6):134, 1-8.
Tal R et al, (Dec. 2010) Effects of hypoxia-inducible factor-1αoverexpression in pregnant mice. American J Pathology 177(6): 2950.
Wang GL & Semenza GL (May 1993) General involvement of hypoxia inducible factor 1 in transcriptional response to hypoxia. *Proc Natl Acad Sci USA*, 90, 4304-4308.
Wang GL, Jiang BH, Rue EA & Semenza GL (Jun. 1995) Hypoxia inducible factor 1 is a basic helix-loop-helix PAS heterodimer regulated by cellular O2 tension. *Proc Natl Acad Sci USA*, 92, 5510-5514.
European Extended Search Report and Opinion dated Oct. 29, 2013 issued in corresponding European Patent Application No. 11800018.1.

\* cited by examiner

Sequences for clone 6A9 Light chain:

```
  1  G  D  Q  S  P  Q  A  V  S  S  G  C  L  L  K  M  K  L  P  V  20
  1  ggTGATCaGTcTCCTCAGGcTGTcTCcTCAGGTTgCCTCCTcAaaatGAAgttGCCtgTT  60

21  R  L  L  V  L  M  F  W  I  P  V  S  S  S  D  V  L  M  T  Q  40
 61  AGGcTgtTGGtGctGATGTTcTGGatTCCtGtTTcCAGCAgtGAtGTTtGAtGAcCCAA  120

41  T  P  L  S  L  P  V  S  L  G  D  Q  A  S  I  S  C  R  S  S  60
121  ACTCCaCTcTCCCTGCCtGTCAGTcTTGGAGaTCAAGCCTCCATcTcTTGCAGATcTAGT  180

61  Q  S  I  V  H  S  N  G  N  T  Y  L  E  W  Y  L  Q  K  P  G  80
181  CAGaGCaTTGTACATAGTAATGGAAACaCCTaTTTaGAATGGTaCCTGCaGAAACCAGGC  240

81  Q  S  P  K  L  L  I  Y  K  V  S  N  R  F  S  G  V  P  D  R  100
241  CAGTCTCCAAAGCTCCTGATtTACAAAGTTTCCAACCGATTTTcTGGGGTcCCAGACAGG  300

101  F  S  G  S  G  S  G  T  D  F  T  L  K  I  S  R  V  E  A  E  120
301  TTCAGTGGCAGTGGATCAGGGACAGATTTCaCACTCAAGATCagCAGAGTGGaGGcTGaG  360

121  D  L  G  V  Y  Y  C  F  Q  G  T  H  V  P  L  T  F  G  A  G  140
361  GaTcTGGGaGTTTATTacTGCTTTCAAGGTaCACATGTTCCGCTCACGTTCGGTGcTGGG  420

141  T  K  L  E  L  K  R  A  D  A  A  P  T  V  S  I  F  P  P  S  160
421  ACCAAGCTGGAgcTGAAACGGGCTGATGcTGCACCAAcTGTAtccatcttcCCaCCATcC  480
```

Sequences for clone 6A9 Heavy chain:

```
  1  S  S  D  R  G  A  K  P  W  I  P  R  S  S  H  S  V  I  S  T  20
  1  AgcTctgacagaggagCCAAgccctgGAtTcCCAGGTCCTCACATTCAGTGATCAGCACT  60

21  E  H  R  P  L  T  M  D  S  R  L  N  L  V  F  L  V  L  I  L  40
 61  gAACACAGaCCACTCACCATGGaCTcCAggcTCAATTTAGTTTTCCTTGTCCTTATTTTA  120

41  K  G  V  Q  C  D  V  Q  L  V  E  S  G  G  G  L  V  Q  P  G  60
121  AAAGGTGTCCAGTGTGATGTGCAGCTGGTGGAGTcTGGGGGAGGCTTAGTGCAGCCTGGA  180

61  G  S  R  K  L  S  C  A  A  S  G  F  T  F  S  S  F  G  M  H  80
181  GGGTCCCGGAAACTCTCCTGTGCAGCCTcTGGATTCACTTTCAGTAGCTTTGGAATGCAC  240

81  W  V  R  Q  A  P  E  K  G  L  E  W  V  A  F  I  S  S  G  S  100
241  TGGGTTcGTCAGGCTCCAGAGAAGGGGCTGGAGTGGGTCGCATTCATTAGTAGTGGCAGT  300

101  H  T  I  F  Y  A  D  T  V  K  G  R  F  T  I  S  R  D  N  P  120
301  CATACCATcTTcTATGCAGACACAGTGAAGGGCCGATTCACCATCTCCCGAGACAATCCC  360

121  K  N  T  L  F  L  Q  M  T  S  L  R  S  E  D  T  A  M  Y  Y  140
361  AAGAACACCCTCTTCCTGCAAATGACCAGTcTAAGGTCTGAGGACACGGCCATGTATTAC  420

141  C  T  R  D  Y  N  A  Y  W  G  Q  G  T  L  V  T  V  S  A  A  160
421  TGTACAAGAGACTATAATGCTTACTGGGgccAAGGGACTCTGGTCACTGTCTCTgcAGcC  480

161  K  T  T  163
481  AAAacAacA  489
```

Figure 12

Sequences for clone 1H1 Light chain:

```
  1 G  D  Q  S  P  Q  A  V  S  S  G  C  L  L  K  M  K  L  P  V   20
  1 ggtGATcAGTcTCCTCaGGcTGTcTcCTCAGGTTGCCTCctcAAAAtgAAgTTgCCTGtT  60

21 R  L  L  V  L  M  F  W  I  P  A  S  S  S  D  V  L  M  T  Q   40
 61 aGGCTGTTGGTGcTGAtGTTcTGGATTccTGcTTcCaGCAGTGATGTTTtGatGaCCCAA 120

41 T  P  L  S  L  P  V  S  L  G  D  Q  A  S  I  S  C  R  S  S   60
121 AcTcCAcTcTcCCTGCCTGTCAGTcTTGGaGATCAAGCCTCCATcTcTTGCAGATcTAGT 180

61 Q  S  I  V  H  S  N  G  N  T  Y  L  E  W  Y  L  Q  K  P  G   80
181 CAGAGCATTGTACATAGTAATGGAAACACcTATTTAGAATGGTaCCTGCAGAAACCaGGc 240

81 Q  S  P  K  V  L  I  Y  K  V  S  N  R  F  S  G  V  P  D  R  100
241 CAGTcTCCAAAGGTCcTGATcTACAAAGTTTCCAACCGATTTTcTGGGgTCCCAGaCAGG 300

101 F  S  G  S  G  S  G  T  D  F  T  L  K  I  S  R  V  E  A  E  120
301 TTCAGtGgCAGtGGaTCAGGGaCaGATTTCaCActCAAGaTCAgCaGAGtGGaGGctGAG 360

121 D  L  G  L  Y  Y  C  F  Q  G  S  H  V  P  W  T  F  G  G  G  140
361 GATcTGGGACTTtATTACTGCTTtCAAGGTTCACATGtTCCgTGGACGTTCGGTgGaGGc 420

141 T  K  L  E  I  K  R  A  D  A  A  P  T  V  S  I  F  P  P  S  160
421 ACCAAGcTGGAgATcAAACGGGCTGATGCTGCACCAACTGTATCCaTCTTCCCACCATCC 480

161 S  E  Q  L  T  S  G  G  A  S  V  V  C  173
481 AGTGAGCAGTTAACATCTGGAGGTGCCTCAGTCGTgTGc 519
```

Figure 13

Sequences for clone 1H1 Heavy chain:

```
  1  G  E  L  *  Q  R  R  P  V  L  D  S  I  P  S  S  S  H  S  V  20
  1  GGGGaGcTctGACAGAGGAgGCCTGTCCTGGATTcGATTcCCAGTTcCTCACATTCAGTC  60

21  S  T  E  H  G  P  L  T  M  N  F  G  L  S  L  I  F  L  V  L  40
 61  AGCAcTGAACACGGACCCCTCACCATGAACTTCGGGcTCAGCtTGATTTTCCTTGTCCTT 120

41  V  L  K  G  V  Q  C  E  V  M  L  V  E  S  G  G  G  L  V  K  60
121  GTTTTAAAAGGTGTCCAGTGTGAAGTGATGCTGGTGGAGTcTGGGGGAGGCTTAGTGAAG 180

61  P  G  G  S  L  K  L  S  C  A  A  S  G  F  T  F  S  N  Y  A  80
181  CCTGGAGGGTCCCTGAAAcTCTCCTGTGCAGCCTCTGGATTCACTTTCAGTAAcTATGCC 240

81  M  S  W  V  R  Q  T  P  E  K  R  L  E  W  V  A  A  I  S  I 100
241  ATGTcTTGGGTTCGCCAGACTCCGGAGAAGAGGCTGGAGTGGGTCGCAGCCATTAGTATT 300

101  G  G  T  Y  T  F  Y  S  D  S  V  K  G  R  F  T  I  S  R  D 120
301  GGtGGTAcTTaCACCTTCTATTCAGACAGTGTGAAGGGGCGATTCACCATCTCCAGaGAC 360

121  N  A  K  N  T  L  Y  L  Q  M  S  S  L  R  S  E  D  T  A  M 140
361  AATGCCAAGAACACCCTTTACCTACAAATGAGCAGTCtGAGGTCTGAGGACACGGCCATG 420

141  Y  Y  C  A  R  R  R  F  D  D  Y  A  M  D  Y  W  G  Q  G  T 160
421  TATTACTGTGCAAGaCGGaGATTcGACGacTaTGCTATGGACTACTGGGGTCAAGGAACC 480

161  S  V  T  V  S  S  A  K  T  T  A  P  S  V  Y  P  L  A  P  V 180
481  TCAGTCACCGTCTCCTCAGCCAAAACAACAGCCCCATCgGTCTATCCACTGGCCCCTGTG 540

181  C  G  D  T  T  G  S  S  V  T  L  G  C  L  V  K  G 197
541  TGTGGAGATACaACTGGCTCCTCgGTGACTCtAGGATGCCtGGtCaAGggT 591
```

Figure 14

Sequences for clone 7E3 Light chain:

```
  1  G  T  D  Q  S  P  Q  A  V  S  S  G  C  L  L  K  M  K  L  P   20
  1  GGGactGATCAGTcTCCTCAGGCTGTCTCCTCAGGTTGCCTCCtCAAAATGAAGTTGCCt  60

21  V  R  L  L  V  L  M  F  W  I  P  A  S  T  S  D  V  L  M  T   40
 61  GtTAGGCTGTTGGTGcTGATGTTcTGGATTCCTGcTTcCACCAGTGATGTTTTGATGACC  120

41  Q  T  P  L  S  L  P  V  S  L  G  D  Q  A  S  I  X  C  R  S   60
121  CAAAcTCCACTCTCCCTGCCtGTCAGTcTTGGAGATCAAGCCTCCATcTNTTGCAGATcT  180

61  S  Q  N  I  L  H  S  S  G  N  T  Y  L  E  W  Y  L  Q  K  P   80
181  AGTCAGAACaTTTTACATAGTAGTGGGAACACCTACTTAGAATGGTACCTGCAGAAGCCA  240

81  G  Q  S  P  K  L  L  I  Y  K  V  S  N  R  F  S  G  V  P  D  100
241  GGCCAGTCTCCAAAgCTCCTgATcTACAAAgTTTCCAACCGATTTTctGgGGTcCCAGAC  300

101  R  F  S  G  S  G  S  G  T  D  F  T  L  K  I  S  R  V  E  G  120
301  AGGtTCAGTGGCAGtgGATCAGGGACAGATTTCaCaCTCaAgatCagCagAgtgGaGGgt  360

121  E  D  L  G  L  Y  F  C  F  Q  G  P  H  V  P  F  T  F  G  S  140
361  GagGaTctggGaCtctAcTtcTgctTtCaAGgtcCaCAtGttcCaTTCACGTTCGGctcG  420

141  G  T  K  L  E  I  K  R  A  D  A  A  P  T  V  S  I  F  P  P  160
421  GGGACaAAGTTGGAAATAAAACGGGCTGATGCTGCACCAACTGTATCCaTcTTCCCaCCA  480

161  S  S  E  Q  L  T  S  G  G  A  S  V  V  C  S            175
481  TCCAGTGAGCAGTTAACATCTGGAGGTGCCTCAGTCGTGTgcTcc           525
```

Figure 15

Sequences for clone 7E3 heavy chain:

```
  1  G  L  *  Q  R  R  Q  V  L  D  S  I  P  S  S  S  H  S  V  S  20
  1  GGGctctGACAGAGGAGGCAGGTCCTGGATTcGATTCCCAGTTCCTCACATTCAGTCAGC  60

21  T  E  H  G  P  L  T  M  N  F  V  L  R  L  I  F  L  A  L  I  40
 61  ACTGAACACGGACCCCTCACCATGAACTTTGTGCTCAGGTTGATTTTCCTTGCCCTCATT 120

41  L  K  G  V  Q  C  E  V  Q  L  V  E  S  G  G  G  L  V  K  P  60
121  TTAAAAGGTGTCCAGTGTGAAGTGCAACTGGTGGAGTCTGGGGGAGGCTTAGTGAAGCCT 180

61  G  G  S  L  Q  L  S  C  A  A  S  G  F  T  F  S  N  F  A  M  80
181  GGAGGGTCCCTGCAGCTcTCCTGTGCAGCCTCGGGATTCACTTTCAGTAACTTTGCCATG 240

81  S  W  V  R  Q  T  P  E  K  R  L  E  W  V  A  A  I  S  F  G 100
241  TcTTGGGTTCGCCAGACTCCGGAGAAGAGGCTGGAGTGGGTCGCAGCCATCAGTTTTGGT 300

101  G  D  Y  T  F  Y  L  D  S  V  K  G  R  F  T  I  S  R  D  N 120
301  GGAGATTACACCTTCTATcTAGACAGTGTGAAGGGTCGATTCACCATTTCCAGAGACAAC 360

121  A  K  N  T  L  Y  L  Q  M  R  S  L  K  S  E  D  T  A  M  Y 140
361  GCCAAGAACACCCTGTACCTACAAATGCGTAGTcTGAAGTCCGAGGACACGGCCATGTAT 420

141  Y  C  V  R  R  E  Y  G  N  F  A  M  A  Y  W  G  Q  G  T  S 160
421  TACTGTGTAAGACGGGAATATGGTAACTTCGCTATGGCCTaCTGGGGtCAAGGAACCTCA 480

161  V  T  V  S  S  A  K  T  T  P  P  S  V  Y  P  L  A  P  G  F 180
481  GTCACCGTCTCCTCAGcCAAAACGaCacCCCCaTcTGTcTATcCcCtgGcCCCcGGaTtT 540

181  A  V  Q  T  N  S  M  V  I 189
541  gcTgtCCaAAcTaAcTCCatGGtgatC 567
```

Figure 16

Sequences for clone 6H4 Light chain:

```
  1 G E S H S Q * G Y T I S M R V L A E L L  20
  1 GGaGaAAGTCActcTCagtGAGGATACACCATCAGCATGAGGGTcCTTGcTGAGcTccTG 60

21 G V L V F C F L G V R C D I Q M N Q S P  40
 61 GGGgTgcTGgtgTTctGcTTTTTAGGTGTGAGATGTGaCATCCAGATGAAcCAGTcTCCA 120

41 S S L S A S X G D T I T I T C Q A S Q N  60
121 TCCAGTcTGTcTGcatCcctNGGaGACACaATTAcCatcacttgcCAaGCCAGTCAGAAC 180

61 I N V W L S W Y Q Q K P G N I P K L M I  80
181 AtTAatGTTTgGTTAAgctGGTaccAgCagAAAcCAgGaAaTATtcCtAAaCtaaTgATc 240

81 S K A S N L H T V V P S R L S R S G C G  100
241 TcTAAGGcTTcCAaCctACACaCAGtcGtgccaTCAaGgctTAgTcgCaGtGGATgtGGA 300

101 T G C T L P I H P L Q R G G G C C H F F  120
301 ACaGgctgcactTTacCCATCcaTcCATTGCAGcGaGGAGGCggatgCtgCcACtTcTtt 360

121 Q P A Q Q G A F T F G G G T K L E I K R  140
361 CagccgGctCAacagggagCTttCACGTTCGGAGGGGGGACCAAGCTGGAAATAAAACGG 420

141 A D A A P T V S I F P P S S E Q L T S G  160
421 GCTGATGCTGCACCAACTGTATCCATcTTCcCaCCATCCAGTGAGCAGTTAACATCTGGA 480

161 G A S V V C  166
481 GGTGCCTCAGTCGTgTgc 498
```

Figure 17

Sequences for clone 6H4 heavy chain:

```
  1 G   N   I   C   P   M   S   S   P   Q   T   L   N   T   L   T   L   T   M   G   20
  1 GGGaAcaTatGTcCaAtgTcCTcTccTcAGACACTGAACACACTGACTcTAACCATGGGA 60

21 W   N   W   I   F   L   F   L   L   S   G   I   A   G   V   L   S   E   V   Q   40
 61 TGGAACTGGATCTTTCTCTTTcTCCTGTCAGGAAtTGCAGGTGTCCTcTcTGAGGTCCAG 120

41 L   Q   Q   S   G   P   E   L   V   K   P   G   A   S   I   K   I   S   C   K   60
121 CTGCAGCAGTcTGGACCTGAGTTGGTGAAGCCTGGGGCTTCAATAAAGATATCCTGCAAG 180

61 T   S   G   Y   T   F   T   E   Y   S   M   H   W   V   K   Q   S   H   G   K   80
181 ACTTcTGGATACACATTCACTGAATACAGCATGCACTGGGTGAAACAGAGCCATGGAAAG 240

81 S   L   E   W   I   G   G   F   N   P   N   N   G   Y   S   H   Y   N   Q   K   100
241 AGCCTTGAGTGGATCGGAGGTTTTAATCCTAACAATGGTTATAGTCACTACAACCAGAAG 300

101 F   K   D   K   A   T   L   T   V   D   K   S   S   S   T   A   Y   M   E   L   120
301 TTCAAGGACAAGGCCACATTGACTGTAGACAAGTCGTCCAGCACAGCCTACATGGAGCTC 360

121 R   S   L   T   S   E   D   S   A   V   F   Y   C   A   R   S   D   K   Y   140
361 CGCAGCCTGACATcTGAGGATTCTGCAGTCTTTTACTGtGCAAGATCGGACTCTAAATAC 420

141 T   Y   F   A   Y   W   G   Q   G   T   L   V   T   V   S   A   A   K   T   T   160
421 ACCTACTTTGCTTACTgggGcCAAGGGACTCTGGTCACTGtCTCTGCAGCCAAAACGaCA 480

161 P   161
481 cCC 483
```

Figure 18

Sequences for clone 5A5 Light chain:

```
  1 G   T   D   Q   S   P   Q   A   V   S   S   G   C   L   L   K   M   K   L   P   20
  1 GGGAcTGATCAGtctcCTCAGGCTGTcTCcTCAGGtTGccTCCTCAAAATGAAGtTgCCT  60

21 V   R   L   L   V   L   M   F   W   I   P   A   F   S   S   D   V   L   M   S   40
 61 GTTAGGctGtTGGtGcTGATGTTctGGAttcCTGCtTtCAGCAGtgATGTcttgATGAgc 120

41 Q   N   P   L   S   L   P   V   S   L   G   D   Q   A   S   I   S   C   R   S   60
121 cAAAatcCACTcTcCcTGCCtGtCAGTcTTGGAGATCAAGCCTCCATcTcTTGCAGATcT 180

61 S   Q   S   I   V   H   S   N   G   N   T   Y   L   E   W   Y   L   Q   K   P   80
181 aGTCAGAgCATTgTACATAgTAAtGGAAACaCcTATTTAGAATgGTACCTGCAGAAACCA 240

81 G   Q   S   P   K   V   L   I   Y   E   V   S   N   R   F   S   G   V   P   D  100
241 GGCCAGTCTCCAAAGGtCcTGATcTACGaAGTTTcCAACCGATTTTcTGGGGTCCCAGAC 300

101 R   F   S   C   T   G   S   G   T   D   L   P   L   K   I   S   R   V   E   A  120
301 AGGTTCAgTtgCactGGatCagGgACaGATctCcCacTCAaGaTCaGcaGaGTGGAGGCT 360

121 E   G   L   G   L   Y   Y   C   F   Q   G   S   H   V   P   W   T   F   G   G  140
361 GAGGgcCTGGGACTTTATTACTGCTTTCAAGGTTCACATGTTCCGTGGACGTTCGGTGGA 420

141 G   T   K   L   E   I   K   R   A   D   A   A   P   T  154
421 GGCAcCaagCtcgaGatCaaacggGCtGaTgcTgcaccaacg 462
```

Sequences for clone 5A5 heavy chain:

```
  1 V   *   Q   R   R   P   V   L   D   S   I   P   S   S   S   H   S   V   S   T   20
  1 gTctGaCaGAGGaGgcctGTCCtggattcGATTccCAGTTcCTCACATTCagtCAGCAcT  60

21 E   H   G   P   L   T   M   N   F   G   L   S   L   I   F   L   V   L   V   L   40
 61 GAACACGGACCCCTCACCATGAACTTCGGGcTCAGCTTGATTTTCCTTGTCCTTGTTTTA 120

41 K   G   V   Q   C   E   V   M   L   V   E   S   G   G   G   L   V   K   P   G   60
121 AAAGGTGTCCAGTGTGAGGTGATGCTGGTGGAGTcTGGGGGAGGCTTAGTGAAGCCTGGA 180

61 G   S   L   K   L   S   C   A   A   S   G   F   T   F   R   N   F   A   M   S   80
181 GGGTCCCTGAAACTCTCCTGTGCAGCCTCTGGATTCACTTTCAGAAACTTTGCCATGTCT 240

81 W   V   R   Q   T   S   E   K   R   L   E   W   V   A   S   I   S   F   G   G  100
241 TGGGTTCGCCAGACTTCGGAGAAGAGGCTGGAGTGGGTCGCAAGCATTAGTTTTGGTGGT 300

101 N   Y   T   F   Y   P   D   S   V   K   G   R   F   T   V   S   K   D   N   A  120
301 AATTaCACCTTCTATCCAGACAGTGTGAAGGGGCGATTCACCGTCTCCAAAGACAATGCC 360

121 K   N   T   L   Y   L   Q   M   S   S   L   R   S   E   D   T   A   M   Y   F  140
361 AAGAACACCCTGTATCTGCAAATGAGTAGTCTGAGGTcTGAGGACACGGCCATGTATTTc 420

141 C   A   R   R   G   Y   S   H   Y   A   M   D   Y   W   G   Q   G   T   S   V  160
421 TGTGCAAGACGAGGTTACTCCCaCTATGCTATGGACTACTGGGGTCAAGGAACCTCAGTC 480

161 S   V   S   S   A   K   T   T   A   P   S   V   Y   P   L   A   P   V   C   G  180
481 TCCGTCTCCTCAGCCAAAACAACAGCCCCATCGGTCTATCCACTGGCCCCtGTGTGTGGA 540
```

Figure 19

Sequences for clone 7D6 Light chain:

```
  1   G   T   D   Q   S   P   Q   A   V   S   S   G   C   L   L   K   M   K   L   P    20
  1 GGGacTGATCAGTCTcCTCAGGCTGTcTccTCAGGtTGCCTCCTCAAAATGAAGTTgCCT  60

21   V   R   L   L   V   L   M   F   W   I   P   A   S   S   S   D   V   L   M   T    40
 61 GTTaGGCTGTTGGTGcTGATGTTcTGGATTcCTGCTTcCAGCAGtGATGTTTTgATGACC 120

41   Q   T   P   L   S   L   P   V   S   L   G   D   Q   A   S   I   S   C   K   S    60
121 CAAAcTcCACTcTcCCTGCCTGTCAGTcTTGGaGATCAAGCCTCCATcTcTTGCAAATcT 180

61   S   Q   S   I   V   H   S   N   G   N   T   Y   L   E   W   Y   L   Q   K   P    80
181 aGTCAGAgCATTGTACATAGTAaTGGAAACaCCTATTTAGAATGGTACCTGCAGAAACCA 240

81   G   Q   P   P   K   V   L   I   Y   K   V   S   N   R   F   S   G   V   P   D   100
241 GGCCAGCCTCCAAAGGTCCTGATcTACAAAGTTTCCAACCGATTTTcTGGGGTcCCAGAC 300

101   R   F   S   G   S   G   S   G   T   D   S   T   L   K   I   S   R   V   E   A   120
301 AGGTTCAgtGGCAGtGGATCAGGGaCAGATTCCaCACTCAAGATCAGCAGAGTGGAGGcT 360

121   E   D   L   G   L   Y   Y   C   F   Q   G   S   H   V   P   W   T   F   G   G   140
361 GAGGATcTGGGaCTTTATTaCTGCTTTCAAGGTTCACATGTTCCGTGGACGTTCGGTGGA 420

141   G   T   K   L   E   I   K   R   A   D   A   A   P   T   V   S   I   F   P   P   160
421 GGCaCCAAgcTGGAGATCAAACGGGCTGAtGcTGCACCAActGTATCCAtcTtcCCgCCA 480
```

Sequences for clone 7D6 heavy chain:

```
  1   V   *   Q   R   R   Q   V   L   D   S   I   P   S   S   S   H   S   V   S   T    20
  1 gtctGACAGAGGAGGCAGGTCCTGGATTCGATTCCCAGTTCCTCACATTCAGTCAGCACT  60

21   E   H   G   P   L   T   M   N   F   V   L   S   L   I   F   L   A   L   I   L    40
 61 GAACACGGACCCCTCACCATGAACTTTGTGCTCAGCTTGATTTTCCTTGCCCTCATTTTA 120

41   K   G   V   Q   C   E   V   Q   L   V   E   S   G   G   G   L   V   K   P   G    60
121 AAAGGTGTCCAGTGTGAAGTGCAGCTGGTGGAGTCTGGGGGAGGCTTAGTGAAGCCTGGA 180

61   G   S   L   K   L   S   C   A   A   S   G   F   T   F   S   S   Y   A   M   S    80
181 GGGTCCCTGAAACTCTCCTGTGCAGCCTCTGGATTCACTTTCAGTAGCTATGCCATGTCT 240

81   W   V   R   Q   T   P   E   K   R   L   E   W   V   A   A   I   S   Y   G   G   100
241 TGGGTTCGCCAGACTCCGGAGAAGAGGCTGGAGTGGGTCGCAGCCATTAGTTATGGTGGT 300

101   N   Y   T   Y   Y   P   D   S   V   K   G   R   F   T   V   S   R   D   N   A   120
301 AATTACACCTACTATCCAGACAGTGTGAAGGGTCGATTCACCGTCTCCAGAGACAATGCC 360

121   K   N   T   L   Y   L   Q   M   S   S   L   R   S   E   D   T   A   M   Y   Y   140
361 AAGAACACCCTGTACCTGCAAATGAGCAGTCTGAGGTCTGAGGACACGGCCATGTATTAC 420

141   C   A   R   R   A   R   A   E   Y   Y   Y   A   M   D   Y   W   G   Q   G   T   160
421 TGTGCAAGAAGAGCTCGGGCCGAGTATTACTATGCTATGGAcTaCtGGGGTCAAGGAACC 480

161   S   V   T   V   S   S   A   T   T   T   A   P   S   V   Y   P   L   V   P   G   180
481 TCTGTCACCGTCTCCTcAGcTACAACAACAGCCCCATCTGTCTAtCCCTTGgtCCCTGgC 540

181   C   S   D   T   S   G   S   S   V   T   L   G   C   L   V   K   G   Y   198
541 TGcAGTGACACATCTGGatCCTCGGTGaCACTGGGATGcCTTGTCAAAGgcTac 594
```

ANTIBODIES AGAINST HUMAN HIF-1α

CROSS-REFERENCE TO RELATED APPLICATIONS

This application is a national stage of International Patent Application No. PCT/CA2011/000763, filed Jun. 30, 2011, which claims the benefit of the priority of U.S. Provisional Patent Application No. 61/360,085, filed Jun. 30, 2010 and U.S. Provisional Patent Application No. 61/381,575, filed Sep. 10, 2010 (both expired), which applications are incorporated herein by reference.

FIELD OF THE INVENTION

The invention relates to reagents and methods for detecting, diagnosing and screening for conditions associated with hydroxylated hypoxia inducible factor 1-α (HIF 1-α).

BACKGROUND OF THE INVENTION

Disorders of pregnancy, including preeclampsia and intrauterine growth restriction (IUGR), are associated with placental hypoxia and elevated expression of HIF-1α [20, 21]. Hypoxia is also an important physiologic inducer of tumor metastasis and HIF-1α levels correlate with hypoxia in solid tumors. Since HIF-1α is central to proper placental development and cancer, early detection of aberrant HIF-1α regulatory mechanisms could impact on the diagnosis of pregnancy-related disorders and cancer.

The highly conserved hypoxia-inducible family of transcription factors is a major player in the physiological response to chronic and acute hypoxia [4]. The family consists of heterodimers comprised of one of three alpha subunits (HIF-1α, HIF-2α and HIF-3α) and a beta subunit (HIF-1β). Under hypoxic conditions the alpha subunits are stable, allowing it to accumulate in the nucleus, where upon binding to HIF-1β it recognises HIF-responsive elements (HRE) within the promoter regions of hypoxia-responsive target genes. Under normoxic conditions, the alpha subunits are rapidly degraded by means of ubiquitination and proteasomal degradation [5,6,7,8]. The ubiquitination process requires the product of the von Hippel-Lindau tumor suppressor gene (VHL), which functions as a substrate recognition component of an E3 ubiquitin ligase complex [5,6,7,8]. The most extensively studied isoform of the α-subunits is HIF-1α. Oxygen-dependent prolyl hydroxylases control the abundance of HIF-1α by hydroxylating two specific proline residues (402 and 564), an event which is required for VHL binding and subsequent HIF-1α degradation [9,10]. The prolyl hydroxylase-domain containing proteins 1, 2 and 3 (PHD1, PHD2 and PHD3) function as oxygen sensors as they require $O_2$ as co-substrate to catalyze the prolyl-hydroxylation reaction, indicating that oxygen levels directly influence their enzymatic activity [11,12,13]. Moreover, in vitro experiments have shown that PHDs mRNA levels are up-regulated in conditions of low oxygen [14], further highlighting their role as $O_2$ sensors. In contrast to HIF-1α, the stability of PHD1 and PHD3 decreases under hypoxic conditions [15]. Recent studies have shown that under hypoxic conditions, PHD1 and 3 are degraded by specific E3-ubiquitin-ligases, termed SIAHs [Seven In Absentia Homologues][15,16]. There are two known human SIAH genes, SIAH-1 (that encodes for two different isoforms: SIAH-1a and SIAH-1b) and SIAH-2. Like PHDs, hypoxia stimulates their transcription and induces the accumulation of these ring finger proteins through an HIF-independent manner [15]. Under hypoxic conditions, SIAHs promote degradation of PHD1 and PHD3 [15,16], leading to an increased accumulation of HIF-1α, whereas under normoxic conditions PHDs are stable and hydroxylate HIF-1α to target it for degradation [9,10].

Another oxygen-dependent mechanism of HIF-1α regulation involves the Factor Inhibiting HIF (FIH), an asparginyl hydroxylase that targets the Asn803 residue in the C-TAD domain for hydroxylation. This post-translational modification prevents C-TAD binding to the transcriptional activator p300/CBP, thereby repressing HIF-1α transcriptional activity [17,18]. Like PHDs, FIH has also been characterized as an oxygen sensor since its enzymatic activity is directly regulated by $O_2$ concentration [19].

SUMMARY OF THE INVENTION

The present invention relates to Hydroxylated HIF Biomarkers (defined herein) and agents that interact with the biomarkers, for detecting, diagnosing, characterizing, and monitoring HIF-1α conditions, and identifying subjects with a predisposition to such conditions. Aspects of the invention relate to Hydroxylated HIF Biomarkers and reagents that interact with same, including monoclonal antibodies specific for Hydroxylated HIF Biomarkers, and their application in the diagnosis of HIF-1α conditions.

The invention relates to a method for detecting or diagnosing a HIF-1α condition comprising determining the status of Hydroxylated HIF Biomarkers in a sample obtained from the patient, wherein an abnormal status indicates the presence of the condition. An aspect of the invention provides a method for detecting or diagnosing a pregnancy-related condition in a patient comprising determining the status of Hydroxylated HIF Biomarkers in a sample obtained from the patient, wherein an abnormal status in the sample indicates the presence of the condition. In an embodiment, the abnormal status is low status or negative status. In another embodiment, the abnormal status is an elevated status.

Hydroxylated HIF Biomarkers may be correlated with specific conditions, in particular specific pregnancy-related disorders (e.g. early onset preeclampsia, late onset preeclampsia, IUGR, molar pregnancy, gestational diabetes or diabetes). Thus, the invention provides a method of diagnosing a HIF-1α condition in a patient comprising determining the status of a Hydroxylated HIF Biomarker in a sample obtained from the patient, wherein an abnormal status of the Hydroxylated HIF Biomarker indicates the presence of a specific HIF-1α condition. In an embodiment, the invention provides a method of diagnosing a pregnancy-related condition in a patient comprising determining the status of a Hydroxylated HIF Biomarker in a sample obtained from the patient, wherein an abnormal status of the Hydroxylated HIF Biomarker indicates the presence of a specific pregnancy-related condition.

Another aspect of the invention provides a method of screening for a HIF-1α condition, in particular a pregnancy-related condition, in a patient comprising identifying a patient at risk of having the condition or in need of screening and determining the status of Hydroxylated HIF Biomarkers in a sample obtained from the patient, wherein an abnormal status of Hydroxylated HIF Biomarkers indicates the presence of the condition. In some embodiments, the patient is at risk of developing a specific type of condition (e.g. pregnancy-related conditions such as early onset preeclampsia, late onset preeclampsia, IUGR, gestational diabetes or diabetes) and the abnormal status indicates the presence of the specific type of condition.

In an embodiment of the invention, a method is provided for detecting Hydroxylated HIF Biomarkers associated with a pregnancy-related condition in a patient comprising or consisting essentially of: (a) detecting or identifying in the sample from the patient one or more Hydroxylated HIF Biomarkers; and (b) comparing the detected amount with an amount detected for a control, standard or cut-off value.

In an embodiment of the invention, a method is provided for detecting Hydroxylated HIF Biomarkers associated with a cancer in a patient comprising or consisting essentially of (a) detecting or identifying in the sample from the patient one or more Hydroxylated HIF Biomarkers; and (b) comparing the detected amount with an amount detected for a control, standard or cut-off value.

In an aspect, the invention provides a method for diagnosing a HIF-1α condition, in particular a pregnancy-related condition, in a subject, the method comprising: (a) contacting a sample from a subject with a reagent capable of determining the status of Hydroxylated HIF Biomarkers, in particular measuring levels of Hydroxylated HIF Biomarkers; and (b) providing a diagnosis of the condition in the subject based on a difference in the status of the Hydroxylated HIF Biomarkers in the sample from the subject over a control or standard obtained from similar samples taken from subjects who do not have the condition or have a different stage of the condition, or from the subject at a different time.

In a particular embodiment of the invention, a method is provided for diagnosing a pregnancy-related condition in a patient comprising, consisting of or consisting essentially of: (a) detecting or identifying in the sample Hydroxylated HIF Biomarkers; and (b) comparing the detected amount with an amount detected for a standard, wherein differences in Hydroxylated HIF Biomarkers or an abnormal status of Hydroxylated HIF Biomarkers, are diagnostic of a pregnancy-related condition.

In a particular embodiment of the invention, a method is provided for diagnosing preeclampsia, in particular early onset preeclampsia, in a patient comprising or consisting essentially of: (a) detecting or identifying in the sample Hydroxylated HIF Biomarkers, and (b) comparing the detected amount with an amount detected for a standard, wherein a decrease in Hydroxylated HIF Biomarkers is diagnostic of preeclampsia.

In a particular embodiment of the invention, a method is provided for diagnosing a cancer in a patient comprising, consisting of or consisting essentially of: (a) detecting or identifying in the sample Hydroxylated HIF Biomarkers; and (b) comparing the detected amount with an amount detected for a standard, wherein differences in Hydroxylated HIF Biomarkers or an abnormal status of Hydroxylated HIF Biomarkers, are diagnostic of the cancer.

The invention provides a method of assessing whether a patient is at risk of, or afflicted with a HIF-1α condition, in particular a pregnancy-related condition, the method comprising comparing: (a) levels of Hydroxylated HIF Biomarkers from a sample of the patient; and (b) standard levels of Hydroxylated HIF Biomarkers in samples of the same type obtained from control patients not afflicted with the condition or with a different stage of the condition or from samples of the subject taken at different times, wherein altered levels of Hydroxylated HIF Biomarkers relative to the corresponding standard levels of Hydroxylated HIF Biomarkers is an indication that the patient is at risk of or afflicted with the condition.

In an aspect the invention provides a method for diagnosing an increased risk of preeclampsia, in particular early onset preeclampsia, in a subject, the method comprising: (a) contacting a sample from a pregnant subject with a diagnostic reagent that measures Hydroxylated HIF Biomarkers; and (b) diagnosing an increased risk of preeclampsia in the subject based upon a difference in the sample (a) from the subject over that of a sample obtained from the same subject at an earlier time in the pregnancy. In an embodiment of this method of the invention, steps (a) and (b) are repeated throughout the pregnancy.

In an embodiment of the invention, a method is provided for diagnosing or identifying an increased risk of preeclampsia in a subject, the method comprising:

a) contacting a sample from a subject at a first time in pregnancy with a diagnostic reagent that measures a first level of a Hydroxylated HIF Biomarker; and b) diagnosing or identifying an increased risk of preeclampsia in the subject based upon a lower level or decrease in the level of the Hydroxylated HIF Biomarker in the sample from the subject over that of an earlier sample level of Hydroxylated HIF Biomarker obtained from samples of the same type taken from the same subject at an earlier time in the pregnancy.

In another embodiment, the invention provides a method for diagnosing or identifying an increased risk of preeclampsia in a subject, the method comprising:

a) contacting a sample taken from a subject at a first time in pregnancy with a diagnostic reagent that measures a first level of a Hydroxylated HIF Biomarker;

b) contacting a sample of the same type taken from a subject at a second time in pregnancy with a diagnostic reagent that measures a second level of the Hydroxylated HIF Biomarker; and c) diagnosing or identifying an increased risk of preeclampsia in the subject based upon a lower level or decreased level of Hydroxylated HIF Biomarker in the sample taken from the subject at the second time, compared to the level of Hydroxylated HIF Biomarker determined in the sample taken at the first time.

The Hydroxylated HIF Biomarker can be measured by detecting, directly or indirectly, the interaction of the Hydroxylated HIF Biomarker with an antibody specific for the Hydroxylated HIF Biomarker (e.g. an antibody of the invention disclosed herein). An antibody may be labeled with an enzyme, fluorescent, luminescent or radioactive material. The method may further comprise performing a step selected from the group consisting of a counter immuno-electrophoresis, a radioimmunoassay, radioimmunoprecipitation assay, an enzyme-linked immunosorbent assay, a dot blot assay or an inhibition of competition assay and a sandwich assay using said antibody.

The invention provides a method of assessing whether a patient is afflicted with or at risk of a HIF-1α condition, in particular a pregnancy-related condition, which comprises comparing: (a) status, in particular levels, of Hydroxylated HIF Biomarkers in a sample from the patient; and (b) status, in particular levels, of Hydroxylated HIF Biomarkers in a sample from a normal subject, a patient with a different stage of condition or from the same subject at a different time, wherein an abnormal status, in particular significantly different levels, of Hydroxylated HIF Biomarkers in the sample from the patient compared with the control is an indication that the patient is afflicted with or at risk of the condition.

In an aspect of a method of the invention for assessing whether a patient is at risk of or afflicted with a HIF-1α condition, in particular a pregnancy-related condition, significant differences in levels of Hydroxylated HIF Biomarkers, in a sample relative to corresponding normal levels or levels from a patient at a different stage of condition or another sample of the patient, is an indication that the patient is at risk of or afflicted with the condition.

In an embodiment of a method of the invention for assessing whether a patient is at risk of or afflicted with a HIF-1α condition, in particular a pregnancy-related condition, levels of Hydroxylated HIF Biomarkers in a sample from the patient are compared to a standard, and significant differences in levels of Hydroxylated HIF Biomarkers compared to a standard are indicative of the condition.

In certain aspects, the invention provides a method for diagnosing or determining or aiding in the determination that a pregnant woman is at risk of developing preeclampsia and/or gestational diabetes or diabetes comprising comparing the expression of one or more Hydroxylated HIF Biomarkers in a sample (e.g., serum or blood sample) from the pregnant woman to be assessed for risk of developing preeclampsia and/or gestational diabetes or diabetes to a standard for each of the Hydroxylated HIF Biomarkers, wherein a significant difference in expression of the one or more Hydroxylated HIF Biomarkers in the sample as compared to a standard of each of the one or more Hydroxylated HIF Biomarkers indicates that the pregnant woman is at risk of developing preeclampsia and/or gestational diabetes or diabetes, thereby determining or aiding in the determination that the pregnant woman is at risk of developing preeclampsia and/or gestational diabetes or diabetes.

In particular aspects, methods of the invention are used to diagnose the stage of a HIF-1α condition, in particular a pregnancy-related condition, in a subject or characterizing a HIF-1α condition in a subject. In an embodiment, the method comprises comparing (a) the status, in particular levels, of Hydroxylated HIF Biomarkers from a sample from the patient; and (b) the status, in particular levels, of the Hydroxylated HIF Biomarkers in control samples of the same type obtained from patients without the condition, with a different stage of condition or from the same patient at a different time. In an aspect, the methods are used to diagnose a pregnancy-related condition. In an aspect, the methods are used to diagnose preeclampsia. In an aspect, the methods are used to diagnose early onset preeclampsia. In an aspect, the methods are used to diagnose a cancer.

The invention provides a method for classifying a patient having a HIF-1α condition, in particular a pregnancy-related condition, the method comprising detecting or determining the status of Hydroxylated HIF Biomarkers in a sample from the patient and correlating the values detected or determined to values measured for the Hydroxylated HIF Biomarkers from patients stratified in classification groups. In various embodiments the values measured can be normalized to provide more accurate quantification and to correct for experimental variations.

The invention further provides a non-invasive non-surgical method for detection or diagnosis of a HIF-1α condition, in particular a pregnancy-related condition, in a subject comprising: obtaining a sample from the subject; subjecting the sample to a procedure to detect Hydroxylated HIF Biomarkers; detecting or diagnosing the condition by comparing the status, in particular levels, of Hydroxylated HIF Biomarkers to the status, in particular levels, of Hydroxylated HIF Biomarkers obtained from a control subject with no condition, a different stage of condition or from the same subject at a different time.

Another aspect provides a diagnostic method comprising identifying a patient who is a candidate for treatment for a HIF-1α condition, in particular a pregnancy-related condition, and determining the status of Hydroxylated HIF Biomarkers in a sample obtained from the patient, wherein an abnormal status of Hydroxylated HIF Biomarkers in the sample indicates that treatment is desirable or necessary.

In aspects of the invention, an abnormal status can be an elevated status, low status or negative status. In an embodiment of the invention for detecting or diagnosing early onset preeclampsia, the abnormal status can be a low or negative status.

The invention provides a method for monitoring the progression of a HIF-1α condition, in particular a pregnancy-related condition, in a patient the method comprising: (a) determining the status of or detecting a Hydroxylated HIF Biomarker in a patient sample at a first time point; (b) repeating step (a) at a subsequent point in time; and (c) comparing the status, in particular levels in (a) and (b), and thereby monitoring the progression of the condition.

The invention also relates to a method for diagnosing or monitoring a pregnancy complication in a subject, the method comprising: (a) detecting or determining Hydroxylated HIF Biomarkers in a sample from the subject; and (b) comparing the value detected or determined in the subject's sample to a control value obtained from one or more samples of the same type in one or more pregnant controls who did not develop the complication; wherein a difference in the value of Hydroxylated HIF Biomarkers in the sample from the subject over that of the control value indicates an increased risk of developing the complication. In embodiments of this aspect of the invention the complication is a condition or an increased risk of a condition selected from the group consisting of intrauterine growth restriction, molar pregnancy, preterm labour, preterm birth, preeclampsia, fetal anomaly, placental abruption, gestational diabetes and diabetes.

The invention further relates to a method of assessing the efficacy of a therapy for a HIF-1α condition, in particular a pregnancy-related condition, in a patient. This method comprises comparing: (a) the status, in particular levels, of Hydroxylated HIF Biomarkers in a first sample obtained from the patient prior to providing at least a portion of the therapy to the patient; and (b) status, in particular levels, of Hydroxylated HIF Biomarkers in a second sample obtained from the patient following therapy. Significantly different levels of Hydroxylated HIF Biomarkers in the second sample, relative to the first sample, can be an indication that the therapy is efficacious for inhibiting the condition. In an embodiment, the method is used to assess the efficacy of a therapy for inhibiting a pregnancy-related condition and lower levels of Hydroxylated HIF Biomarkers in the second sample relative to the first sample, is an indication that the therapy is efficacious for inhibiting the condition. In an embodiment, the method is used to assess the efficacy of a therapy for inhibiting a pregnancy-related condition and higher levels of Hydroxylated HIF Biomarkers in the second sample relative to the first sample, is an indication that the therapy is efficacious for inhibiting the condition. The therapy may be any therapy for treating a HIF-1α condition, in particular a pregnancy-related condition. Therefore, the method can be used to evaluate a patient before, during, and after therapy.

Protein based methods can be used for diagnosing and monitoring a HIF-1α condition, in particular a pregnancy-related condition, in a subject comprising detecting or determining the status of Hydroxylated HIF Biomarkers in a sample from the subject. Hydroxylated HIF Biomarkers may be detected or determined using a binding agent for Hydroxylated HIF Biomarkers. In an aspect the invention provides methods for determining the presence or absence of a HIF-1α condition, in particular a pregnancy-related condition, in a patient comprising the steps of (a) contacting a biological sample obtained from a patient with a binding agent that specifically binds to Hydroxylated HIF Biomarkers; and (b) detecting in the sample Hydroxylated HIF Biomarkers that bind to the binding agent(s), relative to a predetermined standard or cut-off value, and therefrom determining the presence or absence of the condition in the patient.

In an embodiment, the invention relates to a method for detecting, diagnosing, staging and monitoring a HIF-1α condition, in particular a pregnancy-related condition, in a subject by quantitating Hydroxylated HIF Biomarkers in a biological sample from the subject comprising (a) reacting the biological sample with antibodies specific for Hydroxylated HIF Biomarkers which are directly or indirectly labeled with a detectable substance; and (b) detecting the detectable substance.

In another embodiment the invention provides a method of using antibodies to detect expression of Hydroxylated HIF Biomarkers in a sample, the method comprising: (a) combining antibodies that specifically bind Hydroxylated HIF Biomarkers with a sample under conditions which allow the formation of antibody:protein complexes; and (b) detecting complex formation, wherein complex formation indicates expression of Hydroxylated HIF Biomarkers in the sample. Expression may be compared with standards and is diagnostic of the condition.

In an aspect the invention provides a method for detecting or diagnosing a HIF-1α condition, in particular a pregnancy-related condition, or risk of such condition, comprising contacting a sample from a subject with an antibody comprising an antigen recognition domain capable of specifically binding to an epitope of HIF-1α comprising or consisting of hydroxylated proline 402 and/or hydroxylated proline 564, under conditions which allow immunocomplex formation wherein presence of said immunocomplex or level thereof is indicative of the condition or risk of the condition.

The invention also provides binding agents that specifically bind to Hydroxylated HIF Biomarkers. In an aspect, the invention provides an isolated antibody or fragment thereof that specifically binds to a Hydroxylated HIF Biomarker. In aspects of the invention, the isolated antibody or fragment thereof binds an epitope of HIF-1α comprising or consisting of hydroxylated proline 402 and/or hydroxylated proline 564. In an embodiment, a monoclonal antibody is provided that specifically binds human HIF-1α comprising hydroxylated proline 402 and/or hydroxylated proline 564. Aspects of the invention provide amino acid sequences that bind to an epitope of HIF-1α comprising or consisting of hydroxylated proline 402 and/or hydroxylated proline 564. In embodiments the invention provides amino acids sequences of a variable region of a heavy chain or a light chain of an antibody that binds to an epitope of HIF-1α comprising or consisting of hydroxylated proline 402 and/or hydroxylated proline 564. In some aspects the antibody is a human antibody. The invention also provides nucleic acid molecules encoding an antibody, antibody fragment or amino acid sequence of the invention. In an aspect, the invention provides nucleic acid molecules encoding the heavy and/or light chain of an antibody of the invention or the variable region or non-variable region thereof or antigen-binding portion thereof.

The invention provides novel Hydroxylated HIF Biomarker binding antibodies or fragments thereof. In aspects of the invention, the Hydroxylated HIF Biomarker binding antibodies or fragments alternatively or additionally bind to substantially the same epitope as one or more of the exemplary antibodies described herein. Alternatively or additionally, the Hydroxylated HIF Biomarker binding antibodies or fragments compete with the binding of an antibody disclosed herein. The antibodies of the invention can be full-length (for example, an IgG1 or IgG2 antibody), or may comprise only an antigen recognition domain (for example, a Fab, Fab$_2$ or scFv fragment), and may be modified to affect functionality (e.g. to eliminate residual effector functions). Exemplary Hydroxylated HIF Biomarker binding antibodies include the antibodies designated 6A9, 1H1, 6H4, 5A5, 7D6 and 7E3 herein.

Further provided are vectors and host cells comprising nucleic acids encoding the antibodies or fragments or portions thereof. The invention also provides non-human transgenic animals and plants that express antibodies, including antibody fragments, disclosed herein, in particular the heavy or light chains of such antibodies, in particular a variable region of a heavy and/or light chain of an antibody or antibody fragment disclosed herein.

Also provided are methods of making antibodies that specifically bind an epitope of HIF-1α comprising or consisting of hydroxylated proline 402 and/or hydroxylated proline 564, or fragments of the antibodies. The invention further provides a cell line that produces an antibody or fragment thereof that specifically binds to an epitope of HIF-1α comprising or consisting of hydroxylated proline 402 and/or hydroxylated proline 564. The invention also provides methods of recombinantly producing the polypeptides encoded by the nucleic acids disclosed herein.

The invention also provides a composition for diagnosing a HIF-1α condition, in particular a pregnancy-related condition, comprising Hydroxylated HIF Biomarkers or agents that interact with Hydroxylated HIF Biomarkers. In particular, the invention provides a composition for diagnosing a HIF-1α condition, in particular pregnancy-related condition, comprising Hydroxylated HIF Biomarkers, or agents that bind to Hydroxylated HIF Biomarkers. In an embodiment, the composition comprises a binding agent(s) (e.g. antibody) that binds to a Hydroxylated HIF Biomarker or a fragment thereof. In an embodiment, a composition of the invention comprises an antibody or antibody fragment thereof that specifically binds to a Hydroxylated HIF Biomarker. In an embodiment a composition of the invention comprises antibodies that specifically bind an HIF-1α peptide comprising hydroxylated proline 402. In an embodiment a composition of the invention comprises antibodies that specifically bind an HIF-1α peptide comprising hydroxylated proline 564. In an embodiment a composition of the invention comprises antibodies that specifically bind an HIF-1α peptide comprising hydroxylated proline 564 and hydroxylated proline 402. In an embodiment, a composition of the invention comprises an antibody or antibody fragment comprising an antigen recognition domain that specifically binds to an epitope of HIF-1α comprising or consisting of hydroxylated proline 402 of HIF-1α. In an embodiment, a composition of the invention comprises an antibody or antibody fragment comprising an antigen recognition domain that specifically binds to an epitope of HIF-1α comprising or consisting of hydroxylated proline 564 of HIF-1α. In an embodiment, a composition of the invention comprises an antibody or antibody fragment comprising an antigen recognition domain that specifically binds to an epitope of HIF-1α comprising or consisting of hydroxylated proline 402 and 564 of HIF-1α. In an embodiment a composition of the invention comprises a variable region of a heavy and/or light chain of an antibody that specifically binds to a Hydroxylated HIF Biomarker.

Compositions of the invention may further comprise another component, for example a pharmaceutically acceptable carrier, excipient or diluents, or a diagnostic agent. In an aspect, a composition of the invention comprises a heavy and/or light chain of an antibody disclosed herein or the variable region or other antigen-binding portion or antigen recognition domain thereof, or nucleic acid molecules encoding any of the foregoing and a pharmaceutically acceptable carrier.

In another aspect, the invention relates to use of an agent that interacts with a Hydroxylated HIF Biomarker in the manufacture of a composition for diagnosing a disclosed condition. In another aspect, the invention relates to use of an agent that interacts with a Hydroxylated HIF Biomarker in the manufacture of a composition for treating a disclosed condition.

Diagnostic methods of the invention for a HIF-1α condition may also comprise detecting additional markers associated with a HIF-1α condition.

In embodiments of the methods of the invention for diagnosing pregnancy-related conditions, the additional markers may comprise, or can be chosen from, or selected from the group consisting of, PHD1, PHD2 and PHD3, or polynucleotides encoding same. In embodiments of the methods of the invention, the additional markers comprise or are selected from the group consisting of SIAH1a and SIAH1b, or polynucleotides encoding same. In embodiments of the methods of the invention, the additional marker is FIH, or a polynucleotide encoding same. In embodiments of the methods of the invention, the additional marker is endoglin (e.g. soluble endoglin), or a polynucleotide encoding same. In embodiments of the methods of the invention, the additional markers comprise, are chosen from or are selected from the group consisting of PHD1, PHD2, PHD3, SIAH1, SIAH2 and FIH, or polynucleotides encoding same. In embodiments of the methods of the invention, the additional markers comprise, are chosen from or are selected from the group consisting of PHD1, PHD2, PHD3, VHL, SIAH1, SIAH2, FIH, TGFβ3 and endoglin, or polynucleotides encoding same. In embodiments of the methods of the invention, the additional markers comprise, are chosen from or are selected from the group consisting of Mcl-1 isoforms (in particular Mcl-1S or Mcl-1L, or caspase cleaved Mcl-1S or Mcl-1L, in particular caspase cleaved Mcl-1L), TGFβ3, PHD1, PHD2, PHD3, VHL, cullin 2, NEDD8, VEGF, FIH, syncytin, cleaved caspase (e.g., caspase-3), Fas, p53, SMAD2, phospho-SMAD2, SMAD-3, phospho-SMAD3, SMAD7, SIAH1, SIAH2, ceruloplasmin, sFlt, a Mtd polypeptide (e.g. Mtd-L, Mtd-S and/or Mtd-P) and endoglin, or polynucleotides encoding same. In embodiments of the methods of the invention, the additional markers comprise, are chosen from or are selected from the group consisting of Mcl1-L, Mcl1-C, Mtd-L, Mtd-P, TGFβ3, VHL, PHD2, PHD3, FIH, endoglin, sFlt-1, ceruloplasmin, TGFβ-type I receptor (ALK5), TGFβ-type II receptor, TGFβ-1, cleaved caspase, syncytin, VEGF, Fas and HIF1α.

In embodiments of the methods of the invention for diagnosing a cancer the additional markers may comprise, or can be chosen from, or selected from the group consisting of alpha-fetoprotein, Bcr-abl, Beta-2-microglobulin (B2M), Beta-HCG, CA 15-3, CA 27.29, CA 19-9, CA 125, CA 72-4, calcitonin, carcinoembryonic antigen (CEA), chromogranin A, chromogranin A (CgA), epidermal growth factor receptor (EGFR), hormone receptors, HER2 (also known as HER2/neu, erbB-2, or EGFR2), human chorionic gonadotropin (HCG), immunoglobulins, free light chains, KRAS, lactate dehydrogenase (LDH), neuron-specific enolase (NSE), NMP22, prostate-specific antigen (PSA), prostatic acid phosphatase (PAP), prostate-specific membrane antigen (PSMA), S-100, TA-90, progesterone receptor, estrogen receptor and thyroglobulin. In an embodiment for diagnosing breast cancer the additional markers are chosen from CA 15-3, CA 27.29, CA 125, Bcl-2, carcinoembryonic antigen (CEA), HER2, progesterone receptor and estrogen receptor. In an embodiment for diagnosing prostate cancer the additional marker is PSA.

Further, the amount of Hydroxylated HIF Biomarkers may be mathematically combined with other markers of the condition. In an embodiment the invention provides a method for detecting or diagnosing a HIF-1α condition, in particular a pregnancy-related condition, or risk of same in a subject comprising: (a) determining the status, in particular amount, of Hydroxylated HIF Biomarkers in a sample from the subject; (b) determining the status, in particular amount, of other markers associated with the condition; (c) mathematically combining the results of step (a) and step (b) to provide a mathematical combination; and (d) comparing or correlating the mathematical combination to the presence of the condition. The combination is preferably compared to a mathematical combination for a predetermined standard.

In embodiments of methods of the invention, the sample is a fluid comprising or selected from the group consisting of whole blood, plasma, serum, saliva, ocular lens fluid, cerebral spinal fluid, sweat, urine, milk, ascites fluid, amniotic fluid, vaginal fluid, synovial fluid, and peritoneal fluid. In embodiments of the methods of the invention, the sample is whole blood, plasma or serum. In particular embodiments of the methods of the invention, the sample is serum. In embodiments of the methods of the invention, the sample is urine.

In embodiments of the invention, the pregnancy-related condition is early onset preeclampsia.

In embodiments of the invention, the pregnancy-related condition is late onset preeclampsia.

In embodiments of the invention, the pregnancy-related condition is IUGR.

The invention also includes kits for carrying out methods of the invention. In an aspect the invention provides a kit for detecting, diagnosing or characterizing a HIF-1α condition, in particular a pregnancy-related condition, comprising Hydroxylated HIF Biomarkers. In a particular aspect, the invention provides a test kit for diagnosing or characterizing a HIF-1α condition, in particular a pregnancy-related condition, in a subject which comprises an agent that interacts with Hydroxylated HIF Biomarkers. In an embodiment, the kit comprises reagents for identifying and/or assessing levels of Hydroxylated HIF Biomarkers. In an embodiment, the kit comprises antibodies that specifically bind to an epitope of HIF-1α comprising or consisting of hydroxylated proline 402 and/or hydroxylated proline 564, in particular an antibody disclosed herein. The invention provides a diagnostic kit for diagnosing or monitoring a HIF-1α condition, in particular a pregnancy complication, in a subject consisting of a reagent that can measure, directly or indirectly, the levels of Hydroxylated HIF Biomarkers; and one or more positive or negative controls for each measurement obtained from controls not having the condition.

Other objects, features and advantages of the present invention will become apparent from the following detailed description and from the claims. It should be understood, however, that the detailed description and the specific examples while indicating preferred embodiments of the invention are given by way of illustration only, since various changes and modifications within the spirit and scope of the invention will become apparent to those skilled in the art from this detailed description.

DESCRIPTION OF THE DRAWINGS

The invention will now be described in relation to the drawings in which:

FIG. 11 shows amino acid and nucleic acid sequences for light chain variable and non-variable regions [SEQ ID NO: 7, 8, 9, 42, 43 and 44] and heavy chain variable and non-variable regions [SEQ ID NO: 10, 11, 12, 45, 46 and 47] of clone 6A9. The bolded/underlined sequences are the common non-variable sequences of the light and heavy chains. M is the first methionine (i.e. the start point of the amino acid sequence).

FIG. 12 shows amino acid and nucleic acid sequences for light chain variable and non-variable regions of clone 1H1 [SEQ ID NO: 13, 14, 15, 48, 49 and 50]. The bolded/underlined sequences are the common non-variable sequences of the light chain. M is the first methionine (i.e. the start point of the amino acid sequence).

FIG. 13 shows amino acid and nucleic acid sequences for heavy chain variable and non-variable regions of clone 1H1 [SEQ ID NO: 16, 17, 18, 51, 52 and 53]. The bolded/underlined sequences are the common non-variable sequences of the heavy chain. M is the first methionine (i.e. the start point of the amino acid sequence).

FIG. 14 shows amino acid and nucleic acid sequences for light chain variable and non-variable regions of clone 7E3 [SEQ ID NO: 19, 20, 21, 54, 55, and 56]. The bolded/underlined sequences are the common non-variable sequences of the light chain. M is the first methionine (i.e. the start point of the amino acid sequence).

FIG. 15 shows amino acid and nucleic acid sequences for heavy chain variable and non-variable regions of clone 7E3 [SEQ ID NO: 22, 23, 24, 57, 58 and 59]. The bolded/underlined sequences are the common non-variable sequences of the heavy chain. M is the first methionine (i.e. the start point of the amino acid sequence).

FIG. 16 shows amino acid and nucleic acid sequences for light chain variable and non-variable regions of clone 6H4 [SEQ ID NO: 15, 25, 26, 60, 61, and 62]. The bolded/underlined sequence is the common non-variable sequences of the light chain. M is the first methionine (i.e. the start point of the amino acid sequence).

FIG. 17 shows amino acid and nucleic acid sequences for heavy chain variable and non-variable regions of clone 6H4 [SEQ ID NO: 27, 28, 29, 63, 64 and 65]. The bolded/underlined sequences are the common non-variable sequences of the heavy chain. M is the first methionine (i.e. the start point of the amino acid sequence).

FIG. 18 shows amino acid and nucleic acid sequences for light chain variable and non-variable regions [SEQ ID NO: 30, 31, 32, 66, 67 and 68] and heavy chain variable and non-variable regions [SEQ ID NO: 33, 34, 35, 69, 70 and 71] of clone 5A5. The bolded/underlined sequences are the common non-variable sequences of the light and heavy chains. M is the first methionine (i.e. the start point of the amino acid sequence).

FIG. 19 shows sequences for light chain variable and non-variable regions [SEQ ID NO: 36, 37, 38, 72, 73 and 74] and heavy chain variable and non-variable regions [SEQ ID NO: 39, 40, 41, 75, 76 and 77] of clone 7D6. The bolded/underlined sequences are the common non-variable sequences of the light and heavy chains. M is the first methionine (i.e. the start point of the amino acid sequence).

TABLE 3

Figure 1:
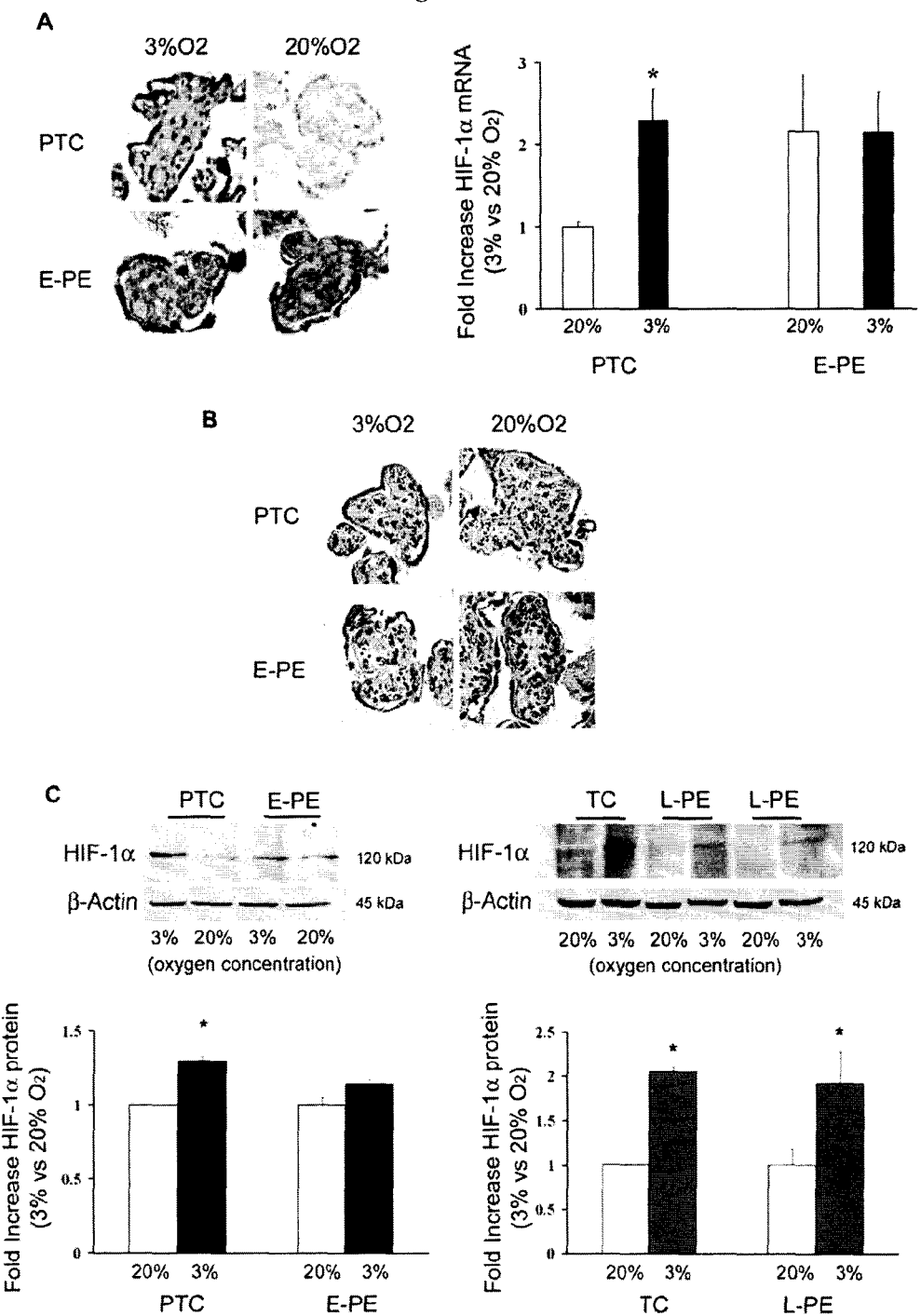
FIG. 1. Expression of HIF-1α in preeclamptic and control placental explants. (A) Left panel: In situ hybridization of HIF-1α mRNA in early preeclamptic (E-PE; n=5) and preterm control (PTC; n=3) explants exposed at 3% and 20% $O_2$. Staining represents positive immunoreactivity for HIF-1α mRNA using a digoxigenin-labeled riboprobe. Right panel: HIF-1α mRNA expression in E-PE (n=4) and PTC (n=3) explants exposed at 3% (black bars) and 20% $O_2$ (open bars) as determined by real-time PCR analysis (values are mean±SEM, *p<0.05). (B) Immunohistochemical analysis of HIF-1α protein on sections of E-PE (n=5) and PTC (n=3) explants exposed at 3% and 20% $O_2$. Staining represents positive immunoreactivity for HIF-1α protein. (C) Left panel: Representative HIF-1α immunoblot of E-PE (n=3) vs PTC (n=3) (upper panel) and densitometric analysis of HIF-1α protein expression in E-PE (n=4) and PTC (n=3) explants exposed at 3% (black bars) and 20% $O_2$ (open bars) (lower panel). (C) Right panel: Representative HIF-1α immunoblot (upper panel) of late preeclamptic (L-PE; n=3) vs term controls (TC; n=3) villous explants cultured at both 3% (gray bars) and 20% $O_2$ (open bars). β-actin was used as loading control. Data are mean±SEM, *p<0.05).

| Figure | Clone | Heavy/Light chain | Seq ID NO | Residue numbers | Coding for SEQ ID NO: X |
|---|---|---|---|---|---|
| 11 | 6A9 | light | 7 | aa 1-145 | N/A |
| | | | 8 | aa 17-145 | N/A |
| | | | 9 | aa 146-160 | N/A |
| | | | 42 | nt 1-435 | 7 |
| | | | 43 | nt 49-435 | 8 |
| | | | 44 | nt 436-480 | 9 |
| | | heavy | 10 | aa 1-146 | N/A |
| | | | 11 | aa 28-146 | N/A |
| | | | 12 | aa 174-163 | N/A |
| | | | 45 | nt 1-439 | 10 |
| | | | 46 | nt 83-439 | 11 |
| | | | 47 | nt 440-489 | 12 |
| 12 | 1H1 | light | 13 | aa 1-145 | N/A |
| | | | 14 | aa 17-145 | N/A |
| | | | 15 | aa 146-173 | N/A |
| | | | 48 | nt 1-435 | 13 |
| | | | 49 | nt 49-435 | 14 |
| | | | 50 | nt 436-519 | 15 |
| 13 | 1H1 | heavy | 16 | aa 1-154 | N/A |
| | | | 17 | aa 30-154 | N/A |
| | | | 18 | aa 155-197 | N/A |
| | | | 51 | nt 1-462 | 16 |
| | | | 52 | nt 88-462 | 17 |
| | | | 53 | nt 463-591 | 18 |
| 14 | 7 E3 | light | 19 | aa 1-146 | N/A |
| | | | 20 | aa 18-146 | N/A |
| | | | 21 | aa 147-175 | N/A |
| | | | 54 | nt 1-458 | 19 |
| | | | 55 | nt 152-458 | 20 |
| | | | 56 | 459-525 | 21 |
| 15 | 7 E3 | heavy | 22 | aa 1-161 | N/A |
| | | | 23 | aa 29-161 | N/A |
| | | | 24 | aa 162-189 | N/A |
| | | | 57 | nt 1-483 | 22 |
| | | | 58 | nt 85-483 | 23 |
| | | | 59 | nt 484-567 | 24 |
| 16 | 6H4 | light | 15 | aa 139-166 | N/A |
| | | | 25 | aa 1-138 | N/A |
| | | | 26 | aa 14-138 | N/A |
| | | | 60 | nt 1-414 | 25 |
| | | | 61 | nt 40-414 | 26 |
| | | | 62 | nt 415-498 | 15 |
| 17 | 6HR | heavy | 27 | aa 1-152 | N/A |
| | | | 28 | aa 20-152 | N/A |
| | | | 29 | aa 153-160 | N/A |
| | | | 63 | nt 1-456 | 27 |
| | | | 64 | nt 58-546 | 28 |
| | | | 65 | nt 457-483 | 29 |
| 18 | 5A5 | light | 30 | aa 1-146 | N/A |
| | | | 31 | aa 18-146 | N/A |
| | | | 32 | aa 147-154 | N/A |
| | | | 66 | nt 1-438 | 30 |
| | | | 67 | nt 52-438 | 31 |
| | | heavy | 33 | aa 1-152 | N/A |
| | | | 34 | aa 28-152 | N/A |
| | | | 35 | aa 153-180 | N/A |
| | | | 69 | nt 1-156 | 33 |
| | | | 70 | nt 82-156 | 34 |
| | | | 71 | nt 157-540 | 35 |
| 19 | 7D6 | light | 36 | aa 1-146 | N/A |
| | | | 37 | aa 18-146 | N/A |
| | | | 38 | aa 147-160 | N/A |
| | | | 72 | nt 1-438 | 36 |
| | | | 73 | nt 52-438 | 37 |
| | | | 74 | nt 439-480 | 38 |
| | | heavy | 39 | aa 1-167 | N/A |
| | | | 40 | aa 28-167 | N/A |
| | | | 41 | aa 168-198 | N/A |
| | | | 75 | nt 1-501 | 39 |
| | | | 76 | nt 83-501 | 40 |
| | | | 77 | nt 502-594 | 41 |

DETAILED DESCRIPTION OF THE INVENTION

Unless defined otherwise, all technical and scientific terms used herein have the same meaning as commonly understood by one of ordinary skill in the art to which this invention belongs. The following definitions supplement those in the art and are directed to the present application and are not to be imputed to any related or unrelated case. Generally, nomenclatures used in connection with, and techniques of, cell and tissue culture, molecular biology, immunology, microbiology, genetics, protein and nucleic acid chemistry and hybridization described herein are those well known and commonly used in the art. Methods and techniques employed in the present invention are generally performed according to conventional methods known in the art and as described, for example, in general references such as Sambrook et al, Molecular Cloning: A Laboratory Manual, $2^{nd}$ ed., Cold Spring Harbor Laboratory Press, Cold Spring Harbor, N.Y. (1989) and Ausubel et al, Current Protocols in Molecular Biology, Greene Publishing Associates (1992) and Harlow and Lane, Antibodies: A Laboratory Manual, Cold Spring Harbor Laboratory Press, Cold Spring Harbor, N.Y., (1990). Although any methods and materials similar or equivalent to those described herein can be used in the practice of the invention, particular materials and methods are described herein.

As used herein, the twenty conventional amino acids and their abbreviations follow conventional usage. (See Immunology—A Synthesis ($2^{nd}$ Edition, E. S. Golub and D. R. Gren, Eds, Sinauer Associates, Sunderland, Mass. (1991). It will also be understood that polypeptides disclosed herein may comprise unconventional amino acids such as alpha and alpha-disubstituted amino acids, N-alkyl amino acids, lactic acid, 4-hydroxyproline, O-phosphoserine, N-acetylserine, 5-hyroxylysine, N-formylmethionine, and the like.

Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." The term "about" means plus or minus 0.1 to 50%, 5-50%, or 10-40%, preferably 10-20%, more preferably 10% or 15%, of the number to which reference is being made. Unless otherwise required by context, singular terms shall include pluralities and plural terms shall include the singular.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

A "HIF-1α condition" refers to a disorder, disease, condition, syndrome or combination of manifestations or symptoms recognized as associated with hydroxylated HIF-1α or aberrant HIF-1α hydroxylation. In aspects of the invention, the term refers to a pregnancy-related condition. In other aspects of the invention the term refers to a condition associated with abnormal cell growth.

A "pregnancy-related condition" refers to a disorder or complication related to pregnancy, including without limitation, conditions associated with or characterized by hypertension and/or conditions, diseases or disorders requiring modulation of, or involving, trophoblast cell death, differentiation, invasion, and/or cell fusion and turnover. Examples of pregnancy-related conditions are preeclampsia including, without limitation, early onset preeclampsia (E-PE), severe early onset preeclampsia placental preeclampsia, late onset preeclampsia (L-PE), maternal preeclampsia, intra-uterine growth restriction (IUGR) or small for gestational age (SGA), preterm labor, preterm birth, fetal anomalies, placental abruption, choriocarcinoma, hydatiform mole, molar pregnancy, eclampsia, gestational hypertension, chronic hypertension, gestational diabetes mellitus, diabetes and HELLP syndrome.

In an embodiment of the invention the condition is preeclampsia. "Preeclampsia" includes a disorder of pregnant women characterized by hypertension, proteinuria and edema. The classical definition of preeclampsia according to the ACOG criteria refers to the onset of high blood pressure (140/90 or higher) after 20 weeks of gestation in a woman with previously normal blood pressure which is accompanied by proteinurea of 0.3-3 gr/day [Redman, C. W., and Sargent, I. L. 2005, *Science* 308:1592-1594; 1, 2, 3]. All forms of preeclampsia, such as premature, mild, moderate, severe preeclampsia, early onset preeclampsia (E-PE), severe early onset preeclampsia placental preeclampsia, late onset preeclampsia (L-PE), and maternal preeclampsia, are included in the definition. In certain embodiments, the invention relates to identifying or aiding in the identification of a pregnant woman at risk of developing preeclampsia.

In an embodiment of the invention the condition is early onset preeclampsia which occurs at <34 wks of gestation. In embodiments, the condition is early onset preeclampsia which occurs at less than 20 weeks of gestation. In embodiments, the condition is early onset preeclampsia which occurs at less than 15 weeks. In embodiments, the condition is early onset preeclampsia which occurs at less than 12 weeks. In embodiments, the condition is early onset preeclampsia which occurs at less than 9 weeks. In embodiments, the condition is early onset preeclampsia which occurs between 9 to 12 weeks of gestation.

In an embodiment of the invention the condition is preeclampsia which occurs after 20 weeks. In an embodiment of the invention the condition is preeclampsia which occurs after 15 weeks. In an embodiment of the invention the condition is preeclampsia which occurs after 12 weeks. In an embodiment of the invention the condition is preeclampsia which occurs after 9 weeks.

In an embodiment, the condition is severe early onset preeclampsia of placental origin which may be due to a defect in trophoblast cell differentiation originating early on in pregnancy.

In an embodiment of the invention, the preeclampsia is placental preeclampsia which is typically early onset (<34 wks) and arises from hypoxic/oxidative stress.

In an embodiment of the invention, the condition is late onset preeclampsia which occurs at >34 wks.

In an embodiment, the condition is maternal preeclampsia which manifests later in gestation ((>34 weeks or >35 weeks) and is indicative of an abnormal maternal response to placentation.

In an embodiment, the condition is severe preeclampsia. Pregnancies complicated by severe preeclampsia are generally characterized by hypertension (blood pressure more than 160/90, proteinurea of 3-5 gr/day, and a variety of other clinical symptoms including headache, visual disturbances, epigastric pain, impaired liver function, thrombocytopenia and fetal growth restriction.

In an embodiment, the condition is severe preeclampsia or early onset severe preeclampsia (EPE) characterized by hypertension (≥140 mmHg; diastolic blood pressure ≥90 mmHg), proteinuria (≥300 mg/24 h) and preterm delivery according to ACOG guidelines.

In an embodiment, the condition is IUGR or small for gestational age (SGA). IUGR is characterized by a birth weight which is less that 10 percent of the predicted fetal weight for the gestational age of the fetus [e.g. a weight less than 2,500 gm (5 lbs. 8 oz.)]. Pregnancies complicated by severe Intrauterine Growth Restriction (sIUGR), disease are generally characterized by fetal growth <5° percentile according to gestational age and sex, pathological umbilical Doppler flow velocimetry waveform (Absent End Diastolic Flow), and pathological bilateral uterine Doppler.

In certain embodiments, the condition is eclampsia which occurs when the preeclampsia is severe and leads to the development of seizures. Dysfunction or damage to several organs or tissues such as the liver (e.g., hepatocellular damage, periportal necrosis) and the central nervous system (e.g., cerebral edema and cerebral hemorrhage) may be associated with eclampsia.

In certain embodiments, the condition is HELLP syndrome (hemolysis, elevated liver enzymes, low platelets). HELLP syndrome is characterized by thrombocytopenia (<100000 cells/muL), increased LDH (>600 IU/L) and increased AST (>70 IU/L).

In an embodiment, the condition is molar pregnancy.

In an embodiment of the invention the condition is gestational diabetes mellitus (GDM). GDM is defined as a glucose intolerance of variable degree which typically develops in the second and third trimester of pregnancy. Risk factors for GDM include without limitation, a previous diagnosis of gestational diabetes or prediabetes; impaired glucose tolerance, impaired fasting glycaemia; a family history of type 2 diabetes; maternal age (particularly women over 35 years of age are high risk); ethnic background (African-Americans, Afro-Caribbeans, Native Americans, Hispanics, Pacific Islanders, and people originating from South Asia have a higher risk of developing GDM); being overweight, obese or severely obese; a previous pregnancy which resulted in a child with a high birth weight (>90th percentile, or >4000 g); and/or a previous poor obstetric history.

In an embodiment of the invention the condition is diabetes. "Diabetes" includes without limitation type I and type II diabetes, early stage diabetes, and a pre-diabetic condition characterized by mildly decreased insulin or mildly elevated blood glucose levels. A "pre-diabetic condition" describes a subject demonstrating a symptom in terms of insulin or glucose level, and/or demonstrating a susceptibilty to diabetes or a related condition due to family history, genetic predisposition, or obesity in the case of type II diabetes, and includes a subject who has previously had diabetes or a related condition and is subject to risk of recurrence.

In aspects of the invention the disorder or disease is a condition associated with abnormal cell growth. In an embodiment, the abnormal cell growth is cancer. The term encompasses tumor invasion, tumor growth, and/or tumor metastasis. The term "cancer" includes without limitation the following cancers: breast, ovary, cervix, prostate, testis, esophagus, glioblastoma, neuroblastoma, stomach, skin, keratoacanthoma, lung, epidermoid carcinoma, bone, pancreas, large cell carcinoma, vagina, vulva, Hodgkin's Disease, thyroid gland, adenocarcinoma, adrenal gland, prostate, chronic or acute leukemia, neoplasms of the central nervous system, primary CNS lymphoma, spinal axis tumors, brain stem glioma, pituitary adenoma, small cell lung, non-small lung, fallopian tubes, endometrium, colon, adenoma, thyroid, parathyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip tongue, mouth, pharynx, small intestine, colon-rectum, large intestine, rectum, brain and central nervous system, and leukemia. In embodiments of the invention, the cancer is prostate cancer. In embodiments of the invention, the cancer is breast cancer. In embodiments of the invention, the cancer is acute myelogenous leukemia.

The term "sample" and the like mean a material known or suspected of expressing or containing Hydroxylated HIF Biomarkers, or binding agents such as antibodies specific for Hydroxylated HIF Biomarkers, and/or in some aspects additional markers of pregnancy related conditions. The sample may be derived from a biological source such as a patient or cell culture ("biological sample"), and includes without limitation, tissues (e.g. placental tissues), tissue extracts, cell cultures, harvested cells, cell lysates, conditioned medium from maternal cells, and biological or physiological fluids, such as, for example, whole blood, plasma, serum, saliva, cerebral spinal fluid, sweat, urine, milk, peritoneal fluid, ascites fluid, amniotic fluid, vaginal fluid, peritoneal fluid, synovial fluid, ocular lens fluid and the like. A sample may be used directly as obtained from the source or following a pretreatment to modify the character of the sample, such as preparing plasma from blood, diluting viscous fluids, and the like. Methods of treatment can involve filtration, distillation, extraction, concentration, inactivation of interfering components, the addition of reagents, and the like. In embodiments of the invention the sample is a mammalian sample, preferably human sample. In certain aspects of the invention, the sample is a human physiological fluid, such as serum or urine. In certain aspects of the invention, the sample is a biopsy sample. In certain aspects of the invention the sample is a placental tissue sample. In an embodiment of the invention, the sample is human serum.

Samples that may be analyzed for markers disclosed herein include polynucleotides from clinically relevant sources, preferably expressed RNA or a nucleic acid derived therefrom (cDNA or amplified RNA derived from cDNA that incorporates an RNA polymerase promoter), The target polynucleotides can comprise RNA, including, without limitation total cellular RNA, poly(A)$^+$ messenger RNA (mRNA) or fraction thereof, cytoplasmic mRNA, or RNA transcribed from cDNA (i.e., cRNA; see, for example, Linsley & Schelter, U.S. patent application Ser. No. 09/411,074, or U.S. Pat. No. 5,545,522, 5,891,636, or 5,716,785). Methods for preparing total and poly(A)$^+$ RNA are well known in the art, and are described generally, for example, in Sambrook et al., (1989, Molecular Cloning—A Laboratory Manual ($2^{nd}$ Ed.), Vols. 1-3, Cold Spring Harbor Laboratory, Cold Spring Harbor, N.Y.) and Ausubel et al, eds. (1994, Current Protocols in Moelcular Biology, vol. 2, Current Protocols Publishing, New York). RNA may be isolated from eukaryotic cells by procedures involving lysis of the cells and denaturation of the proteins contained in the cells. Additional steps may be utilized to remove DNA. Cell lysis may be achieved with a nonionic detergent, followed by microcentrifugation to remove the nuclei and hence the bulk of the cellular DNA. (See Chirgwin et al., 1979, Biochemistry 18:5294-5299). Poly(A)+ RNA can be selected using oligo-dT cellulose (see Sambrook et al., 1989, Molecular Cloning—A Laboratory Manual (2nd Ed.), Vols. 1-3, Cold Spring Harbor Laboratory, Cold Spring Harbor, N.Y.). In the alternative, RNA can be separated from DNA by organic extraction, for example, with hot phenol or phenol/chloroform/isoamyl alcohol. It may be desirable to enrich mRNA with respect to other cellular RNAs, such as transfer RNA (tRNA) and ribosomal RNA (rRNA). Most mRNAs contain a poly(A) tail at their 3' end allowing them to be enriched by affinity chromatography, for example, using oligo(dT) or poly(U) coupled to a solid support, such as cellulose or Sephadex™ (see Ausubel et al., eds., 1994, Current Protocols in Molecular Biology, vol. 2, Current Protocols Publishing, New York). Bound poly(A)+ mRNA is eluted from the affinity column using 2 mM EDTA/ 0.1% SDS.

The terms "subject", "patient" and "individual" are used interchangeably herein and refer to a warm-blooded animal such as a mammal that is afflicted with, or suspected of having, being pre-disposed to, or being screened for a condition disclosed herein. The term includes but is not limited to domestic animals, sports animals, primates and humans. Preferably, the terms refer to a human. In embodiments the term refers to a pregnant female.

A subject at risk for a condition disclosed herein includes a subject with one or more risk factors for developing the condition. Risk factors may include, but are not limited to, age, genetic predisposition, proteinuria, generalized edema and pregnancy-induced hypertension.

As used herein, the term "characterizing a condition in a subject" refers to the identification of one or more properties of a sample in a subject, including but not limited to the subject's prognosis. A condition may be characterized by the identification of the expression of one or more markers, including but not limited to, Hydroxylated HIF Biomarkers disclosed herein.

The term "detect" or "detecting" includes assaying, or otherwise establishing the presence or absence of the target marker(s), subunits, or combinations of reagent bound targets, and the like, or assaying for ascertaining, establishing, characterizing, predicting or otherwise determining one or more factual characteristics of a condition. A standard or control may correspond to amounts determined for samples from control subjects with no disease or early stage disease, or from other samples of the subject.

The term "isolated" refers to molecules separated from other molecules. The term also refers to a nucleic acid or polypeptide that is substantially free of cellular material, viral material, or culture medium when produced by recombinant DNA techniques, or chemical precursors or other chemicals when chemically synthesized. An isolated nucleic acid includes nucleic acid fragments that are not naturally occurring and would not be found in nature. The term "isolated" also refers to polypeptides that are isolated from other cellular proteins, and the term encompasses both purified and recombinant polypeptides. The term "isolated", when used in the context of an antibody refers to an antibody that is (1) not associated with naturally-associated components including other antibodies, (2) free of other proteins from the same species, (3) expressed by a cell from a different species, or (4) not occurring in nature. Examples of isolated antibodies include antibodies produced by hybridomas or cell lines in vitro, affinity purified antibodies, or antibodies generated by transgenic animals or plants.

"Polypeptide" and "protein" are used interchangeably herein and indicate at least one molecular chain of amino acids linked through covalent and/or non-covalent bonds. The terms include peptides, oligopeptides, and proteins, and post-translational modifications of the polypeptides, e.g. glycosylations, acetylations, phosphorylations, and the like. Native or artificial proteins, protein fragments, analogues, mutated or variant proteins, fusion proteins, and the like, are also included within the meaning of the terms. A polypeptide may be monomeric or polymeric. In embodiments of the invention, the polypeptide is an antibody (including fragments thereof) of the invention.

A "native polypeptide" comprises a polypeptide having the same amino acid sequence of a polypeptide derived from nature. Such native-sequence polypeptides can be isolated from nature or can be produced by recombinant or synthetic means. The term specifically encompasses naturally occurring truncated or secreted forms of a polypeptide, polypeptide variants including naturally occurring variant forms (e.g. alternatively spliced forms or splice variants), and naturally occurring allelic variants.

The term "variant" means a polypeptide having at least about 45%, 50%, 55%, 60%, 65%, 70%, 75%, 80%, 85%, 90%, 95%, 97%, 98%, or 99% amino acid sequence identity, particularly at least about 70-80%, more particularly at least about 85%, still more particularly at least about 90%, most particularly at least about 95% or 99% amino acid sequence identity with a reference polypeptide. Such variants include, for instance, polypeptides wherein one or more amino acid residues are added to, or deleted from, the N- or C-terminus of the full-length or mature sequences of the polypeptide, including variants from other species, but excludes a native polypeptide. In an embodiment, a polypeptide is provided having at least about 45%, 50%, 55%, 60%, 65%, 70%, 75%, 80%, 85%, 90%, 95%, 97%, 98%, or 99% amino acid sequence identity, in particular at least 90%, at least 95%, at least 98% or at least 90% sequence identity to SEQ. ID. NO: 7, 8, 10, 11, 13, 14, 16, 17, 19, 20, 22, 23, 25, 26, 27, 28, 30, 31, 33, 34, 36, 37, 39 or 40.

Percent identity of two amino acid sequences, or of two nucleic acid sequences is defined as the percentage of amino acid residues or nucleotides in a candidate sequence that are identical with the amino acid residues in a polypeptide or nucleic acid sequence, after aligning the sequences and introducing gaps, if necessary, to achieve the maximum percent sequence identity, and not considering any conservative substitutions as part of the sequence identity. Alignment for purposes of determining percent amino acid or nucleic acid sequence identity can be achieved in various conventional ways, for instance, using publicly available computer software including the GCG program package (Devereux J. et al., Nucleic Acids Research 12(1): 387, 1984), BLASTP, BLASTN, and FASTA (Atschul, S. F. et al. J. Molec. Biol. 215: 403-410, 1990). The BLAST X program is publicly available from NCBI and other sources (BLAST Manual, Altschul, S. et al. NCBI NLM NIH Bethesda, Md. 20894; Altschul, S. et al. J. Mol. Biol. 215: 403-410, 1990). Skilled artisans can determine appropriate parameters for measuring alignment, including any algorithms needed to achieve maximal alignment over the full length of the sequences being compared. Methods to determine identity and similarity are codified in publicly available computer programs.

A variant may be created by introducing substitutions, additions, or deletions into a polynucleotide such that one or more amino acid substitutions, additions, or deletions are introduced into the encoded protein. Mutations may be introduced by standard methods, such as site-directed mutagenesis and PCR-mediated mutagenesis. In an embodiment, conservative substitutions are made at one or more predicted non-essential amino acid residues. A "conservative amino acid substitution" is one in which an amino acid residue is replaced with an amino acid residue with a similar side chain. Amino acids with similar side chains are known in the art and include amino acids with basic side chains (e.g. Lys, Arg, His), acidic side chains (e.g. Asp, Glu), uncharged polar side chains (e.g. Gly, Asp, Glu, Ser, Thr, Tyr and Cys), nonpolar side chains (e.g. Ala, Val, Leu, Iso, Pro, Trp), beta-branched side chains (e.g. Thr, Val, Iso), and aromatic side chains (e.g. Tyr, Phe, Trp, His). Mutations can also be introduced randomly along part or all of the native sequence, for example, by saturation mutagenesis. Following mutagenesis the variant polypeptide can be recombinantly expressed and the activity of the polypeptide may be determined.

Variants include polypeptides comprising amino acid sequences sufficiently identical to or derived from the amino acid sequence of a polypeptide which contain fewer amino acids than the full length polypeptides. A fragment or portion of a polypeptide can be a polypeptide which is for example, 10, 15, 20, 25, 30, 35, 40, 45, 50, 60, 70, 80, 90, 100 or more amino acids in length. Portions in which regions of a polypeptide are deleted can be prepared by recombinant techniques and can be evaluated for one or more functional activities such as the ability to form antibodies specific for a polypeptide.

A modified form of a polypeptide referenced herein includes modified forms of the polypeptides and derivatives of the polypeptides, including post-translationally modified forms such as glycosylated, phosphorylated, acetylated, methylated or lapidated forms of the polypeptides.

A polypeptide (e.g. an antibody) disclosed herein includes chimeric or fusion proteins. A "chimeric protein" or "fusion protein" comprises all or part (preferably biologically active) of a polypeptide operably linked to a heterologous polypeptide (i.e., a different polypeptide). Within the fusion protein, the term "operably linked" is intended to indicate that the polypeptide and the heterologous polypeptide are fused in-frame to each other. The heterologous polypeptide can be fused to the N-terminus or C-terminus of the polypeptide. Chimeric and fusion proteins can be produced by standard recombinant DNA techniques.

"Polynucleotide(s)" or "nucleic acids" refers to DNA, RNA, mRNA and the like which can be either double stranded or single stranded. Nucleic acid molecules that encode polypeptides referenced herein include native or artificial polypeptides, polypeptide variants including a portion of a polypeptide, an isoform, precursor, complex, a chimeric polypeptide, or modified forms and derivatives of the polypeptides. In aspects of the invention the term refers to nucleic acid molecules encoding antibodies (including fragments thereof) of the invention. A polynucleotide may, but need not, include additional coding or non-coding sequences, or it may, but need not, be linked to other molecules and/or carrier or support materials. The polynucleotides for use in the methods of the invention may be of any length suitable for a particular method.

"Polynucleotides" or "nucleic acids" include complementary nucleic acid sequences, and nucleic acids that are substantially identical to these sequences (e.g. having at least about 45%, 50%, 55%, 60%, 65%, 70%, 75%, 80%, 85%, 90%, 95%, 97%, 98%, or 99% sequence identity). In an embodiment, a nucleic acid is provided having at least about 45%, 50%, 55%, 60%, 65%, 70%, 75%, 80%, 85%, 90%, 95%, 97%, 98%, or 99% sequence identity, in particular at least 90%, at least 95%, at least 98% or at least 90% sequence identity to SEQ. ID. NO: 42, 43, 45, 46, 48, 49, 51, 52, 54, 55, 57, 58, 60, 61, 63, 64, 66, 67, 69, 70, 72, 73, 75, or 76. The terms also include nucleic acid sequences that differ from a native sequence due to degeneracy in the genetic code. Further the terms include nucleic acids that hybridize under stringent conditions, preferably high stringency conditions to a target polynucleotide. Appropriate stringency conditions which promote DNA hybridization are known to those skilled in the art, or can be found in Current Protocols in Molecular Biology, John Wiley & Sons, N.Y. (1989), 6.3.1-6.3.6. For example, 6.0× sodium chloride/sodium citrate (SSC) at about 45° C., followed by a wash of 2.0×SSC at 50° C. may be employed. The stringency may be selected based on the conditions used in the wash step. By way of example, the salt concentration in the wash step can be selected from a high stringency of about 0.2×SSC at 50° C. In addition, the temperature in the wash step can be at high stringency conditions, at about 65° C. Also the terms include truncated nucleic acids or nucleic acid fragments and variant forms of the nucleic acids that arise by alternative splicing of an mRNA corresponding to a DNA.

The term "HIF-1α" refers to hypoxia-inducible factor 1, alpha subunit (basic helix-loop-helix transcription factor) polypeptide encoded by the HIF1α gene. HIF1α comprises a basic helix-loop-helix motif that binds DNA and causes subunit dimerization; a Per-ARNT-Sim (PAS) domain; an oxygen-dependent degradation (ODD) domain (amino acid residues 401-603 in human HIF1α), which is hydroxylated by proline-hydroxylase-2 (PHD-2) rendering the α-subunit vulnerable to proteasomal degradation under normoxic cellular conditions; and two transactivation domains (TAD), which regulate HIF-1 target genes [Ziello et al, 2007, Yale J Biol Med,80(2):51-60]. Under normoxic conditions, HIF-1α is constitutively hydroxylated on two conserved proline residues (Pro-402 and Pro-564 in the case of human HIF-1α). Sequences for two isoforms of human HIF1α are shown in NP_001521.1 and NP_851397.1 and SEQ ID NO: 1 and 2, and a sequence for murine HIF1α is in SEQ ID NO: 78.

"Hydroxylated HIF Biomarkers" refers to HIF-1α hydroxylated at one or both of proline 402 and proline 564, or portions of HIF1α comprising one or both of hydroxylated proline 402 and hydroxylated proline 564. The term also includes native-sequence polypeptides, isoforms, fragments, isolated polypeptides, polypeptide variants and chimeric or fusion proteins of such hydroxylated molecules. In embodiments, the term includes the sequence comprising the oxygen-dependent degradation domain (ODD) of the HIF-1α subunit hydroxylated at one or both of proline 402 and proline 564 in the human sequence. In embodiments, the term includes the sequence comprising the oxygen-dependent degradation domain (ODD) of the HIF-1α subunit hydroxylated at proline 402 in the human sequence. In embodiments, the term includes the sequence comprising the oxygen-dependent degradation domain (ODD) of the HIF-1α subunit hydroxylated at proline 564 in the human sequence. In embodiments, the term includes the sequence comprising amino acid residues 556-574 of SEQ ID NO: 1 or 2. In embodiments, the term includes an ODD sequence comprising amino acid residues 401-603 of SEQ ID NO: 1 or 2.

The "status" of a marker refers to the presence, absence or extent/level of the marker or some physical, chemical or genetic characteristic of the marker. Such characteristics include without limitation, expression level, activity level, structure (sequence information), copy number, post-translational modification etc. The status of a marker may be directly or indirectly determined. In some embodiments status is determined by determining the level of a marker in the sample. The "level" of an element in a sample has its conventional meaning in the art, and includes quantitative determinations (e.g. mg/mL, fold change, etc) and qualitative determinations (e.g. determining the presence or absence of a marker or determining whether the level of the marker is high, low or even present relative to a standard).

The term "abnormal status" means that a marker's status in a sample is different from a reference status for the marker. A reference status may be the status of the marker in samples from normal subjects, averaged samples from subjects with the condition or sample(s) from the same subject taken at different times. An abnormal status includes an elevated, decreased or reduced, present or absent marker(s). Determining the level of a marker in a sample may include determining the level of the marker in a sample and abnormal status could be either lower levels (including undetectable levels) or higher levels (including any amount over zero) compared to a standard. A subject may have an increased likelihood of a condition disclosed herein if the status of a marker in the subject's sample is correlated with the condition (e.g. a level of the marker is closer to a standard or reference or is present in levels that exceed some threshold value where exceeding that value is correlated with the condition). A subject with an increased likelihood of a condition disclosed herein includes a subject with an abnormal status for a marker and as such the subject has a higher likelihood of the condition than if the subject did not have that status.

An "elevated status" means one or more characteristics of a marker are higher than a standard or control. In aspects of the invention, the term refers to an increase in a characteristic as compared to a standard or control. A "low status" means one or more characteristics of a marker are lower than a standard or control. In aspects of the invention, the term refers to a decrease in a characteristic as compared to a standard or control. A "negative status" means that one or more characteristic of a marker is absent or undetectable.

"Significantly different" levels of markers or a "significant difference" in marker levels in a patient sample compared to a control or standard (e.g. normal levels, levels from a different disease stage, or levels in other samples from a patient) may represent levels that are higher or lower than the standard error of the detection assay, preferably the levels are at least about 1.5, 2, 3, 4, 5, 6, 7, 8, 9 or 10 times higher or lower, respectively, than the control or standard.

"Microarray" and "array," refer to nucleic acid or nucleotide arrays or protein or peptide arrays that can be used to detect markers associated with a referenced condition, for instance to measure gene or protein expression.

"Binding agent" refers to a substance such as a polypeptide, antibody, ribosome, or aptamer that specifically binds to a target marker. A binding agent may be a ribosome, with or without a peptide component, RNA or DNA molecule, or a polypeptide. A binding agent may be a polypeptide that comprises a target marker, a peptide variant thereof, or a non-peptide mimetic of such a sequence.

An aptamer includes a DNA or RNA molecule that binds to nucleic acids and proteins. An aptamer that binds to target marker can be produced using conventional techniques, without undue experimentation. [For example, see the following publications describing in vitro selection of aptamers: Klug et al., Mol. Biol. Reports 20:97-107 (1994); Wallis et al., Chem. Biol. 2:543-552 (1995); Ellington, Curr. Biol. 4:427-429 (1994); Lato et al., Chem. Biol. 2:291-303 (1995); Conrad et al., Mol. Div. 1:69-78 (1995); and Uphoff et al., Curr. Opin. Struct. Biol. 6:281-287 (1996)].

"Immunoglobulin" refers to a tetrameric molecule which is generally composed of two identical pairs of polypeptide chains each pair comprising one light chain and one heavy chain. The amino-terminal part of each chain includes a variable region having about 100 or more amino acids which is responsible for antigen recognition, and the carboxy-terminal constant region which is primarily responsible for effector function. Immunoglobulin chains have the same general structure of relatively conserved framework regions (FR) joined by three hypervariable regions (also known as complementarity determining regions or CDRs). The framework regions align the CDRs from the two chains of each pair to form an epitope-specific binding site or antigen recognition domain. The light and heavy chains comprise the domains FR1, CDR1, FR2, CDR2, FR3, CDR3 and FR4 from the N-terminal to C-terminal of the chains. (See generally, Kabat, Sequences of Proteins of Immunological Interest (National Institutes of Health, Bethseda, Md. (1987 and 1991) and Clothia & Lwsk, J Mol Biol, 1987, 196:901-917; and Clothia et al, Nature, 342:878-883, 1989).

An "antibody" includes an intact immunoglobulin or portion thereof. Accordingly, antibodies for use in the present invention include but are not limited to synthetic antibodies, monoclonal antibodies, polyclonal antibodies, recombinantly produced antibodies, antibody fragments, antibody heavy chains, intrabodies, humanized antibodies, human antibodies, antibody light chains, single chain antibody (scFv), diabodies, anti-idiotypic (ant-Id) antibodies, proteins comprising an antibody portion, chimeric antibodies, for example, antibodies which contain the binding specificity of murine antibodies, but in which the remaining portions are of human origin, derivatives, such as enzyme conjugates or labelled derivatives, linear antibodies, disulfide-linked Fvs (sdFv), multispecific antibodies (e.g., bispecific antibodies), epitope-binding fragments of any of the above, and any other modified configuration of an immunoglobulin molecule that comprises an antigen recognition domain of the required specificity. The term also includes immunoadhesions that specifically bind a Hydroxylated HIF Biomarker comprising one or more CDRs covalently or non-covalently incorporated into a molecule. The CDRs may be incorporated as part of a larger polypeptide chain, covalently or non-covalently link the CDRs to another polypeptide chain or incorporate the CDRs non-covalently.

A fragment of an antibody includes without limitation Fab fragments, Fab', F(ab')$_2$ fragments, dAb (domain antibody; see Ward, et. AL, 1989, Nature, 341:544-546), Fd fragments, Fv fragments, single-chain Fv (scFv) molecules, minimal recognition units consisting of the amino acid residues that mimic the hypervariable region of an antibody (e.g., an isolated CDR), and other engineered molecules such as diabodies, triabodies, tetrabodies, and minibodies. A fragment will generally comprise at least one variable region. In aspects of the invention a fragment comprises at least one variable region and at least one constant region. Variable and constant regions may be directly linked to one another or linked by a partial hinge or linker region. A hinge region may comprise about 2, 5, 10, 15, 20, 30, 40 or 60 or more amino acids which result in a flexible or semi-flexible linkage between adjacent variable and/or constant regions in a single polypeptide molecule. A fragment may comprise a homo-dimer or hetero-dimer (or other multimer) of any of the variable and constant regions disclosed herein with one another and/or with one or more monomeric $V_H$ or $V_L$ domains. A fragment may be monospecific or multispecific, for example bispecific. Fragments of an antibody may be obtained using any suitable methods such as proteolytic digestion of a full antibody molecule or recombinant genetic engineering techniques, for example to arrange one or more variable and/or constant regions into a suitable configuration, or to introduce codons, create cysteine residues, modify, add or delete amino acids, etc.

An antibody may have one binding site or more than one identical or non-identical binding site. For example, a single-chain antibody or Fab fragment has one binding site while a bispecific antibody has two different binding sites.

An antibody includes an antibody of any type (e.g. IgA, IgD, IgE, IgG, IgM and IgY), any class (e.g. IgG1, IgG2, IgG3, IgG4, IgA1 and IgA2), or any subclass (e.g. IgG2a and IgG2b), and the antibody need not be of any particular type, class or subclass. In certain embodiments of the invention the antibodies are IgG antibodies or a class or subclass thereof. An antibody may be from any animal origin including birds and mammals (e.g. human, murine, donkey, sheep, rabbit, goat, guinea pig, camel, horse, or chicken).

A "human antibody" refers to an antibody in which the variable and constant region sequences are human sequences. The term also includes sequences derived from human genes which have been altered, for example, to increase affinity, or eliminate cysteines or glycosylation sites. The term also includes recombinant antibodies produced in non-human cells that impart glycosylation sites that are not typical of human cells, or antibodies generated in transgenic animals that have some or all human immunoglobulin heavy and light chain sequences. In some aspects of the invention, humanized antibodies are provided that are derived from a non-human species and have mutated amino acids in the framework and constant regions of the heavy and light chains. In some aspects, a humanized antibody comprises constant domains from a human antibody fused to the variable domains of a non-human species. (See U.S. Pat. Nos. 6,054,297, 5,886,152 and 5,877,293.) In some aspects, a humanized antibody comprises the amino acid sequence of one or more framework regions of one or more human antibodies.

A "chimeric antibody" includes an antibody having one or more regions from one antibody and one or more regions from one or more other antibodies. In an aspect, one or more CDRs of a chimeric antibody are derived from an antibody of the invention. In an aspect, all of the CDRs are derived from an antibody of the invention. In another aspect, the variable regions of a light or heavy chain from more than one antibody of the invention are included in a chimeric antibody. For example, a chimeric antibody may comprise a variable region of a light chain from one antibody of the invention and a variable region of a heavy chain from another antibody. In an embodiment, a chimeric antibody comprises a CDR1 from the light chain of a first antibody combined with CDR2 and CDR3 from the light chain of a second antibody, and the CDRs from the heavy chain may be derived from a third antibody. A chimeric antibody may comprise framework regions from one or the same antibodies or from one or more different antibodies.

An "antigen recognition domain" or "antigen recognition site" refers to the portion of an antibody which comprises the amino acid residues that interact with an antigen or epitope and confer on the antibody specificity and affinity for the antigen or epitope (e.g. the complementarity determining regions (CDR)).

An "epitope" refers to a localized region on an antigen such as a Hydroxylated HIF Biomarker that is capable of being bound to one or more antigen recognition domains of an antibody. In embodiments of the invention, an epitope comprises hydroxylated proline 402 of HIF-1α and/or hydroxylated proline 564 of HIF-1α. In embodiments of the invention, an epitope comprises hydroxylated proline 402 of HIF-1α. In embodiments of the invention, an epitope comprises hydroxylated proline 564 of HIF-1α. In embodiments of the invention, an epitope comprises hydroxylated proline 402 of HIF-1α and hydroxylated proline 564 of HIF-1α.

A "recombinant antibody" includes antibodies that are prepared, expressed, created or isolated by recombinant means, such as antibodies expressed using a recombinant expression vector transfected into a host cell, antibodies isolated from recombinant, combinatorial antibody libraries, antibodies isolated from an animal (e.g. a mouse or cow) that is transgenic and/or transchromosomal for human immunoglobin genes, or antibodies prepared, expressed, created or isolated by any other means that involves slicing of immunoglobulin gene sequences to other DNA sequences.

A "monoclonal antibody" refers to an antibody obtained from a population of homogenous or substantially homogenous antibodies. Generally each monoclonal antibody recognizes a single epitope on an antigen. In aspects of the invention, a monoclonal antibody is an antibody produced by a single hybridoma or other cell, and it specifically binds to only a Hydroxylated HIF Biomarker, in particular an epitope of HIF-1α comprising or consisting of hydroxylated proline 402 and/or hydroxylated proline 564 as determined, for example by ELISA or other antigen-binding or competitive binding assay known in the art. The term is not limited to a particular method for making the antibody and for example they may be produced by the hybridoma method or isolated from phage libraries using methods known in the art.

Antibodies, including monoclonal and polyclonal antibodies, fragments and chimeras, may be prepared using methods well known to those skilled in the art. Isolated native or recombinant polypeptides may be utilized to prepare antibodies. See, for example, Kohler et al. (1975) Nature 256:495-497; Kozbor et al. (1985) J. Immunol. Methods 81:31-42; Cote et al. (1983) Proc Natl Acad Sci 80:2026-2030; and Cole et al. (1984) Mol Cell Biol 62:109-120 for the preparation of monoclonal antibodies; Huse et al. (1989) Science 246:1275-1281 for the preparation of monoclonal Fab fragments; and, Pound (1998) Immunochemical Protocols, Humana Press, Totowa, N.J., for the preparation of phagemid or B-lymphocyte immunoglobulin libraries to identify antibodies. Antibodies specific for selected markers may also be obtained from scientific or commercial sources.

A binding agent, in particular an antibody, that "specifically binds" or "binds" (used interchangeably herein) to a target or an antigen or epitope is a term well understood in the art, and methods to determine specific binding are also well known in the art, for example, equilibrium dialysis, surface plasmon resonance, ELISA, RIA and the like. A binding agent "specifically binds" to a target if it binds with greater affinity, avidity, more readily, and/or with greater duration than it binds to other substances. It will be appreciated that an antibody that specifically binds to a first target may or may not specifically or preferentially bind to a second target. Thus, specific binding does not necessarily require (although it can include) exclusive binding but generally refers to preferential binding.

The term "$K_d$" refers to the dissociation constant of a particular antibody-antigen interaction.

In an embodiment of the invention, antibodies are reactive against a polypeptide marker if they bind an antigen with a $K_d$ of less than about 1000 nM, in particular less than about 200 nM, less than about 100 nM, less than about 90 nM, less than about 80 nM, less than about 70 nM, less than about 60 nM, less than about 50 nM, less than about 40 nM, less than about 20 nM, less than about 10 nM, less than about 5 nM, less than about 3 nM, less than about 2 nM, or less than about 1 nM, preferably measured by surface plasmon resonance assay.

A "host cell" may be a naturally occurring cell or a transformed cell that comprises a vector and supports the replication of the vector. The term includes cells into which an expression vector is initially introduced, and also to the progeny or potential progeny of such cells. Host cells may be cultured cells, explants, in vivo cells and the like.

The term "vector" refers to a nucleic acid capable of transporting another nucleic acid to which it has been linked. A vector includes those capable of autonomous replication and expression of nucleic acids to which they are linked. A vector can be used to deliver a polynucleotide or nucleic acid of interest to the interior of a cell. Numerous vectors are known in the art including, but not limited to, linear polynucleotides, polynucleotides associated with ionic or amphiphilic compounds, plasmids, and viruses. The term "vector" includes an autonomously replicating plasmid or a virus. Examples of viral vectors include, but are not limited to, adenoviral vectors, adeno-associated virus vectors, retroviral vectors, and the like.

A vector comprises regulatory sequences operatively linked to a polynucleotide or nucleic acid of interest. An expression vector generally comprises a promoter, enhancer, transcription termination sequences, origins of replication, selectable marker genes, and sequences required for proper expression of a nucleotide sequence. A construct comprising a nucleotide sequence of interest can be chimeric, or it can be one that is naturally occurring but has been obtained in a recombinant form useful for heterologous expression. The design of a vector including the selection of regulatory sequences may depend on factors such as the type of host cell, the level of expression of the desired polypeptide, etc. (See, for example, U.S. Pat. Nos. 5,168,062, 4,510,245, 4968,615, and 6,517,529 for descriptions of regulatory sequences, and U.S. Pat. Nos. 4,399,216, 4,634,665 and 5,179,017 for descriptions of selectable marker genes.)

The phrase "operatively linked", when describing the relationship between two nucleic acid regions, refers to a juxtaposition wherein the regions are in a relationship permitting them to function in their intended manner. For example, a regulatory sequence "operatively linked" to a coding sequence can be ligated in such a way that expression of the coding sequence is achieved under conditions compatible with the regulatory sequences. In some embodiments, the phrase refers to a promoter connected to a coding sequence such that transcription of that coding sequence is controlled and regulated by the promoter. Techniques for operatively linking a promoter to a coding sequence are known in the art. The phrase "operatively linked" may also refer to a transcription termination sequence that is connected to a nucleic acid sequence in such a way that termination of transcription of that sequence is controlled by that transcription termination sequence.

The term "regulatory sequence" refers to polynucleotide sequences, such as initiation signals, enhancers, regulators, promoters, and termination sequences, which are necessary or desirable to affect the expression of coding and non-coding sequences to which they are operatively linked. The term "regulatory sequence" is intended to include, at a minimum, components the presence of which can influence expression, and can also include additional components the presence of which is advantageous, for example, leader sequences and fusion partner sequences. Exemplary regulatory sequences are described in the art (see for example Goeddel, 1990, Methods Enzymol. 185:3-7). In certain embodiments, the regulatory sequence is a promotor. The regulatory sequence may be a transcription termination sequence (for example, an RNA polymerase III termination sequence). In certain instances, transcriptional terminators are also responsible for correct mRNA polyadenylation.

Markers

The invention contemplates compositions comprising markers and sets of markers that can be used for detection, diagnosis, prevention and therapy of conditions disclosed herein. In an aspect, the invention provides a composition comprising one or more Hydroxylated HIF Biomarkers or a set of Hydroxylated HIF Biomarkers correlated with or that distinguish a condition disclosed herein, in particular a pregnancy-related condition, more particularly early onset preeclampsia, late onset preeclampsia, IUGR, gestational diabetes or diabetes.

In addition to Hydroxylated HIF Biomarkers, a composition or marker set may also comprise one or more of the following markers: Mtd-S, Mtd-P or Mtd-L, (Soleymanlou N. et al, Cell Death Differ 12:441-452, 2005; Gene ID No. 51800; Accession No. NM_032515; NP_115904), sFlt (Accession number: U01134); SMAD2 (Gene ID 4087; NM_001003652; NP_001003652), SMAD3 (Gene ID No. 4088; NP_005893; NM_005902); SMAD7 (Gene ID No. 4092; NM_005904; NP_005895), ceruloplasmin (Gene ID. 1356; NM_000096; NP_000087), transforming growth factor β3 (TGβ3) (e.g., Accession No. NP_003230); transforming growth factor β1 (TGFβ1) (e.g., Accession No. NP_000651); hypoxia-inducible factor 1, beta subunit (HIF-1β) (e.g., Accession No. NP_001659; NP_848513; NP_848514); hypoxia-inducible factor 2, alpha subunit (HIF-2α) (e.g., Accession No. Q99814); endoglin (Gene ID. No. 2022; NP_000109; NM_000118; UniProt No. P17813); von Hippel-Lindau tumor suppressor (VHL) (e.g., Accession Nos. NP_000542 and NP_937799); myeloid cell leukemia sequence 1 (Mcl-1) (e.g., Accession Nos. NP_068779—isoform 1; NP_877495—isoform 2); prolyl-4-hydroxylase 1 (PHD1) (e.g., Accession No. NP_071334); prolyl-4-hydroxylase 2 (PHD2) (e.g., Accession No. NP_0600251; NP_542770; and NP_444274); prolyl-4-hydroxylase 3 (PHD3) (e.g., Accession No. NP_071356); seven in absentia homolog 1 (Siah 1) (e.g., Accession No. NP_001006611 and NP_003022); seven in absentia homolog 2 (Siah2) (e.g., Accession No. NP_005058); vascular endothelial growth factor (VEGF) (e.g., Accession No. NP_001020537 to NP_001020541, NP_003367); syncytin (e.g., Accession No. NP_055405); cullin 2 (e.g., Accession No. NP_003582); neural precursor cell expressed, developmentally down-regulated 8 (NEDD) (e.g. Accession No. NP_006147); factor inhibiting HIF(FIH) (e.g., Accession No. Q9NWT6); Fas (TNF receptor superfamily, member 6) (e.g., Accession No. NP_000034; NP_690610 through NP_690616); cleaved caspase-3 (e.g., capase-3: Accession No. NP_004337; NP_116786; AA025654); HIF-1α (e.g., Accession No. NM_001530, NP_851397); SMAD2 (Gene ID. No. 4087; Accession Nos. NM_001003652 and NM_005901); and tumor protein p53 (e.g., Accession No. NM_000546); or, polynucleotides encoding these polypeptides. Exemplary nucleic acid sequences encoding the polypeptides are as follows: Mtd-P (NM_016778), Mtd-L (NM_016778), TGFβ3 (e.g. Accession No. NM_003239, NM_181054); TGFβ1 (e.g., Accession No. NM_000660); endoglin (Gene ID. 2022, NM_000118); SMAD3 (Gene ID No. 4058; Accession No. NM_005902); SMAD7 (Gene ID No. 4092; Accession No. NM_005904); ceruloplasmin (Gene ID No. 1356; Accession No. NM_000096); VHL (e.g. Accession Nos. NM_000551, NM_198156); Mcl-1 (e.g., Accession Nos. NM_021960—variant 1; NM_182763—variant 2); PHD1 (e.g., Accession No. NM_022051); PHD2 (e.g., Accession Nos. NM_053046, NM_017555, NM_080732); PHD3 (e.g., Accession No. NM_022073); HIF-1β (e.g., Accession No. NM_001668; NM_178426; NM_178427); seven in absentia homolog 1 (Siah1) (e.g., Accession Nos. NM_001006610; NM_0030311 and NM_001006611); Siah2 (e.g., Accession No. NM_005067); VEGF (e.g., Accession No. NM_001025366 to NM_001025370, NM_003376), FIH-1 (e.g. Accession No. AF395830), syncytin (e.g., Accession No. NG_004112), CUL2 (e.g., Accession No. NM_003591); NEDD8 (e.g.

Accession No. NM_006156), Fas (e.g., Accession Nos. NM_000043; NM_152871; NM_152872; NM_152873 152877); cleaved caspase-3 (e.g., caspase-3: Accession No. NM_004346; NM_032991; AY219866); and, p53 (e.g., Accession No. NP_000537).

In an embodiment, the invention provides a composition or set of markers that can be used for detection, diagnosis, prevention and therapy of pregnancy-related conditions comprising a Hydroxylated HIF Biomarker and optionally one or more of ceruloplasmin, sFlt, Mtd-P, Mtd-L, Mtd-S, Mcl-1 isoforms (in particular Mcl-1S or Mcl-1L, or caspase cleaved Mcl-1S or Mcl-1L, in particular caspase cleaved Mcl-1L), TGFβ1, TGFβ3, HIF-1α, HIF-1β, HIF-2α, VHL, cullin 2, NEDD8, PHD1, PHD2, PHD3, SIAH1, SIAH2, cleaved caspase (e.g. caspase-3), syncytin, Fas, VEGF, FIH, p53, and polynucleotides encoding same.

In an embodiment the invention provides a composition or set of markers that can be used for detection, diagnosis, prevention and therapy of pregnancy-related conditions comprising a Hydroxylated HIF Biomarker and optionally one or more of SMAD2, phospho-SMAD2, SMAD-3, phospho-SMAD3, SMAD7, ceruloplasmin, sFlt, Mtd-P, Mtd-L, Mtd-S, Mcl-1 isoforms (in particular Mcl-1S or Mcl-1L, or caspase cleaved Mcl-1S or Mcl-1L, in particular caspase cleaved Mcl-1L), TGFβ1, TGFβ3, HIF-1α, HIF-β3, HIF-2α, VHL, cullin 2, NEDD8, PHD1, PHD2, PHD3, SIAH1, SIAH2, cleaved caspase (e.g. caspase-3), syncytin, Fas, VEGF, FIH, p53, and polynucleotides encoding same.

In an embodiment the invention provides a composition or set of markers that can be used for detection, diagnosis, prevention and therapy of pregnancy-related conditions comprising a Hydroxylated HIF Biomarker and optionally at least one, two, three, four, five, six, seven, eight, nine, or ten or more of SMAD2, phospho-SMAD2, SMAD-3, phospho-SMAD3, SMAD7, ceruloplasmin, sFlt, Mtd-P, Mtd-L, Mtd-S, Mcl-1 isoforms (in particular Mcl-1S or Mcl-1L, or caspase cleaved Mcl-1S or Mcl-1L, in particular caspase cleaved Mcl-1L), TGFβ3, HIF-1α, HIF-1β, HIF-2α, VHL, cullin 2, NEDD8, PHD1, PHD2, PHD3, SIAH1, SIAH2, cleaved caspase (e.g. caspase-3), syncytin, Fas, VEGF, FIH, p53, and polynucleotides encoding same.

In an aspect the marker set comprises Hydroxylated HIF Biomarkers, and SMAD2, phospho-SMAD2, SMAD-3, phospho-SMAD3, SMAD7, ceruloplasmin, sFlt, Mtd-P and/or Mtd-L, and one or more Mcl-1 isoform (in particular Mcl-1S or Mcl-1L, endoglin, or caspase cleaved Mcl-1S or Mcl-1L, in particular caspase cleaved Mcl-1L), TGFβ1, TGFβ3, HIF-1α, HIF-1β, HIF-2α, VHL, cullin 2, NEDD8, PHD1, PHD2, PHD3, SIAH1, SIAH2, cleaved caspase (e.g. caspase-3), syncytin, Fas, VEGF, FIH, and/or p53, and/or polynucleotides encoding same.

In an embodiment the invention provides a composition or set of markers that can be used for detection, diagnosis, prevention and therapy of pregnancy-related conditions comprising a Hydroxylated HIF Biomarker, and a marker chosen from PHD1, PHD2, PHD3, SIAH1, SIAH2, FIH, and/or polynucleotides encoding PHD1, PHD2, PHD3, SIAH1, SIAH2 and FIH.

In another aspect the marker set comprises Hydroxylated HIF Biomarkers, and PHD1, PHD2, PHD3, SIAH1, SIAH2, FIH, and/or polynucleotides encoding PHD1, PHD2, PHD3, SIAH1, SIAH2 and FIH.

In another aspect the marker set comprises Hydroxylated HIF Biomarkers, and endoglin and/or polynucleotides encoding endoglin.

In an embodiment the invention provides a set of markers that can be used for detection, diagnosis, prevention and therapy of pregnancy-related conditions comprising a Hydroxylated HIF Biomarker, and PHD1, PHD2 and/or a polynucleotide encoding PHD1, PHD2 and/or PHD3.

In an embodiment the invention provides a composition or set of markers that can be used for detection, diagnosis, prevention and therapy of pregnancy-related conditions comprising a Hydroxylated HIF Biomarker and optionally SIAH1, SIAH2, and/or a polynucleotide encoding SIAH1 or SIAH2, in particular SIAH1a and SIAH1b.

In an embodiment the invention provides a composition or set of markers that can be used for detection, diagnosis, prevention and therapy of pregnancy-related conditions comprising a Hydroxylated HIF Biomarker and FIH and/or a polynucleotide encoding FIB.

In an embodiment the invention provides a composition or set of markers that can be used for detection, diagnosis, prevention and therapy of pregnancy-related conditions comprising a Hydroxylated HIF Biomarker and optionally one or more of Mcl1-L, Mcl1-C, Mtd-L, Mtd-P, TGFβ3, VHL, PHD2, PHD3, FIH, endoglin, sFlt-1, ceruloplasmin, TGFβ-type I receptor (ALK5), TGFβ-type II receptor, TGFβ-1, cleaved caspase, syncytin, VEGF, Fas and HIF1α, and/or polynucleotides encoding same.

In an embodiment the invention provides a composition or set of markers that can be used for detection, diagnosis, prevention and therapy of pregnancy-related conditions comprising a Hydroxylated HIF Biomarker and optionally one or more of ceruloplasmin, sFlt, Mtd-P, Mtd-L, Mtd-S, Mcl-1, TGFβ3, TGFβ1, HIF-1α, PHD1, PHD2, PHD3, SIAH1, SIAH2, VEGF, FIH, endoglin, and polynucleotides encoding same.

In another aspect the marker set comprises Hydroxylated HIF Biomarkers, and SMAD2, phospho-SMAD2, SMAD-3, phospho-SMAD3, SMAD7, ceruloplasmin, sFlt, Mtd-P, Mtd-L, Mcl-1L, Mcl-1c, TGFβ3, HIF-1α, VHL, PHD1, PHD2, PHD3, SIAH1, SIAH2, FIH, endoglin and VEGF, and/or polynucleotides encoding same.

In embodiments of the invention, the marker sets are used for detection or diagnosis of preeclampsia. In embodiments of the invention, the marker sets are used for detection or diagnosis of IUGR. In embodiments of the invention, the marker sets are used for detection or diagnosis of gestational diabetes. In embodiments of the invention, the marker sets are used for detection or diagnosis of molar pregnancy.

Antibodies

The invention provides antibodies that specifically bind to a Hydroxylated HIF Biomarker. In an aspect, the invention provides an antibody comprising an antigen recognition domain that specifically binds to an epitope of a Hydroxylated HIF Biomarker comprising, consisting of, or consisting essentially of hydroxylated proline 402 and/or hydroxylated proline 564. In aspects, the antibodies are isolated antibodies, in particular recombinant antibodies. In aspects, the antibodies are fragments. In aspects of the invention the antibodies are human antibodies. In an aspect, the invention provides monoclonal antibodies that specifically bind to an epitope of a Hydroxylated HIF Biomarker comprising, consisting of or consisting essentially of hydroxylated proline 402 and/or hydroxylated proline 564. In an aspect, the invention pertains to an isolated monoclonal antibody or an antigen-binding portion thereof wherein the antibody specifically binds to an epitope of a Hydroxylated HIF Biomarker comprising or consisting of hydroxylated proline 402 and/or hydroxylated proline 564. In an embodiment, the invention provides a monoclonal antibody that specifically binds to an epitope of a Hydroxylated HIF Biomarker comprising or consisting of hydroxylated proline 402. In an embodiment, the invention provides a monoclonal antibody that specifically binds to an epitope of a Hydroxylated HIF Biomarker comprising, or consisting of hydroxylated proline 564. In embodiments of the invention, the antibodies have desirable properties including without limitation high affinity binding to an epitope of a Hydroxylated HIF Biomarker comprising or, consisting of hydroxylated proline 402 and/or hydroxylated proline 564, the ability to specifically and/or selectively detect HIF-1α hydroxylated at proline 402 and/or hydroxylated proline 564 in samples, and/or the antibodies are not cross-reactive with other antigens or epitopes, in particular HIF-1α which is not hydroxylated at proline 402 and/or proline 564.

An antibody that specifically binds to an epitope of a Hydroxylated HIF Biomarker comprising or consisting of hydroxylated proline 402 and/or hydroxylated proline 564 can be identified, for example by immunoassays or surface plasmon resonance (e.g. BIAcore). An antibody may be considered to bind specifically to an epitope of a Hydroxylated HIF Biomarker comprising or consisting of hydroxylated proline 402 and/or hydroxylated proline 564 when it binds to the epitope with higher affinity than to any cross-reactive antigen or epitope as determined using experimental techniques such as radioimmunoassay (RIA) and enzyme-linked immunosorbent assays (ELISAs). A specific or selective reaction is generally at least twice the background signal or noise and preferably more than 10 times background. (See, for example, Paul, W. E. ed., 1989, Fundamental Immunology Second Edition, Raven Press, New York at pages 332-336.)

The antibodies of the invention include polypeptides having amino acid sequences that vary from those of the described antibodies but that retain the ability to specifically bind a Hydroxylated HIF Biomarker. Such variants comprise one or more additions, deletions or substitutions of amino acids when compared to a parent sequence but exhibit activity that is substantially equivalent to that of the parent. Antibodies or binding agents may be considered bioequivalent if there are no clinically meaningful differences in their safety, purity and/or potency. Bioequivalence may be demonstrated by methods well known in the art.

In an aspect, the invention provides antibodies which interact with hydroxylated proline 402 and/or hydroxylated proline 564 of HIF-1α, and in particular SEQ ID NO: 1 or 2 hydroxylated at proline 402 and proline 564.

In an aspect, the invention provides anti-hydroxylated HIF-1α antibodies that have affinity and specificity for an epitope of HIF-1α comprising or consisting of hydroxylated proline 402. In an aspect, the invention provides anti-hydroxylated HIF-1α antibodies that have affinity and specificity for an epitope of HIF-1α comprising or consisting of hydroxylated proline 564. In an aspect, the invention provides an antibody comprising an antigen recognition domain capable of binding to an epitope of HIF-1α comprising or consisting of hydroxylated proline 402. In an aspect, the invention provides an antibody comprising an antigen recognition domain capable of binding to an epitope of HIF-1α comprising or consisting of hydroxylated proline 564.

In an aspect, the invention pertains to an isolated monoclonal antibody or an antigen-recognition domain or site thereof wherein the antibody specifically binds an epitope of HIF-1α comprising or consisting of or consisting essentially of hydroxylated proline 402 and/or hydroxylated proline 564.

In an aspect, anti-hydroxylated HIF-1α antibodies of the present invention specifically bind to human HIF-1α hydroxylated at proline 402 and/or hydroxylated at proline 564.

In an aspect the invention provides an isolated antibody or antigen recognition domain thereof comprising a light chain variable sequence of SEQ ID NO: 7, 8, 13, 14, 19, 20, 25, 26, 30, 31, 36 or 37, or a substantially similar sequence thereof having at least 90%, at least 95%, at least 98% or at least 99% sequence identity, or any sequence encoding a light chain variable sequence of SEQ ID NO: 7, 8, 13, 14, 19, 20, 25, 26, 30, 31, 36 or 37, or a substantially similar sequence thereof having at least 90%, at least 95%, at least 98% or at least 99% sequence identity.

In an aspect the invention provides an isolated antibody or antigen recognition domain thereof comprising a heavy chain variable sequence of SEQ ID NO: 10, 11, 16, 17, 22, 23, 27, 28, 33, 34, 39 or 40, or a substantially similar sequence thereof having at least 90%, at least 95%, at least 98% or at least 99% sequence identity, or any sequence encoding a heavy chain variable sequence of SEQ ID NO: 10, 11, 16, 17, 22, 23, 27, 28, 33, 34, 39 or 40, or a substantially similar sequence thereof having at least 90%, at least 95%, at least 98% or at least 99% sequence identity.

In an aspect the invention provides an isolated antibody comprising a light chain variable sequence of SEQ ID NO: 7, 8, 13, 14, 19, 20, 25, 26, 30, 31, 36 or 37, or a substantially similar sequence thereof having at least 90%, at least 95%, at least 98% or at least 99% sequence identity, and a heavy chain variable sequence of SEQ ID NO: 10, 11, 16, 17, 22, 23, 27, 28, 33, 34, 39 or 40, or a substantially similar sequence thereof having at least 90%, at least 95%, at least 98% or at least 99% sequence identity.

In an aspect, the invention provides a monoclonal antibody having affinity and specificity for HIF-1α comprising or consisting of hydroxylated proline 402 and/or hydroxylated proline 564 comprising or consisting of or consisting essentially of variable regions of a light and/or heavy chain variable domain sequence as depicted in SEQ ID NO: 7, 8, 10, 11, 13, 14, 16, 17, 19, 20, 22, 23, 25, 26, 27, 28, 30, 31, 33, 34, 36, 37, 39, or 40, or a substantially similar sequence thereof having at least 90%, at least 95%, at least 98% or at least 99% sequence identity, or any sequence encoding a light and/or heavy chain variable domain sequence as depicted in SEQ ID NO: 7, 8, 10, 11, 13, 14, 16, 17, 19, 20, 22, 23, 25, 26, 27, 28, 30, 31, 33, 34, 36, 37, 39, or 40, or a substantially similar sequence thereof having at least 90%, at least 95%, at least 98% or at least 99% sequence identity.

In an aspect, the invention provides a monoclonal antibody comprising, consisting of or consisting essentially of a light chain and/or heavy chain variable domain sequence as depicted in SEQ ID NO: 7, 8, 10, 11, 13, 14, 16, 17, 19, 20, 22, 23, 25, 26, 27, 28, 30, 31, 33, 34, 36, 37, 39, or 40, or a substantially similar sequence thereof having at least 90%, at least 95%, at least 98% or at least 99% sequence identity, or any sequence encoding a light and/or heavy chain variable domain sequence as depicted in SEQ ID NO: 7, 8, 10, 11, 13, 14, 16, 17, 19, 20, 22, 23, 25, 26, 27, 28, 30, 31, 33, 34, 36, 37, 39, or 40, or a substantially similar sequence thereof having at least 90%, at least 95%, at least 98% or at least 99% sequence identity.

In an aspect, the invention provides a monoclonal antibody comprising or consisting of or consisting essentially of variable regions of a light chain variable domain sequence as depicted in SEQ ID NO: 19, 20, 36 or 37, or a substantially similar sequence thereof having at least 90%, at least 95%, at least 98% or at least 99% sequence identity. In an embodiment, the invention provides a monoclonal antibody having affinity and specificity for HIF-1α comprising or consisting of hydroxylated proline 402 and hydroxylated proline 564 comprising or consisting of or consisting essentially of variable regions of a light chain variable domain sequence as depicted in SEQ ID NO: 19, 20, 36 or 37, or a substantially similar sequence thereof having at least 90%, at least 95%, at least 98% or at least 99% sequence identity.

In an aspect, the invention provides a monoclonal antibody comprising or consisting of or consisting essentially of variable regions of a heavy chain variable domain sequence as depicted in SEQ ID NO: 22, 23, 39 or 40, or a substantially similar sequence thereof having at least 90%, at least 95%, at least 98% or at least 99% sequence identity. In an embodiment, the invention provides a monoclonal antibody having affinity and specificity for HIF-1α comprising or consisting of hydroxylated proline 402 and a hydroxylated proline 564 comprising or consisting of or consisting essentially of variable regions of a heavy chain variable domain sequence as depicted in SEQ ID NO: 22, 23, 39 or 40, or a substantially similar sequence thereof having at least 90%, at least 95%, at least 98% or at least 99% sequence identity.

In an aspect, the invention provides a monoclonal antibody comprising or consisting of or consisting essentially of variable regions of a light chain variable domain sequence as depicted in SEQ ID NO: 13, 14, 25, 26, 30 or 31, or a substantially similar sequence thereof having at least 90%, at least 95%, at least 98% or at least 99% sequence identity. In an embodiment, the invention provides a monoclonal antibody having affinity and specificity for HIF-1α comprising or consisting of hydroxylated proline 402 comprising or consisting of or consisting essentially of variable regions of a light chain variable domain sequence as depicted in SEQ ID NO: 13, 14, 25, 26, 30 or 31, or a substantially similar sequence thereof having at least 90%, at least 95%, at least 98% or at least 99% sequence identity.

In an aspect, the invention provides a monoclonal antibody comprising or consisting of or consisting essentially of variable regions of a heavy chain variable domain sequence as depicted in SEQ ID NO:16, 17, 27, 28, 33 or 34, or a substantially similar sequence thereof having at least 90%, at least 95%, at least 98% or at least 99% sequence identity. In an embodiment, the invention provides a monoclonal antibody having affinity and specificity for HIF-1α comprising or consisting of hydroxylated proline 402 comprising or consisting of or consisting essentially of variable regions of a heavy chain variable domain sequence as depicted in SEQ ID NO:16, 17, 27, 28, 33 or 34, or a substantially similar sequence thereof having at least 90%, at least 95%, at least 98% or at least 99% sequence identity.

In an aspect, the invention provides a monoclonal antibody comprising or consisting of or consisting essentially of variable regions of a light chain variable domain sequence as depicted in SEQ ID NO: 7 or 8, or a substantially similar sequence thereof having at least 90%, at least 95%, at least 98% or at least 99% sequence identity. In an embodiment, the invention provides a monoclonal antibody having affinity and specificity for HIF-1α comprising or consisting of hydroxylated proline 564 comprising or consisting of or consisting essentially of variable regions of a light chain variable domain sequence as depicted in SEQ ID NO: 7 or 8, or a substantially similar sequence thereof having at least 90%, at least 95%, at least 98% or at least 99% sequence identity.

In an aspect, the invention provides a monoclonal antibody comprising or consisting of or consisting essentially of variable regions of a heavy chain variable domain sequence as depicted in SEQ ID NO: 10 or 11, or a substantially similar sequence thereof having at least 90%, at least 95%, at least 98% or at least 99% sequence identity. In an embodiment, the invention provides a monoclonal antibody having affinity and specificity for HIF-1α comprising or consisting of hydroxylated proline 564 comprising or consisting of or consisting essentially of variable regions of a heavy chain variable domain sequence as depicted in SEQ ID NO: 10 or 11, or a substantially similar sequence thereof having at least 90%, at least 95%, at least 98% or at least 99% sequence identity.

In one embodiment, the invention provides a monoclonal antibody having affinity and specificity for HIF-1α comprising or consisting of hydroxylated proline 402 and/or hydroxylated proline 564 wherein the antibody comprises a variable sequence of a light chain selected from the group consisting of SEQ ID NO: 7, 8, 13, 14, 19, 20, 25, 26, 30, 31, 36 and 37, or a variant of one of SEQ ID NO: 7, 8, 13, 14, 17, 20, 25, 26, 30, 31, 36 and 37 wherein the variant comprises an insertion, deletion or substitution of at least one amino acid residue of the sequence depicted in SEQ ID NO: 7, 8, 13, 14, 19, 20, 25, 26, 30, 31, 36 and 37.

In one embodiment, the invention provides a monoclonal antibody having affinity and specificity for HIF-1α comprising or consisting of hydroxylated proline 402 and/or hydroxylated proline 564 wherein the antibody comprises a variable sequence of a heavy chain selected from the group consisting of SEQ ID NO: 10, 11, 16, 17, 22, 23, 27, 28, 33, 34, 39 and 40, or a variant of one of SEQ ID NO: 10, 11, 16, 17, 22, 23, 27, 28, 33, 34, 39 and 40, wherein the variant comprises an insertion, deletion or substitution of at least one amino acid residue of the sequence depicted in SEQ ID NO: 10, 11, 16, 17, 22, 23, 27, 28, 33, 34, 39 and 40.

In one embodiment, the invention provides a monoclonal antibody having affinity and specificity for HIF-1α comprising or consisting of hydroxylated proline 402 wherein the antibody comprises a variable sequence of a light chain selected from the group consisting of SEQ ID NO: 13, 14, 25, 26, 30 and, 31 or a variant of one of SEQ ID NO: 13, 14, 25, 26, 30 and 31, wherein the variant comprises an insertion, deletion or substitution of at least one amino acid residue of the sequence depicted in SEQ ID NO: 13, 14, 25, 26, 30 and 31.

In one embodiment, the invention provides a monoclonal antibody having affinity and specificity for HIF-1α comprising or consisting of hydroxylated proline 402 wherein the antibody comprises a variable sequence of a heavy chain selected from the group consisting of SEQ ID NO: 16, 17, 27, 28, 33 and 34, or a variant of one of SEQ ID NO: 16, 17, 27, 28, 33 and 34 and 31, wherein the variant comprises an insertion, deletion or substitution of at least one amino acid residue of the sequence depicted in SEQ ID NO: 16, 17, 27, 28, 33 and 34.

In one embodiment, the invention provides a monoclonal antibody having affinity and specificity for HIF-1α comprising or consisting of hydroxylated proline 402 and hydroxylated proline 564 wherein the antibody comprises a variable sequence of a light chain selected from the group consisting of SEQ ID NO: 19, 20, 36 and 37, or a variant of one of SEQ ID NO: 10, 19, 20, 36 and 37, wherein the variant comprises an insertion, deletion or substitution of at least one amino acid residue of the sequence depicted in SEQ ID NO: 19, 20, 36 and 37.

In one embodiment, the invention provides a monoclonal antibody having affinity and specificity for HIF-1α comprising or consisting of hydroxylated proline 402 and hydroxylated proline 564 wherein the antibody comprises a variable sequence of a heavy chain selected from the group consisting of SEQ ID NO: 22, 23, 39 and 40, or a variant of one of SEQ ID NO: 22, 23, 39 and 40, wherein the variant comprises an insertion, deletion or substitution of at least one amino acid residue of the sequence depicted in SEQ ID NO: 22, 23, 39 and 40.

In one embodiment, the invention provides a monoclonal antibody having affinity and specificity for HIF-1α comprising or consisting of hydroxylated proline 402 and/or hydroxylated proline 564 wherein the antibody comprises a non-variable sequence of a light chain selected from the group consisting of:
  i) KRADAAPTVSIFPPS (SEQ ID NO: 9),
  ii) KRADAAPTVSIFPPSSEQLTSGGASVVC (SEQ ID NO: 15),
  iii) KRADAAPTVSIFPPSSEQLTSGGASVVCS (SEQ ID NO: 21),
  iv) KRADAAPT (SEQ ID NO: 32),
  v) KRADAAPTVSIFPP (SEQ ID NO: 38), and
  vi) a variant of one of i) to v) wherein the variant comprises an insertion, deletion or substitution of at least one amino acid residue of the sequence depicted in SEQ ID NO: 9, 15, 21, 32 or 38.

In one embodiment, the invention provides a monoclonal antibody having affinity and specificity for HIF-1α comprising or consisting of hydroxylated proline 402 and/or hydroxylated proline 564 wherein the antibody comprises a non-variable sequence of a heavy chain selected from the group consisting of:
  i) AYWGQGTLVTVSAA (SEQ ID NO: 12),
  ii) YWGQGTSVTVSSAKTTAPSVYPLAPVCGDTTGSSVTLGCLVKG (SEQ ID NO: 18),
  iii) TVSSAKTTPPSVYPLAPGFAVQTNSMVI (SEQ ID NO: 24),
  iv) TVSAAKTTP (SEQ ID NO: 29),
  v) YWGQGTSVSVSSAKTTAPSVYPL (SEQ ID NO: 35),
  vi) TTTAPSVYPLVPGCSDTSGSSVT (SEQ ID NO: 41), and
  vii) a variant of one of i) to vi) wherein the variant comprises an insertion, deletion or substitution of at least one amino acid residue of the sequence depicted in SEQ ID NO: 12, 18, 24, 29, 35 or 41.

One aspect of the invention is a monoclonal antibody comprising the variable region of the light chain of 6A9 (SEQ ID NO: 7 or 8), 1H1 (SEQ ID NO: 13 or 14), 7E3 (SEQ ID NO: 19 or 20), 6H4 (SEQ ID NO: 25 or 26), 5A5 (SEQ ID NO: 30 or 31) or 7D6 (SEQ ID NO: 36 or 37).

One aspect of the invention is a monoclonal antibody comprising the variable region of the heavy chain of 6A9 (SEQ ID NO: 10 or 11), 1H1 (SEQ ID NO: 16 or 17), 7E3 (SEQ ID NO: 22 or 23), 6H4 (SEQ ID NO: 27 or 28), 5A5 (SEQ ID NO: 33 or 34) or 7D6 (SEQ ID NO: 39 or 40).

Another aspect of the invention is a monoclonal antibody comprising the variable region of a light chain of 6A9 (SEQ ID NO: 7 or 8), 1H1 (SEQ ID NO: 13 or 14), 7E3 (SEQ ID NO: 19 or 20), 6H4 (SEQ ID NO: 25 or 26), 5A5 (SEQ ID NO: 30 or 31) or 7D6 (SEQ ID NO: 36 or 37), and the variable region of a heavy chain of 6A9 (SEQ ID NO: 10 or 11), 1H1 (SEQ ID NO: 16 or 17), 7E3 (SEQ ID NO: 22 or 23), 6H4 (SEQ ID NO: 27 or 28), 5A5 (SEQ ID NO: 33 or 34) or 7D6 (SEQ ID NO: 39 or 40).

Another aspect of the invention is a monoclonal antibody comprising the variable region of a light chain of 1H1 (SEQ ID NO: 13 or 14), 6H4 (SEQ ID NO: 25 or 26), or 5A5 (SEQ ID NO: 30 or 31), and the variable region of the heavy chain of 1H1 (SEQ ID NO: 16 or 17), 6H4 (SEQ ID NO: 27 or 28), or 5A5 (SEQ ID NO: 33 or 34).

Another aspect of the invention is a monoclonal antibody comprising the variable region of a light chain of 7E3 (SEQ ID NO: 19 or 20) or 7D6 (SEQ ID NO: 36 or 37), and the variable region of the heavy chain of 7E3 (SEQ ID NO: 22 or 23), or 7D6 (SEQ ID NO: 39 or 40).

In one embodiment, the invention provides an antibody or an antigen recognition domain or antigen-binding fragment comprising a light chain variable region having an amino acid sequence of SEQ ID NO: 7, 8, 13, 14, 19, 20, 25, 26, 30, 31, 36 or 37, or a substantially similar sequence thereof having at least 90%, at least 95%, at least 98% or at least 99% sequence identity.

In one embodiment, the invention provides an antibody or an antigen-binding fragment comprising a heavy chain variable region having an amino acid sequence of SEQ ID NO: 10, 11, 16, 17, 22, 23, 27, 28, 33, 34, 39 or 40, or a substantially similar sequence thereof having at least 90%, at least 95%, at least 98% or at least 99% sequence identity.

Another embodiment is a monoclonal antibody or antigen-binding fragment thereof comprising (a) a light chain of the amino acid sequence of SEQ ID NO: 7, and a heavy chain of the amino acid sequence of SEQ ID NO: 10, 11, 16, 17, 22, 23, 27, 28, 33, 34, 39 or 40; or (b) a light chain of the amino acid sequence of SEQ ID NO: 8, and a heavy chain of the amino acid sequence of SEQ ID NO: 10, 11, 16, 17, 22, 23, 27, 28, 33, 34, 39 or 40; or (c) a light chain of the amino acid sequence of SEQ ID NO: 13, and a heavy chain of the amino acid sequence of SEQ ID NO: 10, 11, 16, 17, 22, 23, 27, 28, 33, 34, 39 or 40; or (d) a light chain of the amino acid sequence of SEQ ID NO: 14, and a heavy chain of the amino acid sequence of SEQ ID NO: 10, 11, 16, 17, 22, 23, 27, 28, 33, 34, 39 or 40; or (e) a light chain of the amino acid sequence of SEQ ID NO: 19, and a heavy chain of the amino acid sequence of SEQ ID NO: 10, 11, 16, 17, 22, 23, 27, 28, 33, 34, 39 or 40; or (f) a light chain of the amino acid sequence of SEQ ID NO: 20 and a heavy chain of the amino acid sequence of SEQ ID NO: 10, 11, 16, 17, 22, 23, 27, 28, 33, 34, 39 or 40; or (g) a light chain of the amino acid sequence of SEQ ID NO: 25 and a heavy chain of the amino acid sequence of SEQ ID NO: 10, 11, 16, 17, 22, 23, 27, 28, 33, 34, 39 or 40; or (h) a light chain of the amino acid sequence of SEQ ID NO: 26 and the heavy chain of the amino acid sequence of SEQ ID NO: 10, 11, 16, 17, 22, 23, 27, 28, 33, 34, 39 or 40; or (i) a light chain of the amino acid sequence of SEQ ID NO: 30 and a heavy chain of the amino acid sequence of SEQ ID NO: 10, 11, 16, 17, 22, 23, 27, 28, 33, 34, 39 or 40; or (j) a light chain of the amino acid sequence of SEQ ID NO: 31 and a heavy chain of the amino acid sequence of SEQ ID NO: 10, 11, 16, 17, 22, 23, 27, 28, 33, 34, 39 or 40; or (k) a light chain of the amino acid sequence of SEQ ID NO: 36 and a heavy chain of the amino acid sequence of SEQ ID NO: 10, 11, 16, 17, 22, 23, 27, 28, 33, 34, 39 or 40; or 1) a light chain of the amino acid sequence of SEQ ID NO: 37 and a heavy chain of the amino acid sequence of SEQ ID NO: 10, 11, 16, 17, 22, 23, 27, 28, 33, 34, 39 or 40.

Another embodiment is a monoclonal antibody or antigen-binding fragment thereof comprising (a) a light chain of the amino acid sequence of SEQ ID NO: 7 or 8, and a heavy chain of the amino acid sequence of SEQ ID NO: 10 or 11 or (b) a light chain of the amino acid sequence of SEQ ID NO: 13, 14, 25, 26, 30 or 31, and a heavy chain of the amino acid sequence of SEQ ID NO: 16, 17, 27, 28, 33 or 34, or (c) a light chain of the amino acid sequence of SEQ ID NO: 19, 20, 36 or 37 and a heavy chain of the amino acid sequence of SEQ ID NO: 22, 23, 39 or 40.

Another embodiment is a monoclonal antibody or antigen-binding fragment thereof comprising (a) a heavy chain of the amino acid sequence of SEQ ID NO: 10, and a light chain of the amino acid sequence of SEQ ID NO: 7, 8, 13, 14, 19, 20, 25, 26, 30, 31, 36, or 37; (b) a heavy chain of amino acid sequence of SEQ ID NO: 11, and a light chain of the amino acid sequence of SEQ ID NO: 7, 8, 13, 14, 19, 20, 25, 26, 30, 31, 36, or 37 (c) a heavy chain of the amino acid sequence of SEQ ID NO: 16, and a light chain of the amino acid sequence of SEQ ID NO: 7, 8, 13, 14, 19, 20, 25, 26, 30, 31, 36, or 37; or (d) a heavy chain of the amino acid sequence of SEQ ID NO: 17, and a light chain of the amino acid sequence of SEQ ID NO: 7, 8, 13, 14, 19, 20, 25, 26, 30, 31, 36, or 37; or (e) a heavy chain of the amino acid sequence of SEQ ID NO: 22, and a light chain of the amino acid sequence of SEQ ID NO: 7, 8, 13, 14, 19, 20, 25, 26, 30, 31, 36, or 37; or (f) a heavy chain of the amino acid sequence of SEQ ID NO: 23 and a light chain of the amino acid sequence of SEQ ID NO: 7, 8, 13, 14, 19, 20, 25, 26, 30, 31, 36, or 37; or (g) a heavy chain of the amino acid sequence of SEQ ID NO: 27 and a light chain of the amino acid sequence of SEQ ID NO: 7, 8, 13, 14, 19, 20, 25, 26, 30, 31, 36, or 37; or (h) a heavy chain of the amino acid sequence of SEQ ID NO: 28 and a light chain of the amino acid sequence of SEQ ID NO: 7, 8, 13, 14, 19, 20, 25, 26, 30, 31, 36, or 37; or (i) a heavy chain of the amino acid sequence of SEQ ID NO: 33 and a light chain of the amino acid sequence of SEQ ID NO: 7, 8, 13, 14, 19, 20, 25, 26, 30, 31, 36, or 37; or (j) a heavy chain of the amino acid sequence of SEQ ID NO: 34 and a light chain of the amino acid sequence of SEQ ID NO: 7, 8, 13, 14, 19, 20, 25, 26, 30, 31, 36, or 37; or (k) a heavy chain of the amino acid sequence of SEQ ID NO: 39 and a light chain of the amino acid sequence of SEQ ID NO: 7, 8, 13, 14, 19, 20, 25, 26, 30, 31, 36, or 37; or (l) a heavy chain of the amino acid sequence of SEQ ID NO: 40 and a light chain of the amino acid sequence of SEQ ID NO: 7, 8, 13, 14, 19, 20, 25, 26, 30, 31, 36, or 37.

In an embodiment, the invention provides an antibody having affinity and specificity for HIF-1α comprising or consisting of hydroxylated proline 402 and/or hydroxylated proline 564 or an antigen-binding fragment thereof wherein the antibody or fragment comprises the light and heavy chain CDR domains contained with the light and heavy chain sequences selected from the group consisting of SEQ ID. NO: 7, 8, 10, 11, 13, 14, 16, 17, 19, 20, 22, 23, 25, 26, 27, 28, 30, 31, 33, 34, 36, 37, 39, and 40. Methods and techniques for identifying CDRs within light chain variable and heavy chain variable regions are well known in the art and can be used to identify CDRs within the specified variable regions disclosed herein. For example, the Kabat definition based on sequence variability, Chothia definition based on the location of structural loop regions, and the AbM definition may be used to identify the boundaries of CDRs [Kabat, "Sequences of Proteins of Immunological Interest,", National Institutes of Health, Bethesda, Md. (1991); Al-Lazikani et al, J. Mol. Biol. 273: 927-948, 1997, and Martin et al, Proc. Natl. Acad. Sci. USA 86:9368-9272, 1989].

Another embodiment is a monoclonal antibody or antigen recognition domain thereof comprising (a) a sequence of SEQ ID NO: 7, 8 and 9; (b) a sequence of SEQ ID NO: 10, 11 and 12; (c) a sequence of SEQ ID NO: 13, 14 and 15; (d) a sequence of SEQ ID NO: 16, 17 and 18; (e) a sequence of SEQ ID NO: 19, 20 and 21; (f) a sequence of SEQ ID NO: 22, 23 and 24; (g) a sequence of SEQ ID NO: 15, 25 and 26; (h) a sequence of SEQ ID NO: 27, 28, and 29; (i) a sequence of SEQ ID NO: 30, 31 and 32; (j) a sequence of SEQ ID NO: 33, 34 and 35; (k) a sequence of SEQ ID NO. 36, 37 and 38; or (l) a sequence of SEQ ID NO: 39, 40 and 41.

Another embodiment is an antibody or antigen recognition domain thereof, or a sequence encoding an antibody or antigen recognition domain thereof, comprising a sequence depicted in any one of FIGS. 11 to 19.

Another aspect of the invention is a monoclonal antibody which is an IgG. A further aspect of the invention is a monoclonal antibody which is an IgG2a. A further aspect of the invention is a monoclonal antibody which is an IgG1. A further aspect of the invention is a monoclonal antibody which is an IgG3.

An aspect of the invention is an IgG, in particular an IgG1 or IgG2a, monoclonal antibody specific for a Hydroxylated HIF Biomarker comprising or consisting of hydroxylated proline 402. An aspect of the invention is an IgG, in particular an IgG1 or IgG3, monoclonal antibody specific for a Hydroxlyated HIF Biomarker comprising or consisting of hydroxylated proline 402 and hydroxylated proline 564. An aspect of the invention is an IgG, in particular an IgG2a, monoclonal antibody specific for a Hydroxlyated HIF Biomarker comprising or consisting of hydroxylated proline 564.

A further aspect of the invention is a monoclonal antibody comprising a kappa light chain. A further aspect of the invention is a monoclonal antibody comprising a lambda light chain.

An antibody of the invention may bind a Hydroxylated HIF Biomarker with a $K_d$ of less than about 1000 nM, in particular less than about 200 nM, less than about 100 nM, less than about 90 nM, less than about 80 nM, less than about 70 nM, less than about 60 nM, less than about 50 nM, less than about 40 nM, less than about 20 nM, less than about 10 nM, less than about 5 nM, less than about 3 nM, less than about 2 nM, or less than about 1 nM, preferably measured by immunoassay or surface plasmon resonance assay.

Also provided are isolated nucleic acids encoding antibodies of the invention. In an aspect, the invention provides a nucleic acid that encodes an antibody or antibody fragment comprising an antigen recognition domain capable of binding to an epitope of a Hydroxylated HIF Biomarker comprising or consisting of hydroxylated proline 402 and/or hydroxylated proline 564. In an aspect, the invention pertains to a nucleic acid encoding a monoclonal antibody or an antigen recognition domain thereof wherein the antibody specifically binds to an epitope of a Hydroxylated HIF Biomarker comprising or consisting of hydroxylated proline 402 and hydroxylated proline 564.

In embodiments, the invention relates to an isolated nucleic acid comprising (a) a nucleic acid sequence encoding a polypeptide comprising an amino acid sequence of any one of SEQ ID NO: 7 to 41;

(b) a nucleic acid sequence of any one of SEQ ID NO: 42 to 77;

(c) a nucleic acid sequence complementary to (a) or (b);

(d) a degenerate form of a nucleic acid sequence of (a) or (b);

(e) a nucleic acid sequence capable of hybridizing under stringent conditions to polynucleotide (a), (b), or (c);

(f) a nucleic acid sequence encoding a truncation, an analog, an allelic or species variation of a polypeptide comprising an amino acid sequence of any one of SEQ ID NO: 7 to 41;

(g) a fragment, or allelic or species variation of polynucleotide (a), (b), or (c); or (h) a variant of a polynucleotide (a); or (i) a sequence of (a), (b) or (c) having at least 90%, at least 95%, at least 98% or at least 99% sequence identity.

In an aspect, a nucleic acid sequence encodes a polypeptide comprising an amino acid sequence of SEQ ID NO:7 or 8 and/or 10 or 11. In an aspect, a nucleic acid sequence encodes a polypeptide comprising an amino acid sequence of SEQ ID NO: 13 or 14 and/or 16 or 17. In an aspect, a nucleic acid sequence encodes a polypeptide comprising an amino acid sequence of SEQ ID NO: 19 or 20 and/or 22 or 23. In an aspect, a nucleic acid sequence encodes a polypeptide comprising an amino acid sequence of SEQ ID NO: 25 or 26 and/or 27 or 28. In an aspect, a nucleic acid sequence encodes a polypeptide comprising an amino acid sequence of SEQ ID NO: 30 or 31 and/or 33 or 34. In an aspect, a nucleic acid sequence encodes a polypeptide comprising an amino acid sequence of SEQ ID NO: 36 or 37 and/or 39 or 40.

Another aspect of the invention is a monoclonal antibody that specifically binds a Hydroxylated HIF Biomarker, wherein the antibody is selected from the group consisting of: (a) an antibody comprising the light chain variable regions encoded by the nucleic acid sequences set forth in SEQ ID NO: 42 or 43; (b) an antibody comprising the light chain variable regions encoded by the nucleic acid sequences set forth in SEQ ID NO: 48 or 49; (c) an antibody comprising the light chain variable regions encoded by the nucleic acid sequences set forth in SEQ ID NO: 54 or 55; (d) an antibody comprising the light chain variable regions encoded by the nucleic acid sequences set forth in SEQ ID NO: 60 or 61; (e) an antibody comprising the light chain variable regions encoded by the nucleic acid sequences set forth in SEQ ID NO: 66 or 67; and (f) an antibody comprising the light chain variable regions encoded by the nucleic acid sequences set forth in SEQ ID NO: 72 or 73.

Another aspect of the invention is a monoclonal antibody that specifically binds a Hydroxylated HIF Biomarker, wherein the antibody is selected from the group consisting of: (a) an antibody comprising the heavy chain variable regions encoded by the nucleic acid sequences set forth in SEQ ID NO: 45 or 46; (b) an antibody comprising the heavy chain variable regions encoded by the nucleic acid sequences set forth in SEQ ID NO: 51 or 52; (c) an antibody comprising the heavy chain variable regions encoded by the nucleic acid sequences set forth in SEQ ID NO: 57 or 58; (d) an antibody comprising the heavy chain variable regions encoded by the nucleic acid sequences set forth in SEQ ID NO: 63 or 64; (e) an antibody comprising the heavy chain variable regions encoded by the nucleic acid sequences set forth in SEQ ID NO: 69 or 70; and (f) an antibody comprising the heavy chain variable regions encoded by the nucleic acid sequences set forth in SEQ ID NO: 75 or 76.

In one embodiment, the invention provides an antibody comprising the non-variable sequence of a light chain encoded by the nucleic acid sequence of SEQ ID NO: 44, 50, 56, 62, 68, or 74. In one embodiment, the invention provides an antibody comprising the non-variable sequence of a heavy chain encoded by the nucleic acid sequence of SEQ ID NO: 47, 53, 59, 65, 71, or 77.

A nucleic acid encoding a light chain of an antibody of the invention may be produced by fusing a nucleic acid encoding the variable region of a light chain or antigen-binding domain or antigen recognition domain thereof with a constant domain of a light chain. A nucleic acid encoding a heavy chain of an antibody of the invention may be produced by fusing a nucleic acid encoding the variable region of a heavy chain or antigen-binding domain or antigen recognition domain thereof with a constant domain of a heavy chain. Nucleic acid molecules encoding the variable light and variable heavy chains of an antibody of the invention may provide a full-length antibody nucleic acid by inserting them into vectors already encoding light chain constant and heavy chain constant regions, wherein the light chain variable region is operatively linked to the light chain constant region within the vector and the heavy chain variable region is operatively linked to the heavy chain constant region within the vector. In addition, nucleic acids encoding the light chain or heavy chain variable regions can be converted into full-length light chain and heavy chain nucleic acids by ligating the nucleic acids to nucleic acids encoding light chain constant and heavy chain constant regions, respectively. Further, nucleic acids encoding a light chain, heavy chain or portions thereof (e.g., antigen recognition domains or sites) may be prepared by synthesizing the nucleic acids using sequence information and splicing them together with nucleic acids encoding the appropriate constant regions. Nucleic acids encoding light chain and heavy chain constant regions are known in the art. (See, for example, Kabat et al, Sequences of Proteins of Immunological Interest, 5$^{th}$ Ed., NIH Publ. No. 91-3242 (1991).) Heavy and/or light chain nucleic acids may be expressed in host cells to provide an antibody of the invention, and they may be used to recombinantly manufacture antibodies on a large scale. The nucleic acids may also be used to construct chimeric antibodies, single chain antibodies, immunoadhesions, diabodies, and modified antibodies.

The invention provides a method of preparing an affinity matured polypeptide that binds a Hydroxylated HIF Biomarker comprising (a) providing a first nucleic acid comprising a nucleic acid sequence encoding a polypeptide that binds a Hydroxylated HIF Biomarker that comprises the amino acid sequence of any of SEQ ID NOS: 7 to 41 and a second nucleic acid comprising a nucleic acid sequence that differs from the first nucleic acid sequence by at least one nucleotide, (b) performing nucleic acid shuffling to provide two or more mutated nucleic acids, (c) selecting for a mutated nucleic acid that encodes a polypeptide that (i) binds to the Hydroxylated HIF Biomarker with a greater affinity than the polypeptide encoded by the first nucleic acid, (ii) has a selectivity for the Hydroxylated HIF Biomarker that is greater than that of the polypeptide encoded by the first nucleic acid, (iii) has an equilibrium binding dissociation constant ($K_d$) for the Hydroxylated HIF Biomarker that is lower than that of the polypeptide encoded by the first nucleic acid, and (d) expressing the selected mutated nucleic acid, whereby an affinity matured Hydroxylated HIF Biomarker binding polypeptide is produced.

The invention also provides vectors comprising nucleic acids of the invention that encode a light chain, heavy chain or fragments or portions thereof (e.g. antigen recognition domains or sites), chimeric antibodies and modified antibodies. Nucleic acids encoding the antibodies, or fragments or portions thereof may be incorporated into a vector such that the nucleic acids are operatively linked to regulatory sequences. Examples of vectors include without limitation, plasmids, viruses such as retroviruses, adenoviruses, adeno-associated viruses (AAV), plant viruses (e.g., cauliflower mosaic virus, tobacco mosaic virus), cosmids, YACs, EBV derived episomes, and the like. A vector and regulatory sequences are selected that are compatible with the host cell. A nucleic acid encoding a light chain and a nucleic acid encoding a heavy chain may be inserted into separate vectors or into the same vector. Methods known in the art are used to insert the nucleic acids into the vectors, for example, ligation of complementary restriction sites on a nucleic acid encoding the antibody or portion thereof and vector, or blunt end ligation in the absence of restriction sites.

In aspects, the invention provides vectors that encode a functional constant heavy chain or constant light chain sequences, in particular complete human constant heavy chain or constant light chain sequences, with selected restriction sites engineered so that any variable light chain or heavy chain sequence can be readily inserted and expressed. A vector may also comprise a nucleic acid encoding a signal peptide to facilitate secretion and/or isolation of the antibody chain from a host cell. A signal peptide sequence may be linked in-frame to the amino terminal end of an antibody nucleic acid. In aspects of the invention, the signal peptide is an immunoglobulin signal peptide. In other aspects, the signal peptide is from a non-immunoglobulin polypeptide.

An aspect of the invention provides a vector comprising (a) a nucleic acid sequence encoding a light chain variable region of SEQ ID NO: 7, 8, 13, 14, 19, 20, 25, 26, 30, 31, 33, 34, 36 or 37; (b) a nucleic acid sequence of SEQ ID NO: 42, 43, 48, 49, 54, 55, 60, 61, 66, 67, 72 or 73; (c) nucleic acid sequence encoding a heavy chain variable region of SEQ ID NO: 10, 11, 16, 17, 22, 23, 27, 28, 33, 34, 39 or 40; or (d) a nucleic acid sequence of any one of SEQ ID NO: 45, 46, 51, 52, 57, 58, 63, 64, 69, 70, 75 or 76.

The invention also provides host cells comprising nucleic acids encoding the antibodies or fragments or portions thereof of the invention. Host cells can be transformed with the nucleic acids using any known method for introducing polynucleotides into a host cell. Transformation methods include without limitation, dextran-mediated transfection, calcium phosphate precipitation, polybrene-mediated transfecton, protoplast fusion, electroporation, encapsulation of the polynucleotides in liposomes, biolistic injection and direct microinjection into nuclei. Vectors may also be used to introduce polynucleotides into host cells. (See also, for example, U.S. Pat. Nos. 4,399,216, 4,912,040, 4,740,461 and 4,959,455 for descriptions of methods of transforming cells.)

Host cells that may be used to express antibodies of the invention include many immortalized cell lines available from the American Type Culture Collection (ATCC). Examples of host cells include, without limitation, Chinese hamster ovary (CHO) cells, NSO, SP2 cells, HEK-293T cells, NIH03T3 cells, HeLa cell, baby hamster kidney (BHK) cells, monkey kidney cells (COS), human hepatocellular carcinoma cells (e.g., Hap G2), A549 cells and 3T3 cells. Mammalian host cells include cells from human, mouse, rat, dog, monkey, pig, goat, bovine, horse and hamster cells, and the like. Insect cell lines (e.g., Sf9), amphibian cells, bacterial cells (e.g., *E. coli, Streptomyces* species), plant cells (e.g., *Nicotiana, Arabidopsis*, duckweed, corn, wheat, potato) and fungal cells (e.g., *Schizosaccharomyces pombe, Saccharomyces cerevisiae, Pichia pastoris*) may also be employed to express antibodies of the invention.

Also provided are methods of making antibodies or antibody fragments that specifically bind an epitope of a Hydroxylated HIF Biomarker comprising or consisting of hydroxylated proline 402 and/or hydroxylated proline 564. Antibodies can be produced by culturing a host cell comprising a vector encoding the heavy chain and light chain (or antigen recognition domains or sites thereof) under suitable conditions sufficient to allow for expression of the antibodies in the host cell, or for secretion of the antibodies into the culture medium. Standard purification methods can be used to recover the antibodies from the culture medium. Production of antibodies can be enhanced using techniques known in the art such as the glutamine synthetase gene expression system (for example, see European Pat Nos. 0216846, 0256055, 0338841 and 0323997).

Transgenic non-human animals and plants may be used to produce antibodies of the invention. A nucleic acid encoding a light chain and/or heavy chain or antigen recognition domains thereof, may be introduced into a non-human transgenic animal or plant by methods known in the art. (See, for example, Hogan et al, Manipulating the Mouse Embryo: A Laboratory Manual 2ed., Cold Spring Harbor Press (1999); Jackson et al, Mouse Genetics and Transgenics: A Practical Approach, Oxford University Press (2000), and Pinkert, Trangenic Animal Technology: A Laboratory Handbook, Academic Press (1999). A transgenic animal or plant may comprise and express a nucleic acid encoding a light chain and a heavy chain that combine to specifically bind to a Hydroxylated HIF Biomarker. A transgenic animal or plant may also comprise and express a modified antibody (e.g. single-chain antibody), a chimeric antibody or a humanized antibody. Examples of non-human animals that may be used to produce antibodies include without limitation, mice, rats, sheep, pigs, goats, bovines or horses. The antibodies may be expressed in the bodily fluids of the animals including without limitation blood, milk, urine, saliva, tears and mucus.

Diagnostic Methods

A variety of methods can be employed for the detection, diagnosis, monitoring, and prognosis of conditions disclosed herein, in particular pregnancy-related conditions, or status of such conditions, and for the identification of subjects with a predisposition to such conditions. Such methods may, for example, use binding agents (e.g. antibodies, in particular the antibodies of the invention) against a Hydroxylated HIF Biomarker. In particular, antibodies may be used, for example, for detection of either an over- or an under-abundance of a Hydroxylated HIF Biomarker relative to a normal state or a different stage of a condition, or the presence of a modified Hydroxylated HIF Biomarker which correlates with a condition or state, or a progression toward a condition, or a particular type or stage of a condition. The methods of the invention disclosed herein preferably employ antibodies of the invention.

The methods described herein can be adapted for diagnosing and monitoring a condition disclosed herein in samples from a subject. Such applications may involve comparing the amount of a Hydroxylated HIF Biomarker, and optionally other markers, quantitated in a sample from a subject being tested to a predetermined standard or cut-off value. The standard may correspond to levels quantitated for another sample or an earlier sample from the subject, or levels quantitated for a control sample. Levels for control samples from healthy subjects, different stages or types of condition, may be established by prospective and/or retrospective statistical studies. Healthy subjects who have no clinical evidence of a condition or abnormalities may be selected for statistical studies. A control can comprise markers derived from a pool of samples from individual patients with no disease, or individuals with a known condition. Diagnosis may be made by a finding of an abnormal status or altered levels, in particular statistically or significantly different levels of detected Hydroxylated HIF Biomarkers associated with a condition (e.g., preeclampsia) compared to a control sample or previous levels quantitated for the same subject.

If the status of Hydroxylated HIF Biomarkers is abnormal or if the levels of Hydroxylated HIF Biomarkers are significantly different as compared to levels typical for a patient who does not suffer from the condition or from levels in samples of the patient taken at a different time, the patient may be diagnosed as having the condition or a subpathology thereof, or an increased risk of the condition or a subpathology thereof. Abnormal levels or levels significantly different from those typical for subjects who do not suffer from the condition or from other samples of the patient may be suspect and further monitoring and measurement of Hydroxylated HIF Biomarkers and optionally other markers may be appropriate. The information from the diagnostic method may be used to identify subjects who may benefit from a course of treatment.

In an aspect, the invention provides methods for diagnosing or determining the presence or absence of a pregnancy-related condition disclosed herein in a subject comprising detecting Hydroxylated HIF Biomarkers in a sample from the subject. In particular aspects, the methods of the invention are employed to diagnose preeclampsia or an increased risk of preeclampsia, determine the presence or absence of preeclampsia or determine the likelihood of occurrence of preeclampsia in a subject, or to distinguish subpathologies, including early onset severe preeclampsia (EPE) from late onset preeclampsia, or intrauterine growth restriction (IUGR).

In an embodiment of the invention, a method is provided for diagnosing preeclampsia in a subject comprising detecting Hydroxylated HIF Biomarkers in a sample from the subject wherein significantly different levels or status of Hydroxylated HIF Biomarkers or hydroxylation of HIF-1α at proline 402 and/or proline 564 compared with a control is diagnostic or indicative of preeclampsia. In a particular embodiment, the control comprises levels in a subject with a normal pregnancy. In another particular embodiment, the control comprises levels from the samples of the same type taken at the same stage of pregnancy from women who did not develop preeclampsia. In another particular embodiment, the control comprises levels from samples of the same type taken from the same subject at a different time.

Hydroxylated HIF Biomarkers (and additional markers) may be detected at different times during a pregnancy. In aspects of the invention, the markers are measured during the first trimester of pregnancy (approximately 1 to 15 weeks, 1 to 14 weeks, 1 to 12 weeks, 5 to 12 weeks, 5 to 8 weeks, 5 to 9 weeks, 9 to 12 weeks, 10 to 14 weeks, or 10 to 15 weeks). In aspects of the invention, the markers are measured during the second trimester of pregnancy (approximately 13 to 27 weeks, in particular 18 weeks or 20 to 24 weeks). In aspects of the invention, the markers are measured during the third trimester of pregnancy (approximately 28 to 42 weeks). In aspects of the invention the markers are measured at 5 to 9 weeks. In aspects of the invention for diagnosing preeclampsia the markers are measured at less than 34 weeks, less than 20 weeks, less than 14 weeks, less than 12 weeks, less than 10 weeks, less than 9 weeks or less than 8 weeks, or between about 5 to 8 weeks, 5 to 9 weeks, 9 to 12 weeks, or 10 to 14 weeks of gestation. In other aspects of the invention for diagnosing preeclampsia the markers are measured after 9 weeks, after 12 weeks, after 15 weeks, after 20 weeks or after 34 weeks of gestation.

Hydroxylated HIF Biomarkers may be detected in a patient multiple or repeat times during one or more periods. For example, one or more measurements may be taken during the first trimester period, and subsequently one or more measurements may be taken during the second or third trimester. In embodiments of the invention, the biomarkers are measured during the first trimester of pregnancy and during the second trimester of pregnancy.

The invention provides a method for diagnosing a pregnancy-related condition in a subject comprising detecting Hydroxylated HIF Biomarkers and one or more additional markers of a pregnancy-related condition in a sample from the subject. In an aspect for diagnosing a pregnancy-related condition, the additional marker is endoglin. In an aspect for diagnosing a pregnancy-related condition, the additional marker is TGFβ3. In an aspect for diagnosing a pregnancy-related condition, the additional marker is Mcl-1L. In an aspect for diagnosing a pregnancy-related condition, the additional markers comprise, are chosen from or are selected from the group consisting of Mcl1-L, Mcl1-C, Mtd-L, Mtd-P, TGFβ3, VHL, PHD2, PHD3, FIH, endoglin, sFlt-1, ceruloplasmin, TGFβ3-type I receptor (ALK5), TGFβ3-type II receptor, TGFβ-1, cleaved caspase, syncytin, VEGF, Fas and HIF1α, and/or polynucleotides encoding same. In an embodiment the additional markers comprise, are chosen from or selected from the group consisting of SMAD2, phospho-SMAD2, SMAD-3, phospho-SMAD3, SMAD7, sFlt, Mtd-L, Mtd-P, Mcl-1c, Mcl-1L, TGFβ3, HIF1α, endoglin, PHD1, PHD2, PHD3, VHL, SIAH1, SIAH2, FIH and VEGF, and/or polynucleotides encoding same. In an aspect for diagnosing a pregnancy-related condition, the additional markers comprise, are chosen from or are selected from the group consisting of sFlt, ceruloplasmin, Mtd-L, Mtd-P, Mcl-1c, Mcl-1L, TGFβ3, endoglin, HIF1α, PHD1, PHD2, PHD3, VHL, SIAH1, SIAH2, and VEGF, and/or polynucleotides encoding same.

In an embodiment of the diagnostic method of the invention, a method is provided for diagnosing preeclampsia in a subject comprising detecting Hydroxylated HIF Biomarkers, and one or more of Mcl1-L, Mcl1-C, Mtd-L, Mtd-P, TGFβ3, VHL, PHD2, PHD3, FIH, endoglin, sFlt-1, ceruloplasmin, TGFβ-type I receptor (ALK5), TGFβ-type II receptor, TGFβ-1, cleaved caspase, syncytin, VEGF, Fas and HIF1α, and/or polynucleotides encoding same.

In an aspect, the invention contemplates a method for determining the likelihood of occurrence of preeclampsia in a pregnant mammal comprising detecting Hydroxylated HIF Biomarkers, and optionally additional markers disclosed herein in a sample from the subject.

The invention in embodiments provides a method for diagnosing or identifying early onset preeclampsia, late onset preeclampsia, and intra-uterine growth restriction (IUGR) in a subject comprising detecting Hydroxylated HIF Biomarkers and optionally additional markers disclosed herein in a sample from the subject.

In an aspect, the invention relates to a method for diagnosing early onset preeclampsia in a subject comprising detecting Hydroxylated HIF Biomarkers in a sample from the subject. In embodiments of the invention, a low status or lower levels of Hydroxylated HIF Biomarkers or HIF1α hydroxylated at proline 402 and/or proline 564, in particular significantly lower levels of Hydroxylated HIF Biomarkers, in patients compared to a control (e.g. normal or other sample(s) of the patient) is indicative of early onset preeclampsia, or the likelihood of occurrence of early onset preeclampsia.

In another aspect, the invention relates to a method for diagnosing early onset severe preeclampsia in a subject comprising detecting Hydroxylated HIF Biomarkers in a sample from the subject. In embodiments of the invention, a low status or lower levels of Hydroxylated HIF Biomarkers or HIF1α hydroxylated at proline 402 and/or proline 564, in particular significantly lower levels of Hydroxylated HIF Biomarkers, in patients compared to a control (e.g. normal or other sample(s) of the patient) is indicative of early severe onset preeclampsia, or the likelihood of occurrence of early severe onset preeclampsia.

In aspects of the invention for diagnosing early onset or early onset severe preeclampsia, samples may be obtained at less than 9 weeks or less than 12 weeks, or between about 5 to 8 weeks, 5 to 9 weeks, 9 to 12 weeks, or 10 to 14 weeks. Samples may be taken at multiple times and in particular during the first and second trimesters.

Methods for diagnosing early onset preeclampsia or early onset severe preeclampsia may comprise detecting or comparing one or more additional marker. In an embodiment, the additional marker is endoglin. In another embodiment, the additional marker is TGFβ3. In another embodiment, the additional marker is Mcl-1L. In an embodiment, additional markers may comprise, are chosen from or are selected from the group consisting of SMAD2, phospho-SMAD2, SMAD-3, phospho-SMAD3, SMAD7, sFlt, ceruloplasmin, Mtd-L, Mtd-P, Mcl-1c, TGFβ3, endoglin, SIAH1, SIAH2, FIH, PHD1, PHD2, PHD3 and/or VEGF and/or polynucleotides encoding same. In another embodiment, the additional markers comprise, are chosen from or are selected from the group consisting of Mcl1-L, Mcl1-C, Mtd-L, Mtd-P, TGFβ3, VHL, PHD2, PHD3, FIH, endoglin, sFlt-1, ceruloplasmin, TGFβ-type I receptor (ALK5), TGFβ-type II receptor, TGFβ-1, cleaved caspase, syncytin, VEGF, Fas and HIF1α and/or polynucleotides encoding same.

The diagnostic methods can comprise diagnosing early onset preeclampsia using a panel of markers comprising Hydroxylated HIF Biomarkers and markers comprising, chosen from or selected from the group consisting of Mcl1-L, Mcl1-C, Mtd-L, Mtd-P, TGFβ3, VHL, PHD2, PHD3, FIH, endoglin, sFlt-1, ceruloplasmin, TGFβ-type I receptor (ALK5), TGFβ-type II receptor, TGFβ-1, cleaved caspase, syncytin, VEGF, Fas and HIF1α, and/or polynucleotides encoding same. In an embodiment the panel of markers comprise Hydroxylated HIF Biomarkers and markers comprising, chosen from or selected from the group consisting of SMAD2, phospho-SMAD2, SMAD-3, phospho-SMAD3, SMAD7, ceruloplasmin, sFlt, Mtd (in particular Mtd-P and Mtd-L), and Mcl-1 isoforms (in particular Mcl-1S or Mcl-1L, or caspase cleaved Mcl-1S or Mcl-1L, in particular caspase cleaved Mcl-1L, i.e., Mcl-1c), TGFβ3, TGFβ1, HIF1β, HIF2α, endoglin, PHD1, PHD2, PHD3, VHL, SIAH1, SIAH2, syncytin, cullin 2, cleaved caspase (e.g. caspase-3), VEGF, FIH, NEDD8, Fas, and/or p53, and/or polynucleotides encoding same. The diagnostic methods can comprise diagnosing early onset preeclampsia using a panel of markers comprising Hydroxylated HIF Biomarkers, SMAD2, phospho-SMAD2, SMAD-3, phospho-SMAD3, SMAD7, ceruloplasmin, sFlt, Mtd-L, Mtd-P, Mcl-1c, TGFβ3, endoglin, PHD1, PHD2, VHL, SIAH1, SIAH2, FIH, cullin 2 and/or VEGF, and/or polynucleotides encoding same.

In an aspect, the invention relates to a method for diagnosing early onset preeclampsia in a subject comprising detecting Hydroxylated HIF Biomarkers, ceruloplasmin, sFlt, Mtd-L, Mtd-P, Mcl-1c, TGFβ3, VHL, endoglin and/or VEGF, and/or polynucleotides encoding same, in a sample from the subject.

The invention provides a method for diagnosing early onset preeclampsia comprising comparing levels of (a) Hydroxylated HIF Biomarkers; and optionally (b) at least two, three, four, five, six, seven, eight, nine or ten additional markers comprising, chosen from or selected from the group consisting of SMAD2, phospho-SMAD2, SMAD-3, phospho-SMAD3, SMAD7, ceruloplasmin, sFlt, Mtd-P, Mtd-L, Mcl-1S, Mcl-1L, Mcl-1L truncation, TGFβ3, endoglin, PHD1, PHD2, PHD3, NEDD8, cullin 2, cleaved caspase (e.g. caspase-3), SIAH1, SIAH2, FIH, PHD3, and VHL, and/or polynucleotides encoding same, in a sample from a subject to the corresponding levels in a control. In a particular embodiment, the invention provides a method for diagnosing early onset peeclampsia comprising comparing in a sample taken from a subject in the first trimester of pregnancy, in particular before 14, 12, 10, 9, 8, or 5 weeks, levels of (a) Hydroxylated HIF Biomarkers; and optionally (b) at least two, three, four, five, six, seven, eight, nine, or ten additional markers comprising, chosen from or selected from the group consisting of ceruloplasmin, sFlt, Mtd-P, Mtd-L, Mcl-1c, Mcl-1L, Mcl-1L truncation, TGFβ3, endoglin, PHD1, PHD2, PHD3, NEDD8, cullin 2, cleaved caspase (e.g. caspase-3), SIAH1, SIAH2, FIH, and VHL, and/or polynucleotides encoding same, to the corresponding levels in a control. In a particular embodiment, the additional markers comprise, are chosen from or are selected from the group consisting of SMAD2, SMAD7, sFlt, Mtd-P, Mtd-L, Mcl-1c, TGFβ3, VHL, endoglin and/or VEGF, and/or polynucleotides encoding same. In another particular embodiment, the additional markers comprise, are chosen from or are selected from the group consisting of Mcl1-L, Mcl1-C, Mtd-L, Mtd-P, TGFβ3, VHL, PHD2, PHD3, FIH, endoglin, sFlt-1, ceruloplasmin, TGFβ-type I receptor (ALK5), TGFβ-type II receptor, TGFβ-1, cleaved caspase, syncytin, VEGF, Fas and HIF1α, and/or polynucleotides encoding same. The control may be a pre-term or normotensive age-matched control or a sample from the patient taken at a different time or a different stage of pregnancy (e.g. the second trimester).

The invention also provides a method for diagnosing late onset preeclampsia comprising comparing levels of Hydroxylated HIF Biomarkers, and optionally additional markers, in a sample from a subject to the corresponding levels in a control. In embodiments of the invention, normal levels, or an absence of a decrease in levels or low status, of Hydroxylated HIF Biomarkers or levels of hydroxylation of HIF1α at position proline 402 and/or proline 564 compared to controls, is indicative of late onset preeclampsia. In embodiments of the invention, a sample(s) may be taken from a subject in the third trimester of pregnancy, in particular after week 14, 18, 20, 24, 25, 26, 28, 30, 34 or 35. In embodiments of the invention, levels of Hydroxylated HIF Biomarkers are compared in samples taken from the patient during the first trimester and second and/or third trimesters. In an embodiment, the additional markers comprise, are chosen from or are selected from the group consisting of Mcl1-L, Mcl1-C, Mtd-L, Mtd-P, TGFβ3, VHL, PHD2, PHD3, FIH, endoglin, sFlt-1, ceruloplasmin, TGFβ-type I receptor (ALK5), TGFβ-type II receptor, TGFβ-1, cleaved caspase, syncytin, VEGF, Fas and HIF1α, and/or polynucleotides encoding same. In another embodiment, the additional markers comprise, are chosen from or are selected from the group consisting of Mtd-P, Mtd-L, ceruloplasmin, sFlt, SMAD2, SMAD3, SMAD7, VEGF, Mcl-1c, TGFβ3, VHL, SIAH1, SIAH2, FIH, PHD1, PHD2, and/or PHD3 and/or polynucleotides encoding same. In another embodiment, the additional markers comprise, are chosen from or are selected from the group consisting of Mtd-P, Mtd-L, sFlt, SMAD2, SMAD7, Mcl-1c, Mcl-1L, TGFβ3, VEGF, VHL, SIAH1, SIAH2, FIH, PHD1, PHD2 and/or PHD3, and polynucleotides encoding same.

The invention also provides a method for diagnosing intrauterine growth restriction (IUGR) comprising comparing levels of Hydroxylated HIF Biomarkers in a sample from a subject to the corresponding levels in a control. In an embodiment, the subject has no clinical signs of preeclampsia. In embodiments of the invention for diagnosing IUGR, samples may be taken from a subject at or later than about 14, 18, 20, 25, 28, 30, 34 or 35 weeks of gestation. In embodiments of the invention, levels of Hydroxylated HIF Biomarkers are compared in samples taken from the patient during the first trimester and second and/or third trimesters. In embodiments of the invention, an increase or elevated status, in particular a significant increase in Hydroxylated HIF Biomarkers or levels of hydroxylation of HIF1α at position proline 564, or positions proline 402 and proline 564, compared to controls is indicative of IUGR. A method for diagnosing IUGR may comprise detecting additional markers. In an embodiment, the additional markers comprise, are chosen from or are selected from the group consisting of cyclin D1, Mtd-L, Mtd-P, sFLt, SMAD2, phospho-SMAD2, SMAD-3, phospho-SMAD3, SMAD7, VEGF, Mcl-1L, Mcl-1c, VHL, TGFβ3, PHD1, PHD2, PHD3, endoglin, SIAH1 and/or SIAH2, and/or polynucleotides encoding same. In another embodiment, the additional markers comprise, are chosen from or are selected from the group consisting of sFLt, SMAD2, SMAD7, VEGF, HIF1α, VHL, TGFβ3, PHD1, PHD2, PHD3, FIH, SIAH1 and/or SIAH2, and/or polynucleotides encoding same. In another embodiment, the additional markers comprise, are chosen from or are selected from the group consisting of Mcl1-L, Mcl1-C, Mtd-L, Mtd-P, TGFβ3, VHL, PHD2, PHD3, FIH, endoglin, sFlt-1, ceruloplasmin, TGFβ-type I receptor (ALK5), TGFβ-type II receptor, TGFβ-1, cleaved caspase, syncytin, VEGF, Fas and HIF1α, and/or polynucleotides encoding same. An increase in TGFβ3, phospho-SMAD2, phospho-SMAD3, sFlt, endoglin, PHD1, PHD2, PHD3, SIAH and/or SIAH2, and a decrease in cyclin D1, VEGF, SMAD7, and/or ceruloplasmin may be indicative of IUGR.

The invention further provides a method for diagnosing severe IUGR, comprising comparing levels of Hydroxylated HIF Biomarkers in a sample from a subject to the corresponding levels in a control. In embodiments of the invention, an increase or elevated status, in particular a significant increase in Hydroxylated HIF Biomarkers or levels of hydroxylation of HIF1α at position proline 564, or positions proline 402 and proline 564, compared to controls is indicative of severe IUGR. In embodiments of the invention for diagnosing severe IUGR, a sample(s) may be taken from a subject at or later than about 18, 20, 25, 28, 30, 34 or 35 weeks of gestation. In embodiments of the invention for diagnosing severe IUGR, levels of Hydroxylated HIF Biomarkers are compared in samples taken from the patient during the first trimester and second and/or third trimesters. A method for diagnosing severe IUGR may comprise detecting additional markers. In an embodiment, the additional markers comprise or are chosen from, or are selected from the group consisting of cyclin D1, phospho-SMAD2, SMAD2, phospho-SMAD3, SMAD3, SMAD7, sFlt, TGFβ3, PHD1, PHD2, PHD3, SIAH1, SIAH2, VEGF, FIH, endoglin, and/or HIF1α, and/or polynucleotides encoding same. An increase, in particular a significant increase, in levels of phospho-SMAD2, phospho-SMAD3, PHD1, PHD2, PHD3, SIAH1, SIAH2, sFlt, TGFβ3, endoglin and FIH and decreased levels of cyclin D1, SMAD7 and/or VEGF may be indicative of IUGR.

The invention further provides a method for diagnosing gestational diabetes, comprising comparing levels of Hydroxylated HIF Biomarkers in a sample from a subject to the corresponding levels in a control. In an embodiment, the subject does not have preeclampsia. In another embodiment, the subject has preeclampsia. In embodiments of the invention, an increase or elevated status, in particular a significant increase in Hydroxylated HIF Biomarkers compared to controls is indicative of gestational diabetes. In aspects of the invention, an increase of levels or elevated status of hydroxylation of HIF1α in position proline 402 compared to controls is indicative of gestational diabetes.

It will also be appreciated that the diagnostic methods disclosed herein may also be useful in the diagnosis or monitoring of choriocarcinoma or hydatiform mole which involves uncontrolled trophoblast invasion. Further, the methods may be used to diagnose or monitor other pregnancy complications including molar pregnancy, preterm labour, preterm birth, fetal anomalies, and placental abruption.

In an aspect, the invention provides a method for diagnosing a molar pregnancy comprising comparing levels of Hydroxylated HIF Biomarkers, and optionally other markers disclosed herein, in a sample from a subject to the corresponding levels in a control. In embodiments of the invention, an increase or elevated status, in particular a significant increase in Hydroxylated HIF Biomarkers compared to controls is indicative of a molar pregnancy. In embodiments of the invention, an increase of levels or elevated status of hydroxylation of HIF1α in position proline 402 and position proline 564 compared to controls is indicative of molar pregnancy.

In an aspect, the invention provides a method for diagnosing cancer comprising comparing levels of Hydroxylated HIF Biomarkers, and optionally other cancer markers disclosed herein, in a sample from a subject to the corresponding levels in a control. In one embodiment of the invention, the cancer is a solid tumor. In one embodiment of the invention the cancer is prostate cancer. In one embodiment of the invention the cancer is breast cancer. In one embodiment of the invention the cancer is acute myeloid leukemia. In embodiments of the invention, an increase in levels or elevated status, in particular a significant increase in Hydroxylated HIF Biomarkers compared to controls is indicative of a benign and/or precancerous condition. In embodiments of the invention, a decrease in levels or low status compared to controls is indicative of a malignant condition. In other embodiments of the invention, an increase or elevated status, in particular a significant increase in Hydroxylated HIF Biomarkers, compared to controls is indicative of a cancer.

In an aspect, the invention provides a method for assessing the aggressiveness or indolence of a cancer (e.g. staging), the method comprising comparing:

(a) levels of Hydroxylated HIF Biomarkers in a patient sample; and
(b) control levels of the Hydroxylated HIF Biomarkers.

In an embodiment, a significant difference between the levels in the sample and the control levels is an indication that the cancer is aggressive or indolent. In a particular embodiment, the levels of Hydroxylated HIF Biomarkers are higher than control levels. In a particular embodiment, the levels of Hydroxylated HIF Biomarkers are lower than control levels.

In an aspect, the invention provides a method for determining whether a cancer has metastasized or is likely to metastasize in the future, the method comprising comparing:

(a) levels of Hydroxylated HIF Biomarkers in a patient sample; and
(b) control levels of the Hydroxylated HIF Biomarkers.

In an embodiment, a significant difference between the levels in the patient sample and the control levels is an indication that the cancer has metastasized or is likely to metastasize in the future.

Polypeptide Methods

Hydroxylated HIF Biomarkers and optionally other polypeptide markers used in the present invention may be detected using binding agents. Binding agents may be used for a variety of diagnostic and assay applications. There are a variety of assay formats known to the skilled artisan for using a binding agent to detect a target molecule in a sample. (For example, see Harlow and Lane, Antibodies: A Laboratory Manual, Cold Spring Harbor Laboratory, 1988). In general, the presence or absence of a Hydroxylated HIF Biomarker and optionally other polypeptide markers in a sample may be determined by (a) contacting the sample with binding agents that interact with the marker(s); and (b) determining the status of the marker(s) or binding agents in the sample wherein an abnormal status in the sample indicates the presence of the condition.

In the context of certain methods of the invention, a sample or binding agents (e.g. antibodies) may be immobilized on a carrier or support. For example, an antibody or sample may be immobilized on a carrier or solid support which is capable of immobilizing cells, antibodies, etc. Suitable carriers or supports may comprise nitrocellulose, or glass, polyacrylamides, gabbros, and magnetite. The support material may have any possible configuration including spherical (e.g. bead), cylindrical (e.g. inside surface of a test tube or well, or the external surface of a rod), or flat (e.g. sheet, test strip). Immobilization typically entails separating the binding agent from any free analytes (e.g. free markers or free complexes thereof) in the reaction mixture.

Binding agents may be labeled using conventional methods with a detectable substance. Examples of detectable substances include, but are not limited to, the following: radioisotopes (e.g., $^3$H, $^{14}$C, $^{35}$S, $^{125}$I, $^{131}$I), fluorescent labels (e.g., FITC, rhodamine, lanthanide phosphors), luminescent labels such as luminol, enzymatic labels (e.g., horseradish peroxidase, beta-galactosidase, luciferase, alkaline phosphatase, acetylcholinesterase), biotinyl groups (which can be detected by marked avidin e.g., streptavidin containing a fluorescent marker or enzymatic activity that can be detected by optical or calorimetric methods), and predetermined polypeptide epitopes recognized by a secondary reporter (e.g., leucine zipper pair sequences, binding sites for secondary antibodies, metal binding domains, epitope tags). In some embodiments, labels are attached via spacer arms of various lengths to reduce potential steric hindrance. Antibodies may also be coupled to electron dense substances, such as ferritin or colloidal gold, which are readily visualised by electron microscopy. Where a radioactive label is used as a detectable substance, a polypeptide may be localized by radioautography. The results of radioautography may be quantitated by determining the density of particles in the radioautographs by various optical methods, or by counting the grains.

Binding agents, including antibodies or protein complexes comprising polypeptide markers, or peptides that interact with polypeptide markers or complexes thereof, may also be indirectly labeled with a ligand binding partner. For example, the antibodies, or peptides may be conjugated to one partner of a ligand binding pair, and the polypeptide may be coupled to the other partner of the ligand binding pair. Representative examples include avidin-biotin, and riboflavin-riboflavin binding protein. In an embodiment the binding agents (e.g. antibodies) are biotinylated. Methods for conjugating binding agents such as antibodies with a ligand binding partner may be readily accomplished by one of ordinary skill in the art (see Wilchek and Bayer, "The Avidin-Biotin Complex in Bioanalytical Applications," Anal. Biochem. 171:1-32, 1988).

Binding agents can directly or indirectly interact with polypeptide markers. Indirect methods may be employed in which a primary binding agent-binding partner interaction is amplified by introducing a second agent. For example, a primary polypeptide-antibody reaction may be amplified by the introduction of a second antibody, having specificity for the antibody reactive against the primary polypeptide. By way of example, if the antibody having specificity against a polypeptide marker is a rabbit IgG antibody, the second antibody may be goat anti-rabbit gamma-globulin labeled with a detectable substance as described herein.

The presence of a polypeptide marker may be determined by measuring the binding of the polypeptide marker to molecules (or parts thereof) which are known to interact with the polypeptide. In aspects of the invention, peptides derived from sites on a polypeptide which bind to a polypeptide may be used. A peptide derived from a specific site on a binding polypeptide may encompass the amino acid sequence of a naturally occurring binding site, any portion of that binding site, or other molecular entity that functions to bind an associated molecule. A peptide derived from such a site will interact directly or indirectly with an associated molecule in such a way as to mimic the native binding site. Such peptides may include competitive inhibitors, enhancers, peptide mimetics, and the like.

In aspects of the invention, the binding agent is an antibody. Antibodies specifically reactive with polypeptide markers, or derivatives, such as enzyme conjugates or labeled derivatives, may be used to detect polypeptides in various samples (e.g. biological materials). They may be used as diagnostic or prognostic reagents and they may be used to detect abnormalities in the level of polypeptide expression, or abnormalities in the structure, and/or temporal, tissue, cellular, or subcellular location of a polypeptide. Antibodies may also be used to screen potentially therapeutic compounds in vitro to determine their effects on conditions referenced herein (e.g., preeclampsia). In vitro immunoassays may also be used to assess or monitor the efficacy of particular therapies. Antibodies may also be used in vitro to determine the level of expression in cells genetically engineered to produce a polypeptide.

In particular the invention provides a diagnostic method for monitoring or diagnosing a condition disclosed herein in a subject by quantitating Hydroxylated HIF Biomarkers and optionally other markers, or complexes thereof, in a biological sample from the subject comprising reacting the sample with antibodies specific for the markers or complexes thereof, which are directly or indirectly labeled with detectable substances and detecting the detectable substances. In a particular embodiment of the invention, Hydroxylated HIF Biomarkers and optionally other polypeptide markers disclosed herein are quantitated or measured.

In an aspect of the invention, a method for detecting a condition disclosed herein is provided comprising:
 (a) obtaining a sample suspected of containing Hydroxylated HIF Biomarkers or complexes thereof;
 (b) contacting the sample with antibodies that specifically bind to Hydroxylated HIF Biomarkers or complexes thereof under conditions effective to bind the antibodies and form complexes;
 (c) measuring the amount of Hydroxylated HIF Biomarkers or complexes thereof present in the sample by quantitating the amount of the antibody-polypeptide complexes; and
 (d) comparing the amount of Hydroxylated HIF Biomarkers or complexes thereof present in the sample with the amount of Hydroxylated HIF Biomarkers or complexes thereof in a control, wherein a change or significant difference in the amount of Hydroxylated HIF Biomarkers or complexes thereof in the sample compared with the amount in the control is indicative of the condition.

The amount of antibody complexes may also be compared to a value representative of the amount of antibody complexes from an individual not at risk of, or afflicted with, a condition or having a condition at different stages, or from the same individual at different times. A significant difference in antibody complex formation may be indicative of an advanced condition or an unfavourable prognosis.

In embodiments of the methods of the invention, Hydroxylated HIF Biomarkers or complexes thereof are detected in samples and lower levels, in particular significantly lower levels compared to a control (e.g. normal) is indicative of a condition (e.g. early onset preeclampsia).

In an embodiment, the invention contemplates a method for monitoring the progression of a condition disclosed herein, in particular pregnancy-related condition, in an individual, comprising:
 (a) contacting antibodies which bind to Hydroxylated HIF Biomarkers or complexes thereof with a sample from the individual so as to form complexes comprising the antibodies and Hydroxylated HIF Biomarkers or complexes thereof in the sample;

(b) determining or detecting the presence or amount of complex formation in the sample;

(c) repeating steps (a) and (b) at a point later in time; and (d) comparing the result of step (b) with the result of step (c), wherein a difference in the amount of complex formation is indicative of the condition, condition stage, and/or progression of the condition in the individual.

In an embodiment, a method is provided for monitoring the progression of preeclampsia or subpathologies thereof in an individual, comprising:

(a) contacting an amount of binding agents (e.g., an antibody) which bind to Hydroxylated HIF Biomarkers and optionally other markers referenced herein with a sample from the individual so as to form a binary complex comprising the binding agents and Hydroxylated HIF Biomarker and optionally other markers referenced herein in the sample;

(b) determining or detecting the presence or amount of complex formation in the sample;

(c) repeating steps (a) and (b) at a point later in time; and (d) comparing the result of step (b) with the result of step (c), wherein a difference in the amount of complex formation is indicative of the progression of the preeclampsia in said individual.

The amount of complexes may also be compared to a value representative of the amount of the complex. In an embodiment a decrease in complexes in (c) is indicative of preeclampsia.

In methods of the invention the step of contacting a sample with a binding agent (e.g. antibodies) may be accomplished by any suitable technique so that detection can occur. A method of the invention using antibodies may utilize Countercurrent Immuno-Electrophoresis (CIEP), Radioimmunoassays, Radioimmunoprecipitations, and Enzyme-Linked Immuno-Sorbent Assays (ELISA), Dot Blot assays, inhibition or competition assays and sandwich assays as described herein and known in the art.

Antibodies may be used in any known immunoassays that rely on the binding interaction between antigenic determinants of a Hydroxylated HIF Biomarker and optionally other markers disclosed herein, or complexes thereof and the antibodies. Immunoassay procedures for in vitro detection of antigens in fluid samples are well known in the art, as well as widely established and used in the commercial diagnostic industry. [See for example, Paterson et al., Int. J. Can. 37:659 (1986) and Burchell et al., Int. J. Can. 34:763 (1984) for a general description of immunoassay procedures]. Qualitative and/or quantitative determinations of polypeptide markers or complexes thereof in a sample may be accomplished by competitive or non-competitive immunoassay procedures in either a direct or indirect format. Detection of polypeptide markers or complexes thereof using antibodies can be done utilizing immunoassays which are run in either the forward, reverse or simultaneous modes. Examples of immunoassays are radioimmunoassays (RIA), enzyme immunoassays (e.g. ELISA), immunofluorescence, immunoprecipitation, latex agglutination, hemagglutination, histochemical tests, and sandwich (immunometric) assays. These terms are well understood by those skilled in the art. A person skilled in the art will know, or can readily discern, other immunoassay formats without undue experimentation.

Thus, the present invention provides means for determining Hydroxylated HIF Biomarkers, and optionally other markers disclosed herein, in a sample by measuring the polypeptides by immunoassay. According to an embodiment of the invention, an immunoassay for detecting Hydroxylated HIF Biomarkers, and optionally other markers disclosed herein in a biological sample comprises contacting antibodies that specifically bind to Hydroxylated HIF Biomarkers, and optionally other markers disclosed herein or complexes thereof in the sample under conditions that allow the formation of complexes comprising antibodies and Hydroxylated HIF Biomarkers, and optionally other markers disclosed herein, or complexes, and determining the presence or amount of the complexes as a measure of the amount of Hydroxylated HIF Biomarkers, and optionally other markers disclosed herein, or complexes contained in the sample.

In an aspect of the invention a competitive method is provided employing immobilized or immobilizable antibodies to target markers, and labeled forms of the target markers. Sample markers and labeled markers compete for binding to antibodies to the target markers. After separation of the resulting labeled markers that have become bound to antibodies (bound fraction) from that which has remained unbound (unbound fraction), the amount of the label in either bound or unbound fraction is measured and may be correlated with the amount of markers in the test sample in any conventional manner, e.g., by comparison to a standard curve.

In another aspect, a non-competitive method is used for the determination of a polypeptide marker with the most common method being the "sandwich" method. In this assay, two antibodies to a polypeptide marker are employed. One of the antibodies to a polypeptide marker is directly or indirectly labeled (sometimes referred to as the "detection antibody") and the other is immobilized or immobilizable (sometimes referred to as the "capture antibody"). The capture and detection antibodies can be contacted simultaneously or sequentially with the test sample. Sequential methods can be accomplished by incubating the capture antibody with the sample, and adding the detection antibody at a predetermined time thereafter (sometimes referred to as the "forward" method); or the detection antibody can be incubated with the sample first and then the capture antibody added (sometimes referred to as the "reverse" method). After the necessary incubation(s) have occurred, to complete the assay, the capture antibody is separated from the liquid test mixture, and the label is measured in at least a portion of the separated capture antibody phase or the remainder of the liquid test mixture. Generally it is measured in the capture antibody phase since it comprises polypeptide markers bound by ("sandwiched" between) the capture and detection antibodies. In an embodiment, the label may be measured without separating the capture antibodies and liquid test mixture.

In aspects of the invention, antibodies of the invention are used in the disclosed methods, in particular the antibodies designated 6A9, 1H1, 6H4, 5A5, 7D6 and 7E3 herein, or fragments thereof.

The above-described immunoassay methods and formats are intended to be exemplary and are not limiting. Other methods now or hereafter developed for the determination of polypeptide markers or complexes thereof are included within the scope hereof.

Polynucleotide Methods

Methods for diagnosing a condition disclosed herein, in particular a pregnancy-related condition, or stage or type of same, disclosed herein may comprise detecting polynucleotides encoding markers referenced herein. Techniques for detecting polynucleotides such as polymerase chain reaction (PCR) and hybridization assays are well known in the art.

Probes may be used in hybridization techniques to detect genes that encode a polynucleotide encoding a marker. The probes may be useful in the diagnosis of conditions disclosed herein, in monitoring the progression of such conditions; or monitoring a therapeutic treatment. In aspects of the invention the probes are useful in the diagnosis, prediction, management and control of preeclampsia involving polynucleotide markers referenced herein, in monitoring the progression of preeclampsia, or monitoring a therapeutic treatment. The hybridization techniques generally involve contacting and incubating polynucleotides (e.g. recombinant DNA molecules, cloned genes) obtained from a sample from a patient or other cellular source with a probe under conditions favourable for the specific annealing of the probes to complementary sequences in the polynucleotides. After incubation, the non-annealed nucleic acids are removed, and the presence of polynucleotides that have hybridized to the probe if any are detected.

Nucleotide probes for use in the detection of nucleic acid sequences in samples may be constructed using conventional methods known in the art. A nucleotide probe may be labeled with a detectable substance such as a radioactive label which provides for an adequate signal and has sufficient half-life such as $^{32}P$, $^{3}H$, $^{14}C$ or the like. Other detectable substances which may be used include antigens that are recognized by a specific labeled antibody, fluorescent compounds, enzymes, antibodies specific for a labeled antigen, and luminescent compounds. An appropriate label may be selected having regard to the rate of hybridization and binding of the probe to the nucleotide to be detected and the amount of nucleotide available for hybridization. Labeled probes may be hybridized to nucleic acids on solid supports such as nitrocellulose filters or nylon membranes as generally described in Sambrook et al, 1989, Molecular Cloning, A Laboratory Manual (2nd ed.).

The levels of mRNA or polynucleotides derived therefrom can be determined using hybridization methods known in the art. For example, RNA can be isolated from a sample and separated on a gel. The separated RNA can then be transferred to a solid support and nucleic acid probes representing one or more markers can be hybridized to the solid support and the amount of marker-derived RNA can be determined. Such determination can be visual or machine-aided (e.g. use of a densitometer). Dot-blot or slot-blot may also be used to determine RNA. RNA or nucleic acids derived therefrom from a sample are labeled, and then hybridized to a solid support containing oligonucleotides derived from one or more marker genes that are placed on the solid support at discrete, easily-identifiable locations. Hybridization or the lack thereof, of the labeled RNA to the solid support oligonucleotides is determined visually or by densitometer.

The detection of polynucleotide markers may involve the amplification of specific gene sequences using an amplification method such as polymerase chain reaction (PCR), followed by the analysis of the amplified molecules using techniques known to those skilled in the art. Suitable primers can be routinely designed by one of skill in the art. By way of example, at least two oligonucleotide primers may be employed in a PCR based assay to amplify a portion of a polynucleotide(s) derived from a sample, wherein at least one of the oligonucleotide primers is specific for (i.e. hybridizes to) a polynucleotide marker. The amplified cDNA is then separated and detected using techniques well known in the art, such as gel electrophoresis.

In order to maximize hybridization under assay conditions, primers and probes employed in the methods of the invention generally have at least about 60%, preferably at least about 75%, and more preferably at least about 90% identity to a portion of a polynucleotide marker; that is, they are at least 10 nucleotides, and preferably at least 20 nucleotides in length. In an embodiment the primers and probes are at least about 10-40 nucleotides in length.

Hybridization and amplification techniques described herein may be used to assay qualitative and quantitative aspects of polynucleotide expression. For example, RNA may be isolated from a cell type or tissue known to express a polynucleotide marker and tested utilizing the hybridization (e.g. standard Northern analyses) or PCR techniques referred to herein. The techniques may be used to detect differences in transcript size which may be due to normal or abnormal alternative splicing. The techniques may be used to detect quantitative differences between levels of full length and/or alternatively spliced transcripts detected in normal individuals relative to those individuals exhibiting symptoms of a condition disclosed herein.

A method may employ reverse transcriptase-polymerase chain reaction (RT-PCR), in which PCR is applied in combination with reverse transcription. Generally, RNA is extracted from a sample using standard techniques (for example, guanidine isothiocyanate extraction as described by Chomcynski and Sacchi, Anal. Biochem. 162:156-159, 1987) and is reverse transcribed to produce cDNA. The cDNA is used as a template for a polymerase chain reaction. The cDNA is hybridized to a set of primers, at least one of which is specifically designed against a polynucleotide sequence of a marker. Once the primer and template have annealed a DNA polymerase is employed to extend from the primer, to synthesize a copy of the template. The DNA strands are denatured, and the procedure is repeated many times until sufficient DNA is generated to allow visualization by ethidium bromide staining and agarose gel electrophoresis.

The invention provides a method wherein polynucleotides that are mRNA are detected by (a) isolating mRNA from a sample and combining the mRNA with reagents to convert it to cDNA; (b) treating the converted cDNA with amplification reaction reagents and nucleic acid primers that hybridize to a polynucleotide marker, to produce amplification products; (d) analyzing the amplification products to detect an amount of mRNA; and (e) comparing the amount of mRNA to an amount detected for a control or standard.

Positive samples containing a polynucleotide marker in patient samples compared to controls (e.g. normal sample) may be indicative of a condition, (e.g., preeclampsia), and/or that the patient is not responsive to or tolerant of a therapy. Alternatively, negative samples or lower levels compared to a control (e.g. normal samples or negative samples) may also be indicative of a condition, and/or that a patient is not responsive to or tolerant of a therapy.

Amplification may be performed on samples obtained from a subject with a suspected condition described herein (e.g. suspected preeclampsia) and an individual who is not predisposed to such condition. The reaction may be performed on several dilutions of cDNA spanning at least two orders of magnitude. A significant difference in expression in several dilutions of the subject sample as compared to the same dilutions of the normal sample may be considered positive for the presence of the condition (e.g. preeclampsia).

The primers and probes may be used in the above-described methods in situ i.e. directly on tissue sections (fixed and/or frozen) of patient tissue obtained from biopsies.

Oligonucleotides or longer fragments derived from a polynucleotide marker may be used as targets in a micro-array. The micro-array can be used to simultaneously monitor the expression levels of polynucleotide marker(s). The micro-array can also be used to identify genetic variants, mutations, and polymorphisms. The information from the micro-array may be used to determine gene function, to understand the genetic basis of a condition, to diagnose a condition, and to develop and monitor the activities of therapeutic agents. Thus, the invention also includes an array comprising one or more polynucleotide marker or a marker set referenced herein. The array can be used to assay expression of polynucleotides in the array or to quantitate expression of one or more polynucleotides. Arrays are also useful for ascertaining differential expression patterns of polynucleotide markers in normal and abnormal samples. This may provide a battery of nucleic acids that could serve as molecular targets for diagnosis or therapeutic intervention.

The preparation, use, and analysis of micro-arrays are well known to a person skilled in the art. (See, for example, Brennan, T. M. et al. (1995) U.S. Pat. No. 5,474,796; Schena, et al. (1996) Proc. Natl. Acad. Sci. 93:10614-10619; Baldeschweiler et al. (1995), PCT Application WO95/251116; Shalon, D. et al. (1995) PCT application WO95/35505; Heller, R. A. et al. (1997) Proc. Natl. Acad. Sci. 94:2150-2155; and Heller, M. J. et al. (1997) U.S. Pat. No. 5,605,662). A variety of arrays are made in research and manufacturing facilities worldwide, some of which are available commercially. By way of example, spotted arrays and in situ synthesized arrays are two kinds of nucleic acid arrays that differ in the manner in which the nucleic acid materials are placed onto the array substrate. A widely used in situ synthesized oligonucleotide array is GeneChip™ made by Affymetrix, Inc. Examples of spotted cDNA arrays include LifeArray™ made by Incyte Genomics and DermArray made by IntegriDerm (or Invitrogen). Presynthesized and amplified cDNA sequences are attached to the substrate of spotted arrays. Protein and peptide arrays also are known [(see for example, Zhu et al., *Science* 293:2101 (2001)].

The invention provides an array for use in combination with methods for detecting Hydroxylated HIF Biomarkers comprising one or more polynucleotide markers associated with a condition disclosed herein. In an aspect an array is provided for use in combination with methods for detecting Hydroxylated HIF Biomarkers comprising one or more polynucleotide markers associated with a pregnancy-related condition including one or more of the following: SMAD2, phospho-SMAD2, SMAD-3, phospho-SMAD3, SMAD7, ceruloplasmin, sFlt, Mtd-P, Mtd-L, Mtd-S, Mcl-1 isoforms (in particular Mcl-1S or Mcl-1L, or caspase cleaved Mcl-1S or Mcl-1L, in particular caspase cleaved Mcl-1L), TGFβ3, HIF-1α, endoglin, HIF-2α, HIF-1β, VHL, PHD1, PHD2, PHD3, Siah1/2, VEGF, FIH, syncytin, cleaved caspase (e.g. caspase-3), cullin 2, NEDD8, Fas, and/or p53. The array can be used to assay expression of the markers in the array. The invention allows the quantitation of expression of one or more markers.

The invention provides microarrays comprising a marker set referenced herein. In one embodiment, the invention provides a microarray for distinguishing a pregnancy-related condition, comprising a positionally-addressable array of polynucleotide probes bound to a support, the polynucleotide probes comprising a plurality of polynucleotide probes of different nucleotide sequences, each of the different nucleotide sequences comprising a sequence complementary and hybridizable to a plurality of genes, the plurality comprising or consisting essentially of at least 2, 3, 4, 5, 6, 7, 8, 9, 10, 11, 12, 13, 14, 15, 16, 17, 18, 19, 20, or 25, polynucleotide markers, in particular genes corresponding to at least two markers chosen from Hydroxylated HIF Biomarker, SMAD2, SMAD-3, SMAD7, ceruloplasmin, sFlt, Mtd-P, Mtd-L, Mtd-S, Mcl-1 isoforms (in particular Mcl-1S or Mcl-1L, or caspase cleaved Mcl-1S or Mcl-1L, in particular caspase cleaved Mcl-1L), TGFβ3, TGFβ1, HIF-1α, HIF-1β, HIF-2α, VHL, cleaved caspase (e.g. caspase-3), PHD1, PHD2, PHD3, SIAH1, SIAH2, syncytin, endoglin, VEGF, FIH, cullin 2, NEDD8, Fas, and/or p53. An aspect of the invention provides microarrays comprise at least 5, 10, 15, 20, or 25 polynucleotide markers or a set of markers disclosed herein.

In an aspect, the invention provides a method for classifying a pregnancy-related condition disclosed herein comprising in addition to detecting Hydroxylated HIF Biomarkers, detecting a difference in the expression of a plurality of genes in a sample from a subject relative to a control, the plurality of genes comprising at least 2, 5, 6, 7, 8, 9, 10, 15, 20, or 25 polynucleotide markers, in particular at least 3, 4, 5, 10, 15, or 20 of the genes encoding the markers SMAD2, SMAD-3, phospho-SMAD3, SMAD7, ceruloplasmin, sFlt, Mtd-P, Mtd-L, Mtd-S, Mcl-1 isoforms (in particular Mcl-1S or Mcl-1L, or caspase cleaved Mcl-1S or Mcl-1L, in particular caspase cleaved Mcl-1L), GFβ3, TGFβ1, HIF-1α, HIF-2α, HIF-1β, endoglin, VHL, cleaved caspase (e.g. caspase-3), PHD1, PHD2, PHD3, SIAH1, SIAH2, syncytin, VEGF, FIH, cullin 2, NEDD8, Fas, and/or p53. In specific aspects, the plurality of genes consists of at least 10 or 15 of the genes encoding the markers SMAD2, SMAD-3, phospho-SMAD3, SMAD7, ceruloplasmin, or sFlt, Mtd-P, Mtd-L, Mtd-S, Mcl-1 isoforms (in particular Mcl-1S, Mcl-1c or Mcl-1L, or caspase cleaved Mcl-1S or Mcl-1L, in particular caspase cleaved Mcl-1L), TGFβ3, TGFβ1, HIF-1α, HIF-2α, HIF-1β, endoglin, VHL, cleaved caspase (e.g. caspase-3), PHD1, PHD2, PHD3, Siah1/2, syncytin, VEGF, FIH, cullin 2, NEDD8, Fas, and/or p53. In another specific aspect, the control comprises nucleic acids derived from a pool of samples from individual control patients, or from similar samples from the same patient taken at different times.

The invention provides a method for classifying a pregnancy-related condition by calculating the similarity between the expression of Hydroxylated HIF Biomarkers and at least 5, 10, 15, 20, or 25, polynucleotide markers comprising or selected from the group consisting of SMAD2, phospho-SMAD2, phospho-SMAD2, SMAD-3, phospho-SMAD3, SMAD7, ceruloplasmin, sFlt, Mtd-P, Mtd-L, Mtd-S, Mcl-1 isoforms (in particular Mcl-1S, Mcl-1c, or Mcl-1L, or caspase cleaved Mcl-1S or Mcl-1L, in particular caspase cleaved Mcl-1L), TGFβ3, TGFβ1, HIF-1α, HIF-2α, HIF-1β, endoglin, VHL, cleaved caspase (e.g. caspase-3), PHD1, PHD2, PHD3, Siah1/2, syncytin, VEGF, FIH, cullin 2, NEDD8, Fas, and/or p53, in a sample to the expression of the same markers in a control pool.

In an embodiment, the array can be used to monitor the time course of expression of one or more markers in the array. This can occur in various biological contexts such as disease progression. The array is also useful for ascertaining differential expression patterns of markers, and optionally other markers, in normal and abnormal cells. This may provide a battery of nucleic acids that could serve as molecular targets for diagnosis or therapeutic intervention.

Microarrays typically contain at separate sites nanomolar quantities of individual genes, cDNAs, or ESTs on a substrate (e.g., nitrocellulose or silicon plate, or photolithographically prepared glass substrate). The arrays are hybridized to cDNA probes using conventional techniques with gene-specific primer mixes. The target polynucleotides to be analyzed are isolated, amplified and labeled, typically with fluorescent labels, radiolabels or phosphorous label probes. After hybridization is completed, the array is inserted into the scanner, where patterns of hybridization are detected. Data are collected as light emitted from the labels incorporated into the target, which becomes bound to the probe array. Probes that completely match the target generally produce stronger signals than those that have mismatches. The sequence and position of each probe on the array are known, and thus by complementarity, the identity of the target nucleic acid applied to the probe array can be determined.

In accordance with embodiments of the invention, a microarray is provided comprising a support or surface with an ordered array of hybridization sites or "probes" each representing one polynucleotide marker. The microarrays can be addressable arrays, and in particular positionally addressable arrays. Each probe of the array is typically located at a known, predetermined position on the solid support such that the identity of each probe can be determined from its position in the array. In particular embodiments, each probe is covalently attached to the solid support at a single site.

Microarrays used in the present invention are preferably (a) reproducible, allowing multiple copies of a given array to be produced and easily compared with each other; (b) made from materials that are stable under hybridization conditions; (c) small, (e.g., between 1 $cm^2$ and 25 $cm^2$, between 12 $cm^2$ and 13 $cm^2$, or 3 $cm^2$; and (d) comprise a unique set of binding sites that will specifically hybridize to the product of a single gene in a cell (e.g., to a specific mRNA, or to a specific cDNA derived therefrom). However, it will be appreciated that larger arrays may be used particularly in screening arrays, and other related or similar sequences will cross hybridize to a given binding site.

In accordance with an aspect of the invention, the microarray is an array in which each position represents one polynucleotide marker. Each position of the array can comprise a DNA or DNA analogue based on genomic DNA to which a particular RNA or cDNA transcribed from a genetic marker can specifically hybridize. A DNA or DNA analogue can be a synthetic oligomer or a gene fragment. In an embodiment, probes representing polynucleotide markers are present on the array. In an embodiment, the array comprises at least 5, 10, 15, 20, or 25 polynucleotide markers.

Microarrays can be prepared by selecting polynucleotide probes and immobilizing them to a solid support or surface. The probes may comprise DNA sequences, RNA sequences, copolymer sequences of DNA and RNA, DNA and/or RNA analogues, or combinations thereof. The probe sequences may be full or partial fragments of genomic DNA, or they may be synthetic oligonucleotide sequences synthesized either enzymatically in vivo, enzymatically in vitro (e.g., by PCR), or non-enzymatically in vitro.

Probes for the microarray can be synthesized using N-phosphonate or phosphoramidite chemistries (Froehler et al., 1986, Nucleic Acid Res. 14:5399-5407; McBride et al., 1983, Tetrahedron Lett. 24:246-248). Synthetic sequences are typically between about 10 and about 500 bases, 20-100 bases, or 40-70 bases in length. Synthetic nucleic acid probes can include non-natural bases, such as, without limitation, inosine. Nucleic acid analogues such as peptide nucleic acid may be used as binding sites for hybridization. (See, e.g., Egholm et al., 1993, Nature 363:566-568; U.S. Pat. No. 5,539,083).

Probes can be selected using an algorithm that takes into account binding energies, base composition, sequence complexity, cross-hybridization binding energies, and secondary structure (see Friend et al., International Patent Publication WO 01/05935, published Jan. 25, 2001).

Positive control probes, (e.g., probes known to be complementary and hybridize to sequences in the target polynucleotides), and negative control probes, (e.g., probes known to not be complementary and hybridize to sequences in the target polynucleotides) are typically included on the array. Positive controls can be synthesized along the perimeter of the array or synthesized in diagonal stripes across the array. A reverse complement for each probe can be next to the position of the probe to serve as a negative control.

The probe or primers used in the nucleic acid methods of the invention can be immobilized to a solid support or surface which may be either porous or non-porous at either the 3' or the 5' end of the probe. In an aspect of the invention, hybridization levels are measured to microarrays of probes consisting of a solid support on the surface of which are immobilized a population of polynucleotides, such as a population of DNA or DNA mimics, or, alternatively, a population of RNA or RNA mimics. A solid support may be a nonporous or, optionally, a porous material such as a gel.

The probes can be attached to a solid support or surface, which may be made from glass, plastic (e.g., polypropylene, nylon), polyacrylamide, nitrocellulose, gel, filter, or other porous or nonporous material. The probes can be printed on surfaces such as glass plates (see Schena et al., 1995, Science 270:467-470). This method may be particularly useful for preparing microarrays of cDNA (See also, DeRisi et al., 1996, Nature Genetics 14:457-460; Shalon et al., 1996, Genome Res. 6:639-645; and Schena et al., 1995, Proc. Natl. Acad. Sci. U.S.A. 93:10539-11286).

High-density oligonucleotide arrays containing oligonucleotides complementary to defined sequences, at defined locations on a surface can be produced using photolithographic techniques for synthesis in situ (see, Fodor et al., 1991, Science 251:767-773; Pease et al., 1994, Proc. Natl. Acad. Sci. U.S.A. 91:5022-5026; Lockhart et al., 1996, Nature Biotechnology 14:1675; U.S. Pat. Nos. 5,578,832; 5,556,752; and 5,510,270) or other methods for rapid synthesis and deposition of defined oligonucleotides (Blanchard et al., Biosensors & Bioelectronics 11:687-690). Using these methods oligonucleotides (e.g., 60-mers) of known sequence are synthesized directly on a surface such as a derivatized glass slide. The array produced may be redundant, with several oligonucleotide molecules per RNA. Microarrays can be made by other methods including masking (Maskos and Southern, 1992, Nuc. Acids. Res. 20:1679-1684). Microarrays can be produced by synthesizing polynucleotide probes on a support wherein the nucleotide probes are attached to the support covalently at either the 3' or the 5' end of the polynucleotide.

Kits

The invention also relates to kits for carrying out the methods of the invention. In an aspect, the invention provides a test kit for diagnosing a condition disclosed herein, in particular a pregnancy-related condition, in particular preeclampsia, IUGR, choriocarcinoma, hydatiform mole, or a molar pregnancy, which comprises a binding agent that interacts with Hydroxylated HIF Biomarkers, and optionally binding agents that interact with other markers disclosed herein. A kit can comprise instructions, negative and positive controls, and means for direct or indirect measurement of markers. Kits may typically comprise two or more components required for performing a diagnostic assay. Components include but are not limited to compounds, reagents, containers, and/or equipment. In an embodiment, a kit comprises an antibody, including an antibody fragment, of the invention.

The methods described herein may be performed by utilizing pre-packaged diagnostic kits comprising binding agents (e.g. antibody) described herein, which may be conveniently used, e.g., in clinical settings to screen and diagnose patients and to screen and identify those individuals exhibiting a predisposition to a condition disclosed herein, in particular preeclampsia. In an embodiment, a container with a kit comprises one or more binding agent as described herein. By way of example, the kit may contain antibodies or antibody fragments which bind specifically to epitopes of Hydroxylated HIF Biomarkers (and optionally other polypeptide markers); antibodies against the antibodies labelled with an enzyme; and, a substrate for the enzyme. The kit may also contain microtiter plate wells, standards, assay diluent, wash buffer, adhesive plate covers, and/or instructions for carrying out a method of the invention using the kit.

In an aspect of the invention, the kit includes antibodies or fragments of antibodies which bind specifically to an epitope of a Hydroxylated HIF Biomarker (and optionally one or more polypeptide marker), and means for detecting binding of the antibodies to their epitope associated with a condition disclosed herein, either as concentrates (including lyophilized compositions), which may be further diluted prior to use or at the concentration of use, where the vials may include one or more dosages.

A kit may additionally be designed to detect the level of polynucleotides encoding one or more polynucleotide markers disclosed herein in a sample. Such kits generally comprise oligonucleotide probes or primers, as described herein, that hybridize to polynucleotide markers. Such an oligonucleotide may be used, for example, within a PCR or hybridization procedure.

The invention provides a kit containing a micoarray described herein ready for hybridization to target polynucleotide markers plus software for the data analysis of the results. The software to be included with the kit comprises data analysis methods, in particular mathematical routines for marker discovery, including the calculation of correlation coefficients between clinical categories and marker expression. The software may also include mathematical routines for calculating the correlation between sample marker expression and control marker expression, using array-generated fluorescence data, to determine the clinical classification of the sample.

In an aspect, the invention provides a kit comprising a reagent that detects polypeptide markers or polynucleotide markers, and instructions or package insert or label for assaying whether a pregnant mammal is at risk of early onset preeclampsia. The kit may further comprise a detection means and/or microtiter plates, standard or tracer, and an immobilized reagent that detects polypeptide markers or polynucleotide markers and is used to capture the polypeptide markers or polynucleotide markers.

The invention relates to a kit for assessing the suitability of each of a plurality of test compounds for inhibiting a condition disclosed herein. In an aspect, the kit comprises reagents for assessing one or more polypeptide markers or polynucleotide markers, and optionally a plurality of test agents or compounds.

Additionally the invention provides a kit for assessing the potential of a test compound to contribute to a condition disclosed herein. In an aspect, the kit comprises cells and tissues associated with the condition and reagents for assessing one or more polypeptide markers or polynucleotide markers.

Computer Systems

Analytic methods contemplated herein can be implemented by use of computer systems and methods described below and known in the art. Thus, the invention provides computer readable media comprising one or more markers disclosed herein. "Computer readable media" refers to any medium that can be read and accessed directly by a computer, including but not limited to magnetic storage media, such as floppy discs, hard disc storage medium, and magnetic tape; optical storage media such as CD-ROM; electrical storage media such as RAM and ROM; and hybrids of these categories such as magnetic/optical storage media. Thus, the invention contemplates computer readable medium having recorded thereon markers identified for patients and controls.

"Recorded" refers to a process for storing information on computer readable medium. The skilled artisan can readily adopt any of the presently known methods for recording information on computer readable medium to generate manufactures comprising information on one or more markers disclosed herein.

A variety of data processor programs and formats can be used to store information on one or more markers. For example, the information can be represented in a word processing text file, formatted in commercially-available software such as WordPerfect and MicroSoft Word, or represented in the form of an ASCII file, stored in a database application, such as DB2, Sybase, Oracle, or the like. Any number of dataprocessor structuring formats (e.g., text file or database) may be adapted in order to obtain computer readable medium having recorded thereon the marker information.

By providing the marker information in computer readable form, one can routinely access the information for a variety of purposes. For example, one skilled in the art can use the information in computer readable form to compare marker information obtained during or following therapy with the information stored within the data storage means.

The invention provides a medium for holding instructions for performing a method for determining whether a patient has a condition disclosed herein or a pre-disposition to a condition disclosed herein, comprising determining the presence or absence of one or more markers, and based on the presence or absence of the markers, determining the condition or a pre-disposition to a condition, optionally recommending a procedure or treatment.

The invention also provides in an electronic system and/or in a network, a method for determining whether a subject has a condition disclosed herein, or a pre-disposition to a condition disclosed herein, comprising determining the presence or absence of one or more markers, and based on the presence or absence of the markers, determining whether the subject has the condition or a pre-disposition to the condition, and optionally recommending a procedure or treatment.

The invention further provides in a network, a method for determining whether a subject has a condition disclosed herein or a pre-disposition to a condition disclosed herein comprising: (a) receiving phenotypic information on the subject and information on one or more markers (i.e. Hydroxylated HIF Biomarkers and optionally other markers disclosed herein) associated with samples from the subject; (b) acquiring information from the network corresponding to the markers; and (c) based on the phenotypic information and information on the markers, determining whether the subject has the condition or a pre-disposition to the condition, and (d) optionally recommending a procedure or treatment.

The invention still further provides a system for identifying selected records that identify a diseased cell or tissue. A system of the invention generally comprises a digital computer; a database server coupled to the computer; a database coupled to the database server having data stored therein, the data comprising records of data comprising one or more markers, and a code mechanism for applying queries based upon a desired selection criteria to the data file in the database to produce reports of records which match the desired selection criteria.

The invention contemplates a business method for determining whether a subject has a condition disclosed herein or a pre-disposition to a condition disclosed herein comprising: (a) receiving phenotypic information on the subject and information on one or more markers associated with samples from the subject; (b) acquiring information from a network corresponding to the markers; and (c) based on the phenotypic information, information on the markers and acquired information, determining whether the subject has the condition or a pre-disposition to the condition, and optionally recommending a procedure or treatment.

In an aspect of the invention, the computer systems, components, and methods described herein are used to monitor a condition or determine the stage of a condition.

The following non-limiting examples are illustrative of the present invention:

Example 1

Abnormalities in Oxygen Sensing Define Early and Late Onset Preeclampsia as Distinct Pathologies The following materials and methods were used in the study described in this example:

Tissue Collection:

First and second trimester human placental tissues (6-15 weeks' gestation, n=18) were obtained from elective terminations of pregnancies. Seventy six placentae were collected from pregnancies complicated by preeclampsia (PE). The diagnosis of PE was made according to the following criteria: presence of pregnancy-induced hypertension (systolic ≥140 mmHg, diastolic ≥90 mmHg) and proteinuria (≥300 mg/24 h) after the $20^{th}$ weeks of gestation in normotensive women [2]. Differential diagnosis of early-severe preeclampsia and late-onset preeclampsia was made according to the ACOG criteria [2]. Fifty-eight age-matched control placentae were obtained from normal pregnancies that did not show any signs of preeclampsia or other placental disease. Patients with diabetes, infections and kidney disease were excluded. Clinical data are summarized in Table 1. Maternal age, gestational age and parity were comparable between E-PE vs preterm controls (PTC) and L-PE vs term controls (TC) groups. Ethnical origins were similar among the four study groups. Only 19.6% of the babies from early-onset preeclamptic pregnancies were growth restricted. Samples were collected randomly from central and peripheral placental areas and snap frozen immediately after delivery. Calcified, necrotic and visually ischemic areas were excluded from collection. Analysis for mRNA and protein were performed in the same samples.

Human Villous Explant Culture:

Early (n=12) and late-onset (n=3) preeclamptic and age-matched control (n=8) villous explant cultures were established as previously described [27]. Villous explants were cultured for 4 days under standard tissue culture conditions of 5% $CO_2$ in 95% air (20% $O_2$ environment) or maintained in an atmosphere of either 3% $O_2$/92% $N_2$/5% $CO_2$. Twenty and 3% $O_2$ concentrations were chosen since they represent the standard culturing condition and the physiological placental $O_2$ environment before 10 weeks of gestation respectively. Hence, when using third trimester tissue that is physiologically at 5-8% $O_2$, oxygen concentration of 3% can be efficiently used to mimic hypoxia. For each treatment, tissue samples from the same placenta were used and in each experiment, explant cultures were set up in triplicate.

In-Situ Hybridization:

Antisense and sense digoxigenin-labeled HIF-1α riboprobes were generated according to manufacturer's protocol (Boehringer Mannheim, Montreal, QC, Canada). In situ hybridization to preeclamptic (n=5) and normal age-matched control (n=3) placental tissue sections was performed as previously described [27]. Endogenous alkaline phosphatase was blocked by the addition of 2 mM levamisole. Sections were counter-stained with methyl green.

FIH Silencing:

JEG-3 choriocarcinoma cells (ATCC, Manassas, Va., USA) were plated at a density of $2 \times 10^5$ cells/well in 6 well plates and cultured in Eagle's minimal essential medium (EMEM) (ATCC, Manassas, Va., USA) at standard conditions (5% $CO_2$ in 95% air). When cells reached 50-70% confluency they were transfected with 30 nM of Silencer® siRNA directed against the human FIH gene (Ambion, Inc., Austin, Tex., USA) using Lipofectamine™ 2000 (Invitrogen, Carlsbad, Calif., USA) following manufacturer's protocol. Silencer® Negative Control siRNA (Ambion, Inc., Austin, Tex., USA), which does not target any gene product was used as a control.

RNA Isolation and Real Time PCR:

Total RNA, extracted from placental tissues and FIH siRNA-treated JEG-3 cells using TRIZOL (Invitrogen Canada Inc, Burlington, ON, Canada), was treated with DNAse I to remove genomic DNA contamination. One μg of total RNA was reverse transcribed using random hexamers (Applied Biosystems (ABI), Foster City, Calif., USA). The resulting templates (30 ng of cDNA for our target genes and 1.5 ng for 18S) were quantified by real-time PCR (DNA Engine Opticon2 R system, MJ Research, Waltham, Mass.). TaqMan probes for PHD1, PHD2, and PHD3 were purchased from ABI. Primers were obtained from the oligosynthesis service at the Hospital for Sick Children (Toronto, Canada). SIAH1, SIAH2, FIH and ribosomal 18S probes and primers were purchased from ABI as Assays-on-Demand™ for human genes. For each probe a dilution series determined the efficiency of amplification of each primer/probe set and the relative quantification method was employed [28]. For the relative quantitation, PCR signals were compared among groups after normalization using 18S as internal reference. Relative expression and fold change was calculated according to Livak and Schmittgen [28].

Semi-Quantitative RT-PCR for SIAH-1b Isoform:

One μg of total RNA was reverse transcribed using random hexamers (Applied Biosystems). Semi-quantitative PCR was performed using primer sets specific for SIAH-1b (NM 001006610; gi: 55749556): forward primer, 5'-ATGACGG-GAAAGGCTACTCCA-3' [SEQ ID NO: 3]; reverse primer, 5'-AGTTGCGAATGGATCCCAAA-3' [SEQ ID NO: 4] (predicted amplicon of 346 bp). Human β-Actin (forward primer: 5'-CGAGAAGATGACCCA GATCATGT-3' [SEQ ID NO: 5]; reverse primer: 5'-CCACAGGACTCCATGC-CCAGGAA-3' [SEQ ID NO: 6]) was used as housekeeping gene to normalize the data. DNA contamination was excluded by performing PCR on each sample without first transcribing mRNA with reverse transcriptase.

Preparation of HIF Mutants:

The human full-length HIF-1α cDNA construct (generous gift of Dr. Semenza, Johns Hopkins University) was used as template to generate single (HIF-1α$_{P402R}$, HIF-1α$_{P564R}$) and double (HIF-1α$_{P402R,P564R,P}$) HIF-1α mutants using the QuickChange kit (Stratagene, Montreal, QE, Canada). All mutations were confirmed by DNA sequencing.

Antibodies:

Mouse monoclonal antibodies (anti-HIF-1α$_{P402}^{OH}$ or anti-HIF-1α$_{P564}^{OH}$) were raised against either hydroxylated proline residue 402 or 564 containing peptides of the HIF-1αODD region (Monoclonal Antibody Facility, Hospital for Sick Children).

Properties of the antibodies are summarized in Table 2. All the clones have kappa light chains. Amino acid sequences of the monoclonal antibodies are shown in SEQ ID NO: 7 to 41, and nucleic acid sequences of the monoclonal antibodies are shown in SEQ ID NO: 42 to 77.

Western Blot Analysis:

Western blot analyses were performed as previously described [25]. Primary antibodies were mouse monoclonal anti-human HIF-1α (1:250: Affinity Bioreagents Inc., Golden, Colo., USA) rabbit polyclonal anti-human PHD1, PHD2 and PHD3 (1:1000; Novus Biologicals, Littleton, Colo., USA), goat polyclonal anti-human SIAH1 and SIAH2 (1:200 dilution for SIAH1 and 1:100 dilution for SIAH2; Santa Cruz Biotechnology, Santa Cruz, Calif., USA), and FIH (1:500, Abcam Inc, Cambridge, Mass., USA). Horseradish peroxidase-conjugated secondary antibodies were goat anti-mouse for HIF-1α (1:5000), donkey anti-rabbit for PHDs and FIH (1:10000) and donkey anti-goat for SIAHs (1:5000). Specificity of SIAHs antibodies was determined using Siah-1 and Siah-2 blocking-peptides (Santa Cruz Biotechnology). HISM and IL4-treated Ramos cell lysates (Santa Cruz Biotechnology) were used as positive controls for SIAH-1 and SIAH-2, respectively.

Statistical Analysis:

All data are represented as mean±SEM. For comparison of data between multiple groups the Kruskal-Wallis test was used and for comparison between two groups the Mann-Whitney U test was used. Statistical tests were carried out using Prism statistical software and significance was accepted at P<0.05.

The results of the study are discussed below.

Oxygen Sensing in Normal and Preeclamptic Placentae:

Striking similarities in global patterns of gene expression have recently been reported between preeclamptic and high altitude placental tissue as well as low oxygen-treated first trimester placental explants [29]. HIF-1α exhibited greater expression in all three low oxygen conditions relative to control [29]. Whether hypoxia or altered oxygen-dependent regulatory mechanisms are responsible for the up-regulated HIF-1α expression in PE placentae is unknown. Therefore, villous explants from early onset (E-PE) and late onset (L-PE) preeclamptic placentae and from age-matched control tissues (pre-term: PTC; term control: TC) were maintained in either 3% or 20% $O_2$. The expression and localization of HIF-1α mRNA and protein was determined. In situ hybridization (ISH) revealed HIF-1α transcripts in trophoblasts and stroma of PTC control explants cultured at 3% $O_2$ (FIG. 1A, upper left panel). HIF-1α mRNA was abundant in E-PE explants maintained at 3% $O_2$, but in contrast to PTC control explants, HIF-1α transcript levels remained high in E-PE explants cultured at 20% $O_2$ (FIG. 1A, bottom left panel). No specific staining was observed in control sections hybridized with sense HIF-1α probes (data not shown). Real-time PCR confirmed the ISH data (FIG. 1A, right panel). Immunohistochemical (IHC) analysis showed strong positive immunoreactivity for HIF-1α protein in villous trophoblasts of both E-PE and PTC explants maintained at 3% $O_2$ (FIG. 1B). Low/absent immunoreactivity for HIF-1α was noted in PTC explants cultured at 20% $O_2$, while E-PE trophoblasts exhibited strong positive HIF-1α immunoreactivity even when maintained in 20% $O_2$. Western blot analysis verified the IHC findings (PTC explants: 3% vs. 20% 1.3-fold increase, p=0.04; E-PE explants: 3% vs. 20% 1.14-fold increase, ns) (FIG. 1C, left panel). These data suggest that E-PE placentae have lost their ability to properly respond to variations in oxygen tension. HIF-1α expression was next examined in placentae from late-onset preeclampsia. Term control explants showed increased HIF-1α protein expression at 3% $O_2$ (2.05-fold increase, p<0.01), which was markedly down regulated when the explants were maintained at 20% $O_2$ (FIG. 1C, right panel). In contrast to E-PE placentae, L-PE explants showed a similar $O_2$ response, namely elevated HIF-1α protein at 3% $O_2$ (1.92-fld increase, p<0.01) and reduced levels at 20% $O_2$.

Figure 2:
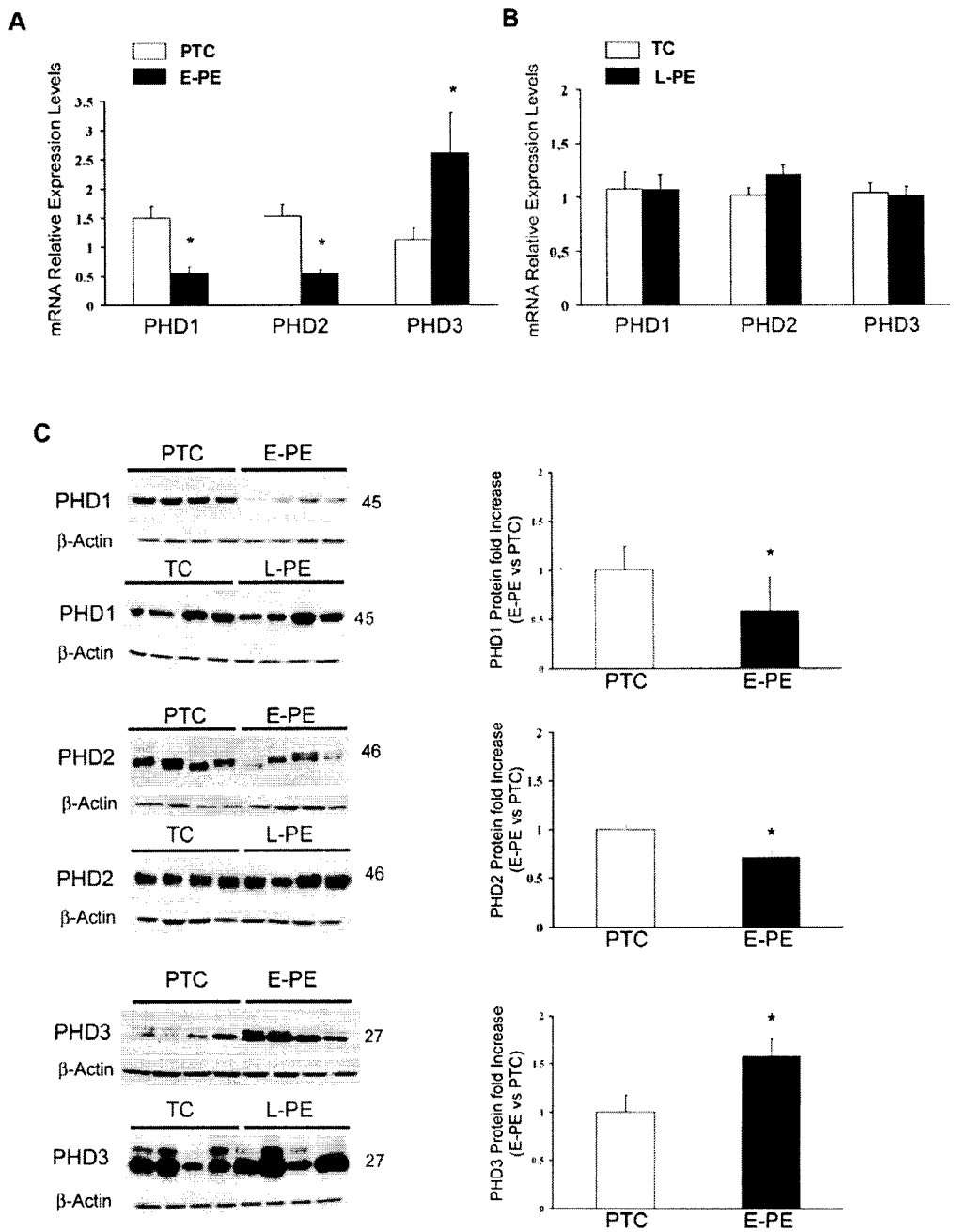
FIG. 2. PHDs expression in early preeclamptic (E-PE), late preeclamptic (L-PE), preterm control (PTC) and term control (TC) placentae. (A) Expression of PHD1-3 mRNA in E-PE (n=18) and PTC (n=15) placentae as assessed by real-time PCR analysis (values are mean±SEM, *p<0.05). (B) Expression of PHD1-3 mRNA in L-PE (n=12) and TC (n=10) placentae. (C) Left panel: Representative immunoblots for PHDs of E-PE (n=25), L-PE (n=11), PTC (n=19) and TC (n=8) placental tissues. β-actin was used as loading control. Right panel: Densitometric analysis for PHDs protein levels of E-PE and PTC placentae. Data are mean±SEM, *p<0.05.

Expression of Prolyl Hydroxylases 1, 2 and 3 in Normal and Preeclamptic Placentae:

PHDs hydroxylate HIF-1α, thereby targeting it for degradation [11]. In addition, as they utilize molecular oxygen to elicit their function, they have been shown to function as oxygen sensors in a variety of systems [13,14], including the human placenta [24]. Since E-PE explants showed a lack of oxygen sensing with respect to HIF-1α expression, the expression of PHD1, PHD2 and PHD3 was next investigated in early (E-PE) and late (L-PE) onset preeclamptic placentae. Real-time PCR analysis showed that PHD1 and PHD2, mRNA expressions were decreased in placentae from early preeclamptic pregnancies compared to pre-term controls (FIG. 2A). Similar to the mRNA findings, PHD1 (1.7-fold decrease, p=0.001) and PHD2 (1.69-fold decrease, p=0.028) protein content was significantly reduced in E-PE placentae compared to PTC controls (FIG. 2C). Notably, both PHD3 mRNA and protein expression levels were significantly increased in E-PE placentae relative to controls (FIGS. 2A, and 2C). Neither mRNA nor protein expression of any PHDs was altered in placentae from pregnancies complicated by late-onset preeclampsia (L-PE) compared to term-control (TC) placentae (FIGS. 2B and 2C). Because of the high percentage of caesarean section deliveries (CS) in the early- and late-onset preeclamptic population, the expression of PHDs was also examined in normal placentae from CS and spontaneous vaginal deliveries. No differences in PHDs mRNA and protein expression were found between the 2 (control) groups, indicating that changes in PHDs expression do not reflect the mode of delivery.

Figure 3:
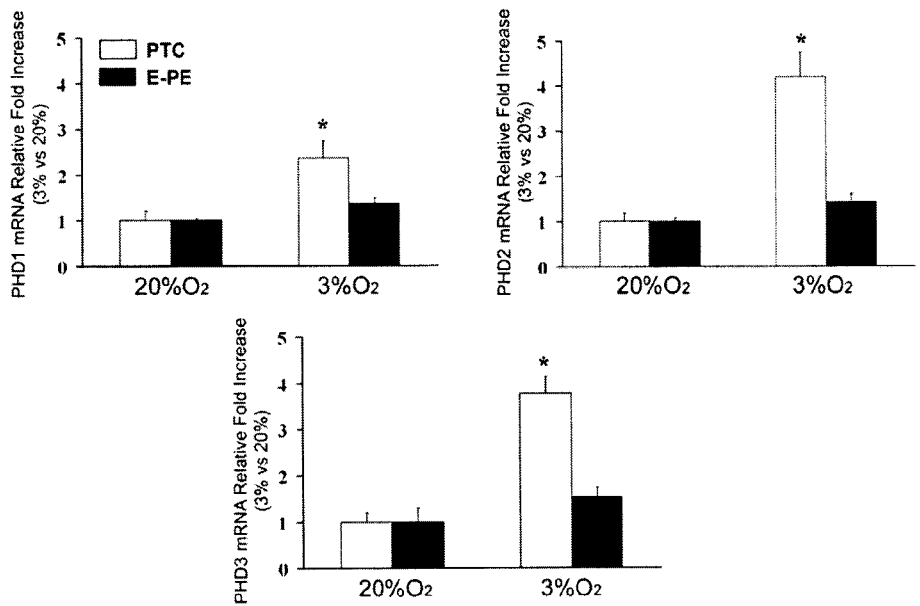
FIG. 3. Expression of PHDs in early preeclamptic (E-PE) and preterm Control (PTC) placental explants. (A) Expression of PHDs mRNA in E-PE (black bars, n=4) and PTC (open bars, n=3) explants exposed at 3% and 20% $O_2$ as assessed by real-time PCR analysis (values are mean±SEM, *p<0.05). (B) Left panel: Representative immunoblots for PHDs of E-PE (n=4) and PTC (n=3) villous explants cultured at either 3% or 20% oxygen. β-actin was used as loading control. Right panel: Densitometric analysis for PHDs protein levels of E-PE and PTC explants. Data are mean±SEM, *p<0.05.
Figure 3:
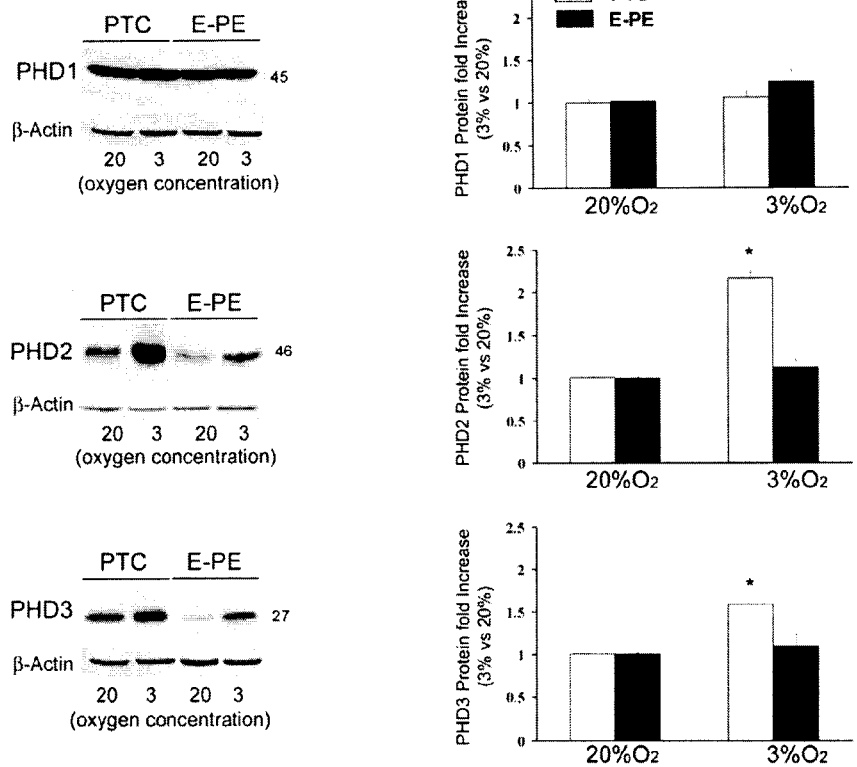

Next, whether the reduction in PHD1 and PHD2 expression in early onset PE was due to a lack of proper oxygen sensing was investigated. E-PE and PTC villous explants were cultured at 3% and 20% $O_2$ and PHD expression was assessed. Low oxygen (3% $O_2$) induced a significant increase in PHD1, PHD2 and PHD3 mRNA expression in normal PTC explants when compared to 20% $O_2$ (FIG. 3A). The highest induction was observed for PHD2 and 3. No significant oxygen-dependent changes in PHDs mRNA expression were observed in E-PE explants (FIG. 3A), suggesting that E-PE placentae fail to sense changes in oxygenation. At the protein level, control explants responded to variations in $O_2$ tension by increasing PHD2 (2.17-fold increase, p<0.01) and, to a lesser extent, PHD3 (1.5-fold increase, p<0.05) at 3% $pO_2$. E-PE explants showed a modest increase in PHD2 and PHD3 protein expression at 3% $pO_2$, while the overall protein levels of PHD2 and 3 were decreased in E-PE when compared to PTC explants. These data confirm the lack of oxygen sensing observed in vivo. No changes in response to varying oxygen concentrations were found for PHD I in both PTC and E-PE explants (FIG. 3B).

Figure 4:
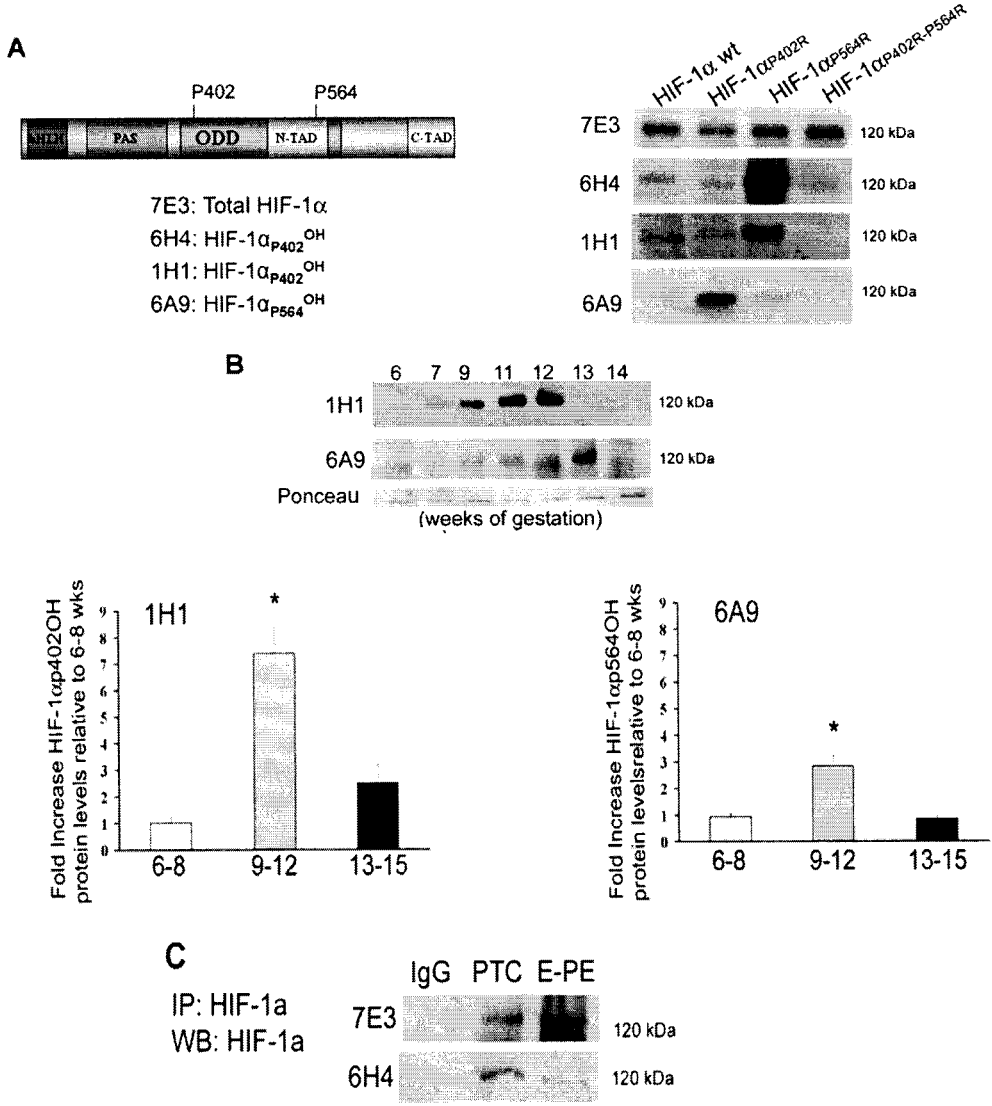
FIG. 4. HIF-1α hydroxylation during normal placentation and in preeclampsia. (A) Validation of monoclonal antibodies against hydroxylated proline 402 or 564 containing peptides of the HIF-1αODD region. Clones 6H4 and 1H1 recognized specifically HIF-1α hydroxylated at proline 402 as demonstrated by Western blotting of lysates of JEG-3 cells transfected with a HIF-1α single or double mutated construct at P402 and/or P564, while clone 6A9 was specific for hydroxylated proline 564. (B) Upper panel: Representative immunoblots for HIF-1α hydroxylated at either proline 402 or 564 during early placental development (6-14 weeks, n=18), Ponceau staining demonstrated equal protein loading. Lower panel: Densitometric analysis; data are mean±SEM, *p<0.05. (C) HIF-1α immunoprecipitation followed by immunoblotting with monoclonals either recognizing total HIF-1α (7E3) or HIF-1α hydroxylated at proline 402 (6H4). (D) Upper panel: Representative immunoblots showing reduced HIF-1α hydroxylation at P402 (1H1) and P564 (6A9) in preeclamptic placentae (E-PE, n=12) relative to preterm controls (PTC n=12). Ponceau staining demonstrated equal protein loading. Lower panel: Densitometric analysis of clones recognizing HIF-1α hydroxylation at either P402 (1H1) or P564 (6A9) in preeclamptic placentae vs preterm controls; data are mean±SEM, *p<0.05.
Figure 4:
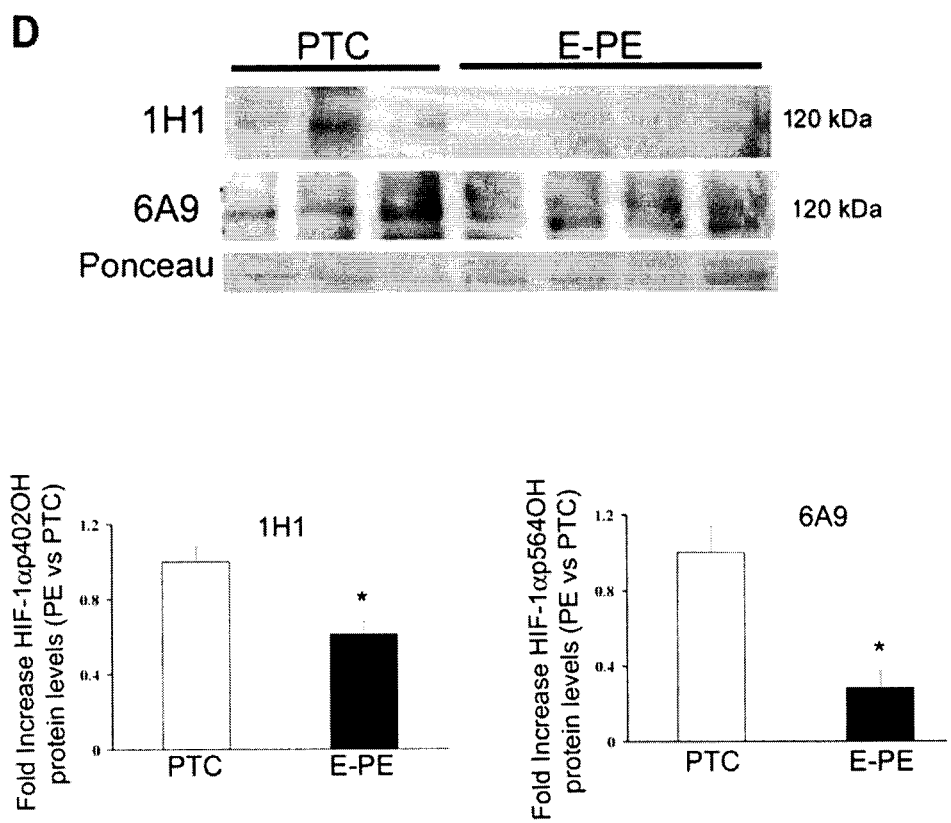

HIF-1α Hydroxylation During Human Placental Development and in Preeclampsia:

To establish PHD activities HIF-1α hydroxylation was examined using specific mouse monoclonal antibodies raised against either hydroxylated proline 402 or 564 containing peptides of the HIF-1αODD region. To validate the various clones specific HIF-1α expression constructs were generated including full-length HIF-1αHIF-1α$_{P402R}$, HIF-1α$_{P564R}$ and HIF-1α$_{P402R,P564R}$. In the latter constructs proline residues 402 or 564 alone or together were mutated to alanine, thereby preventing hydroxylation at those sites. Following transfection with the various HIF-1α constructs, JEG-3 choriocarcinoma cells were cultured for 24 h with proteosomal inhibitor MG-132 to prevent HIF degradation. Subsequent Western blot analysis revealed specificity of clones 6H4 and 1H1, respectively, for HIF-1α hydroxylated at P402 while clone 6A9 was specific for hydroxylated HIF-1α at P564 (FIG. 4A). Immunoblotting of placental lysates from first trimester gestation (6-14 weeks of gestation, n=18) showed increased HIF-1α hydroxylation at P402 at 9-12 weeks of gestation (7.39-fold increase, p<0.01) and a peak of hydroxylation at P564 at 11-13 (2.83-fold increase, p<0.01) (FIG. 4B). In E-PE, HIF-1α hydroxylation at proline residue 402 was markedly decreased relative to preterm controls (FIGS. 4C and 4D) (E-PE vs. PTC, 1H1: 1.40-fold decrease; 6H4: 1.44-fold decrease; *p<0.01). A similar decrease was noted for HIF-1α hydroxylation at proline residue 564 (E-PE vs. PTC, 6A9: 1.72-fold decrease). (FIG. 4D).

Figure 5:
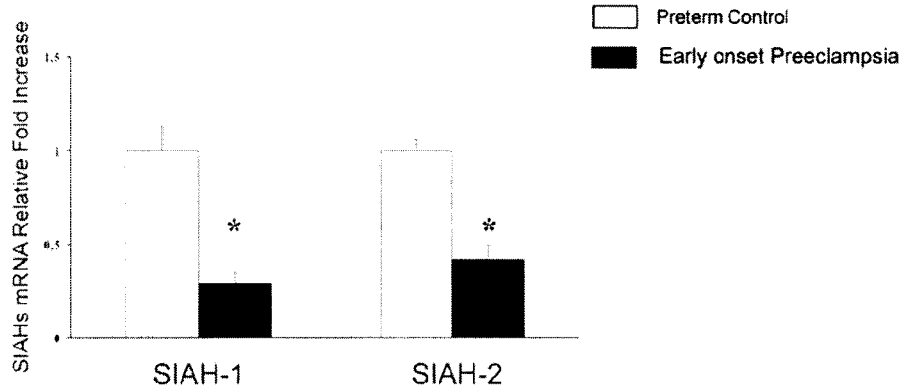
FIG. 5. Expression of SIAH-1 and SIAH-2 in early preeclamptic (E-PE), late preeclamptic (L-PE), preterm control (PTC) and term control (TC) placentae. (A) Expression of SIAH-1 and SIAH-2 mRNA in E-PE (n=18, black bars) and PTC (n=15, open bars) placental tissues as assessed by real-time PCR analysis (values are mean±SEM, *p<0.05). (B) Upper panel: Representative immunoblots for SIAHs in E-PE (n=25) and PTC (n=19) placentae. Ponceau staining demonstrated equal protein loading. Lower panel: Densitometric analysis of SIAHs protein levels in PTC and E-PE placental lysates (data are mean±SEM, *p<0.05). (C) Upper panel: Representative immunoblots for SIAHs in L-PE (n=12) and TC (n=10) placentae. Ponceau staining demonstrated equal protein loading. Lower panel: Densitometric analysis of SIAHs protein levels in TC and L-PE placental lysates (data are mean±SEM, *p<0.05). (D) SIAH-1b transcript levels as assessed by semi-quantitative RT-PCR in E-PE (n=18) vs PTC (n=15) placentae. Human β-Actin was used as housekeeping gene to normalize the data (lower panel) (E) SIAH-1 transcript levels in preeclamptic (n=4) vs term control placental explants (n=3) exposed at 3% (gray bars) and 20% (open bars) $O_2$; *p<0.05.
Figure 5:
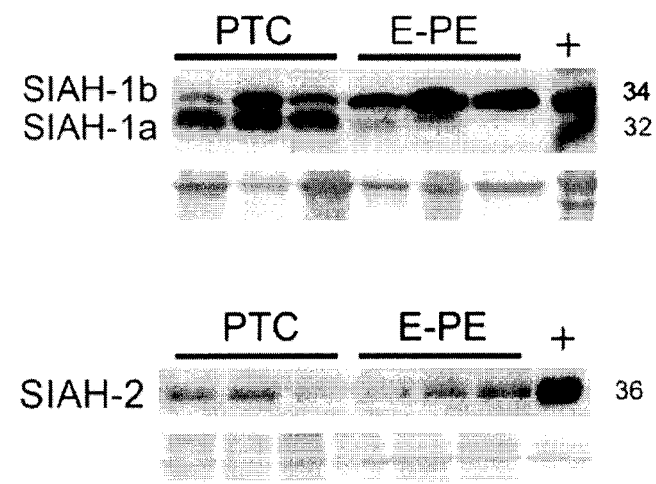
Figure 5:
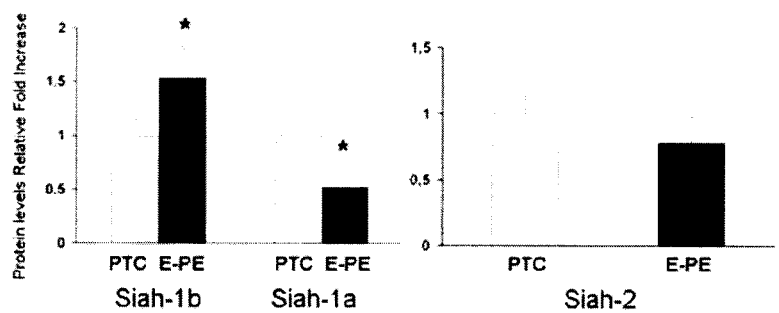
Figure 5:
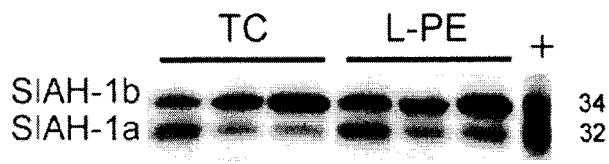
Figure 5:
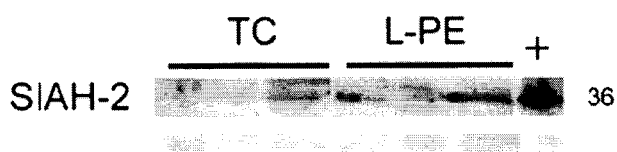
Figure 5:
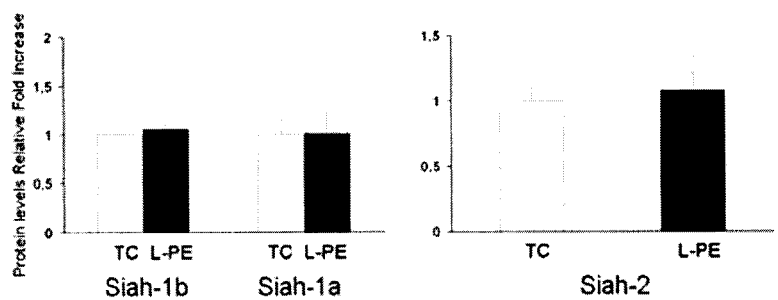
Figure 5:
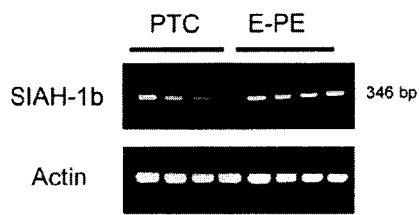
Figure 5:
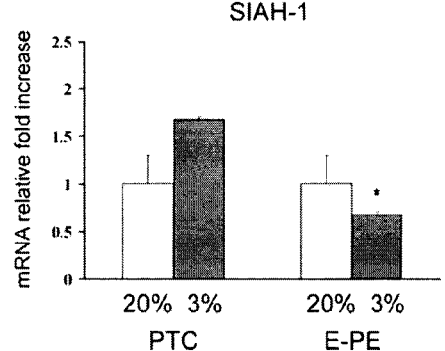

Expression of Seven in Absentia Homologues 1 and 2 in Normal and Preeclamptic Placentae:

The ubiquitin E3 ligases SIAH-1 and SIAH-2 are also oxygen sensors as they are induced by hypoxia [16]. Therefore, their expression was evaluated in placentae from pregnancies complicated by early- and late-onset preeclampsia. Compared to PTC placentae, E-PE placentae showed a significant decrease in both SIAH-1 and SIAH-2 message levels (FIG. 5A). Western blot analysis of placental tissues using SIAH-1 antibody revealed the presence of two bands with $M_r$ of 32 and 34 kDa (FIG. 5B top panel). The SIAH-1 gene is located on chromosome 16q12 and encodes two different isoforms, called SIAH-1a and SIAH-1b, with predicted molecular weights of 32 kDa and 34 kDa, respectively. To demonstrate that the two protein bands represented the two SIAH1 isoforms, the antibody was incubated with competing SIAH-1 peptide prior to Western blotting. Both bands disappeared in positive control and placental tissues, confirming that the antibody recognizes both SIAH-1 isoforms (data not shown). Western blot analysis showed differential changes in SIAH-1a and SIAH-1b protein content between E-PE and PTC tissues (FIG. 5B). SIAH-1a protein content was significantly decreased in E-PE placentae relative to preterm controls (1.89-fold decrease, p=0.004), while SIAH-1b protein showed a significant increase in E-PE vs. PTC controls (1.52-fold increase p<0.05). No differences were found in SIAH-2 protein (36 kDa) content between the two groups (FIG. 5B bottom panel). In contrast to early-onset PE, late-onset PE did not exhibit an altered protein expression of either SIAH-1 or SIAH-2 (FIG. 5C). To determine whether the changes in SIAH-1a and SIAH-1b protein expression between E-PE and PTC placentae were due to altered mRNA expression, semi-quantitative RT-PCR analysis was performed using specific primers for SIAH-1b. Transcript levels of SIAH-1b increased in E-PE placentae in comparison to PTC controls, reflecting the protein pattern (FIG. 5D). Hence, the observed reduction in total SIAH-1 mRNA expression (FIG. 5A) is likely due to a decrease in SIAH-1a expression.

As for PHDs, whether the overall reduction of SIAHs was due to a lack of proper oxygen sensing in early-onset preeclamptic placentae was investigated. As described earlier, E-PE and PTC villous explants were used which were cultured at 3% and 20% $O_2$ and SIAH-1 and –2 mRNA expression levels were quantified by real-time PCR. Low oxygen increased SIAH-1 mRNA expression in control explants (FIG. 5E). A non-significant increase in SIAH-2 message was noted (data not shown). In contrast, mRNA expression of SIAH-1 (FIG. 5E) and SIAH-2 (data not shown) was decreased in E-PE explants cultured at 3% $O_2$ compared to explants maintained at 20% $O_2$, confirming the in vivo findings.

Figure 6:
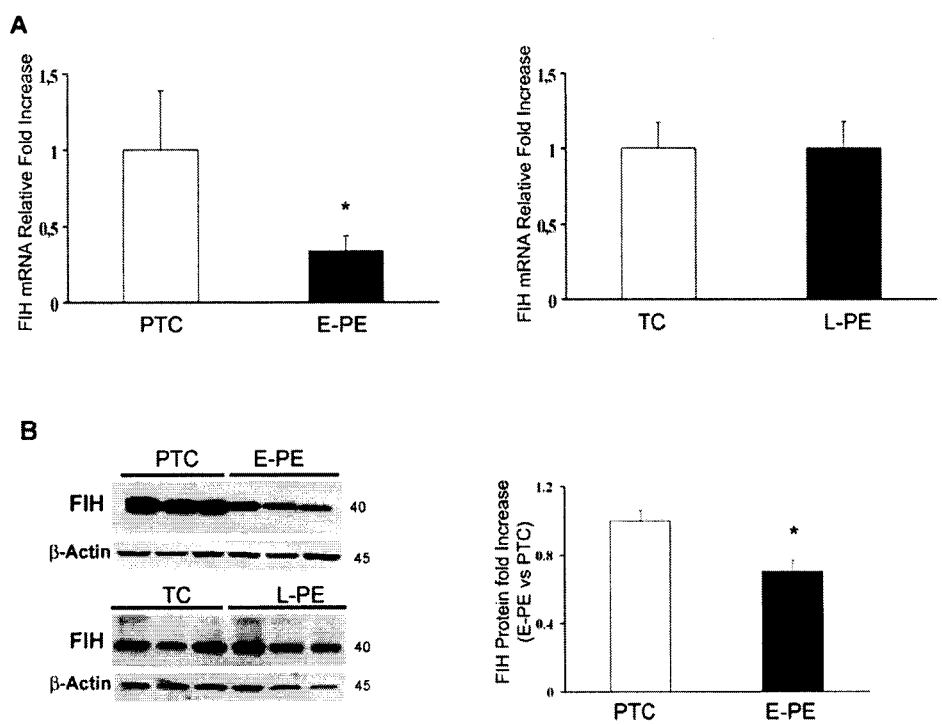
FIG. 6. Expression of Factor Inhibiting HIF (FIH) in Preeclamptic Placentae and Pre-term control placentae. (A) Expression of FIH mRNA in early onset preeclamptic (E-PE, n=18) vs pre-term control (PTC, n=15) placentae (left panel) and late onset preeclamptic (L-PE, n=12) vs term control (TC, n=10) placentae (right panel) as assessed by real-time PCR analysis (values are mean±SEM, *p<0.05). (B) Left panel: Representative FIH immunoblots in E-PE (n=25) vs PTC (n=19) placentae (left panel) and L-PE (n=11) vs TC (n=8) placentae (right panel). β-actin was used as loading control. Right panel: Densitometric analysis of FIH protein expression in E-PE vs. PTC placentae (data are mean±SEM, *p<0.05). (C) Upper panels: FIH mRNA and protein expression levels in FIH siRNA-treated JEG-3 cells maintained at 20, 8 and 3% $O_2$. Lower panels: PHD2 and PHD3 expression in JEG-3 cells treated with FIH siRNA. Data are mean±SEM, *p<0.05. β-actin was used as loading control.
Figure 6:
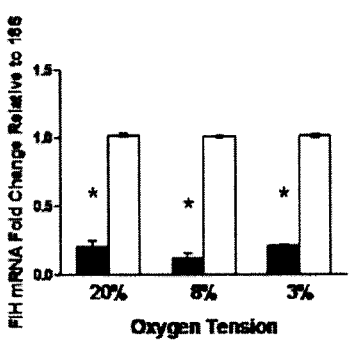
Figure 6:
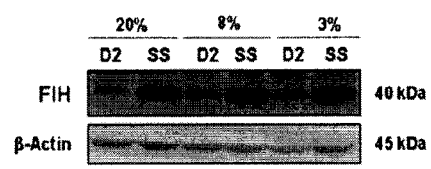
Figure 6:
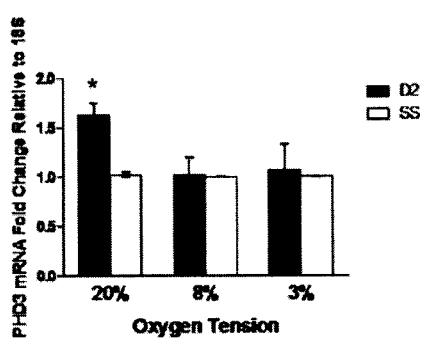
Figure 6:
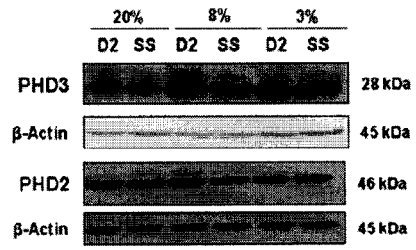

Expression of Factor Inhibiting Hif-1 in Normal and Preeclamptic Placentae:

The asparginyl hydroxylase FIH regulates HIF-1α by repressing its transcriptional activity [17,18]. FIH enzymatic activity is directly influenced by oxygen concentration within the cell, making FIH an oxygen sensing molecule [19]. Herein, it was observed that FIH gene expression was significantly decreased (2.9-fold decrease, p=0.0005) in E-PE placentae relative to preterm controls (FIG. 5A left panel), while, as observed before for PHDs and SIAHs, FIH mRNA expression in L-PE placentae was not different from controls (FIG. 6A right panel). These results were confirmed at the protein level. FIH protein levels were markedly reduced in E-PE placental tissues relative to preterm controls (FIG. 6B), while no changes were observed in L-PE placentae vs. term controls (FIG. 6B).

FIH Regulation of PHD3 Expression in JEG-3 Choriocarcinoma Cells:

In order to determine the functional significance of FIH in regulating PHD3 expression in the placenta, the consequences of inhibiting FIH on PHD3 expression by employing siRNA technology was examined. As FIH has been shown to regulate PHD3 in an oxygen-dependent manner [30], siRNA experiments were conducted at 20%, 8%, and 3% $O_2$ to assess the effect of FIH along an oxygen gradient. Real-time PCR (qRT-PCR) and Western blot analyses demonstrated that FIH expression was significantly silenced at all oxygen tensions tested, at the level of both mRNA (20% $O_2$: 0.20±0.05-fold, p<0.05; 8% $O_2$: 0.12±0.04-fold, p<0.05; 3% $O_2$: 0.21±0.01-fold, p<0.05) and protein (20% $O_2$: 0.20±0.05-fold, p<0.05; 8% $O_2$: 0.17±0.08-fold, p<0.05; 3% $O_2$: 0.32±0.11, p<0.05), relative to their respective scramble sequence controls (SS) (FIG. 6C upper panels). Decreased FIH levels were associated with a statistical significant increase in PHD3 mRNA and protein (although not significant) expression at 20% $O_2$ (1.63±0.13-fold, p<0.05), but not at 8 and 3% $O_2$ (FIG. 6C, bottom panels). To confirm that FIH selectively regulates PHD3 in JEG-3 cells, the expression of PHD2, also a HIF-1 target hydroxylase were further examined. PHD2 expression was not affected by FIH silencing, providing further support that PHD3 is selectively subjected to FIH-mediated HIF-1 inactivation in JEG-3 cells (FIG. 6C).

In the present study a disruption of oxygen sensing in early-onset, but not late-onset, preeclamptic placentae is reported. In E-PE placentae, decreased expression was found of PHD1, PHD2, SIAHs and FIH, molecules that are known to be up-regulated in response to low oxygen tensions and to be key regulators of HIF-1α, the major player in the cellular response to hypoxia. The diminished expression and function of these oxygen-sensing molecules contributes to decreased HIF-1α hydroxylation and breakdown, leading to its accumulation in early-onset preeclamptic placenta, thereby affecting the expression of molecules that orchestrate proper trophoblast cell differentiation/invasion [25,26,31,32].

Other classical oxygen sensors such as NADPH oxidase and Heme-oxygenase (HO) have also been found to be disrupted in placentae from pregnancies complicated by preeclampsia. Nox1, a gene encoding a novel NADPH oxidase isoform, is expressed in a variety of placental cells [33] and its protein expression has been reported to be increased in placental syncytium and villous endothelial cells from preeclamptic patients [33]. The expression of the HO-2, one of the three isoenzymes that compose HO, has been found to be reduced in the villous endothelial cells of PE placentae, while no differences were found in trophoblast cells [34]. Together these data suggest that impaired oxygen sensing is an important feature of preeclampsia.

PHDs are key regulators of HIF-1α stability [9,11]. PHDs are also oxygen-sensing molecules as they respond to low $pO_2$ by up-regulating their transcript levels, as demonstrated in several systems, including the human placenta [11,24]. In HeLa cells, both PHD2 and 3, but not PHD1, transcripts are induced by hypoxia [11]. In the human placenta, exposure of first trimester placental explants to low $pO_2$ resulted in an increase in PHD2 and PHD3 transcripts [24]. The finding of decreased PHD2 mRNA expression suggests that in E-PE placenta PHD2 is not sensing the low oxygenated environment.

It has been reported that in normoxic conditions only PHD2 controls HIF-1α stability, while PHD1 and 3 do not contribute to HIF-1α hydroxylation [14]. Thus, the decreased PHD2 protein levels in E-PE placentae likely leads to the reported increase in HIF-1α [25,26]. Supporting this concept are recent findings obtained with PHD knockout mice [35]. Disruption of the PHD2, but not PHD1 and 3, gene led to embryonic lethality and caused placental HIF1-α over-expression that was associated with placental defects such as diminished villous branching [35]. HIF-1α was not up-regulated in the embryonic heart of PHD2 mutant mouse [35], suggesting a specific role for PHD2 as a regulator of HIF-1α stability in murine placenta. Since early placental development occurs in a hypoxic environment [36,37], the PHD2 knockout results imply an active role of PHD2 during early development, although it has been thought that PHD2 is not functional during hypoxia [38]. Interestingly, the PHD2$^{-/-}$ mouse placenta exhibited significantly decreased levels of GCM1, a molecule implicated in placental branching morphogenesis [39]. GCM1 has been found to be decreased in placenta from pregnancies complicated by preeclampsia [40]. The influence of PHD2 on GCM1 expression further emphasises the importance of this HIF specific prolyl hydroxylase in human placental development and disease.

PHD3 also controls the stability of the HIF alpha subunit [11,12], although it is more specific for HIF-2α than HIF-1α [41]. Moreover, while PHD2 is the primary enzyme that affects HIF-1α hydroxylation in normoxia, PHD3 seems to be partially active even in conditions of low $pO_2$, thereby controlling HIF-1α levels during hypoxia [16]. In the present study, increased PHD3 expression levels in E-PE placentae relative to controls was observed. This finding together with the increased HIF-1α expression in E-PE suggests that this prolyl hydroxylase does not compensate for the reduction in PHD2 expression and further underscores the low affinity of PHD3 for HIF-1α [41].

Reduced PHD expression is generally indicative of reduced activity, but so far no direct or indirect examination of PHDs function in placenta has been reported. Using specific monoclonal antibodies against HIF-1α hydroxylated at residue P402 or P564, this study shows for the first time that during placental development HIF-1α hydroxylation is maximal at 9-12 weeks of gestation. These data agree with previously published observation of increased PHDs and decreased HIF1α expression at this specific window of gestation when trophoblast cells experience a rapid increased in oxygenation. Of clinical significance, it was found that HIF-1α hydroxylation is markedly reduced in preeclampsia. Since PHD2 appears to be the primary regulator of HIF-1α stability by hydroxylating P402 and 564, it is plausible that the decreased amount of PHD2 protein and activity in E-PE is the main cause of aberrant HIF-1α expression.

Since PHD2 and 3 are induced by low $O_2$ via HIF-1 [42], it was surprising that in E-PE placentae the hypoxic environment [29] together with its elevated HIF-1α expression [25,26,31,32] was associated with high levels of PHD3 and not PHD2. However, studies using either pVHL-deficient cells, which have high HIF-1α levels due to fact that HIF-1α is not degraded, or cell lines over-expressing HIF-1α, have shown increases in expression of PHD3 but not PHD2 [43]. Hence, increases in HIF-1α alone are not sufficient to induce PHD2 expression in E-PE placentae. A recent study reports that TGFβ1 negatively regulates PHD2 gene expression [44]. In preliminary experiments, it was found that exposure of human villous explants to both TGFβ1 and TGFβ$_3$ results in decreased PHD2 mRNA expression. Moreover, TGFβ3 [22] levels are increased in severe preeclamptic placentae and this may explain the reduced PHD2 levels found in this pathology.

While PHD2 and PHD3 are induced by hypoxia via a mechanism that involves HIF-1α PHD 1 appears not to be an HIF-1 target gene [11,41] and may even be inhibited by hypoxia [45]. Other studies have reported that PHD1 expression is regulated by estrogen [41,45] and it is plausible that the decreased PHD1 expression in preeclampsia is due to an alteration in the hormonal milieu. In rats with hypoxia-induced hypertension PHD1 expression negatively correlated with HIF-3α, but not HIF-1α, expression, suggesting that PHD1 has a greater specificity for HIF-3α [46]. Thus, the low expression of PHD1 in E-PE placentae does likely not contribute to the increase in HIF-1α levels in E-PE.

SIAHs have recently been characterized as novel oxygen-sensing molecules as hypoxia stimulates their transcription and accumulation albeit in a HIF-independent manner [16]. This study shows for the first time the expression of both SIAH-1 and SIAH-2 in the human placenta. In particular, decreased SIAH-1 and SIAH-2 mRNA levels were found in early-onset, but not late-onset, preeclamptic placentae, further emphasising the lack of placental oxygen sensing in the most severe form of preeclampsia. Recently, a novel splicing variant of SIAH-1, called SIAH-1L, has been reported [47]. This variant corresponds to the placental SIAH-1b isoform that was found in the present study. SIAH-1L has been demonstrated to be induced by p53 and to enhance the degradation of β-catenin, thereby promoting cell apoptosis [47]. Thus, the observed increase in SIAH-1b protein in E-PE placentae may contribute to the increased placental apoptosis seen in preeclampsia [48]. Both SIAH-1 and SIAH-2 mRNA levels were decreased in E-PE, supporting abnormal oxygen sensing, but only SIAH-1a protein was reduced while no changes in SIAH-2 were found in E-PE compared to control placentae. It has been reported that both SIAH-1 and SIAH-2 decrease the abundance of PHD1 and PHD3 [16] and that SIAH-2 is more efficient in degrading PHD3 than PHD1 [49] implicating other proteolytic pathways in regulating PHD1 stability [50].

In conditions of hypoxia PHD3 forms hetero-complexes with PHD2, thereby reducing PHD2 ability to hydroxylate HIF-1α and enhancing its degradation by SIAH-1 and 2 [49]. In preliminary experiments, PHD3 was found to dimerize with PHD2 in both normal and pathological placental tissues. Thus, the normal SIAH-2 and high PHD3 protein levels found in E-PE placentae likely contribute to the reduced PHD2 levels and increased amount of HIF-1α.

Another important level of HIF-1α regulation involves FIH [17,18,19]. Like PHDs, FIH is an oxygen-dependent molecule as its enzymatic activity is directly influenced by $pO_2$ within the cell [19,51]. It has been reported that PHDs and FIH have different $K_m$ for oxygen [51]. Since these $O_2$-dependent molecules act on different HIF-1α domains, an interesting O₂ regulatory model for HIF-1α activity has been proposed [30]. Along a decreasing gradient of O₂ tension PHDs are the first sensors to be inactivated, leading to stabilization of HIF-1α and activation of HIF-1α N-TAD transcriptional activity, followed by inhibition of FIH at severe hypoxia, which will lead to the activation of HIF-1α C-TAD transcriptional activity [30]. FIH controls the expression of a variety of genes via its action on C-TAD domain [30] that can be divided in FIH-inhibited and non-FIH-inhibited genes. Vascular endothelial growth factor (VEGF), which expression has been reported to be increased in preeclamptic placentae [29,52,53,54,55] belongs to the FIH-inhibited genes [30]. PHD3 is also inhibited by FIH [30]. In the present study, a dramatic decrease of FIH expression was observed in E-PE placentae, which could explain the increased PHD3 levels found in this pathology. In support of the in vivo data it was found that FIH silencing in trophoblastic JEG-3 cells increased PHD3, but not PHD2, expression at 20%, but not 3%, O₂. This discrepancy with the hypoxic E-PE is likely due to the complex in vivo placental model versus the simpler JEG-3 system. Recently, it was demonstrated that FIH expression is increased in high altitude placentae, a unique physiological model of adaptation to chronic hypoxia [56]. Thus, the low FIH mRNA levels in E-PE placentae accentuate the inability of these placentae to properly sense O₂. Reduced amounts of FIH protein in combination with increased HIF-1α levels in E-PE placentae probably contributes to the increased VEGF levels previously reported in preeclamptic placentae [29].

Interestingly, normal gene and protein expression of PHDs, SIAHs and FIH was observed in late-onset preeclamptic placentae relative to controls. In stark contrast with E-PE explants, L-PE placentae showed a normal regulation of HIF-1α levels, with higher expression at 3% O₂ and down-regulation at 20% O₂. Redman et al. [57] theorized on the basis of clinical features that there are two main categories of preeclampsia, placental (early PE) and maternal (late PE). The data provide the first molecular evidence for this theory. In preeclampsia of placental origin (E-PE), it was demonstrated that PHDs, SIAHs and FIH are unable to properly sense and respond to hypoxia. The consequence is aberrant HIF-1α over-expression typical of E-PE. These features contribute to the morphological, molecular and functional alterations of preeclamptic trophoblasts that characterize early onset preeclampsia as pathology of placental origin. Maternal preeclampsia arises from the interaction between a normal placenta and a maternal constitution that is susceptible to, or suffers from, microvascular disease [57] and as such the late-onset preeclamptic placenta is a system that is able to properly sense and respond to oxygen tension variations.

The previous findings of placental hypoxia in preeclampsia [27] together with the present data on disruption of oxygen sensing mechanisms explain the elevated HIF-1α levels found in preeclamptic placenta. [25,26,31,32] and the high expression of known HIF-1 targets such as VEGF [29,52,53,54,55] and sFlt-1 [58,59,60,61]. However, it is possible that the defect in oxygen sensing in the E-PE placenta is an effect and not the cause of the preeclamptic disease and that the HIF-1α response is triggered by other mechanisms [62,63]. The notion of placental hypoxia as leading cause of placental pathologies is disputed. Others have suggested hypoxia/reoxygenation [64,65] or hyperoxia as etiological factors in preeclampsia. [66,67,68]. Both conditions lead to the generation of reactive oxygen species (ROS) [64,65] and mitochondrial ROS have been shown to increase HIF-1α levels [69,70, 71] and to alter expression of PHDs [72] although the findings are controversial as the ROS effect appears to vary between different biological systems. ROS generation is also high during hypoxia and thus may contribute to HIF-1α stabilization under low-oxygen conditions [69,70,71,73,74].

The molecular data emphasize the existence of two preeclamptic subtypes, early and late onset, respectively, and further highlight the key role of PHD2 in human placental physiology and pathology. Importantly disruption of the oxygen-sensing machinery may be of diagnostic value. Since HIF-1α is crucial for proper placental development, early detection of aberrant HIF-1α regulatory mechanisms could impact on the differential diagnosis between high risk and low risk pregnancies. This may impact on the disease management during pregnancy and may ultimately be translated into novel therapeutic targets. In fact, in cancer research a variety of therapeutic tools aimed at targeting the HIF pathway are currently being developed, hence increasing HIF hydroxylation in order to prevent its accumulation may reduce its detrimental consequences in placental pathologies.

Figure 7:
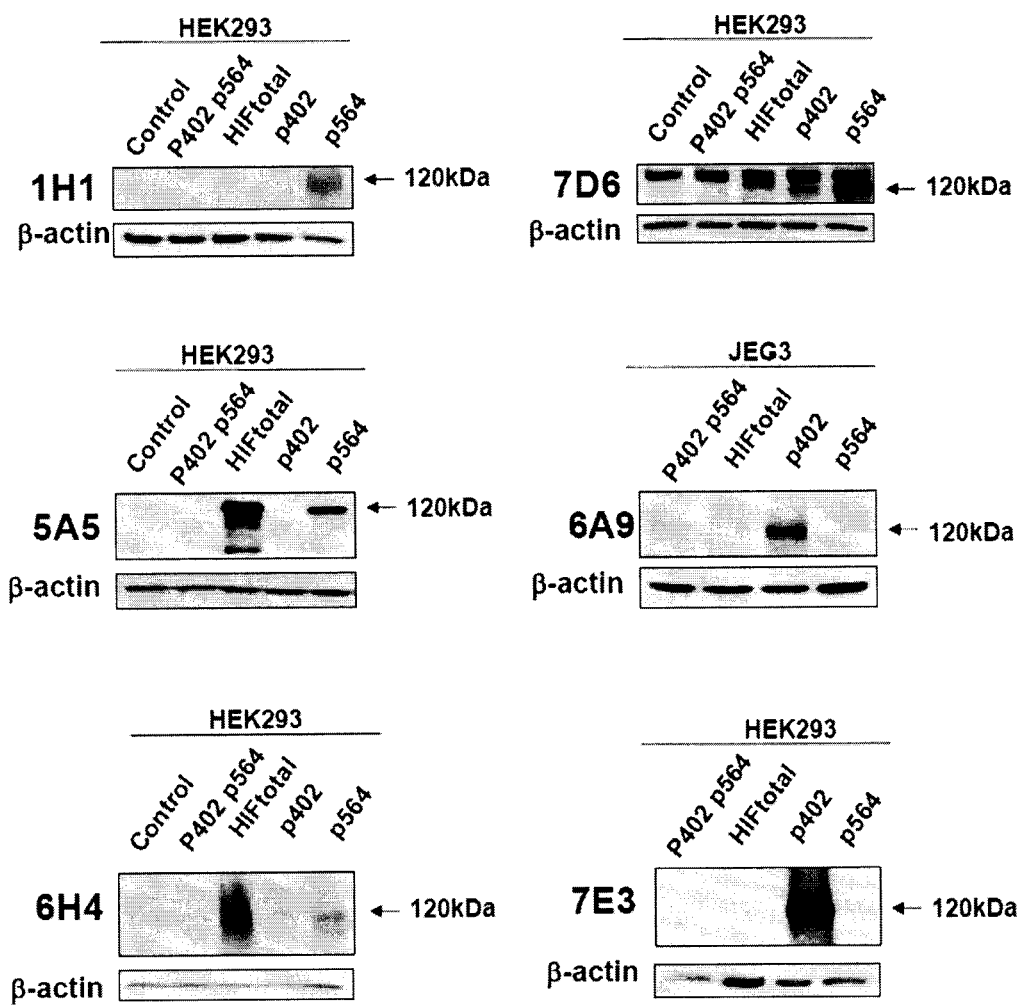
FIG. 7 are graphs showing the results of tests of antibodies 1H1, 5A5, 6H4, 7D6, 7E3 tested on HEK 293 cells and antibody 6A9 on JEG3 cells transfected with overexpression of mutated and total HIF-1α.
Figure 8:
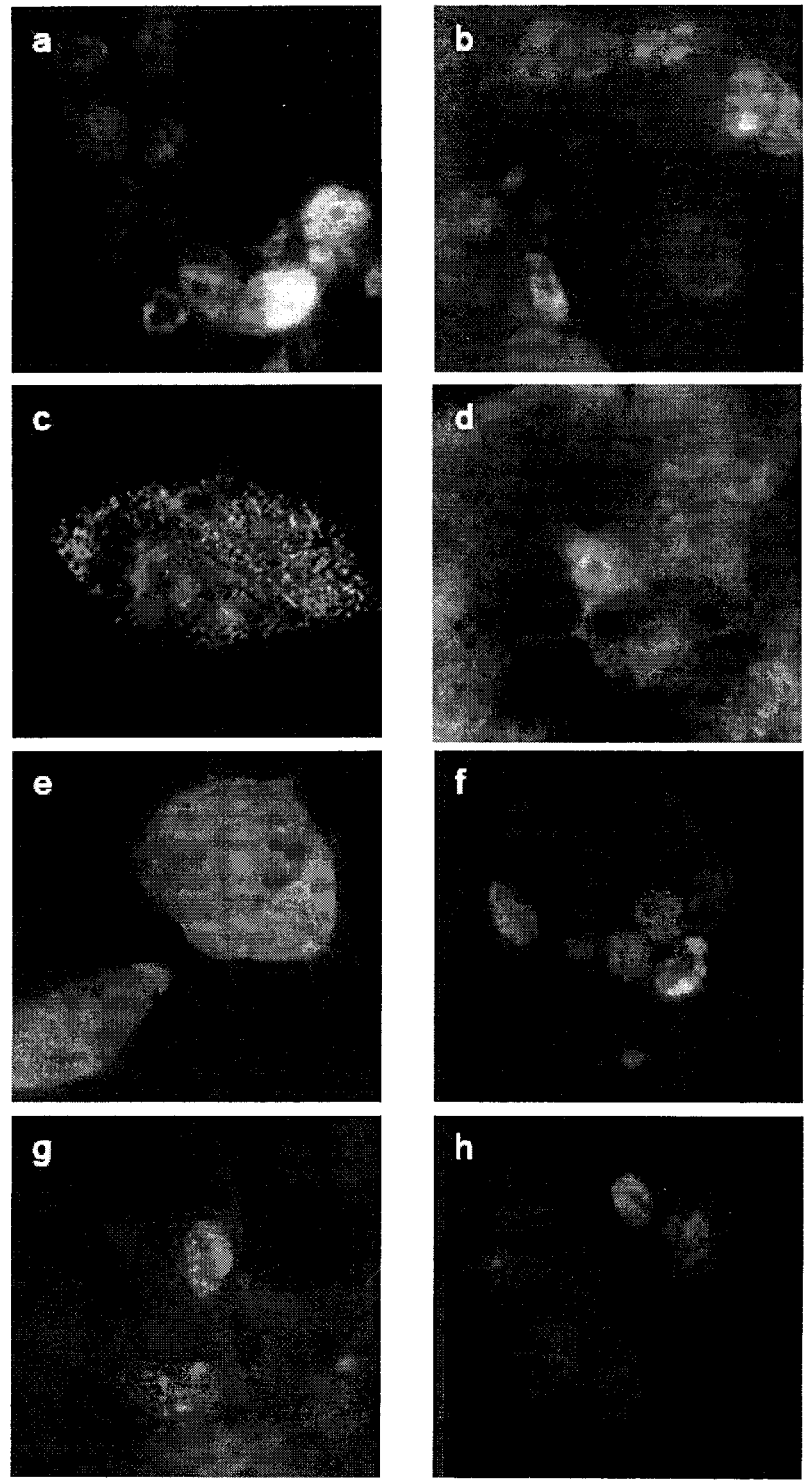
FIG. 8 shows images of a) antibody 7E3 tested on HEK 293 cells transfected with HIF1α, b) antibody 6A9 tested on HEK 293 cells transfected with HIF1α mutP402, c) antibody 5A5 tested on HEK 293 cells transfected with HIF1α mut P564, d) antibody 6H4 tested on HEK 293 cells transfected with HIF1α mutP564, e) antibody 1H1 tested on HEK 293 cells transfected with HIF1α mutP564, f) antibody 7D6 tested on HEK 293 cells transfected with HIF1α mut P564, g) antibody 7D6 tested on EK 293 cells transfected with HIF1α mut P402, and h) Negative.

Monoclonal antibodies against hydroxylated proline residues 402 and/or 564 containing peptides of HIF-1α were generated. Using these antibodies changes in HIF-1α hydroxylation status during normal placental development were reported and HIF-1α hydroxylation was found to be markedly reduced in early (the most severe form), but not late, onset preeclampsia. Thus, the antibodies may be useful in predicting the severity of preeclampsia. The monoclonal antibodies were affinity purified, their IgG isotype was determined and their specificity validated (see Table 2 and FIGS. 7 and 8). The antibodies were validated using the following strategy. Several HIF-1α and mutated HIF-1α$_{P402R}$, HIF-1α$_{P564R}$ and HIF-1α$_{P402RP564R}$ (in the latter constructs proline residues 402 or 564 alone or together were mutated to alanine, thereby preventing hydroxylation at those sites) were generated. Following transfection with the various HIF-1α constructs, JEG-3 choriocarcinoma and HEK293 cells were cultured with proteosomal inhibitor MG-132 to prevent HIF degradation and Western blot and immunofluorescence analyses were used to establish the specificity and utility of the various clones. Validation experiments were run in parallel using both purified and non-purified clones to rule out potential changes in antibody performance following purification. The Western blot results unequivocally indicate that clones 1H1, 6H4 and 5A5 recognize HIF-P402$^{OH}$; clone 6A9 recognizes HIF-P564$^{OH}$; clone 7D6 recognizes both HIF-P402$^{OH}$ and HIF-P64$^{OH}$; and clone 7E3 is excellent to detect total HIF-1α. Experiments using the purified clones for immunofluorescence analysis demonstrated the validity of the various clones for this technique. Immunofluorescence analysis was conducted in cells and tissue sections. Overall the validation indicates that the various purified clones possess high specificity and sensitivity.

The variable and non-variable regions of the heavy and light chains of the antibodies have been sequenced (see SEQ ID NO: 7 to 77).

Figure 9:
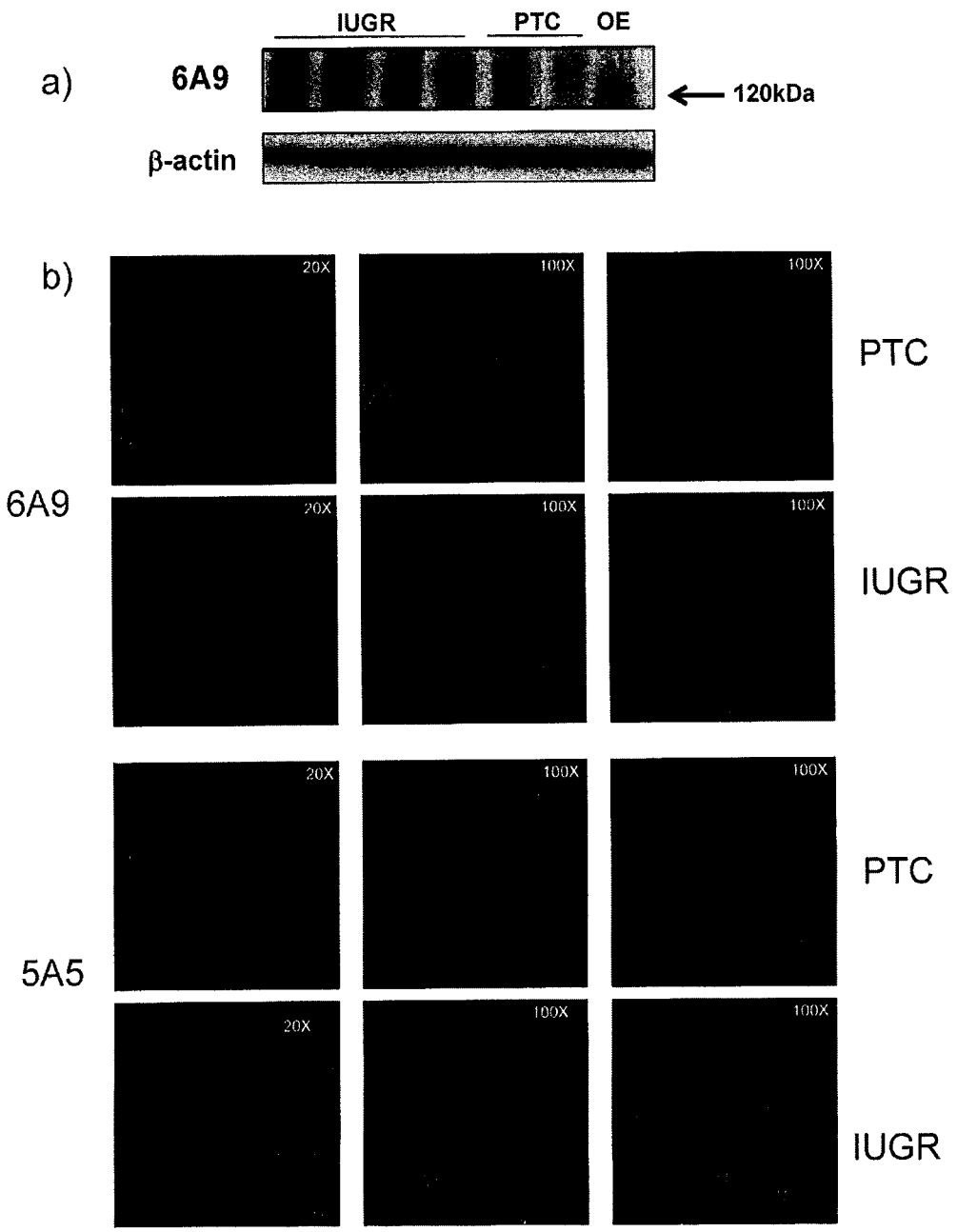
FIG. 9 are images showing expression of hydroxylated HIF1α in position P402 and P564 in IUGR. a) HIF1α hydroxylated in position P564 is increased in IUGR compared to term controls. b) Immunofluorescence staining of HIF1α hydroxylated at both positions P402 and P564 in IUGR and age matched preterm control [PTC] placenta sections shows an increase in IUGR compared to PTC; OE=overexpression.
Figure 10:
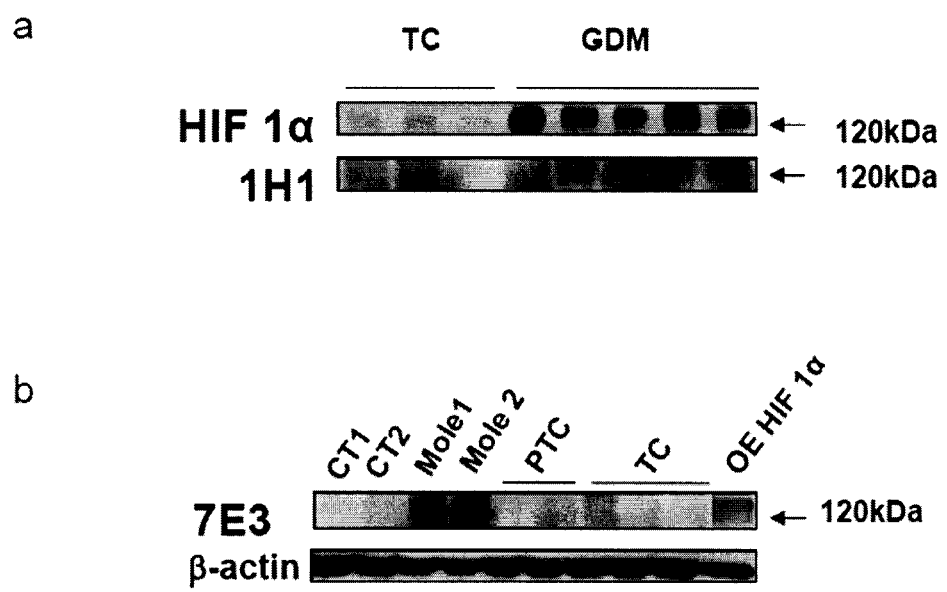
FIG. 10 are images showing expression of hydroxylated HIF1α in Gestational Diabetes and Molar Pregnancy. a) HIF1α hydroxylated in position P402 is increased in Gestational diabetes compared to term controls. b) HIF1α hydroxylated in both position P402 and P564 is increased in molar pregnancy compared to its control twin and age-matched and term controls. TC=term control; GDM=gestational diabetes; CT1/CT2=control twin ½; OE=over-expression.

Using the antibodies it was also found that in IUGR with no clinical signs of preeclampsis and in Gestational Diabetes (GDM) placentae with and without preeclampsia, HIF expression and hydroxylated status differs relative to age-matched controls and pathological preeclamptic cases. In particular, FIG. 9a illustrates that HIF1α hydroxylated in position P564 is increased in IUGR compared to term controls. FIG. 9b shows that HIF1α hydroxylated in both positions P402 and P564 is increased in IUGR compared to age matched preterm control [PTC] placenta sections. FIG. 10a shows that expression of HIF1α hydroxylated in position P402 is increased in gestational diabetes compared to term controls. In addition, FIG. 10b shows that total hydroxylated HIF1α (e.g. HIF1α hydroxylated in both positions P402 and P564) is increased in molar pregnancy, a precancerous condition of pregnancy characterized by the presence of placenta in the absence of the conceptus that in following pregnancy may lead to the development of the highly invasive choriocarcinoma. Since during pregnancy placental/fetal debris is constantly shed in the maternal circulation (3 gr/day), altered placental total and hydroxylated HIF-1α expression may be correlated with that of serum.

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

All publications, patents and patent applications referred to herein are incorporated by reference in their entirety to the same extent as if each individual publication, patent or patent application was specifically and individually indicated to be incorporated by reference in its entirety. All publications, patents and patent applications mentioned herein are incorporated herein by reference for the purpose of describing and disclosing the antibodies, methodologies etc. which are reported therein which might be used in connection with the invention. Nothing herein is to be construed as an admission that the invention is not entitled to antedate such disclosure by virtue of prior invention.

TABLE 1

Clinical Parameters of Control and Preeclamptic Participants.

| | Pre-Term Controls (n = 53) | Early Onset Preeclampsia (n = 58) | Term Controls (n = 16) | Late Onset Preeclampsia (n = 18) |
|---|---|---|---|---|
| Mean Maternal Age (yr) | 33.4 ± 4.8 | 29.9 ± 5.2 | 29 ± 4.6 | 28 ± 4.2 |
| Mean Gestational Age at delivery [wk (range)] | 29 ± 3.3 (25-35) | 28.6 ± 2.86 (24-35) | 39.6 ± 0.6 (39-41) | 38 ± 1.5 (36-41) |
| Parity | 0.6 ± 0.7 | 0.63 ± 1.1 | 0.2 ± 0.4 | 0.33 ± 0.57 |
| Blood Pressure (mmHg) | Systolic: 112 ± 7.5 Diastolic: 68.7 ± 5.7 | Systolic: 175.5 ± 16 Diastolic: 108 ± 14.4 | Systolic: 110.6 ± 6.5 Diastolic: 67.3 ± 6.9 | Systolic: 155 ± 11 Diastolic: 96 ± 4.2 |
| Proteinuria (g/24 h) | Absent | 3.0 ± 1 | Absent | 3.0 ± 1 |
| Fetal Weight (g) | A.G.A. (n = 46): 1488.2 ± 668.2 | A.G.A.(n = 41): 1250 ± 387 IUGR (n = 10): 816.5 ± 394 | A.G.A. (n = 12): 3603 ± 329 | A.G.A. (n = 18): 3556.6 ± 588 |
| Fetal Sex | Males = 45% Females = 55% | Males = 66% Females = 34% | Males = 33% Females 67% | Males = 83% Females 17% |
| Mode of delivery | CS 41% VD 59% | CS 90% VD 10% | CS 33% VD 67% | CS 71% VD 29% |

Footnotes:
Data are represented as mean ± standard deviation.
A.G.A.: Appropriate for Gestational Age.
IUGR: Intra-Uterine Growth Restriction (<5%).
VD: Vaginal Delivery.
CS: Caesarean Section delivery.

TABLE 2

Summary of Monoclonal Antibody Clones

| Ab Clones[i] | Purification | Isotyping | Specificity | Validation WB* (Cell Lysates:Tissue Lysates) | IF** (Cells:Tissue Sections) | Sequenced |
|---|---|---|---|---|---|---|
| 6A9 | Affinity Purified on HIF P564$^{OH}$ column | IgG2a | HIF-p564$^{OH}$ | 1:200 | 1:100 | YES |
| 1H1 | Affinity Purified on HIF P402$^{OH}$ column | IgG2a | HIF-P402$^{OH}$ | 1:300 | 1:300 | YES |
| 6H4 | Affinity Purified on HIF P402$^{OH}$ column | IgG1 | HIF-P402$^{OH}$ | 1:100 | 1:100 | YES |
| 5A5 | Affinity Purified on HIF P402$^{OH}$ column | IgG2a | HIF-P402$^{OH}$ | 1:200 | 1:100 | YES |
| 7D6 | Purification on G column | IgG3 | HIF-P402$^{OH}$ HIF-P564$^{OH}$ | 1:50 | 1:100 | YES |

TABLE 2-continued

Summary of Monoclonal Antibody Clones

| Ab Clones[i] | Purification | Isotyping | Specificity | Validation | | Sequenced |
| --- | --- | --- | --- | --- | --- | --- |
| | | | | WB* (Cell Lysates:Tissue Lysates) | IF** (Cells:Tissue Sections) | |
| 7E3 | Purification on G column | IgG1 | HIF-P402$^{OH}$ HIF-P564$^{OH}$ | 1:200 | 1:100 | YES |

*Western Blot Analysis
**Immunofluorescence Analysis
[i]Note: All clones have Kappa Light chain

CITATIONS FOR PUBLICATIONS

1. Chesley L C (1985) Diagnosis of preeclampsia. Obstet Gynecol 65: 423-425.
2. (2002) ACOG practice bulletin. Diagnosis and management of preeclampsia and eclampsia. Number 33, January 2002. Obstet Gynecol 99: 159-167.
3. Pijnenborg R, Vercruysse L, Verbist L, Van Assche F A (1998) Interaction of interstitial trophoblast with placental bed capillaries and venules of normotensive and pre-eclamptic pregnancies. Placenta 19: 569-575.
4. Semenza G L (1998) Hypoxia-inducible factor 1: master regulator of $O_2$ homeostasis. Curr Opin Genet Dev 8: 588-594.
5. Maxwell P H, Wiesener M S, Chang G W, Clifford S C, Vaux E C, et al. (1999) The tumour suppressor protein VHL targets hypoxia-inducible factors for oxygen-dependent proteolysis. Nature 399: 271-275.
6. Cockman M E, Masson N, Mole D R, Jaakkola P, Chang G W, et al. (2000) Hypoxia inducible factor-alpha binding and ubiquitylation by the von Hippel-Lindau tumor suppressor protein. J Biol Chem 275: 25733-25741.
7. Ohh M, Park C W, Ivan M, Hoffman M A, Kim T Y, et al. (2000) Ubiquitination of hypoxia-inducible factor requires direct binding to the beta-domain of the von Hippel-Lindau protein. Nat Cell Biol 2: 423-427.
8. Kibel A, Iliopoulos O, DeCaprio J A, Kaelin W G, Jr. (1995) Binding of the von Hippel-Lindau tumor suppressor protein to Elongin B and C. Science 269: 1444-1446.
9. Ivan M, Kondo K, Yang H, Kim W, Valiando J, et al. (2001) HIFalpha targeted for VHL-mediated destruction by proline hydroxylation: implications for $O_2$ sensing. Science 292: 464-468.
10. Jaakkola P, Mole D R, Tian Y M, Wilson M I, Gielbert J, et al. (2001) Targeting of HIF-alpha to the von Hippel-Lindau ubiquitylation complex by O2-regulated prolyl hydroxylation. Science 292: 468-472.
11. Epstein A C, Gleadle J M, McNeill L A, Hewitson K S, O'Rourke J, et al. (2001) C. elegans EGL-9 and mammalian homologs define a family of dioxygenases that regulate HIF by prolyl hydroxylation. Cell 107: 43-54.
12. Bruick R K, McKnight S L (2002) Transcription. Oxygen sensing gets a second wind. Science 295: 807-808.
13. Masson N, Ratcliffe P J (2003) HIF prolyl and asparaginyl hydroxylases in the biological response to intracellular O(2) levels. J Cell Sci 116: 3041-3049.
14. Berra E, Benizri E, Ginouves A, Volmat V, Roux D, et al. (2003) HIF prolyl-hydroxylase 2 is the key oxygen sensor setting low steady-state levels of HIF-1alpha in normoxia. Embo J 22: 4082-4090.
15. Nakayama K, Frew I J, Hagensen M, Skals M, Habelhah H, et al. (2004) Siah2 regulates stability of prolyl-hydroxylases, controls HIF1alpha abundance, and modulates physiological responses to hypoxia. Cell 117: 941-952.
16. Nakayama K, Ronai Z (2004) Siah: new players in the cellular response to hypoxia. Cell Cycle 3: 1345-1347.
17. Mahon P C, Hirota K, Semenza G L (2001) FIH-1: a novel protein that interacts with HIF-1alpha and VHL to mediate repression of HIF-1 transcriptional activity. Genes Dev 15: 2675-2686.
18. Lando D, Peet D J, Gorman J J, Whelan D A, Whitelaw M L, et al. (2002) FIH-1 is an asparaginyl hydroxylase enzyme that regulates the transcriptional activity of hypoxia-inducible factor. Genes Dev 16: 1466-1471.
19. Hewitson K S, McNeill L A, Riordan M V, Tian Y M, Bullock A N, et al. (2002) Hypoxia-inducible factor (HIF) asparagine hydroxylase is identical to factor inhibiting HIF (FIH) and is related to the cupin structural family. J Biol Chem 277: 26351-26355.
20. Adelman D M, Gertsenstein M, Nagy A, Simon M C, Maltepe E (2000) Placental cell fates are regulated in vivo by HIF-mediated hypoxia responses. Genes Dev 14: 3191-3203.
21. Kozak K R, Abbott B, Hankinson O (1997) ARNT-deficient mice and placental differentiation. Dev Biol 191: 297-305.
22. Caniggia I, Mostachfi H, Winter J, Gassmann M, Lye S J, et al. (2000) Hypoxia-inducible factor-1 mediates the biological effects of oxygen on human trophoblast differentiation through TGFbeta(3). J Clin Invest 105: 577-587.
23. Rajakumar A, Conrad K P (2000) Expression, ontogeny, and regulation of hypoxia-inducible transcription factors in the human placenta. Biol Reprod 63: 559-569.
24. Ietta F, Wu Y, Winter J, Xu J, Wang J, et al. (2006) Dynamic HIF1A regulation during human placental development. Biol Reprod 75: 112-121.
25. Caniggia I, Winter J L (2002) Adriana and Luisa Castellucci Award lecture 2001. Hypoxia inducible factor-1: oxygen regulation of trophoblast differentiation in normal and pre-eclamptic pregnancies—a review. Placenta 23 Suppl A: S47-57.
26. Rajakumar A, Brandon H M, Daftary A, Ness R, Conrad K P (2004) Evidence for the functional activity of hypoxia-inducible transcription factors overexpressed in preeclamptic placentae. Placenta 25: 763-769.
27. Caniggia I, Grisaru-Gravnosky S, Kuliszewsky M, Post M, Lye S J (1999) Inhibition of TGF-beta 3 restores the invasive capability of extravillous trophoblasts in preeclamptic pregnancies. J Clin Invest 103: 1641-1650.
28. Livak K J, Schmittgen T D (2001) Analysis of relative gene expression data using real-time quantitative PCR and the 2(−Delta Delta C(T)) Method. Methods 25: 402-408.

29. Soleymanlou N, Jurisica I, Nevo O, letta F, Zhang X, et al. (2005) Molecular evidence of placental hypoxia in preeclampsia. J Clin Endocrinol Metab 90: 4299-4308.
30. Dayan F, Roux D, Brahimi-Horn M C, Pouyssegur J, Mazure N M (2006) The oxygen sensor factor-inhibiting hypoxia-inducible factor-1 controls expression of distinct genes through the bifunctional transcriptional character of hypoxia-inducible factor-1 alpha. Cancer Res 66: 3688-3698.
31. Genbacev O, Joslin R, Damsky C H, Polliotti B M, Fisher S J (1996) Hypoxia alters early gestation human cytotrophoblast differentiation/invasion in vitro and models the placental defects that occur in preeclampsia. J Clin Invest 97: 540-550.
32. Caniggia I, Winter J, Lye S J, Post M (2000) Oxygen and placental development during the first trimester: implications for the pathophysiology of pre-eclampsia. Placenta 21 Suppl A: S25-30.
33. Cui X L, Brockman D, Campos B, Myatt L (2006) Expression of NADPH oxidase isoform 1 (Nox1) in human placenta: involvement in preeclampsia. Placenta 27: 422-431.
34. Barber A, Robson S C, Myatt L, Bulmer J N, Lyall F (2001) Heme oxygenase expression in human placenta and placental bed: reduced expression of placenta endothelial HO-2 in preeclampsia and fetal growth restriction. Faseb J 15: 1158-1168.
35. Takeda K, Ho V C, Takeda H, Duan L J, Nagy A, et al. (2006) Placental but not heart defects are associated with elevated hypoxia-inducible factor alpha levels in mice lacking prolyl hydroxylase domain protein 2. Mol Cell Biol 26: 8336-8346.
36. Rodesch F, Simon P, Donner C, Jauniaux E (1992) Oxygen measurements in endometrial and trophoblastic tissues during early pregnancy. Obstet Gynecol 80: 283-285.
37. Burton G J, Jauniaux E, Watson A L (1999) Maternal arterial connections to the placental intervillous space during the first trimester of human pregnancy: the Boyd collection revisited. Am J Obstet Gynecol 181: 718-724.
38. D'Angelo G, Duplan E, Boyer N, Vigne P, Frelin C (2003) Hypoxia up-regulates prolyl hydroxylase activity: a feedback mechanism that limits HIF-1 responses during reoxygenation. J Biol Chem 278: 38183-38187.
39. Anson-Cartwright L, Dawson K, Holmyard D, Fisher S J, Lazzarini R A, et al. (2000) The glial cells missing-1 protein is essential for branching morphogenesis in the chorioallantoic placenta. Nat Genet. 25: 311-314.
40. Chen C P, Chen C Y, Yang Y C, Su T H, Chen H (2004) Decreased placental GCM1 (glial cells missing) gene expression in pre-eclampsia. Placenta 25: 413-421.
41. Appelhoff R J, Tian Y M, Raval R R, Turley H, Harris A L, et al. (2004) Differential function of the prolyl hydroxylases PHD1, PHD2, and PHD3 in the regulation of hypoxia-inducible factor. J Biol Chem 279: 38458-38465.
42. Aprelikova O, Chandramouli G V, Wood M, Vasselli J R, Riss J, et al. (2004) Regulation of HIF prolyl hydroxylases by hypoxia-inducible factors. J Cell Biochem 92: 491-501.
43. del Peso L, Castellanos M C, Temes E, Martin-Puig S, Cuevas Y, et al. (2003) The von Hippel Lindau/hypoxia-inducible factor (HIF) pathway regulates the transcription of the HIF-proline hydroxylase genes in response to low oxygen. J Biol Chem 278: 48690-48695.
44. McMahon S, Charbonneau M, Grandmont S, Richard D E, Dubois C M (2006) Transforming growth factor beta 1 induces hypoxia-inducible factor-1 stabilization through selective inhibition of PHD2 expression. J Biol Chem 281: 24171-24181.
45. Tian Y M, Mole D R, Ratcliffe P J, Gleadle J M (2006) Characterization of different isoforms of the HIF prolyl hydroxylase PHD1 generated by alternative initiation. Biochem J 397: 179-186.
46. Chen Y R, Dai A G, Hu R C, Jiang Y L (2006) Differential and reciprocal regulation between hypoxia-inducible factor-alpha subunits and their prolyl hydroxylases in pulmonary arteries of rat with hypoxia-induced hypertension. Acta Biochim Biophys Sin (Shanghai) 38: 423-434.
47. Iwai A, Marusawa H, Matsuzawa S, Fukushima T, Hijikata M, et al. (2004) Siah-1L, a novel transcript variant belonging to the human Siah family of proteins, regulates beta-catenin activity in a p53-dependent manner. Oncogene 23: 7593-7600.
48. Huppertz B, Kadyrov M, Kingdom J C (2006) Apoptosis and its role in the trophoblast. Am Obstet Gynecol 195: 29-39.
49. Nakayama K, Gazdoiu S, Abraham R, Pan Z Q, Ronai Z (2007) Hypoxia-induced assembly of prolyl hydroxylase PHD3 into complexes: implications for its activity and susceptibility for degradation by the E3 ligase Siah2. Biochem J 401: 217-226.
50. Erez N, Milyaysky M, Eilam R, Shats I, Goldfinger N, et al. (2003) Expression of prolyl-hydroxylase-1 (PHD1/EGLN2) suppresses hypoxia inducible factor-1 alpha activation and inhibits tumor growth. Cancer Res 63: 8777-8783.
51. Koivunen P, Hirsila M, Gunzler V, Kivirikko K I, Myllyharju J (2004) Catalytic properties of the asparaginyl hydroxylase (FIH) in the oxygen sensing pathway are distinct from those of its prolyl 4-hydroxylases. J Biol Chem 279: 9899-9904.
52. Ahmad S, Ahmed A (2004) Elevated placental soluble vascular endothelial growth factor receptor-1 inhibits angiogenesis in preeclampsia. Circ Res 95: 884-891.
53. Li H, Gu B, Zhang Y, Lewis D F, Wang Y (2005) Hypoxia-induced increase in soluble Flt-1 production correlates with enhanced oxidative stress in trophoblast cells from the human placenta. Placenta 26: 210-217.
54. Ahmed A, Li X F, Dunk C, Whittle M J, Rushton D I, et al. (1995) Colocalisation of vascular endothelial growth factor and its Flt-1 receptor in human placenta. Growth Factors 12: 235-243.
55. Chung J Y, Song Y, Wang Y, Magness R R, Zheng J (2004) Differential expression of vascular endothelial growth factor (VEGF), endocrine gland derived-VEGF, and VEGF receptors in human placentas from normal and preeclamptic pregnancies. J Clin Endocrinol Metab 89: 2484-2490.
56. Zamudio S, Wu Y, letta F, Rolfo A, Cross A, et al. (2007) Human placental hypoxia-inducible factor-1alpha expression correlates with clinical outcomes in chronic hypoxia in vivo. Am J Pathol 170: 2171-2179.
57. Redman C W, Sargent I L (2005) Latest advances in understanding preeclampsia. Science 308: 1592-1594.
58. Nevo O, Soleymanlou N, Wu Y, Xu J, Kingdom J, et al. (2006) Increased expression of sFlt-1 in in vivo and in vitro models of human placental hypoxia is mediated by HIF-1. Am J Physiol Regul Integr Comp Physiol 291: R1085-1093.
59. Koga K, Osuga Y, Yoshino O, Hirota Y, Ruimeng X, et al. (2003) Elevated serum soluble vascular endothelial growth factor receptor 1 (sVEGFR-1) levels in women with preeclampsia. Clin Endocrinol Metab 88: 2348-2351.
60. Levine R J, Maynard S E, Qian C, Lim K H, England L J, et al. (2004) Circulating angiogenic factors and the risk of preeclampsia. N Engl J Med 350: 672-683.

61. Zhou Y, McMaster M, Woo K, Janatpour M, Perry J, et al. (2002) Vascular endothelial growth factor ligands and receptors that regulate human cytotrophoblast survival are dysregulated in severe preeclampsia and hemolysis, elevated liver enzymes, and low platelets syndrome. Am J Pathol 160: 1405-1423.
62. Zhou J, Brune B (2006) Cytokines and hormones in the regulation of hypoxia inducible factor-1alpha (HIF-1alpha). Cardiovasc Hematol Agents Med Chem 4: 189-197.
63. Lopez-Lazaro M (2006) HIF-1: hypoxia-inducible factor or dysoxia-inducible factor? Faseb J 20: 828-832.
64. Hung T H, Skepper J N, Charnock-Jones D S, Burton G J (2002) Hypoxia-reoxygenation: a potent inducer of apoptotic changes in the human placenta and possible etiological factor in preeclampsia. Circ Res 90: 1274-1281.
65. Hung T H, Skepper J N, Burton G J (2001) In vitro ischemia-reperfusion injury in term human placenta as a model for oxidative stress in pathological pregnancies. Am J Pathol 159: 1031-1043.
66. Ahmed A, Kilby M D (1997) Hypoxia or hyperoxia in placental insufficiency? Lancet 350: 826-827.
67. Krebs C, Macara L M, Leiser R, Bowman A W, Greer I A, et al. (1996) Intrauterine growth restriction with absent end-diastolic flow velocity in the umbilical artery is associated with maldevelopment of the placental terminal villous tree. Am J Obstet Gynecol 175: 1534-1542.
68. Macara L, Kingdom J C, Kaufmann P, Kohnen G, Hair J, et al. (1996) Structural analysis of placental terminal villi from growth-restricted pregnancies with abnormal umbilical artery Doppler waveforms. Placenta 17: 37-48.
69. Chandel N S, Maltepe E, Goldwasser E, Mathieu C E, Simon M C, et al. (1998) Mitochondrial reactive oxygen species trigger hypoxia-induced transcription. Proc Natl Acad Sci USA 95: 11715-11720.
70. Chandel N S, McClintock D S, Feliciano C E, Wood T M, Melendez J A, et al. (2000) Reactive oxygen species generated at mitochondrial complex III stabilize hypoxia-inducible factor-1alpha during hypoxia: a mechanism of $O_2$ sensing. J Biol Chem 275: 25130-25138.
71. Mansfield K D, Guzy R D, Pan Y, Young R M, Cash T P, et al. (2005) Mitochondrial dysfunction resulting from loss of cytochrome c impairs cellular oxygen sensing and hypoxic HIF-alpha activation. Cell Metab 1: 393-399.
72. Callapina M, Zhou J, Schmid T, Kohl R, Brune B (2005) NO restores HIF-1alpha hydroxylation during hypoxia: role of reactive oxygen species. Free Radic Biol Med 39: 925-936.
73. Brunelle J K, Bell E L, Quesada N M, Vercauteren K, Tiranti V, et al. (2005) Oxygen sensing requires mitochondrial ROS but not oxidative phosphorylation. Cell Metab 1: 409-414.
74. Guzy R D, Hoyos B, Robin E, Chen H, Liu L, et al. (2005) Mitochondrial complex III is required for hypoxia-induced ROS production and cellular oxygen sensing. Cell Metab 1: 401-408.

What is claimed is:

1. An isolated antibody or antibody fragment which binds to the human HIF-1α (SEQ ID NO: 1) comprising hydroxylated proline 402, or hydroxylated proline 402 and hydroxylated proline 564 comprising:
   (a) a variable region of a light chain of 1H1 (SEQ ID NO: 13 or 14) or a sequence sharing 95% identity therewith and a variable region of a heavy chain of 1H1 (SEQ ID NO: 16 or 17) or a sequence sharing 95% identity therewith.

2. The antibody or antibody fragment of claim 1, wherein said sequence sharing 95% identity involves only conservative substitutions at one or more non-essential amino acid residue.

3. An isolated antibody or antibody fragment comprising:
   (a) a variable region of a light chain of 1H1 (SEQ ID NO: 13 or 14) and a variable region of a heavy chain of 1H1 (SEQ ID NO: 16 or 17).

4. The antibody or antibody fragment of claim 3, wherein said antibody is a monoclonal antibody or a single chain variable fragment (scFv), Fab, or F(ab')$_2$.

5. The antibody of claim 3, comprising SEQ ID NO: 14 and SEQ ID NO: 17.

6. The antibody of claim 5, which is the 1H1 monoclonal antibody.

7. The antibody of claim 3, which binds to the human HIF-1α (SEQ ID NO: 1) comprising hydroxylated proline 402, or hydroxylated proline 402 and hydroxylated proline 564.

8. A composition or kit for use in diagnosing a pregnancy-related condition comprising an antibody or antibody fragment of claim 3.

* * * * *

SEQUENCE LISTING

```
<160> NUMBER OF SEQ ID NOS: 78

<210> SEQ ID NO 1
<211> LENGTH: 826
<212> TYPE: PRT
<213> ORGANISM: Homo sapiens
<300> PUBLICATION INFORMATION:
<308> DATABASE ACCESSION NUMBER: NP_001521.1
<309> DATABASE ENTRY DATE: 2011-06-26
<313> RELEVANT RESIDUES IN SEQ ID NO: (1)..(826)

<400> SEQUENCE: 1

Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
                20                  25                  30

Glu Ser Glu Val Phe Tyr Glu Leu Ala His Gln Leu Pro Leu Pro His
            35                  40                  45

Asn Val Ser Ser His Leu Asp Lys Ala Ser Val Met Arg Leu Thr Ile
        50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
                100                 105                 110

Ser Asp Asn Val Asn Lys Tyr Met Gly Leu Thr Gln Phe Glu Leu Thr
            115                 120                 125

Gly His Ser Val Phe Asp Phe Thr His Pro Cys Asp His Glu Glu Met
        130                 135                 140

Arg Glu Met Leu Thr His Arg Asn Gly Leu Val Lys Lys Gly Lys Glu
145                 150                 155                 160
```

-continued

```
Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
                195                 200                 205

Gln Cys Gly Tyr Lys Lys Pro Pro Met Thr Cys Leu Val Leu Ile Cys
        210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
                260                 265                 270

Arg Ser Ile Tyr Glu Tyr Tyr His Ala Leu Asp Ser Asp His Leu Thr
            275                 280                 285

Lys Thr His His Asp Met Phe Thr Lys Gly Gln Val Thr Thr Gly Gln
            290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
            340                 345                 350

Ser Leu Gln Gln Thr Glu Cys Val Leu Lys Pro Val Glu Ser Ser Asp
            355                 360                 365

Met Lys Met Thr Gln Leu Phe Thr Lys Val Glu Ser Glu Asp Thr Ser
        370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                405                 410                 415

Asp Thr Glu Thr Asp Asp Gln Gln Leu Glu Glu Val Pro Leu Tyr Asn
            420                 425                 430

Asp Val Met Leu Pro Ser Pro Asn Glu Lys Leu Gln Asn Ile Asn Leu
        435                 440                 445

Ala Met Ser Pro Leu Pro Thr Ala Glu Thr Pro Lys Pro Leu Arg Ser
    450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Thr Pro Ser Pro Ser Asp Gly Ser Thr Arg Gln Ser Ser Pro Glu
            500                 505                 510

Pro Asn Ser Pro Ser Glu Tyr Cys Phe Tyr Val Asp Ser Asp Met Val
        515                 520                 525

Asn Glu Phe Lys Leu Glu Leu Val Glu Lys Leu Phe Ala Glu Asp Thr
    530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575
```

```
Phe Asp Gln Leu Ser Pro Leu Glu Ser Ser Ala Ser Pro Glu Ser
            580                 585                 590

Ala Ser Pro Gln Ser Thr Val Thr Val Phe Gln Thr Gln Ile Gln
            595                 600                 605

Glu Pro Thr Ala Asn Ala Thr Thr Thr Ala Thr Thr Asp Glu Leu
            610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
                    645                 650                 655

Ser Pro Tyr Arg Asp Thr Gln Ser Arg Thr Ala Ser Pro Asn Arg Ala
        660                 665                 670

Gly Lys Gly Val Ile Glu Gln Thr Glu Lys Ser His Pro Arg Ser Pro
            675                 680                 685

Asn Val Leu Ser Val Ala Leu Ser Gln Arg Thr Thr Val Pro Glu Glu
        690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
                    725                 730                 735

Leu Leu Gln Gln Pro Asp Asp His Ala Ala Thr Thr Ser Leu Ser Trp
            740                 745                 750

Lys Arg Val Lys Gly Cys Lys Ser Glu Gln Asn Gly Met Glu Gln
            755                 760                 765

Lys Thr Ile Ile Leu Ile Pro Ser Asp Leu Ala Cys Arg Leu Leu Gly
770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                    805                 810                 815

Glu Leu Leu Arg Ala Leu Asp Gln Val Asn
            820                 825

<210> SEQ ID NO 2
<211> LENGTH: 735
<212> TYPE: PRT
<213> ORGANISM: Homo sapiens
<300> PUBLICATION INFORMATION:
<308> DATABASE ACCESSION NUMBER: NP_851397.1
<309> DATABASE ENTRY DATE: 2011-06-26
<313> RELEVANT RESIDUES IN SEQ ID NO: (1)..(735)

<400> SEQUENCE: 2

Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
```

-continued

```
            100                 105                 110
Ser Asp Asn Val Asn Lys Tyr Met Gly Leu Thr Gln Phe Glu Leu Thr
            115                 120             125

Gly His Ser Val Phe Asp Phe Thr His Pro Cys Asp His Glu Glu Met
        130                 135             140

Arg Glu Met Leu Thr His Arg Asn Gly Leu Val Lys Lys Gly Lys Glu
145                     150                 155                 160

Gln Asn Thr Gln Arg Ser Phe Phe Leu Arg Met Lys Cys Thr Leu Thr
                165                 170             175

Ser Arg Gly Arg Thr Met Asn Ile Lys Ser Ala Thr Trp Lys Val Leu
            180                 185             190

His Cys Thr Gly His Ile His Val Tyr Asp Thr Asn Ser Asn Gln Pro
        195                 200             205

Gln Cys Gly Tyr Lys Lys Pro Pro Met Thr Cys Leu Val Leu Ile Cys
        210                 215             220

Glu Pro Ile Pro His Pro Ser Asn Ile Glu Ile Pro Leu Asp Ser Lys
225                     230                 235             240

Thr Phe Leu Ser Arg His Ser Leu Asp Met Lys Phe Ser Tyr Cys Asp
                245                 250             255

Glu Arg Ile Thr Glu Leu Met Gly Tyr Glu Pro Glu Glu Leu Leu Gly
            260                 265             270

Arg Ser Ile Tyr Glu Tyr Tyr His Ala Leu Asp Ser Asp His Leu Thr
        275                 280             285

Lys Thr His His Asp Met Phe Thr Lys Gly Gln Val Thr Thr Gly Gln
        290                 295             300

Tyr Arg Met Leu Ala Lys Arg Gly Gly Tyr Val Trp Val Glu Thr Gln
305                     310                 315             320

Ala Thr Val Ile Tyr Asn Thr Lys Asn Ser Gln Pro Gln Cys Ile Val
                325                 330             335

Cys Val Asn Tyr Val Val Ser Gly Ile Ile Gln His Asp Leu Ile Phe
            340                 345             350

Ser Leu Gln Gln Thr Glu Cys Val Leu Lys Pro Val Glu Ser Ser Asp
        355                 360             365

Met Lys Met Thr Gln Leu Phe Thr Lys Val Glu Ser Glu Asp Thr Ser
        370                 375             380

Ser Leu Phe Asp Lys Leu Lys Lys Glu Pro Asp Ala Leu Thr Leu Leu
385                     390                 395                 400

Ala Pro Ala Ala Gly Asp Thr Ile Ile Ser Leu Asp Phe Gly Ser Asn
                405                 410             415

Asp Thr Glu Thr Asp Asp Gln Gln Leu Glu Glu Val Pro Leu Tyr Asn
            420                 425             430

Asp Val Met Leu Pro Ser Pro Asn Glu Lys Leu Gln Asn Ile Asn Leu
        435                 440             445

Ala Met Ser Pro Leu Pro Thr Ala Glu Thr Pro Lys Pro Leu Arg Ser
        450                 455             460

Ser Ala Asp Pro Ala Leu Asn Gln Glu Val Ala Leu Lys Leu Glu Pro
465                     470                 475                 480

Asn Pro Glu Ser Leu Glu Leu Ser Phe Thr Met Pro Gln Ile Gln Asp
                485                 490             495

Gln Thr Pro Ser Pro Ser Asp Gly Ser Thr Arg Gln Ser Ser Pro Glu
            500                 505             510

Pro Asn Ser Pro Ser Glu Tyr Cys Phe Tyr Val Asp Ser Asp Met Val
        515                 520             525
```

Asn Glu Phe Lys Leu Glu Leu Val Glu Lys Leu Phe Ala Glu Asp Thr
            530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Phe Gln Leu Arg Ser
                565                 570                 575

Phe Asp Gln Leu Ser Pro Leu Glu Ser Ser Ala Ser Pro Glu Ser
            580                 585                 590

Ala Ser Pro Gln Ser Thr Val Thr Val Phe Gln Thr Gln Ile Gln
            595                 600                 605

Glu Pro Thr Ala Asn Ala Thr Thr Thr Ala Thr Asp Glu Leu
            610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
                645                 650                 655

Ser Pro Tyr Arg Asp Thr Gln Ser Arg Thr Ala Ser Pro Asn Arg Ala
                660                 665                 670

Gly Lys Gly Val Ile Glu Gln Thr Glu Lys Ser His Pro Arg Ser Pro
            675                 680                 685

Asn Val Leu Ser Val Ala Leu Ser Gln Arg Thr Thr Val Pro Glu Glu
690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Ile
                725                 730                 735

<210> SEQ ID NO 3
<211> LENGTH: 21
<212> TYPE: DNA
<213> ORGANISM: Artificial Sequence
<220> FEATURE:
<223> OTHER INFORMATION: Synthetic

<400> SEQUENCE: 3
atgacgggaa aggctactcc a                                              21

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
agttgcgaat ggatcccaaa                                                20

<210> SEQ ID NO 5
<211> LENGTH: 23
<212> TYPE: DNA
<213> ORGANISM: Artificial Sequence
<220> FEATURE:
<223> OTHER INFORMATION: Synthetic

<400> SEQUENCE: 5
cgagaagatg acccagatca tgt                                            23

<210> SEQ ID NO 6
<211> LENGTH: 23

<212> TYPE: DNA
<213> ORGANISM: Artificial Sequence
<220> FEATURE:
<223> OTHER INFORMATION: Synthetic

<400> SEQUENCE: 6
ccacaggact ccatgcccag gaa                                           23

<210> SEQ ID NO 7
<211> LENGTH: 145
<212> TYPE: PRT
<213> ORGANISM: Artificial Sequence
<220> FEATURE:
<223> OTHER INFORMATION: Synthetic

<400> SEQUENCE: 7

Gly Asp Gln Ser Pro Gln Ala Val Ser Ser Gly Cys Leu Leu Lys Met
1               5                   10                  15

Lys Leu Pro Val Arg Leu Leu Val Leu Met Phe Trp Ile Pro Val Ser
            20                  25                  30

Ser Ser Asp Val Leu Met Thr Gln Thr Pro Leu Ser Leu Pro Val Ser
        35                  40                  45

Leu Gly Asp Gln Ala Ser Ile Ser Cys Arg Ser Gln Ser Ile Val
    50                  55                  60

His Ser Asn Gly Asn Thr Tyr Leu Glu Trp Tyr Leu Gln Lys Pro Gly
65                  70                  75                  80

Gln Ser Pro Lys Leu Leu Ile Tyr Lys Val Ser Asn Arg Phe Ser Gly
                85                  90                  95

Val Pro Asp Arg Phe Ser Gly Ser Gly Ser Gly Thr Asp Phe Thr Leu
            100                 105                 110

Lys Ile Ser Arg Val Glu Ala Glu Asp Leu Gly Val Tyr Tyr Cys Phe
        115                 120                 125

Gln Gly Thr His Val Pro Leu Thr Phe Gly Ala Gly Thr Lys Leu Glu
    130                 135                 140

Leu
145

<210> SEQ ID NO 8
<211> LENGTH: 129
<212> TYPE: PRT
<213> ORGANISM: Artificial Sequence
<220> FEATURE:
<223> OTHER INFORMATION: Synthetic

<400> SEQUENCE: 8

Lys Leu Pro Val Arg Leu Leu Val Leu Met Phe Trp Ile Pro Val Ser
1               5                   10                  15

Ser Ser Asp Val Leu Met Thr Gln Thr Pro Leu Ser Leu Pro Val Ser
            20                  25                  30

Leu Gly Asp Gln Ala Ser Ile Ser Cys Arg Ser Ser Gln Ser Ile Val
        35                  40                  45

His Ser Asn Gly Asn Thr Tyr Leu Glu Trp Tyr Leu Gln Lys Pro Gly
    50                  55                  60

Gln Ser Pro Lys Leu Leu Ile Tyr Lys Val Ser Asn Arg Phe Ser Gly
65                  70                  75                  80

Val Pro Asp Arg Phe Ser Gly Ser Gly Ser Gly Thr Asp Phe Thr Leu
                85                  90                  95

Lys Ile Ser Arg Val Glu Ala Glu Asp Leu Gly Val Tyr Tyr Cys Phe
            100                 105                 110

Gln Gly Thr His Val Pro Leu Thr Phe Gly Ala Gly Thr Lys Leu Glu
            115                 120                 125

Leu

<210> SEQ ID NO 9
<211> LENGTH: 15
<212> TYPE: PRT
<213> ORGANISM: Artificial Sequence
<220> FEATURE:
<223> OTHER INFORMATION: Synthetic

<400> SEQUENCE: 9

Lys Arg Ala Asp Ala Ala Pro Thr Val Ser Ile Phe Pro Pro Ser
1               5                   10                  15

<210> SEQ ID NO 10
<211> LENGTH: 146
<212> TYPE: PRT
<213> ORGANISM: Artificial Sequence
<220> FEATURE:
<223> OTHER INFORMATION: Synthetic

<400> SEQUENCE: 10

Ser Ser Asp Arg Gly Ala Lys Pro Trp Ile Pro Arg Ser Ser His Ser
1               5                   10                  15

Val Ile Ser Thr Glu His Arg Pro Leu Thr Met Asp Ser Arg Leu Asn
            20                  25                  30

Leu Val Phe Leu Val Leu Ile Leu Lys Gly Val Gln Cys Asp Val Gln
        35                  40                  45

Leu Val Glu Ser Gly Gly Gly Leu Val Gln Pro Gly Gly Ser Arg Lys
    50                  55                  60

Leu Ser Cys Ala Ala Ser Gly Phe Thr Phe Ser Ser Phe Gly Met His
65                  70                  75                  80

Trp Val Arg Gln Ala Pro Glu Lys Gly Leu Glu Trp Val Ala Phe Ile
                85                  90                  95

Ser Ser Gly Ser His Thr Ile Phe Tyr Ala Asp Thr Val Lys Gly Arg
            100                 105                 110

Phe Thr Ile Ser Arg Asp Asn Pro Lys Asn Thr Leu Phe Leu Gln Met
        115                 120                 125

Thr Ser Leu Arg Ser Glu Asp Thr Ala Met Tyr Tyr Cys Thr Arg Asp
    130                 135                 140

Tyr Asn
145

<210> SEQ ID NO 11
<211> LENGTH: 119
<212> TYPE: PRT
<213> ORGANISM: Artificial Sequence
<220> FEATURE:
<223> OTHER INFORMATION: Synthetic

<400> SEQUENCE: 11

Asp Ser Arg Leu Asn Leu Val Phe Leu Val Leu Ile Leu Lys Gly Val
1               5                   10                  15

Gln Cys Asp Val Gln Leu Val Glu Ser Gly Gly Gly Leu Val Gln Pro
            20                  25                  30

Gly Gly Ser Arg Lys Leu Ser Cys Ala Ala Ser Gly Phe Thr Phe Ser
        35                  40                  45

Ser Phe Gly Met His Trp Val Arg Gln Ala Pro Glu Lys Gly Leu Glu

```
                 50                  55                  60
Trp Val Ala Phe Ile Ser Ser Gly Ser His Thr Ile Phe Tyr Ala Asp
 65                  70                  75                  80

Thr Val Lys Gly Arg Phe Thr Ile Ser Arg Asp Asn Pro Lys Asn Thr
                 85                  90                  95

Leu Phe Leu Gln Met Thr Ser Leu Arg Ser Glu Asp Thr Ala Met Tyr
                100                 105                 110

Tyr Cys Thr Arg Asp Tyr Asn
            115
```

<210> SEQ ID NO 12
<211> LENGTH: 17
<212> TYPE: PRT
<213> ORGANISM: Artificial Sequence
<220> FEATURE:
<223> OTHER INFORMATION: Synthetic

<400> SEQUENCE: 12

```
Ala Tyr Trp Gly Gln Gly Thr Leu Val Thr Val Ser Ala Ala Lys Thr
 1               5                  10                  15

Thr
```

<210> SEQ ID NO 13
<211> LENGTH: 145
<212> TYPE: PRT
<213> ORGANISM: Artificial Sequence
<220> FEATURE:
<223> OTHER INFORMATION: Synthetic

<400> SEQUENCE: 13

```
Gly Asp Gln Ser Pro Gln Ala Val Ser Ser Gly Cys Leu Leu Lys Met
 1               5                  10                  15

Lys Leu Pro Val Arg Leu Leu Val Leu Met Phe Trp Ile Pro Ala Ser
                 20                  25                  30

Ser Ser Asp Val Leu Met Thr Gln Thr Pro Leu Ser Leu Pro Val Ser
                 35                  40                  45

Leu Gly Asp Gln Ala Ser Ile Ser Cys Arg Ser Ser Gln Ser Ile Val
 50                  55                  60

His Ser Asn Gly Asn Thr Tyr Leu Glu Trp Tyr Leu Gln Lys Pro Gly
 65                  70                  75                  80

Gln Ser Pro Lys Val Leu Ile Tyr Lys Val Ser Asn Arg Phe Ser Gly
                 85                  90                  95

Val Pro Asp Arg Phe Ser Gly Ser Gly Thr Asp Phe Thr Leu
                100                 105                 110

Lys Ile Ser Arg Val Glu Ala Glu Asp Leu Gly Leu Tyr Tyr Cys Phe
            115                 120                 125

Gln Gly Ser His Val Pro Trp Thr Phe Gly Gly Gly Thr Lys Leu Glu
    130                 135                 140

Ile
145
```

<210> SEQ ID NO 14
<211> LENGTH: 129
<212> TYPE: PRT
<213> ORGANISM: Artificial Sequence
<220> FEATURE:
<223> OTHER INFORMATION: Synthetic

<400> SEQUENCE: 14

Lys Leu Pro Val Arg Leu Val Leu Met Phe Trp Ile Pro Ala Ser
1               5                   10                  15

Ser Ser Asp Val Leu Met Thr Gln Thr Pro Leu Ser Leu Pro Val Ser
            20                  25                  30

Leu Gly Asp Gln Ala Ser Ile Ser Cys Arg Ser Ser Gln Ser Ile Val
        35                  40                  45

His Ser Asn Gly Asn Thr Tyr Leu Glu Trp Tyr Leu Gln Lys Pro Gly
    50                  55                  60

Gln Ser Pro Lys Val Leu Ile Tyr Lys Val Ser Asn Arg Phe Ser Gly
65                  70                  75                  80

Val Pro Asp Arg Phe Ser Gly Ser Gly Ser Gly Thr Asp Phe Thr Leu
                85                  90                  95

Lys Ile Ser Arg Val Glu Ala Glu Asp Leu Gly Leu Tyr Tyr Cys Phe
            100                 105                 110

Gln Gly Ser His Val Pro Trp Thr Phe Gly Gly Gly Thr Lys Leu Glu
        115                 120                 125

Ile

<210> SEQ ID NO 15
<211> LENGTH: 28
<212> TYPE: PRT
<213> ORGANISM: Artificial Sequence
<220> FEATURE:
<223> OTHER INFORMATION: Synthetic

<400> SEQUENCE: 15

Lys Arg Ala Asp Ala Ala Pro Thr Val Ser Ile Phe Pro Pro Ser Ser
1               5                   10                  15

Glu Gln Leu Thr Ser Gly Gly Ala Ser Val Val Cys
            20                  25

<210> SEQ ID NO 16
<211> LENGTH: 154
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa can be any naturally occurring amino acid

<400> SEQUENCE: 16

Gly Glu Leu Xaa Gln Arg Arg Pro Val Leu Asp Ser Ile Pro Ser Ser
1               5                   10                  15

Ser His Ser Val Ser Thr Glu His Gly Pro Leu Thr Met Asn Phe Gly
            20                  25                  30

Leu Ser Leu Ile Phe Leu Val Leu Leu Lys Gly Val Gln Cys Glu
        35                  40                  45

Val Met Leu Val Glu Ser Gly Gly Gly Leu Val Lys Pro Gly Gly Ser
    50                  55                  60

Leu Lys Leu Ser Cys Ala Ala Ser Gly Phe Thr Phe Ser Asn Tyr Ala
65                  70                  75                  80

Met Ser Trp Val Arg Gln Thr Pro Glu Lys Arg Leu Glu Trp Val Ala
                85                  90                  95

Ala Ile Ser Ile Gly Gly Thr Tyr Thr Phe Tyr Ser Asp Ser Val Lys
            100                 105                 110

Gly Arg Phe Thr Ile Ser Arg Asp Asn Ala Lys Asn Thr Leu Tyr Leu
        115                 120                 125

```
Gln Met Ser Ser Leu Arg Ser Glu Asp Thr Ala Met Tyr Tyr Cys Ala
    130                 135                 140

Arg Arg Arg Phe Asp Asp Tyr Ala Met Asp
145                 150
```

<210> SEQ ID NO 17
<211> LENGTH: 122
<212> TYPE: PRT
<213> ORGANISM: Artificial Sequence
<220> FEATURE:
<223> OTHER INFORMATION: Synthetic

<400> SEQUENCE: 17

```
Asn Phe Gly Leu Ser Leu Ile Phe Leu Val Leu Val Leu Lys Gly Val
1               5                   10                  15

Gln Cys Glu Val Met Leu Val Glu Ser Gly Gly Gly Leu Val Lys Pro
            20                  25                  30

Gly Gly Ser Leu Lys Leu Ser Cys Ala Ala Ser Gly Phe Thr Phe Ser
        35                  40                  45

Asn Tyr Ala Met Ser Trp Val Arg Gln Thr Pro Glu Lys Arg Leu Glu
    50                  55                  60

Trp Val Ala Ala Ile Ser Ile Gly Gly Thr Tyr Thr Phe Tyr Ser Asp
65                  70                  75                  80

Ser Val Lys Gly Arg Phe Thr Ile Ser Arg Asp Asn Ala Leu Tyr Leu
                85                  90                  95

Gln Met Ser Ser Leu Arg Ser Glu Asp Thr Ala Met Tyr Tyr Cys Ala
            100                 105                 110

Arg Arg Arg Phe Asp Asp Tyr Ala Met Asp
        115                 120
```

<210> SEQ ID NO 18
<211> LENGTH: 43
<212> TYPE: PRT
<213> ORGANISM: Artificial Sequence
<220> FEATURE:
<223> OTHER INFORMATION: Synthetic

<400> SEQUENCE: 18

```
Tyr Trp Gly Gln Gly Thr Ser Val Thr Val Ser Ser Ala Lys Thr Thr
1               5                   10                  15

Ala Pro Ser Val Tyr Pro Leu Ala Pro Val Cys Gly Asp Thr Thr Gly
            20                  25                  30

Ser Ser Val Thr Leu Gly Cys Leu Val Lys Gly
        35                  40
```

<210> SEQ ID NO 19
<211> LENGTH: 146
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (57)..(57)
<223> OTHER INFORMATION: Xaa can be any naturally occurring amino acid

<400> SEQUENCE: 19

```
Gly Thr Asp Gln Ser Pro Gln Ala Val Ser Ser Gly Cys Leu Leu Lys
1               5                   10                  15

Met Lys Leu Pro Val Arg Leu Leu Val Leu Met Phe Trp Ile Pro Ala
            20                  25                  30
```

```
Ser Thr Ser Asp Val Leu Met Thr Gln Thr Pro Leu Ser Leu Pro Val
        35                  40                  45

Ser Leu Gly Asp Gln Ala Ser Ile Xaa Cys Arg Ser Ser Gln Asn Ile
 50                  55                  60

Leu His Ser Ser Gly Asn Thr Tyr Leu Glu Trp Tyr Leu Gln Lys Pro
 65                  70                  75                  80

Gly Gln Ser Pro Lys Leu Leu Ile Tyr Lys Val Ser Asn Arg Phe Ser
                 85                  90                  95

Gly Val Pro Asp Arg Phe Ser Gly Ser Gly Ser Gly Thr Asp Phe Thr
                100                 105                 110

Leu Lys Ile Ser Arg Val Glu Gly Glu Asp Leu Gly Leu Tyr Phe Cys
            115                 120                 125

Phe Gln Gly Pro His Val Pro Phe Thr Phe Gly Ser Gly Thr Lys Leu
        130                 135                 140

Glu Ile
145

<210> SEQ ID NO 20
<211> LENGTH: 129
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (40)..(40)
<223> OTHER INFORMATION: Xaa can be any naturally occurring amino acid

<400> SEQUENCE: 20

Lys Leu Pro Val Arg Leu Leu Val Leu Met Phe Trp Ile Pro Ala Ser
 1               5                  10                  15

Thr Ser Asp Val Leu Met Thr Gln Thr Pro Leu Ser Leu Pro Val Ser
                20                  25                  30

Leu Gly Asp Gln Ala Ser Ile Xaa Cys Arg Ser Ser Gln Asn Ile Leu
            35                  40                  45

His Ser Ser Gly Asn Thr Tyr Leu Glu Trp Tyr Leu Gln Lys Pro Gly
 50                  55                  60

Gln Ser Pro Lys Leu Leu Ile Tyr Lys Val Ser Asn Arg Phe Ser Gly
 65                  70                  75                  80

Val Pro Asp Arg Phe Ser Gly Ser Gly Ser Gly Thr Asp Phe Thr Leu
                 85                  90                  95

Lys Ile Ser Arg Val Glu Gly Glu Asp Leu Gly Leu Tyr Phe Cys Phe
            100                 105                 110

Gln Gly Pro His Val Pro Phe Thr Phe Gly Ser Gly Thr Lys Leu Glu
        115                 120                 125

Ile

<210> SEQ ID NO 21
<211> LENGTH: 29
<212> TYPE: PRT
<213> ORGANISM: Artificial Sequence
<220> FEATURE:
<223> OTHER INFORMATION: Synthetic

<400> SEQUENCE: 21

Lys Arg Ala Asp Ala Ala Pro Thr Val Ser Ile Phe Pro Pro Ser Ser
 1               5                  10                  15

Glu Gln Leu Thr Ser Gly Gly Ala Ser Val Val Cys Ser
```

```
            20                  25

<210> SEQ ID NO 22
<211> LENGTH: 161
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid

<400> SEQUENCE: 22

Gly Leu Xaa Gln Arg Arg Gln Val Leu Asp Ser Ile Pro Ser Ser Ser
1               5                   10                  15

His Ser Val Ser Thr Glu His Gly Pro Leu Thr Met Asn Phe Val Leu
            20                  25                  30

Arg Leu Ile Phe Leu Ala Leu Ile Leu Lys Gly Val Gln Cys Glu Val
        35                  40                  45

Gln Leu Val Glu Ser Gly Gly Gly Leu Val Lys Pro Gly Gly Ser Leu
    50                  55                  60

Gln Leu Ser Cys Ala Ala Ser Gly Phe Thr Phe Ser Asn Phe Ala Met
65                  70                  75                  80

Ser Trp Val Arg Gln Thr Pro Glu Lys Arg Leu Glu Trp Val Ala Ala
                85                  90                  95

Ile Ser Phe Gly Gly Asp Tyr Thr Phe Tyr Leu Asp Ser Val Lys Gly
            100                 105                 110

Arg Phe Thr Ile Ser Arg Asp Asn Ala Lys Asn Thr Leu Tyr Leu Gln
        115                 120                 125

Met Arg Ser Leu Lys Ser Glu Asp Thr Ala Met Tyr Tyr Cys Val Arg
    130                 135                 140

Arg Glu Tyr Gly Asn Phe Ala Met Ala Tyr Trp Gly Gln Gly Thr Ser
145                 150                 155                 160

Val

<210> SEQ ID NO 23
<211> LENGTH: 133
<212> TYPE: PRT
<213> ORGANISM: Artificial Sequence
<220> FEATURE:
<223> OTHER INFORMATION: Synthetic

<400> SEQUENCE: 23

Asn Phe Val Leu Arg Leu Ile Phe Leu Ala Leu Ile Leu Lys Gly Val
1               5                   10                  15

Gln Cys Glu Val Gln Leu Val Glu Ser Gly Gly Gly Leu Val Lys Pro
            20                  25                  30

Gly Gly Ser Leu Gln Leu Ser Cys Ala Ala Ser Gly Phe Thr Phe Ser
        35                  40                  45

Asn Phe Ala Met Ser Trp Val Arg Gln Thr Pro Glu Lys Arg Leu Glu
    50                  55                  60

Trp Val Ala Ala Ile Ser Phe Gly Gly Asp Tyr Thr Phe Tyr Leu Asp
65                  70                  75                  80

Ser Val Lys Gly Arg Phe Thr Ile Ser Arg Asp Asn Ala Lys Asn Thr
                85                  90                  95

Leu Tyr Leu Gln Met Arg Ser Leu Lys Ser Glu Asp Thr Ala Met Tyr
            100                 105                 110
```

```
Tyr Cys Val Arg Arg Glu Tyr Gly Asn Phe Ala Met Ala Tyr Trp Gly
            115                 120                 125

Gln Gly Thr Ser Val
    130

<210> SEQ ID NO 24
<211> LENGTH: 28
<212> TYPE: PRT
<213> ORGANISM: Artificial Sequence
<220> FEATURE:
<223> OTHER INFORMATION: Synthetic

<400> SEQUENCE: 24

Thr Val Ser Ser Ala Lys Thr Thr Pro Pro Ser Val Tyr Pro Leu Ala
1               5                   10                  15

Pro Gly Phe Ala Val Gln Thr Asn Ser Met Val Ile
            20                  25

<210> SEQ ID NO 25
<211> LENGTH: 138
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid

<400> SEQUENCE: 25

Gly Glu Ser His Ser Gln Xaa Gly Tyr Thr Ile Ser Met Arg Val Leu
1               5                   10                  15

Ala Glu Leu Leu Gly Val Leu Val Phe Cys Phe Leu Gly Val Arg Cys
            20                  25                  30

Asp Ile Gln Met Asn Gln Ser Pro Ser Ser Leu Ser Ala Ser Xaa Gly
        35                  40                  45

Asp Thr Ile Thr Ile Thr Cys Gln Ala Ser Gln Asn Ile Asn Val Trp
    50                  55                  60

Leu Ser Trp Tyr Gln Gln Lys Pro Gly Asn Ile Pro Lys Leu Met Ile
65                  70                  75                  80

Ser Lys Ala Ser Asn Leu His Thr Val Val Pro Ser Arg Leu Ser Arg
                85                  90                  95

Ser Gly Cys Gly Thr Gly Cys Thr Leu Pro Ile His Pro Leu Gln Arg
            100                 105                 110

Gly Gly Gly Cys Cys His Phe Phe Gln Pro Ala Gln Gln Gly Ala Phe
        115                 120                 125

Thr Phe Gly Gly Gly Thr Lys Leu Glu Ile
    130                 135

<210> SEQ ID NO 26
<211> LENGTH: 125
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (34)..(34)
<223> OTHER INFORMATION: Xaa can be any naturally occurring amino acid
```

<400> SEQUENCE: 26

Arg Val Leu Ala Glu Leu Leu Gly Val Leu Phe Cys Phe Leu Gly
1               5                   10                  15

Val Arg Cys Asp Ile Gln Met Asn Gln Ser Pro Ser Ser Leu Ser Ala
            20                  25                  30

Ser Xaa Gly Asp Thr Ile Thr Ile Thr Cys Gln Ala Ser Gln Asn Ile
        35                  40                  45

Asn Val Trp Leu Ser Trp Tyr Gln Gln Lys Pro Gly Asn Ile Pro Lys
    50                  55                  60

Leu Met Ile Ser Lys Ala Ser Asn Leu His Thr Val Pro Ser Arg
65                  70                  75                  80

Leu Ser Arg Ser Gly Cys Gly Thr Gly Cys Thr Leu Pro Ile His Pro
                85                  90                  95

Leu Gln Arg Gly Gly Gly Cys Cys His Phe Phe Gln Pro Ala Gln Gln
            100                 105                 110

Gly Ala Phe Thr Phe Gly Gly Gly Thr Lys Leu Glu Ile
            115                 120                 125

<210> SEQ ID NO 27
<211> LENGTH: 152
<212> TYPE: PRT
<213> ORGANISM: Artificial Sequence
<220> FEATURE:
<223> OTHER INFORMATION: Synthetic

<400> SEQUENCE: 27

Gly Asn Ile Cys Pro Met Ser Ser Pro Gln Thr Leu Asn Thr Leu Thr
1               5                   10                  15

Leu Thr Met Gly Trp Asn Trp Ile Phe Leu Phe Leu Leu Ser Gly Ile
            20                  25                  30

Ala Gly Val Leu Ser Glu Val Gln Leu Gln Gln Ser Gly Pro Glu Leu
        35                  40                  45

Val Lys Pro Gly Ala Ser Ile Lys Ile Ser Cys Lys Thr Ser Gly Tyr
    50                  55                  60

Thr Phe Thr Glu Tyr Ser Met His Trp Val Lys Gln Ser His Gly Lys
65                  70                  75                  80

Ser Leu Glu Trp Ile Gly Gly Phe Asn Pro Asn Asn Gly Tyr Ser His
                85                  90                  95

Tyr Asn Gln Lys Phe Lys Asp Lys Ala Thr Leu Thr Val Asp Lys Ser
            100                 105                 110

Ser Ser Thr Ala Tyr Met Glu Leu Arg Ser Leu Thr Ser Glu Asp Ser
            115                 120                 125

Ala Val Phe Tyr Cys Ala Arg Ser Asp Ser Lys Tyr Thr Tyr Phe Ala
            130                 135                 140

Tyr Trp Gly Gln Gly Thr Leu Val
145                 150

<210> SEQ ID NO 28
<211> LENGTH: 133
<212> TYPE: PRT
<213> ORGANISM: Artificial Sequence
<220> FEATURE:
<223> OTHER INFORMATION: Synthetic

<400> SEQUENCE: 28

Gly Trp Asn Trp Ile Phe Leu Phe Leu Leu Ser Gly Ile Ala Gly Val
1               5                   10                  15

```
Leu Ser Glu Val Gln Leu Gln Gln Ser Gly Pro Glu Leu Val Lys Pro
            20                  25                  30

Gly Ala Ser Ile Lys Ile Ser Cys Lys Thr Ser Gly Tyr Thr Phe Thr
        35                  40                  45

Glu Tyr Ser Met His Trp Val Lys Gln Ser His Gly Lys Ser Leu Glu
 50                  55                  60

Trp Ile Gly Gly Phe Asn Pro Asn Asn Gly Tyr Ser His Tyr Asn Gln
 65                  70                  75                  80

Lys Phe Lys Asp Lys Ala Thr Leu Thr Val Asp Lys Ser Ser Ser Thr
                85                  90                  95

Ala Tyr Met Glu Leu Arg Ser Leu Thr Ser Glu Asp Ser Ala Val Phe
            100                 105                 110

Tyr Cys Ala Arg Ser Asp Ser Lys Tyr Thr Tyr Phe Ala Tyr Trp Gly
        115                 120                 125

Gln Gly Thr Leu Val
        130
```

<210> SEQ ID NO 29
<211> LENGTH: 9
<212> TYPE: PRT
<213> ORGANISM: Artificial Sequence
<220> FEATURE:
<223> OTHER INFORMATION: Synthetic

<400> SEQUENCE: 29

```
Thr Val Ser Ala Ala Lys Thr Thr Pro
 1               5
```

<210> SEQ ID NO 30
<211> LENGTH: 146
<212> TYPE: PRT
<213> ORGANISM: Artificial Sequence
<220> FEATURE:
<223> OTHER INFORMATION: Synthetic

<400> SEQUENCE: 30

```
Gly Thr Asp Gln Ser Pro Gln Ala Val Ser Ser Gly Cys Leu Leu Lys
 1               5                  10                  15

Met Lys Leu Pro Val Arg Leu Leu Val Leu Met Phe Trp Ile Pro Ala
            20                  25                  30

Phe Ser Asp Val Leu Met Ser Gln Asn Pro Leu Ser Leu Pro Val
        35                  40                  45

Ser Leu Gly Asp Gln Ala Ser Ile Ser Cys Arg Ser Ser Gln Ser Ile
 50                  55                  60

Val His Ser Asn Gly Asn Thr Tyr Leu Glu Trp Tyr Leu Gln Lys Pro
 65                  70                  75                  80

Gly Gln Ser Pro Lys Val Leu Ile Tyr Glu Val Ser Asn Arg Phe Ser
                85                  90                  95

Gly Val Pro Asp Arg Phe Ser Cys Thr Gly Ser Gly Thr Asp Leu Pro
            100                 105                 110

Leu Lys Ile Ser Arg Val Glu Ala Glu Gly Leu Gly Leu Tyr Tyr Cys
        115                 120                 125

Phe Gln Gly Ser His Val Pro Trp Thr Phe Gly Gly Gly Thr Lys Leu
        130                 135                 140

Glu Ile
145
```

<210> SEQ ID NO 31

<211> LENGTH: 128
<212> TYPE: PRT
<213> ORGANISM: Artificial Sequence
<220> FEATURE:
<223> OTHER INFORMATION: Synthetic

<400> SEQUENCE: 31

Lys Leu Pro Val Arg Leu Leu Val Leu Met Phe Trp Ile Pro Ala Phe
1               5                   10                  15

Ser Ser Asp Val Leu Met Ser Gln Asn Pro Leu Ser Leu Pro Val Ser
            20                  25                  30

Leu Gly Asp Gln Ala Ser Ile Ser Cys Arg Ser Ser Gln Ser Ile Val
        35                  40                  45

His Ser Asn Gly Asn Thr Tyr Leu Glu Trp Tyr Leu Gln Lys Pro Gly
    50                  55                  60

Gln Ser Pro Lys Val Leu Ile Tyr Glu Val Ser Asn Arg Phe Ser Gly
65                  70                  75                  80

Val Pro Asp Arg Phe Ser Cys Thr Gly Ser Gly Thr Asp Leu Pro Leu
                85                  90                  95

Lys Ile Ser Arg Val Glu Ala Glu Gly Leu Gly Leu Tyr Tyr Cys Phe
            100                 105                 110

Gln Gly Ser His Val Pro Trp Thr Phe Gly Gly Thr Lys Leu Glu Ile
        115                 120                 125

<210> SEQ ID NO 32
<211> LENGTH: 8
<212> TYPE: PRT
<213> ORGANISM: Artificial Sequence
<220> FEATURE:
<223> OTHER INFORMATION: Synthetic

<400> SEQUENCE: 32

Lys Arg Ala Asp Ala Ala Pro Thr
1               5

<210> SEQ ID NO 33
<211> LENGTH: 152
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid

<400> SEQUENCE: 33

Val Xaa Gln Arg Arg Pro Val Leu Asp Ser Ile Pro Ser Ser Ser His
1               5                   10                  15

Ser Val Ser Thr Glu His Gly Pro Leu Thr Met Asn Phe Gly Leu Ser
            20                  25                  30

Leu Ile Phe Leu Val Leu Val Leu Lys Gly Val Gln Cys Glu Val Met
        35                  40                  45

Leu Val Glu Ser Gly Gly Gly Leu Val Lys Pro Gly Gly Ser Leu Lys
    50                  55                  60

Leu Ser Cys Ala Ala Ser Gly Phe Thr Phe Arg Asn Phe Ala Met Ser
65                  70                  75                  80

Trp Val Arg Gln Thr Ser Glu Lys Arg Leu Glu Trp Val Ala Ser Ile
                85                  90                  95

Ser Phe Gly Gly Asn Tyr Thr Tyr Tyr Pro Asp Ser Val Lys Gly Arg
            100                 105                 110

Phe Thr Val Ser Lys Asp Asn Ala Lys Asn Thr Leu Tyr Leu Gln Met
            115                 120                 125

Ser Ser Leu Arg Ser Glu Asp Thr Ala Met Tyr Phe Cys Ala Arg Arg
        130                 135                 140

Gly Tyr Ser His Tyr Ala Met Asp
145                 150

<210> SEQ ID NO 34
<211> LENGTH: 125
<212> TYPE: PRT
<213> ORGANISM: Artificial Sequence
<220> FEATURE:
<223> OTHER INFORMATION: Synthetic

<400> SEQUENCE: 34

Asn Phe Gly Leu Ser Leu Ile Phe Leu Val Leu Val Leu Lys Gly Val
1               5                   10                  15

Gln Cys Glu Val Met Leu Val Glu Ser Gly Gly Gly Leu Val Lys Pro
            20                  25                  30

Gly Gly Ser Leu Lys Leu Ser Cys Ala Ala Ser Gly Phe Thr Phe Arg
        35                  40                  45

Asn Phe Ala Met Ser Trp Val Arg Gln Thr Ser Glu Lys Arg Leu Glu
    50                  55                  60

Trp Val Ala Ser Ile Ser Phe Gly Gly Asn Tyr Thr Phe Tyr Pro Asp
65                  70                  75                  80

Ser Val Lys Gly Arg Phe Thr Val Ser Lys Asp Asn Ala Lys Asn Thr
                85                  90                  95

Leu Tyr Leu Gln Met Ser Ser Leu Arg Ser Glu Asp Thr Ala Met Tyr
            100                 105                 110

Phe Cys Ala Arg Arg Gly Tyr Ser His Tyr Ala Met Asp
        115                 120                 125

<210> SEQ ID NO 35
<211> LENGTH: 28
<212> TYPE: PRT
<213> ORGANISM: Artificial Sequence
<220> FEATURE:
<223> OTHER INFORMATION: Synthetic

<400> SEQUENCE: 35

Tyr Trp Gly Gln Gly Thr Ser Val Ser Val Ser Ser Ala Lys Thr Thr
1               5                   10                  15

Ala Pro Ser Val Tyr Pro Leu Ala Pro Val Cys Gly
            20                  25

<210> SEQ ID NO 36
<211> LENGTH: 146
<212> TYPE: PRT
<213> ORGANISM: Artificial Sequence
<220> FEATURE:
<223> OTHER INFORMATION: Synthetic

<400> SEQUENCE: 36

Gly Thr Asp Gln Ser Pro Gln Ala Val Ser Ser Gly Cys Leu Leu Lys
1               5                   10                  15

Met Lys Leu Pro Val Arg Leu Leu Val Leu Met Phe Trp Ile Pro Ala
            20                  25                  30

Ser Ser Ser Asp Val Leu Met Thr Gln Thr Pro Leu Ser Leu Pro Val
        35                  40                  45

-continued

```
Ser Leu Gly Asp Gln Ala Ser Ile Ser Cys Lys Ser Ser Gln Ser Ile
         50                   55                   60

Val His Ser Asn Gly Asn Thr Tyr Leu Glu Trp Tyr Leu Gln Lys Pro
 65                   70                   75                   80

Gly Gln Pro Pro Lys Val Leu Ile Tyr Lys Val Ser Asn Arg Phe Ser
                 85                   90                   95

Gly Val Pro Asp Arg Phe Ser Gly Ser Gly Ser Gly Thr Asp Ser Thr
                100                  105                 110

Leu Lys Ile Ser Arg Val Glu Ala Glu Asp Leu Gly Leu Tyr Tyr Cys
            115                  120                 125

Phe Gln Gly Ser His Val Pro Trp Thr Phe Gly Gly Gly Thr Lys Leu
        130                  135                 140

Glu Ile
145
```

<210> SEQ ID NO 37
<211> LENGTH: 129
<212> TYPE: PRT
<213> ORGANISM: Artificial Sequence
<220> FEATURE:
<223> OTHER INFORMATION: Synthetic

<400> SEQUENCE: 37

```
Lys Leu Pro Val Arg Leu Leu Val Leu Met Phe Trp Ile Pro Ala Ser
 1               5                   10                  15

Ser Ser Asp Val Leu Met Thr Gln Thr Pro Leu Ser Leu Pro Val Ser
                 20                  25                  30

Leu Gly Asp Gln Ala Ser Ile Ser Cys Lys Ser Ser Gln Ser Ile Val
             35                  40                  45

His Ser Asn Gly Asn Thr Tyr Leu Glu Trp Tyr Leu Gln Lys Pro Gly
         50                  55                  60

Gln Pro Pro Lys Val Leu Ile Tyr Lys Val Ser Asn Arg Phe Ser Gly
 65                  70                  75                  80

Val Pro Asp Arg Phe Ser Gly Ser Gly Ser Gly Thr Asp Ser Thr Leu
                 85                  90                  95

Lys Ile Ser Arg Val Glu Ala Glu Asp Leu Gly Leu Tyr Tyr Cys Phe
            100                 105                 110

Gln Gly Ser His Val Pro Trp Thr Phe Gly Gly Gly Thr Lys Leu Glu
        115                 120                 125

Ile
```

<210> SEQ ID NO 38
<211> LENGTH: 14
<212> TYPE: PRT
<213> ORGANISM: Artificial Sequence
<220> FEATURE:
<223> OTHER INFORMATION: Synthetic

<400> SEQUENCE: 38

```
Lys Arg Ala Asp Ala Ala Pro Thr Val Ser Ile Phe Pro Pro
 1               5                   10
```

<210> SEQ ID NO 39
<211> LENGTH: 167
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid

<400> SEQUENCE: 39

Val Xaa Gln Arg Arg Gln Val Leu Asp Ser Ile Pro Ser Ser Ser His
1               5                   10                  15

Ser Val Ser Thr Glu His Gly Pro Leu Thr Met Asn Phe Val Leu Ser
            20                  25                  30

Leu Ile Phe Leu Ala Leu Ile Leu Lys Gly Val Gln Cys Glu Val Gln
        35                  40                  45

Leu Val Glu Ser Gly Gly Gly Leu Val Lys Pro Gly Gly Ser Leu Lys
50                  55                  60

Leu Ser Cys Ala Ala Ser Gly Phe Thr Phe Ser Ser Tyr Ala Met Ser
65                  70                  75                  80

Trp Val Arg Gln Thr Pro Glu Lys Arg Leu Glu Trp Val Ala Ala Ile
                85                  90                  95

Ser Tyr Gly Gly Asn Tyr Thr Tyr Tyr Pro Asp Ser Val Lys Gly Arg
            100                 105                 110

Phe Thr Val Ser Arg Asp Asn Ala Lys Asn Thr Leu Tyr Leu Gln Met
        115                 120                 125

Ser Ser Leu Arg Ser Glu Asp Thr Ala Met Tyr Tyr Cys Ala Arg Arg
130                 135                 140

Ala Arg Ala Glu Tyr Tyr Tyr Ala Met Asp Tyr Trp Gly Gln Gly Thr
145                 150                 155                 160

Ser Val Thr Val Ser Ser Ala
                165

<210> SEQ ID NO 40
<211> LENGTH: 140
<212> TYPE: PRT
<213> ORGANISM: Artificial Sequence
<220> FEATURE:
<223> OTHER INFORMATION: Synthetic

<400> SEQUENCE: 40

Asn Phe Val Leu Ser Leu Ile Phe Leu Ala Leu Ile Leu Lys Gly Val
1               5                   10                  15

Gln Cys Glu Val Gln Leu Val Glu Ser Gly Gly Gly Leu Val Lys Pro
            20                  25                  30

Gly Gly Ser Leu Lys Leu Ser Cys Ala Ala Ser Gly Phe Thr Phe Ser
        35                  40                  45

Ser Tyr Ala Met Ser Trp Val Arg Gln Thr Pro Glu Lys Arg Leu Glu
50                  55                  60

Trp Val Ala Ala Ile Ser Tyr Gly Gly Asn Tyr Thr Tyr Tyr Pro Asp
65                  70                  75                  80

Ser Val Lys Gly Arg Phe Thr Val Ser Arg Asp Asn Ala Lys Asn Thr
                85                  90                  95

Leu Tyr Leu Gln Met Ser Ser Leu Arg Ser Glu Asp Thr Ala Met Tyr
            100                 105                 110

Tyr Cys Ala Arg Arg Ala Arg Ala Glu Tyr Tyr Tyr Ala Met Asp Tyr
        115                 120                 125

Trp Gly Gln Gly Thr Ser Val Thr Val Ser Ser Ala
130                 135                 140

<210> SEQ ID NO 41
<211> LENGTH: 31
<212> TYPE: PRT

<213> ORGANISM: Artificial Sequence
<220> FEATURE:
<223> OTHER INFORMATION: Synthetic

<400> SEQUENCE: 41

```
Thr Thr Thr Ala Pro Ser Val Tyr Pro Leu Val Pro Gly Cys Ser Asp
1               5                   10                  15
Thr Ser Gly Ser Ser Val Thr Leu Gly Cys Leu Val Lys Gly Tyr
            20                  25                  30
```

<210> SEQ ID NO 42
<211> LENGTH: 435
<212> TYPE: DNA
<213> ORGANISM: Artificial Sequence
<220> FEATURE:
<223> OTHER INFORMATION: Synthetic

<400> SEQUENCE: 42

```
ggtgatcagt ctcctcaggc tgtctcctca ggttgcctcc tcaaaatgaa gttgcctgtt      60
aggctgttgg tgctgatgtt ctggattcct gtttccagca gtgatgtttt gatgacccaa     120
actccactct ccctgcctgt cagtcttgga gatcaagcct ccatctcttg cagatctagt     180
cagagcattg tacatagtaa tggaaacacc tatttagaat ggtacctgca gaaaccaggc     240
cagtctccaa agctcctgat ttacaaagtt tccaaccgat tttctggggt cccagacagg     300
ttcagtggca gtggatcagg gacagatttc acactcaaga tcagcagagt ggaggctgag     360
gatctgggag tttattactg ctttcaaggt acacatgttc cgctcacgtt cggtgctggg     420
accaagctgg agctg                                                     435
```

<210> SEQ ID NO 43
<211> LENGTH: 387
<212> TYPE: DNA
<213> ORGANISM: Artificial Sequence
<220> FEATURE:
<223> OTHER INFORMATION: Synthetic

<400> SEQUENCE: 43

```
aagttgcctg ttaggctgtt ggtgctgatg ttctggattc ctgtttccag cagtgatgtt      60
ttgatgaccc aaactccact ctccctgcct gtcagtcttg agatcaagc tccatctct      120
tgcagatcta gtcagagcat tgtacatagt aatggaaaca cctatttaga atggtacctg     180
cagaaaccag gccagtctcc aaagctcctg atttacaaag tttccaaccg attttctggg     240
gtcccagaca ggttcagtgg cagtggatca gggacagatt tcacactcaa gatcagcaga     300
gtggaggctg aggatctggg agtttattac tgctttcaag gtacacatgt tccgctcacg     360
ttcggtgctg ggaccaagct ggagctg                                         387
```

<210> SEQ ID NO 44
<211> LENGTH: 45
<212> TYPE: DNA
<213> ORGANISM: Artificial Sequence
<220> FEATURE:
<223> OTHER INFORMATION: Synthetic

<400> SEQUENCE: 44

```
aaacgggctg atgctgcacc aactgtatcc atcttcccac catcc                      45
```

<210> SEQ ID NO 45
<211> LENGTH: 439
<212> TYPE: DNA
<213> ORGANISM: Artificial Sequence
<220> FEATURE:
<223> OTHER INFORMATION: Synthetic

<400> SEQUENCE: 45

```
agctctgaca gaggagccaa gccctggatt cccaggtcct cacattcagt gatcagcact      60
gaacacagac cactcaccat ggactccagg ctcaatttag ttttccttgt ccttatttta     120
aaaggtgtcc agtgtgatgt gcagctggtg gagtctgggg gaggcttagt gcagcctgga     180
gggtcccgga aactctcctg tgcagcctct ggattcactt tcagtagctt tggaatgcac     240
tgggttcgtc aggctccaga aaggggctg gagtgggtcg cattcattag tagtggcagt      300
cataccatct ctatgcaga cacagtgaag gccgattca ccatctcccg agacaatccc       360
aagaacaccc tcttcctgca aatgaccagt ctaaggtctg aggacacggc catgtattac     420
tgtacaagag actataatg                                                  439
```

<210> SEQ ID NO 46
<211> LENGTH: 358
<212> TYPE: DNA
<213> ORGANISM: Artificial Sequence
<220> FEATURE:
<223> OTHER INFORMATION: Synthetic

<400> SEQUENCE: 46

```
gactccaggc tcaatttagt tttccttgtc cttattttaa aaggtgtcca gtgtgatgtg      60
cagctggtgg agtctggggg aggcttagtg cagcctggag ggtcccggaa actctcctgt    120
gcagcctctg gattcacttt cagtagcttt ggaatgcact gggttcgtca ggctccagag    180
aaggggctgg agtgggtcgc attcattagt agtggcagtc ataccatctt ctatgcagac    240
acagtgaagg ccgattcac catctcccga acaatccca agaacaccct cttcctgcaa     300
atgaccagtc taaggtctga ggacacggcc atgtattact gtacaagaga ctataatg      358
```

<210> SEQ ID NO 47
<211> LENGTH: 50
<212> TYPE: DNA
<213> ORGANISM: Artificial Sequence
<220> FEATURE:
<223> OTHER INFORMATION: Synthetic

<400> SEQUENCE: 47

```
cttactgggg ccaagggact ctggtcactg tctctgcagc caaaacaaca               50
```

<210> SEQ ID NO 48
<211> LENGTH: 435
<212> TYPE: DNA
<213> ORGANISM: Artificial Sequence
<220> FEATURE:
<223> OTHER INFORMATION: Synthetic

<400> SEQUENCE: 48

```
ggtgatcagt ctcctcaggc tgtctcctca ggttgcctcc tcaaaatgaa gttgcctgtt      60
aggctgttgg tgctgatgtt ctggattcct gcttccagca gtgatgtttt gatgacccaa    120
actccactct ccctgcctgt cagtcttgga gatcaagcct ccatctcttg cagatctagt    180
cagagcattg tacatagtaa tggaaacacc tatttagaat ggtacctgca gaaaccaggc    240
cagtctccaa aggtcctgat ctacaaagtt tccaaccgat tttctggggt cccagacagg    300
ttcagtggca gtggatcagg gacagatttc acactcaaga tcagcagagt ggaggctgag    360
gatctgggac tttattactg ctttcaaggt tcacatgttc cgtggacgtt cggtggaggc    420
```
accaagctgg agatc 435

<210> SEQ ID NO 49
<211> LENGTH: 387
<212> TYPE: DNA
<213> ORGANISM: Artificial Sequence
<220> FEATURE:
<223> OTHER INFORMATION: Synthetic

<400> SEQUENCE: 49
aagttgcctg ttaggctgtt ggtgctgatg ttctggattc ctgcttccag cagtgatgtt      60
ttgatgaccc aaactccact ctccctgcct gtcagtcttg gagatcaagc ctccatctct     120
tgcagatcta gtcagagcat tgtacatagt aatggaaaca cctatttaga atggtacctg     180
cagaaaccag gccagtctcc aaaggtcctg atctacaaag tttccaaccg attttctggg     240
gtcccagaca ggttcagtgg cagtggatca gggacagatt tcacactcaa gatcagcaga     300
gtggaggctg aggatctggg actttattac tgctttcaag gttcacatgt tccgtggacg     360
ttcggtggag gcaccaagct ggagatc                                         387

<210> SEQ ID NO 50
<211> LENGTH: 84
<212> TYPE: DNA
<213> ORGANISM: Artificial Sequence
<220> FEATURE:
<223> OTHER INFORMATION: Synthetic

<400> SEQUENCE: 50
aaacgggctg atgctgcacc aactgtatcc atcttcccac catccagtga gcagttaaca      60
tctggaggtg cctcagtcgt gtgc                                             84

<210> SEQ ID NO 51
<211> LENGTH: 462
<212> TYPE: DNA
<213> ORGANISM: Artificial Sequence
<220> FEATURE:
<223> OTHER INFORMATION: Synthetic

<400> SEQUENCE: 51
ggggagctct gacagaggag gcctgtcctg gattcgattc ccagttcctc acattcagtc      60
agcactgaac acggacccct caccatgaac ttcgggctca gcttgatttt ccttgtcctt     120
gttttaaaag gtgtccagtg tgaagtgatg ctggtggagt ctgggggagg cttagtgaag     180
cctggagggt ccctgaaact ctcctgtgca gcctctggat tcactttcag taactatgcc     240
atgtcttggg ttcgccagac tccggagaag aggctggagt gggtcgcagc cattagtatt     300
ggtggtactt acaccttcta ttcagacagt gtgaaggggc gattcaccat ctccagagac     360
aatgccaaga acacccttta cctacaaatg agcagtctga ggtctgagga cacggccatg     420
tattactgtg caagacggag attcgacgac tatgctatgg ac                        462

<210> SEQ ID NO 52
<211> LENGTH: 375
<212> TYPE: DNA
<213> ORGANISM: Artificial Sequence
<220> FEATURE:
<223> OTHER INFORMATION: Synthetic

<400> SEQUENCE: 52
aacttcgggc tcagcttgat tttccttgtc cttgttttaa aaggtgtcca gtgtgaagtg      60
atgctggtgg agtctggggg aggcttagtg aagcctggag ggtccctgaa actctcctgt     120

```
gcagcctctg gattcacttt cagtaactat gccatgtctt gggttcgcca gactccggag    180
aagaggctgg agtgggtcgc agccattagt attggtggta cttacacctt ctattcagac    240
agtgtgaagg ggcgattcac catctccaga gacaatgcca agaacaccct ttacctacaa    300
atgagcagtc tgaggtctga ggacacggcc atgtattact gtgcaagacg agattcgac     360 gactatgcta tggac                                                     375
```

<210> SEQ ID NO 53
<211> LENGTH: 129
<212> TYPE: DNA
<213> ORGANISM: Artificial Sequence
<220> FEATURE:
<223> OTHER INFORMATION: Synthetic

<400> SEQUENCE: 53

```
tactggggtc aaggaacctc agtcaccgtc tcctcagcca aaacaacagc cccatcggtc    60
tatccactgg cccctgtgtg tggagataca actggctcct cggtgactct aggatgcctg    120
gtcaagggt                                                            129
```

<210> SEQ ID NO 54
<211> LENGTH: 438
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (170)..(170)
<223> OTHER INFORMATION: n is a, c, g, or t

<400> SEQUENCE: 54

```
gggactgatc agtctcctca ggctgtctcc tcaggttgcc tcctcaaaat gaagttgcct    60
gttaggctgt tggtgctgat gttctggatt cctgcttcca ccagtgatgt tttgatgacc    120
caaactccac tctccctgcc tgtcagtctt ggagatcaag cctccatctn ttgcagatct    180
agtcagaaca ttttacatag tagtgggaac acctacttag aatggtacct gcagaagcca    240
ggccagtctc caaagctcct gatctacaaa gtttccaacc gattttctgg ggtcccagac    300
aggttcagtg gcagtggatc agggacagat ttcacactca agatcagcag agtggagggt    360
gaggatctgg gactctactt ctgctttcaa ggtccacatg ttccattcac gttcggctcg    420
gggacaaagt tggaaata                                                  438
```

<210> SEQ ID NO 55
<211> LENGTH: 387
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (119)..(119)
<223> OTHER INFORMATION: n is a, c, g, or t

<400> SEQUENCE: 55

```
aagttgcctg ttaggctgtt ggtgctgatg ttctggattc ctgcttccac cagtgatgtt    60
ttgatgaccc aaactccact ctccctgcct gtcagtcttg gagatcaagc ctccatctnt    120
tgcagatcta gtcagaacat tttacatagt agtgggaaca cctacttaga atggtacctg    180
cagaagccag gccagtctcc aaagctcctg atctacaaag tttccaaccg attttctggg    240
```

```
gtcccagaca ggttcagtgg cagtggatca gggacagatt tcacactcaa gatcagcaga    300
gtggagggtg aggatctggg actctacttc tgctttcaag gtccacatgt tccattcacg    360
ttcggctcgg ggacaaagtt ggaaata                                        387
```

<210> SEQ ID NO 56
<211> LENGTH: 87
<212> TYPE: DNA
<213> ORGANISM: Artificial Sequence
<220> FEATURE:
<223> OTHER INFORMATION: Synthetic

<400> SEQUENCE: 56

```
aaacgggctg atgctgcacc aactgtatcc atcttcccac catccagtga gcagttaaca     60
tctggaggtg cctcagtcgt gtgctcc                                        87
```

<210> SEQ ID NO 57
<211> LENGTH: 483
<212> TYPE: DNA
<213> ORGANISM: Artificial Sequence
<220> FEATURE:
<223> OTHER INFORMATION: Synthetic

<400> SEQUENCE: 57

```
gggctctgac agaggaggca ggtcctggat tcgattccca gttcctcaca ttcagtcagc     60
actgaacacg gaccectcac catgaacttt gtgctcaggt tgattttcct tgccctcatt    120
ttaaaaggtg tccagtgtga agtgcaactg gtggagtctg ggggaggctt agtgaagcct    180
ggagggtccc tgcagctctc ctgtgcagcc tcgggattca ctttcagtaa ctttgccatg    240
tcttgggttc gccagactcc ggagaagagg ctggagtggg tcgcagccat cagttttggt    300
ggagattaca ccttctatct agacagtgtg aagggtcgat tcaccatttc cagagacaac    360
gccaagaaca ccctgtacct acaaatgcgt agtctgaagt ccgaggacac ggccatgtat    420
tactgtgtaa gacgggaata tggtaacttc gctatggcct actggggtca aggaaccctca   480 gtc                                                                  483
```

<210> SEQ ID NO 58
<211> LENGTH: 399
<212> TYPE: DNA
<213> ORGANISM: Artificial Sequence
<220> FEATURE:
<223> OTHER INFORMATION: Synthetic

<400> SEQUENCE: 58

```
aactttgtgc tcaggttgat tttccttgcc ctcattttaa aggtgtccca gtgtgaagtg     60
caactggtgg agtctggggg aggcttagtg aagcctggag gtccctgca gctctcctgt    120 gcagcctcgg gattcacttt cagtaacttt gccatgtctt gggttcgcca gactccggag    180
aagaggctgg agtgggtcgc agccatcagt tttggtggag attacaccctt ctatctagac   240 agtgtgaagg gtcgattcac catttccaga gacaacgcca gaacaccct gtacctacaa    300 atgcgtagtc tgaagtccga ggacacggcc atgtattact gtgtaagacg ggaatatggt    360
aacttcgcta tggcctactg gggtcaagga acctcagtc                           399
```

<210> SEQ ID NO 59
<211> LENGTH: 84
<212> TYPE: DNA
<213> ORGANISM: Artificial Sequence
<220> FEATURE:
<223> OTHER INFORMATION: Synthetic

<400> SEQUENCE: 59

```
accgtctcct cagccaaaac gacaccccca tctgtctatc ccctggcccc cggatttgct      60
gtccaaacta actccatggt gatc                                             84
```

<210> SEQ ID NO 60
<211> LENGTH: 414
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (141)..(141)
<223> OTHER INFORMATION: n is a, c, g, or t

<400> SEQUENCE: 60

```
ggagaaagtc actctcagtg aggatacacc atcagcatga gggtccttgc tgagctcctg      60
ggggtgctgg tgttctgctt tttaggtgtg agatgtgaca tccagatgaa ccagtctcca     120
tccagtctgt ctgcatccct nggagacaca attaccatca cttgccaagc cagtcagaac     180
attaatgttt ggttaagctg gtaccagcag aaaccaggaa atattcctaa actaatgatc     240
tctaaggctt ccaacctaca cacagtcgtg ccatcaaggc ttagtcgcag tggatgtgga     300
acaggctgca ctttacccat ccatccattg cagcgaggag gcggatgctg ccacttcttt     360
cagccggctc aacagggagc tttcacgttc ggagggggga ccaagctgga aata           414
```

<210> SEQ ID NO 61
<211> LENGTH: 375
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (102)..(102)
<223> OTHER INFORMATION: n is a, c, g, or t

<400> SEQUENCE: 61

```
agggtccttg ctgagctcct gggggtgctg gtgttctgct ttttaggtgt gagatgtgac      60
atccagatga accagtctcc atccagtctg tctgcatccc tnggagacac aattaccatc     120
acttgccaag ccagtcagaa cattaatgtt tggttaagct ggtaccagca gaaaccagga     180
aatattccta aactaatgat ctctaaggct tccaacctac acacagtcgt gccatcaagg     240
cttagtcgca gtggatgtgg aacaggctgc actttaccca tccatccatt gcagcgagga     300
ggcggatgct gccacttctt tcagccggct caacagggag ctttcacgtt cggagggggg     360
accaagctgg aaata                                                       375
```

<210> SEQ ID NO 62
<211> LENGTH: 84
<212> TYPE: DNA
<213> ORGANISM: Artificial Sequence
<220> FEATURE:
<223> OTHER INFORMATION: Synthetic

<400> SEQUENCE: 62

```
aaacgggctg atgctgcacc aactgtatcc atcttcccac catccagtga gcagttaaca      60
tctggaggtg cctcagtcgt gtgc                                             84
```

<210> SEQ ID NO 63

<211> LENGTH: 456
<212> TYPE: DNA
<213> ORGANISM: Artificial Sequence
<220> FEATURE:
<223> OTHER INFORMATION: Synthetic

<400> SEQUENCE: 63

| | | | | | |
|---|---|---|---|---|---|
| gggaacatat | gtccaatgtc | ctctcctcag | acactgaaca | cactgactct | aaccatggga | 60 |
| tggaactgga | tctttctctt | tctcctgtca | ggaattgcag | gtgtcctctc | tgaggtccag | 120 |
| ctgcagcagt | ctggacctga | gttggtgaag | cctggggctt | caataaagat | atcctgcaag | 180 |
| acttctggat | acacattcac | tgaatacagc | atgcactggg | tgaaacagag | ccatggaaag | 240 |
| agccttgagt | ggatcggagg | ttttaatcct | aacaatggtt | atagtcacta | caaccagaag | 300 |
| ttcaaggaca | aggccacatt | gactgtagac | aagtcgtcca | gcacagccta | catggagctc | 360 |
| cgcagcctga | catctgagga | ttctgcagtc | ttttactgtg | caagatcgga | ctctaaatac | 420 |
| acctactttg | cttactgggg | ccaagggact | ctggtc | | | 456 |

<210> SEQ ID NO 64
<211> LENGTH: 399
<212> TYPE: DNA
<213> ORGANISM: Artificial Sequence
<220> FEATURE:
<223> OTHER INFORMATION: Synthetic

<400> SEQUENCE: 64

| | | | | | |
|---|---|---|---|---|---|
| ggatggaact | ggatctttct | ctttctcctg | tcaggaattg | caggtgtcct | ctctgaggtc | 60 |
| cagctgcagc | agtctggacc | tgagttggtg | aagcctgggg | cttcaataaa | gatatcctgc | 120 |
| aagacttctg | gatacacatt | cactgaatac | agcatgcact | gggtgaaaca | gagccatgga | 180 |
| aagagccttg | agtggatcgg | aggttttaat | cctaacaatg | gttatagtca | ctacaaccag | 240 |
| aagttcaagg | acaaggccac | attgactgta | gacaagtcgt | ccagcacagc | ctacatggag | 300 |
| ctccgcagcc | tgacatctga | ggattctgca | gtcttttact | gtgcaagatc | ggactctaaa | 360 |
| tacacctact | ttgcttactg | gggccaaggg | actctggtc | | | 399 |

<210> SEQ ID NO 65
<211> LENGTH: 27
<212> TYPE: DNA
<213> ORGANISM: Artificial Sequence
<220> FEATURE:
<223> OTHER INFORMATION: Synthetic

<400> SEQUENCE: 65
actgtctctg cagccaaaac gacaccc                                          27

<210> SEQ ID NO 66
<211> LENGTH: 438
<212> TYPE: DNA
<213> ORGANISM: Artificial Sequence
<220> FEATURE:
<223> OTHER INFORMATION: Synthetic

<400> SEQUENCE: 66

| | | | | | |
|---|---|---|---|---|---|
| gggactgatc | agtctcctca | ggctgtctcc | tcaggttgcc | tcctcaaaat | gaagttgcct | 60 |
| gttaggctgt | tggtgctgat | gttctggatt | cctgctttca | gcagtgatgt | cttgatgagc | 120 |
| caaaatccac | tctccctgcc | tgtcagtctt | ggagatcaag | cctccatctc | ttgcagatct | 180 |
| agtcagagca | ttgtacatag | taatggaaac | acctatttag | aatggtacct | gcagaaacca | 240 |
| ggccagtctc | caaaggtcct | gatctacgaa | gtttccaacc | gattttctgg | ggtcccagac | 300 |

```
aggttcagtt gcactggatc agggacagat ctcccactca agatcagcag agtggaggct    360
gagggcctgg gactttatta ctgctttcaa ggttcacatg ttccgtggac gttcggtgga    420
ggcaccaagc tcgagatc                                                  438
```

<210> SEQ ID NO 67
<211> LENGTH: 387
<212> TYPE: DNA
<213> ORGANISM: Artificial Sequence
<220> FEATURE:
<223> OTHER INFORMATION: Synthetic

<400> SEQUENCE: 67

```
aagttgcctg ttaggctgtt ggtgctgatg ttctggattc ctgctttcag cagtgatgtc     60
ttgatgagcc aaaatccact ctccctgcct gtcagtcttg gagatcaagc ctccatctct    120
tgcagatcta gtcagagcat tgtacatagt aatggaaaca cctatttaga atggtacctg    180
cagaaaccag gccagtctcc aaaggtcctg atctacgaag tttccaaccg attttctggg    240
gtcccagaca ggttcagttg cactggatca gggacagatc tcccactcaa gatcagcaga    300
gtggaggctg agggcctggg actttattac tgctttcaag gttcacatgt tccgtggacg    360
ttcggtggag gcaccaagct cgagatc                                        387
```

<210> SEQ ID NO 68
<211> LENGTH: 24
<212> TYPE: PRT
<213> ORGANISM: Artificial Sequence
<220> FEATURE:
<223> OTHER INFORMATION: Synthetic

<400> SEQUENCE: 68

```
Ala Ala Ala Cys Gly Gly Gly Cys Thr Gly Ala Thr Gly Cys Thr Gly
1               5                   10                  15

Cys Ala Cys Cys Ala Ala Cys Gly
            20
```

<210> SEQ ID NO 69
<211> LENGTH: 456
<212> TYPE: DNA
<213> ORGANISM: Artificial Sequence
<220> FEATURE:
<223> OTHER INFORMATION: Synthetic

<400> SEQUENCE: 69

```
gtctgacaga ggaggcctgt cctggattcg attcccagtt cctcacattc agtcagcact     60
gaacacggac ccctcaccat gaacttcggg ctcagcttga ttttccttgt ccttgtttta    120
aaaggtgtcc agtgtgaggt gatgctggtg gagtctgggg gaggcttagt gaagcctgga    180
gggtccctga aactctcctg tgcagcctct ggattcactt tcagaaactt gccatgtctt    240
tgggttcgcc agacttcgga gaagaggctg gagtgggtcg caagcattag ttttggtggt    300
aattacacct tctatccaga cagtgtgaag gggcgattca ccgtctccaa agacaatgcc    360
aagaacaccc tgtatctgca aatgagtagt ctgaggtctg aggacacggc catgtatttc    420
tgtgcaagac gaggttactc ccactatgct atggac                              456
```

<210> SEQ ID NO 70
<211> LENGTH: 375
<212> TYPE: DNA
<213> ORGANISM: Artificial Sequence
<220> FEATURE:

<223> OTHER INFORMATION: Synthetic

<400> SEQUENCE: 70

| aacttcgggc tcagcttgat tttccttgtc cttgttttaa aaggtgtcca gtgtgaggtg | 60 |
| atgctggtgg agtctggggg aggcttagtg aagcctggag ggtccctgaa actctcctgt | 120 |
| gcagcctctg gattcacttt cagaaacttt gccatgtctt gggttcgcca gacttcggag | 180 |
| aagaggctgg agtgggtcgc aagcattagt tttggtggta attacacctt ctatccagac | 240 |
| agtgtgaagg ggcgattcac cgtctccaaa gacaatgcca gaacaccct gtatctgcaa | 300 |
| atgagtagtc tgaggtctga ggacacggcc atgtatttct gtgcaagacg aggttactcc | 360 |
| cactatgcta tggac | 375 |

<210> SEQ ID NO 71
<211> LENGTH: 84
<212> TYPE: DNA
<213> ORGANISM: Artificial Sequence
<220> FEATURE:
<223> OTHER INFORMATION: Synthetic

<400> SEQUENCE: 71

| tactggggtc aaggaacctc agtctccgtc tcctcagcca aaacaacagc cccatcggtc | 60 |
| tatccactgg ccctgtgtg tgga | 84 |

<210> SEQ ID NO 72
<211> LENGTH: 438
<212> TYPE: DNA
<213> ORGANISM: Artificial Sequence
<220> FEATURE:
<223> OTHER INFORMATION: Synthetic

<400> SEQUENCE: 72

| gggactgatc agtctcctca ggctgtctcc tcaggttgcc tcctcaaaat gaagttgcct | 60 |
| gttaggctgt tggtgctgat gttctggatt cctgcttcca gcagtgatgt tttgatgacc | 120 |
| caaactccac tctccctgcc tgtcagtctt ggagatcaag cctccatctc ttgcaaatct | 180 |
| agtcagagca ttgtacatag taatggaaac acctatttag aatggtacct gcagaaacca | 240 |
| ggccagcctc caaaggtcct gatctacaaa gtttccaacc gattttctgg ggtcccagac | 300 |
| aggttcagtg cagtggatc agggacagat tccacactca gatcagcag agtggaggct | 360 |
| gaggatctgg gactttatta ctgctttcaa ggttcacatg ttccgtggac gttcggtgga | 420 |
| ggcaccaagc tggagatc | 438 |

<210> SEQ ID NO 73
<211> LENGTH: 387
<212> TYPE: DNA
<213> ORGANISM: Artificial Sequence
<220> FEATURE:
<223> OTHER INFORMATION: Synthetic

<400> SEQUENCE: 73

| aagttgcctg ttaggctgtt ggtgctgatg ttctggattc ctgcttccag cagtgatgtt | 60 |
| ttgatgaccc aaactccact ctccctgcct gtcagtcttg gagatcaagc ctccatctct | 120 |
| tgcaaatcta gtcagagcat tgtacatagt aatggaaaca cctatttaga atggtacctg | 180 |
| cagaaaccag gccagcctcc aaaggtcctg atctacaaag tttccaaccg attttctggg | 240 |
| gtcccagaca ggttcagtgg cagtggatca gggacagatt ccacactcaa gatcagcaga | 300 |
| gtggaggctg aggatctggg actttattac tgctttcaag gttcacatgt tccgtggacg | 360 |

```
ttcggtggag gcaccaagct ggagatc                                             387
```

<210> SEQ ID NO 74
<211> LENGTH: 42
<212> TYPE: DNA
<213> ORGANISM: Artificial Sequence
<220> FEATURE:
<223> OTHER INFORMATION: Synthetic

<400> SEQUENCE: 74

```
aaacgggctg atgctgcacc aactgtatcc atcttcccgc ca                             42
```

<210> SEQ ID NO 75
<211> LENGTH: 501
<212> TYPE: DNA
<213> ORGANISM: Artificial Sequence
<220> FEATURE:
<223> OTHER INFORMATION: Synthetic

<400> SEQUENCE: 75

```
gtctgacaga ggaggcaggt cctggattcg attcccagtt cctcacattc agtcagcact          60
gaacacggac ccctcaccat gaactttgtg ctcagcttga ttttccttgc cctcatttta         120
aaaggtgtcc agtgtgaagt gcagctggtg gagtctgggg gaggcttagt gaagcctgga         180
gggtccctga actctcctg tgcagcctct ggattcactt tcagtagcta tgccatgtct          240
tgggttcgcc agactccgga agaggctg agtgggtcg cagccattag ttatggtggt            300
aattacaccct actatccaga cagtgtgaag gtcgattca ccgtctccag agacaatgcc         360
aagaacaccc tgtacctgca aatgagcagt ctgaggtctg aggacacggc catgtattac         420
tgtgcaagaa gagctcgggc cgagtattac tatgctatgg actactgggg tcaaggaacc         480
tctgtcaccg tctcctcagc t                                                   501
```

<210> SEQ ID NO 76
<211> LENGTH: 420
<212> TYPE: DNA
<213> ORGANISM: Artificial Sequence
<220> FEATURE:
<223> OTHER INFORMATION: Synthetic

<400> SEQUENCE: 76

```
aactttgtgc tcagcttgat tttccttgcc ctcattttaa aaggtgtcca gtgtgaagtg          60
cagctggtgg agtctggggg aggcttagtg aagcctggag ggtccctgaa actctcctgt        120
gcagcctctg gattcacttt cagtagctat gccatgtctt gggttcgcca gactccggag        180
aagaggctgg agtgggtcgc agccattagt tatggtggta attacaccta ctatccagac        240
agtgtgaagg gtcgattcac cgtctccaga gacaatgcca agaacaccct gtacctgcaa        300
atgagcagtc tgaggtctga ggacacggcc atgtattact gtgcaagaag agctcgggcc        360
gagtattact atgctatgga ctactggggt caaggaacct ctgtcaccgt ctcctcagct        420
```

<210> SEQ ID NO 77
<211> LENGTH: 93
<212> TYPE: DNA
<213> ORGANISM: Artificial Sequence
<220> FEATURE:
<223> OTHER INFORMATION: Synthetic

<400> SEQUENCE: 77

```
acaacaacag ccccatctgt ctatcccttg gtccctggct gcagtgacac atctggatcc          60
```

-continued tcggtgacac tgggatgcct tgtcaaaggc tac    93

<210> SEQ ID NO 78
<211> LENGTH: 836
<212> TYPE: PRT
<213> ORGANISM: Mus musculus
<300> PUBLICATION INFORMATION:
<308> DATABASE ACCESSION NUMBER: NP_034561
<309> DATABASE ENTRY DATE: 2011-06-18
<313> RELEVANT RESIDUES IN SEQ ID NO: (1)..(836)

<400> SEQUENCE: 78

```
Met Glu Gly Ala Gly Gly Glu Asn Lys Lys Met Ser Glu
1               5                   10                  15

Arg Arg Lys Glu Lys Ser Arg Asp Ala Ala Arg Ser Arg Arg Ser Lys
                20                  25                  30

Glu Ser Glu Val Phe Tyr Glu Leu Ala His Gln Leu Pro Leu Pro His
            35                  40                  45

Asn Val Ser Ser His Leu Asp Lys Ala Ser Val Met Arg Leu Thr Ile
        50                  55                  60

Ser Tyr Leu Arg Val Arg Lys Leu Leu Asp Ala Gly Gly Leu Asp Ser
65                  70                  75                  80

Glu Asp Glu Met Lys Ala Gln Met Asp Cys Phe Tyr Leu Lys Ala Leu
                85                  90                  95

Asp Gly Phe Val Met Val Leu Thr Asp Asp Gly Asp Met Val Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
130                 135                 140

Arg Glu Met Leu Thr His Arg Asn Gly Pro Val Arg Lys Gly Lys Glu
                145                 150                 155                 160

Leu Asn Thr Gln Arg Ser Phe Phe Leu Arg Met Lys Cys Thr Leu Thr
            165                 170                 175

Ser Arg Gly Arg Thr Met Asn Ile Lys Ser Ala Thr Trp Lys Val Leu
        180                 185                 190

His Cys Thr Gly His Ile His Val Tyr Asp Thr Asn Ser Asn Gln Pro
    195                 200                 205

Gln Cys Gly Tyr Lys Lys Pro Pro Met Thr Cys Leu Val Leu Ile Cys
210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
    290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
            340                 345                 350
```

```
Ser Leu Gln Gln Thr Glu Ser Val Leu Lys Pro Val Glu Ser Asp
        355                 360                 365

Met Lys Met Thr Gln Leu Phe Thr Lys Val Glu Ser Glu Asp Thr Ser
    370                 375                 380

Cys Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asp
                405                 410                 415

Asp Thr Glu Thr Glu Asp Gln Gln Leu Glu Asp Val Pro Leu Tyr Asn
            420                 425                 430

Asp Val Met Phe Pro Ser Ser Asn Glu Lys Leu Asn Ile Asn Leu Ala
                435                 440                 445

Met Ser Pro Leu Pro Ser Ser Glu Thr Pro Lys Pro Leu Arg Ser Ser
    450                 455                 460

Ala Asp Pro Ala Leu Asn Gln Glu Val Ala Leu Lys Leu Glu Ser Ser
465                 470                 475                 480

Pro Glu Ser Leu Gly Leu Ser Phe Thr Met Pro Gln Ile Gln Asp Gln
                485                 490                 495

Pro Ala Ser Pro Ser Asp Gly Ser Thr Arg Gln Ser Ser Pro Glu Arg
                500                 505                 510

Leu Leu Gln Glu Asn Val Asn Thr Pro Asn Phe Ser Gln Pro Asn Ser
                515                 520                 525

Pro Ser Glu Tyr Cys Phe Asp Val Asp Ser Asp Met Val Asn Val Phe
    530                 535                 540

Lys Leu Glu Leu Val Glu Lys Leu Phe Ala Glu Asp Thr Glu Ala Lys
545                 550                 555                 560

Asn Pro Phe Ser Thr Gln Asp Thr Asp Leu Asp Leu Glu Met Leu Ala
                565                 570                 575

Pro Tyr Ile Pro Met Asp Asp Asp Phe Gln Leu Arg Ser Phe Asp Gln
                580                 585                 590

Leu Ser Pro Leu Glu Ser Asn Ser Pro Ser Pro Ser Met Ser Thr
    595                 600                 605

Val Thr Gly Phe Gln Gln Thr Gln Leu Gln Lys Pro Thr Ile Thr Ala
                610                 615                 620

Thr Ala Thr Thr Thr Ala Thr Asp Glu Ser Lys Thr Glu Thr Lys
625                 630                 635                 640

Asp Asn Lys Glu Asp Ile Lys Ile Leu Ile Ala Ser Pro Ser Ser Thr
                645                 650                 655

Gln Val Pro Gln Glu Thr Thr Ala Lys Ala Ser Ala Tyr Ser Gly
                660                 665                 670

Thr His Ser Arg Thr Ala Ser Pro Asp Arg Ala Gly Lys Arg Val Ile
                675                 680                 685

Glu Gln Thr Asp Lys Ala His Pro Arg Ser Leu Asn Leu Ser Ala Thr
    690                 695                 700

Leu Asn Gln Arg Asn Thr Val Pro Glu Glu Leu Asn Pro Lys Thr
705                 710                 715                 720

Ile Ala Ser Gln Asn Ala Gln Arg Lys Arg Lys Met Glu His Asp Gly
                725                 730                 735

Ser Leu Phe Gln Ala Ala Gly Ile Gly Thr Leu Leu Gln Gln Pro Gly
                740                 745                 750

Asp Cys Ala Pro Thr Met Ser Leu Ser Trp Lys Arg Val Lys Gly Phe
                755                 760                 765
```

```
Ile Ser Ser Glu Gln Asn Gly Thr Glu Gln Lys Thr Ile Ile Leu Ile
    770             775             780
Pro Ser Asp Leu Ala Cys Arg Leu Leu Gly Gln Ser Met Asp Glu Ser
785             790             795             800
Gly Leu Pro Gln Leu Thr Ser Tyr Asp Cys Glu Val Asn Ala Pro Ile
            805             810             815
Gln Gly Ser Arg Asn Leu Leu Gln Gly Glu Glu Leu Leu Arg Ala Leu
            820             825             830
Asp Gln Val Asn
        835
```